United States Patent
Subramanian et al.

(10) Patent No.: US 12,428,487 B2
(45) Date of Patent: *Sep. 30, 2025

(54) COMPLEXES COMPRISING AN ANTI-TRANSFERRIN RECEPTOR ANTIBODY LINKED TO AN OLIGONICLEOTIDE AND METHOD OF DELIVERING OLIGONUCLEOTIDE TO A SUBJECT

(71) Applicant: Dyne Therapeutics, Inc., Waltham, MA (US)

(72) Inventors: Romesh R. Subramanian, Framingham, MA (US); Mohammed T. Qatanani, Waltham, MA (US); Timothy Weeden, Waltham, MA (US); Cody A. Desjardins, Waltham, MA (US)

(73) Assignee: Dyne Therapeutics, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/211,660

(22) Filed: May 19, 2025

(65) Prior Publication Data

US 2025/0276083 A1 Sep. 4, 2025

Related U.S. Application Data

(63) Continuation of application No. 19/066,035, filed on Feb. 27, 2025, now Pat. No. 12,370,264, which is a continuation of application No. 18/939,894, filed on Nov. 7, 2024, now Pat. No. 12,319,743, which is a continuation of application No. 18/656,654, filed on May 7, 2024, now Pat. No. 12,173,078, which is a continuation of application No. 18/468,580, filed on Sep. 15, 2023, now Pat. No. 12,018,087, which is a continuation-in-part of application No. 18/184,741, filed on Mar. 16, 2023, now Pat. No. 11,795,233, which is a continuation of application No. 17/936,483, filed on Sep. 29, 2022, now Pat. No. 11,787,869, which is a continuation of application No. 17/846,738, filed on Jun. 22, 2022, now Pat. No. 11,518,816, which is a continuation of application No. 17/671,707, filed on Feb. 15, 2022, now Pat. No. 11,390,682, which is a continuation of application No. 17/400,295, filed on Aug. 12, 2021, now Pat. No. 11,286,305, which is a continuation of application No. 17/205,123, filed on Mar. 18, 2021, now Pat. No. 11,111,309, said application No. 18/468,580 is a continuation-in-part of application No. 17/265,019, filed as application No. PCT/US2019/044959 on Aug. 2, 2019, now abandoned, said application No. 18/468,580 is a continuation-in-part of application
(Continued)

(51) Int. Cl.
A61K 47/68 (2017.01)
A61P 21/00 (2006.01)
C07K 16/28 (2006.01)
C12N 15/113 (2010.01)

(52) U.S. Cl.
CPC .......... *A61K 47/6849* (2017.08); *A61P 21/00* (2018.01); *C07K 16/2881* (2013.01); *C12N 15/113* (2013.01); *C07K 2317/24* (2013.01); *C07K 2317/524* (2013.01); *C07K 2317/526* (2013.01); *C07K 2317/565* (2013.01); *C07K 2317/567* (2013.01); *C07K 2317/71* (2013.01); *C12N 2310/11* (2013.01); *C12N 2310/315* (2013.01); *C12N 2310/321* (2013.01); *C12N 2310/322* (2013.01); *C12N 2320/32* (2013.01)

(58) Field of Classification Search
CPC . A61K 47/6849; A61P 21/00; C07K 16/2881; C07K 2317/24; C07K 2317/524; C07K 2317/526; C07K 2317/565; C07K 2317/567; C07K 2317/71; C12N 15/113; C12N 2310/11; C12N 2310/315; C12N 2310/322; C12N 2320/32
See application file for complete search history.

(56) References Cited

U.S. PATENT DOCUMENTS 2,631,173 A 3/1953 Hillyer et al.
6,100,099 A 8/2000 Hoijer et al.
(Continued)

FOREIGN PATENT DOCUMENTS

CN 102459597 A 11/2010
CN 103443125 A 12/2013
(Continued)

OTHER PUBLICATIONS

[No Author Listed], Alessandra Baleyew—Abstract. MDA National Scientific Conference. Neuromuscular Therapeutic Strategies: Overcoming the Barriers from Microscope to Marketplace. Mar. 13-16, 2011. Las Vegas, Nevada. 2 pages.
(Continued)

*Primary Examiner* — Robert S Landsman
(74) *Attorney, Agent, or Firm* — Wolf, Greenfield & Sacks, P.C.

(57) ABSTRACT

Aspects of the disclosure relate to complexes comprising a muscle-targeting agent covalently linked to a molecular payload. In some embodiments, the muscle-targeting agent specifically binds to an internalizing cell surface receptor on muscle cells. In some embodiments, the molecular payload inhibits activity of a disease allele associated with muscle disease. In some embodiments, the molecular payload is an oligonucleotide, such as an antisense oligonucleotide or RNAi oligonucleotide.

30 Claims, 21 Drawing Sheets

Specification includes a Sequence Listing.

Related U.S. Application Data

No. 17/264,972, filed as application No. PCT/US2019/044961 on Aug. 2, 2019, now abandoned, said application No. 18/468,580 is a continuation-in-part of application No. 17/264,998, filed as application No. PCT/US2019/044982 on Aug. 2, 2019, now abandoned, said application No. 18/468,580 is a continuation-in-part of application No. 17/264,905, filed as application No. PCT/US2019/044987 on Aug. 2, 2019, now abandoned, said application No. 18/468,580 is a continuation-in-part of application No. 17/265,024, filed as application No. PCT/US2019/044949 on Aug. 2, 2019, now abandoned, said application No. 18/468,580 is a continuation-in-part of application No. 17/265,044, filed as application No. PCT/US2019/044955 on Aug. 2, 2019, now abandoned, said application No. 17/205,123 is a continuation of application No. 17/264,948, filed as application No. PCT/US2019/044990 on Aug. 2, 2019, now abandoned, said application No. 18/468,580 is a continuation-in-part of application No. 17/265,016, filed as application No. PCT/US2019/044960 on Aug. 2, 2019, now abandoned.

(60) Provisional application No. 62/859,694, filed on Jun. 10, 2019, provisional application No. 62/859,672, filed on Jun. 10, 2019, provisional application No. 62/858,925, filed on Jun. 7, 2019, provisional application No. 62/858,888, filed on Jun. 7, 2019, provisional application No. 62/855,781, filed on May 31, 2019, provisional application No. 62/855,761, filed on May 31, 2019, provisional application No. 62/855,766, filed on May 31, 2019, provisional application No. 62/779,161, filed on Dec. 13, 2018, provisional application No. 62/779,173, filed on Dec. 13, 2018, provisional application No. 62/714,025, filed on Aug. 2, 2018, provisional application No. 62/714,031, filed on Aug. 2, 2018, provisional application No. 62/713,959, filed on Aug. 2, 2018, provisional application No. 62/713,933, filed on Aug. 2, 2018, provisional application No. 62/713,914, filed on Aug. 2, 2018, provisional application No. 62/714,010, filed on Aug. 2, 2018, provisional application No. 62/714,034, filed on Aug. 2, 2018, provisional application No. 62/714,035, filed on Aug. 2, 2018.

(56) References Cited

U.S. PATENT DOCUMENTS

| | | | |
|---|---|---|---|
| 6,136,603 | A | 10/2000 | Dean et al. |
| 6,210,898 | B1 | 4/2001 | Hoijer et al. |
| 6,214,345 | B1 | 4/2001 | Firestone et al. |
| 7,015,315 | B1 | 3/2006 | Cook et al. |
| 7,064,142 | B2 | 6/2006 | Sato et al. |
| 7,250,496 | B2 | 7/2007 | Bentwich |
| 7,265,131 | B2 | 9/2007 | Johnson et al. |
| 7,442,372 | B2 | 10/2008 | Kakkis et al. |
| 7,534,879 | B2 | 5/2009 | van Deutekom et al. |
| 7,575,886 | B2 | 8/2009 | Venkataraman et al. |
| 7,785,856 | B2 | 8/2010 | Lebowitz et al. |
| 7,902,160 | B2 | 3/2011 | Matsuo et al. |
| 7,960,541 | B2 | 6/2011 | Wilton et al. |
| 7,973,015 | B2 | 7/2011 | van Ommen et al. |
| 8,084,601 | B2 | 12/2011 | Graham et al. |
| 8,232,384 | B2 | 7/2012 | Wilton et al. |
| 8,324,371 | B2 | 12/2012 | Popplewell et al. |
| 8,361,979 | B2 | 1/2013 | van Ommen et al. |
| 8,409,573 | B2 | 4/2013 | Boumsell et al. |
| 8,455,636 | B2 | 6/2013 | Fletcher et al. |
| 8,466,340 | B2 | 6/2013 | Khanna et al. |
| 8,486,907 | B2 | 7/2013 | Wilton et al. |
| 8,524,880 | B2 | 9/2013 | Mcclorey et al. |
| 8,580,756 | B2 | 11/2013 | Hansen et al. |
| 8,637,483 | B2 | 1/2014 | Wilton et al. |
| 8,759,501 | B2 | 6/2014 | Zhu et al. |
| 8,759,507 | B2 | 6/2014 | van Deutekom et al. |
| 8,785,168 | B2 | 7/2014 | Lebowitz et al. |
| 8,802,437 | B2 | 8/2014 | Tremblay et al. |
| 8,835,614 | B2 | 9/2014 | Avila et al. |
| 8,846,639 | B2 | 9/2014 | Swayze et al. |
| 8,859,629 | B2 | 10/2014 | van Delft et al. |
| 8,865,883 | B2 | 10/2014 | Kole et al. |
| 8,952,147 | B2 | 2/2015 | Bouchard et al. |
| 9,018,368 | B2 | 4/2015 | Wilton et al. |
| 9,024,007 | B2 | 5/2015 | Wilton et al. |
| 9,035,040 | B2 | 5/2015 | Wilton et al. |
| 9,044,473 | B2 | 6/2015 | Kakkis et al. |
| 9,045,754 | B2 | 6/2015 | Bhanot et al. |
| 9,050,333 | B2 | 6/2015 | Chen et al. |
| 9,078,911 | B2 | 7/2015 | Lu et al. |
| 9,079,934 | B2 | 7/2015 | Takeda et al. |
| 9,186,420 | B2 | 11/2015 | Koeberl et al. |
| 9,217,148 | B2 | 12/2015 | Bestwick et al. |
| 9,222,940 | B2 | 12/2015 | van Delft et al. |
| 9,228,187 | B2 | 1/2016 | Meloni et al. |
| 9,243,245 | B2 | 1/2016 | De Kimpe et al. |
| 9,249,399 | B2 | 2/2016 | Vervecken et al. |
| 9,260,371 | B2 | 2/2016 | Bertozzi et al. |
| 9,416,361 | B2 | 8/2016 | Iversen et al. |
| 9,422,555 | B2 | 8/2016 | Wilton et al. |
| 9,428,534 | B2 | 8/2016 | Christensen et al. |
| 9,447,415 | B2 | 9/2016 | Wilton et al. |
| 9,447,416 | B2 | 9/2016 | Sazani et al. |
| 9,469,850 | B2 | 10/2016 | Zhu et al. |
| 9,493,498 | B2 | 11/2016 | Avila et al. |
| 9,504,758 | B2 | 11/2016 | van Delft et al. |
| 9,506,058 | B2 | 11/2016 | Kaye |
| 9,512,424 | B2 | 12/2016 | Watanabe et al. |
| 9,528,109 | B2 | 12/2016 | De Kimpe et al. |
| 9,550,834 | B2 | 1/2017 | Shirai et al. |
| 9,550,988 | B2 | 1/2017 | Swayze |
| 9,610,362 | B2 | 4/2017 | Armstrong |
| 9,611,323 | B2 | 4/2017 | Dennis et al. |
| 9,617,540 | B2 | 4/2017 | Bhanot et al. |
| 9,650,632 | B2 | 5/2017 | Popplewell et al. |
| 9,657,049 | B2 | 5/2017 | Koizumi et al. |
| 9,657,050 | B2 | 5/2017 | Koizumi et al. |
| 9,695,418 | B2 | 7/2017 | Seth et al. |
| 9,708,361 | B2 | 7/2017 | Takeda et al. |
| 9,708,406 | B2 | 7/2017 | Zhang et al. |
| 9,708,614 | B2 | 7/2017 | Christensen et al. |
| 9,758,783 | B2 | 9/2017 | Meloni et al. |
| 9,765,338 | B2 | 9/2017 | Bennett et al. |
| 9,840,706 | B2 | 12/2017 | Watanabe et al. |
| 9,850,474 | B2 | 12/2017 | Chen et al. |
| 9,890,381 | B2 | 2/2018 | Watanabe et al. |
| 9,926,557 | B2 | 3/2018 | De Kimpe et al. |
| 9,970,010 | B2 | 5/2018 | Graham et al. |
| 9,988,628 | B2 | 6/2018 | Belayew et al. |
| 9,988,629 | B2 | 6/2018 | Takeda et al. |
| 9,994,851 | B2 | 6/2018 | Wilton et al. |
| 10,098,905 | B2 | 10/2018 | Koeberl et al. |
| 10,100,304 | B2 | 10/2018 | van Deutekom et al. |
| 10,131,682 | B2 | 11/2018 | Zhao |
| 10,144,931 | B2 | 12/2018 | Enya et al. |
| 10,179,912 | B2 | 1/2019 | De Visser et al. |
| 10,190,116 | B2 | 1/2019 | Van Deutekom et al. |
| 10,208,299 | B2 | 2/2019 | Gotschall et al. |
| 10,227,577 | B2 | 3/2019 | Do et al. |
| 10,227,590 | B2 | 3/2019 | Wilton et al. |
| 10,238,753 | B2 | 3/2019 | Armstrong |
| 10,239,807 | B2 | 3/2019 | van Delft et al. |
| 10,266,502 | B2 | 4/2019 | van Delft et al. |
| 10,266,827 | B2 | 4/2019 | Wilton et al. |
| 10,287,586 | B2 | 5/2019 | Wilson et al. |
| 10,329,319 | B2 | 6/2019 | Watanabe et al. |

(56) References Cited

U.S. PATENT DOCUMENTS

| | | |
|---|---|---|
| 10,337,003 B2 | 7/2019 | Kaye |
| 10,364,431 B2 | 7/2019 | Kaye |
| 10,385,092 B2 | 8/2019 | Watanabe et al. |
| 10,407,461 B2 | 9/2019 | Watanabe et al. |
| 10,421,966 B2 | 9/2019 | Wilton et al. |
| 10,434,111 B2 | 10/2019 | Bertozzi et al. |
| 10,450,568 B2 | 10/2019 | Butler et al. |
| 10,457,944 B2 | 10/2019 | Popplewell et al. |
| RE47,691 E | 11/2019 | Wilton et al. |
| 10,464,962 B2 | 11/2019 | Avila et al. |
| 10,487,106 B2 | 11/2019 | Watanabe et al. |
| RE47,751 E | 12/2019 | Wilton et al. |
| 10,493,092 B2 | 12/2019 | Swayze |
| 10,512,676 B2 | 12/2019 | Char et al. |
| 10,533,171 B2 | 1/2020 | van Deutekom et al. |
| 10,533,174 B2 | 1/2020 | Iversen et al. |
| 10,538,763 B2 | 1/2020 | Rigo et al. |
| 10,550,188 B2 | 2/2020 | Geall et al. |
| 10,647,969 B2 | 5/2020 | Chen et al. |
| 10,648,044 B2 | 5/2020 | Vervecken et al. |
| 10,662,217 B2 | 5/2020 | Watanbe et al. |
| 10,704,060 B2 | 7/2020 | Gersbach et al. |
| 10,722,559 B2 | 7/2020 | Concino et al. |
| 10,752,898 B2 | 8/2020 | Pietri et al. |
| 10,781,448 B2 | 9/2020 | Watanabe et al. |
| 10,781,450 B2 | 9/2020 | Wilton et al. |
| 10,781,451 B2 | 9/2020 | Wilton et al. |
| 10,865,445 B2 | 12/2020 | van Der Maarel et al. |
| 10,876,114 B2 | 12/2020 | van Deutekom et al. |
| 10,881,743 B2 | 1/2021 | Geall et al. |
| 10,907,142 B2 | 2/2021 | Zhu et al. |
| 10,907,157 B2 | 2/2021 | Belayew et al. |
| 10,913,946 B2 | 2/2021 | De Visser et al. |
| 10,940,125 B2 | 3/2021 | Koeberl et al. |
| 10,940,185 B2 | 3/2021 | Yasukawa et al. |
| 10,961,522 B2 | 3/2021 | Gotschall et al. |
| 10,968,450 B2 | 4/2021 | Wilton et al. |
| 10,994,020 B2 | 5/2021 | Levin et al. |
| 10,995,337 B2 | 5/2021 | Wilton et al. |
| 11,028,122 B1 | 6/2021 | Watanabe et al. |
| 11,111,309 B2 | 9/2021 | Subramanian et al. |
| 11,168,141 B2 | 11/2021 | Subramanian et al. |
| 11,179,472 B2 | 11/2021 | Levin et al. |
| 11,208,458 B2 | 12/2021 | Baik et al. |
| 11,214,782 B2 | 1/2022 | Chen et al. |
| 11,230,605 B2 | 1/2022 | Launay et al. |
| 11,248,056 B1 | 2/2022 | Subramanian et al. |
| 11,253,485 B2 | 2/2022 | Dodge et al. |
| RE48,960 E | 3/2022 | Wilton et al. |
| 11,279,725 B2 | 3/2022 | Avila et al. |
| 11,286,305 B2 | 3/2022 | Subramanian et al. |
| 11,311,627 B1 | 4/2022 | Levin et al. |
| 11,339,406 B2 | 5/2022 | Mingozzi et al. |
| 11,369,689 B2 | 6/2022 | Subramanian et al. |
| 11,390,682 B2 | 7/2022 | Subramanian et al. |
| 11,400,163 B2 | 8/2022 | Levin et al. |
| 11,421,211 B2 | 8/2022 | Mingozzi et al. |
| 11,491,211 B2 | 11/2022 | Char et al. |
| 11,497,815 B2 | 11/2022 | Subramanian et al. |
| 11,518,816 B2 | 12/2022 | Subramanian et al. |
| 11,525,137 B2 | 12/2022 | Malecova et al. |
| 11,547,717 B2 | 1/2023 | Koeberl et al. |
| 11,555,190 B2 | 1/2023 | Malecova et al. |
| 11,591,583 B2 | 2/2023 | Gotschall et al. |
| 11,633,496 B2 | 4/2023 | Subramanian et al. |
| 11,633,498 B2 | 4/2023 | Subramanian et al. |
| 11,638,761 B2 | 5/2023 | Subramanian et al. |
| 11,648,318 B2 | 5/2023 | Subramanian et al. |
| 11,672,872 B2 | 6/2023 | Subramanian et al. |
| 11,679,161 B2 | 6/2023 | Subramanian et al. |
| 11,690,812 B2 | 7/2023 | Koeberl et al. |
| 11,708,569 B2 | 7/2023 | Kristensen et al. |
| 11,753,632 B2 | 9/2023 | Gotschall et al. |
| 11,759,525 B1 | 9/2023 | Subramanian et al. |
| 11,771,776 B2 | 10/2023 | Subramanian et al. |
| 11,787,869 B2 | 10/2023 | Subramanian et al. |
| 11,795,233 B2 | 10/2023 | Subramanian et al. |
| 11,795,234 B2 | 10/2023 | Subramanian et al. |
| 11,833,217 B2 | 12/2023 | Subramanian et al. |
| 11,839,660 B2 | 12/2023 | Subramanian et al. |
| 11,844,843 B2 | 12/2023 | Subramanian et al. |
| 11,911,484 B2 | 2/2024 | Subramanian et al. |
| 11,912,779 B2 | 2/2024 | Malecova et al. |
| 11,931,421 B2 | 3/2024 | Hilderbrand et al. |
| 11,969,475 B2 | 4/2024 | Subramanian et al. |
| 11,970,722 B2 | 4/2024 | Hallows et al. |
| 11,986,537 B2 | 5/2024 | Subramanian et al. |
| 12,005,124 B2 | 6/2024 | Subramanian et al. |
| 12,012,460 B2 | 6/2024 | Subramanian et al. |
| 12,018,087 B2 | 6/2024 | Subramanian et al. |
| 12,064,483 B2 | 8/2024 | Levin et al. |
| 12,097,263 B2 | 9/2024 | Subramanian et al. |
| 12,102,687 B2 | 10/2024 | Subramanian et al. |
| 12,128,109 B2 | 10/2024 | Weeden et al. |
| 12,144,867 B2 | 11/2024 | Subramanian et al. |
| 12,144,868 B2 | 11/2024 | Subramanian et al. |
| 12,173,078 B2 | 12/2024 | Subramanian et al. |
| 12,173,079 B2 | 12/2024 | Subramanian et al. |
| 12,239,716 B2 | 3/2025 | Subramanian et al. |
| 12,239,717 B2 | 3/2025 | Subramanian et al. |
| 12,263,225 B2 | 4/2025 | Subramanian et al. |
| 12,280,122 B2 | 4/2025 | Subramanian et al. |
| 12,319,743 B2 | 6/2025 | Subramanian et al. |
| 12,325,753 B2 | 6/2025 | Subramanian et al. |
| 2004/0063654 A1 | 4/2004 | Davis et al. |
| 2005/0004026 A1 | 1/2005 | Kashibatla et al. |
| 2005/0084906 A1 | 4/2005 | Goetsch et al. |
| 2005/0255487 A1 | 11/2005 | Khvorova et al. |
| 2005/0282252 A1 | 12/2005 | Siegel |
| 2006/0110782 A1 | 5/2006 | Bertozzi et al. |
| 2006/0252107 A1 | 11/2006 | Kubota et al. |
| 2007/0050146 A1 | 3/2007 | Bentwich et al. |
| 2007/0082861 A1 | 4/2007 | Matsuo et al. |
| 2007/0105805 A1 | 5/2007 | Kmiec et al. |
| 2008/0199960 A1 | 8/2008 | Juliano et al. |
| 2009/0269755 A1 | 10/2009 | Aartsma-Rus et al. |
| 2010/0130591 A1 | 5/2010 | Sazani et al. |
| 2010/0168212 A1 | 7/2010 | Popplewell et al. |
| 2011/0256157 A1 | 10/2011 | Howard et al. |
| 2011/0263682 A1 | 10/2011 | De Kimpe et al. |
| 2012/0059042 A1 | 3/2012 | Platenburg et al. |
| 2012/0077860 A1 | 3/2012 | Garcia et al. |
| 2012/0122801 A1 | 5/2012 | Platenburg |
| 2012/0201809 A1 | 8/2012 | Bhat et al. |
| 2012/0225034 A1 | 9/2012 | Belayew et al. |
| 2012/0270925 A1 | 10/2012 | Wilton et al. |
| 2013/0028891 A1 | 1/2013 | Penichet et al. |
| 2013/0041017 A1 | 2/2013 | Kaplan et al. |
| 2013/0066063 A1 | 3/2013 | Berry et al. |
| 2013/0072541 A1 | 3/2013 | Garcia et al. |
| 2013/0137763 A1 | 5/2013 | van Delft et al. |
| 2013/0177579 A1 | 7/2013 | Lin et al. |
| 2013/0237585 A1 | 9/2013 | Bennett et al. |
| 2014/0105873 A1 | 4/2014 | Belayew et al. |
| 2014/0193436 A1 | 7/2014 | Prudent |
| 2014/0323552 A1 | 10/2014 | Burghes et al. |
| 2014/0336178 A1 | 11/2014 | Kazantsev et al. |
| 2014/0363455 A1 | 12/2014 | Stull et al. |
| 2015/0064181 A1 | 3/2015 | Armstrong |
| 2015/0191725 A1 | 7/2015 | van Deutekom et al. |
| 2015/0196670 A1 | 7/2015 | Dickson et al. |
| 2015/0225722 A1 | 8/2015 | Ozsolak |
| 2015/0258210 A1 | 9/2015 | van Delft et al. |
| 2016/0032286 A1 | 2/2016 | Montgomery et al. |
| 2016/0053262 A1 | 2/2016 | Platenburg et al. |
| 2016/0090598 A1 | 3/2016 | Oestergaard et al. |
| 2016/0107999 A1 | 4/2016 | Debets et al. |
| 2016/0175460 A1 | 6/2016 | Arathoon et al. |
| 2016/0201064 A1 | 7/2016 | Ozsolak |
| 2016/0235861 A1 | 8/2016 | van Delft et al. |
| 2016/0250347 A1 | 9/2016 | van Delft et al. |
| 2016/0264976 A1 | 9/2016 | Laporte et al. |
| 2016/0272973 A1 | 9/2016 | Shehadeh |
| 2016/0304864 A1 | 10/2016 | De Kimpe et al. |

(56) References Cited

U.S. PATENT DOCUMENTS

| | | |
|---|---|---|
| 2016/0355599 A1 | 12/2016 | Sagert et al. |
| 2017/0002012 A1 | 1/2017 | van Delft et al. |
| 2017/0008858 A1 | 1/2017 | van Delft et al. |
| 2017/0029849 A1 | 2/2017 | Harper et al. |
| 2017/0072068 A1 | 3/2017 | Verkade et al. |
| 2017/0130256 A1 | 5/2017 | van Berkel et al. |
| 2017/0151348 A1 | 6/2017 | Kaspar et al. |
| 2017/0226554 A1 | 8/2017 | Wasiel et al. |
| 2017/0281795 A1 | 10/2017 | Geall et al. |
| 2017/0283799 A1 | 10/2017 | Kaye et al. |
| 2017/0348416 A1 | 12/2017 | Hasler et al. |
| 2018/0002433 A1 | 1/2018 | Zhang et al. |
| 2018/0021449 A1 | 1/2018 | Armstrong |
| 2018/0028554 A1 | 2/2018 | De Visser et al. |
| 2018/0094262 A1 | 4/2018 | Montgomery et al. |
| 2018/0111983 A1 | 4/2018 | Hatsell et al. |
| 2018/0134797 A1 | 5/2018 | Zhang et al. |
| 2018/0142245 A1 | 5/2018 | Watanabe et al. |
| 2018/0171333 A1 | 6/2018 | Meloni et al. |
| 2018/0179538 A1 | 6/2018 | Takeda et al. |
| 2018/0216111 A1 | 8/2018 | Wilton et al. |
| 2018/0265859 A1 | 9/2018 | Tremblay et al. |
| 2018/0265870 A1 | 9/2018 | Belayew et al. |
| 2018/0369400 A1 | 12/2018 | Levin et al. |
| 2019/0000986 A1 | 1/2019 | Levin et al. |
| 2019/0008986 A1 | 1/2019 | Butler et al. |
| 2019/0038765 A1 | 2/2019 | van Berkel et al. |
| 2019/0060488 A1 | 2/2019 | Tadin-Strapps et al. |
| 2019/0092833 A1 | 3/2019 | Lin et al. |
| 2019/0092870 A1 | 3/2019 | Launay et al. |
| 2019/0112604 A1 | 4/2019 | De Kimpe et al. |
| 2019/0119679 A1 | 4/2019 | De Kimpe et al. |
| 2019/0127733 A1 | 5/2019 | Butler et al. |
| 2019/0153083 A1 | 5/2019 | Juste et al. |
| 2019/0177723 A1 | 6/2019 | Dickson et al. |
| 2019/0177725 A1 | 6/2019 | De Kimpe et al. |
| 2019/0209604 A1 | 7/2019 | Zhang et al. |
| 2019/0211362 A1 | 7/2019 | Lundberg et al. |
| 2019/0240346 A1 | 8/2019 | Sugo et al. |
| 2019/0249173 A1 | 8/2019 | Vargeese et al. |
| 2019/0270994 A1 | 9/2019 | Wilton et al. |
| 2019/0284556 A1 | 9/2019 | Sazani et al. |
| 2019/0298847 A1 | 10/2019 | Geall et al. |
| 2019/0323010 A1 | 10/2019 | Wilton et al. |
| 2019/0330626 A1 | 10/2019 | Rigo et al. |
| 2019/0336615 A1 | 11/2019 | Thompson et al. |
| 2019/0338043 A1 | 11/2019 | Sonoda et al. |
| 2019/0338311 A1 | 11/2019 | Amoasii et al. |
| 2019/0359982 A1 | 11/2019 | Kaye et al. |
| 2019/0364862 A1 | 12/2019 | Amoasii et al. |
| 2019/0390197 A1 | 12/2019 | Butler et al. |
| 2020/0040337 A1 | 2/2020 | Kaye et al. |
| 2020/0046742 A1 | 2/2020 | Bertozzi et al. |
| 2020/0046854 A1 | 2/2020 | Zhang et al. |
| 2020/0048174 A1 | 2/2020 | van Delft et al. |
| 2020/0123267 A1 | 4/2020 | Zhang et al. |
| 2020/0239886 A1 | 7/2020 | De Kimpe et al. |
| 2020/0248179 A1 | 8/2020 | Harper |
| 2020/0282074 A1 | 9/2020 | Levin et al. |
| 2020/0325237 A1 | 10/2020 | Darimont et al. |
| 2020/0385457 A1 | 12/2020 | McNally et al. |
| 2021/0038739 A1 | 2/2021 | Takahashi et al. |
| 2021/0130486 A1 | 5/2021 | Darimont et al. |
| 2021/0145852 A1 | 5/2021 | Passini et al. |
| 2021/0163941 A1 | 6/2021 | Belayew et al. |
| 2021/0187082 A1 | 6/2021 | Yasukawa et al. |
| 2021/0187116 A1 | 6/2021 | Geall et al. |
| 2021/0206868 A1 | 7/2021 | Subramanian et al. |
| 2021/0220479 A1 | 7/2021 | Subramanian et al. |
| 2021/0228730 A1 | 7/2021 | Subramanian et al. |
| 2021/0230290 A1 | 7/2021 | Subramanian et al. |
| 2021/0261680 A1 | 8/2021 | Subramanian et al. |
| 2021/0308272 A1 | 10/2021 | Subramanian et al. |
| 2021/0308273 A1 | 10/2021 | Subramanian et al. |
| 2021/0308274 A1 | 10/2021 | Subramanian et al. |
| 2021/0317226 A1 | 10/2021 | Subramanian et al. |
| 2021/0322562 A1 | 10/2021 | Subramanian et al. |
| 2021/0322563 A1 | 10/2021 | Subramanian et al. |
| 2021/0324101 A1 | 10/2021 | Subramanian et al. |
| 2021/0371860 A1 | 12/2021 | Hagedorn et al. |
| 2021/0380709 A1 | 12/2021 | Subramanian et al. |
| 2022/0025066 A1 | 1/2022 | Subramanian et al. |
| 2022/0106592 A1 | 4/2022 | Harper et al. |
| 2022/0143206 A1 | 5/2022 | Subramanian et al. |
| 2022/0169743 A1 | 6/2022 | Subramanian et al. |
| 2022/0193250 A1 | 6/2022 | Subramanian et al. |
| 2022/0288220 A1 | 9/2022 | Subramanian et al. |
| 2022/0306685 A1 | 9/2022 | Weeden et al. |
| 2022/0324992 A1 | 10/2022 | Subramanian et al. |
| 2022/0378934 A1 | 12/2022 | Subramanian et al. |
| 2023/0001002 A1 | 1/2023 | Subramanian et al. |
| 2023/0044278 A1 | 2/2023 | Subramanian et al. |
| 2023/0045002 A1 | 2/2023 | Subramanian et al. |
| 2023/0045314 A1 | 2/2023 | Subramanian et al. |
| 2023/0047754 A1 | 2/2023 | Geall et al. |
| 2023/0049450 A1 | 2/2023 | Subramanian et al. |
| 2023/0050911 A1 | 2/2023 | Subramanian et al. |
| 2023/0051954 A1 | 2/2023 | Subramanian et al. |
| 2023/0088865 A1 | 3/2023 | Subramanian et al. |
| 2023/0103793 A1 | 4/2023 | Subramanian et al. |
| 2023/0111147 A1 | 4/2023 | Subramanian et al. |
| 2023/0111212 A1 | 4/2023 | Subramanian et al. |
| 2023/0113823 A1 | 4/2023 | Subramanian et al. |
| 2023/0117883 A1 | 4/2023 | Subramanian et al. |
| 2023/0118799 A1 | 4/2023 | Subramanian et al. |
| 2023/0144436 A1 | 5/2023 | Subramanian et al. |
| 2023/0203180 A1 | 6/2023 | Subramanian et al. |
| 2023/0203181 A1 | 6/2023 | Subramanian et al. |
| 2023/0226212 A1 | 7/2023 | Subramanian et al. |
| 2023/0227569 A1 | 7/2023 | Subramanian et al. |
| 2023/0256112 A1 | 8/2023 | Subramanian et al. |
| 2023/0256113 A1 | 8/2023 | Subramanian et al. |
| 2023/0270873 A1 | 8/2023 | Subramanian et al. |
| 2023/0272065 A1 | 8/2023 | Subramanian et al. |
| 2023/0285582 A1 | 9/2023 | Subramanian et al. |
| 2023/0285586 A1 | 9/2023 | Subramanian et al. |
| 2023/0287108 A1 | 9/2023 | Subramanian et al. |
| 2023/0321264 A1 | 10/2023 | Subramanian et al. |
| 2023/0330247 A1 | 10/2023 | Hildebrand et al. |
| 2023/0330562 A1 | 10/2023 | Weeden et al. |
| 2023/0346966 A1 | 11/2023 | Subramanian et al. |
| 2023/0346967 A1 | 11/2023 | Subramanian et al. |
| 2024/0016950 A1 | 1/2024 | Weeden et al. |
| 2024/0016952 A1 | 1/2024 | Subramanian et al. |
| 2024/0066139 A1 | 2/2024 | Subramanian et al. |
| 2024/0066140 A1 | 2/2024 | Subramanian et al. |
| 2024/0067743 A1 | 2/2024 | Subramanian et al. |
| 2024/0067744 A1 | 2/2024 | Subramanian et al. |
| 2024/0100177 A1 | 3/2024 | Hildebrand et al. |
| 2024/0110184 A1 | 4/2024 | Brown et al. |
| 2024/0117356 A1 | 4/2024 | Subramanian et al. |
| 2024/0148891 A1 | 5/2024 | Subramanian et al. |
| 2024/0197901 A1 | 6/2024 | Subramanian et al. |
| 2024/0197905 A1 | 6/2024 | Subramanian et al. |
| 2024/0207430 A1 | 6/2024 | Subramanian et al. |
| 2024/0209119 A1 | 6/2024 | Subramanian et al. |
| 2024/0216522 A1 | 7/2024 | Subramanian et al. |
| 2024/0238435 A1 | 7/2024 | Subramanian et al. |
| 2024/0252666 A1 | 8/2024 | Hilderbrand et al. |
| 2024/0287201 A1 | 8/2024 | Subramanian et al. |
| 2024/0293568 A1 | 9/2024 | Subramanian et al. |
| 2024/0294921 A1 | 9/2024 | Subramanian et al. |
| 2024/0301416 A1 | 9/2024 | Tone et al. |
| 2024/0309107 A1 | 9/2024 | Subramanian et al. |
| 2024/0318176 A1 | 9/2024 | Desjardins et al. |
| 2024/0318177 A1 | 9/2024 | Desjardins et al. |
| 2024/0325558 A1 | 10/2024 | Zanotti et al. |
| 2024/0368296 A1 | 11/2024 | Desjardins et al. |
| 2024/0382513 A1 | 11/2024 | Subramanian et al. |
| 2024/0382609 A1 | 11/2024 | Desjardins et al. |
| 2024/0398967 A1 | 12/2024 | Subramanian et al. |
| 2024/0398968 A1 | 12/2024 | Subramanian et al. |
| 2024/0408227 A1 | 12/2024 | Subramanian et al. |
| 2025/0018050 A1 | 1/2025 | Desjardins et al. |

(56) References Cited

U.S. PATENT DOCUMENTS

| | | |
|---|---|---|
| 2025/0025570 A1 | 1/2025 | Hsia et al. |
| 2025/0032634 A1 | 1/2025 | Subramanian et al. |
| 2025/0057972 A1 | 2/2025 | Subramanian et al. |
| 2025/0066495 A1 | 2/2025 | Subramanian et al. |
| 2025/0066496 A1 | 2/2025 | Subramanian et al. |
| 2025/0099603 A9 | 3/2025 | Subramanian et al. |
| 2025/0152727 A1 | 5/2025 | Subramanian et al. |
| 2025/0177549 A1 | 6/2025 | Subramanian et al. |

FOREIGN PATENT DOCUMENTS

| | | |
|---|---|---|
| CN | 103732259 A | 4/2014 |
| CN | 105142672 A | 12/2015 |
| CN | 107001473 A | 8/2017 |
| CN | 107849555 A | 3/2018 |
| CN | 110381980 A | 10/2019 |
| EP | 1619249 A1 | 1/2006 |
| EP | 2149605 A2 | 2/2010 |
| EP | 1716232 B1 | 4/2010 |
| EP | 2203173 B1 | 7/2010 |
| EP | 2284264 A1 | 2/2011 |
| EP | 2410053 A1 | 1/2012 |
| EP | 2410054 A1 | 1/2012 |
| EP | 2426203 A2 | 3/2012 |
| EP | 2121713 B1 | 6/2013 |
| EP | 2614827 A2 | 7/2013 |
| EP | 1673104 B1 | 10/2013 |
| EP | 2801618 A1 | 11/2014 |
| EP | 2344637 B1 | 12/2014 |
| EP | 2318037 B1 | 1/2015 |
| EP | 2465542 B1 | 1/2015 |
| EP | 2612917 B1 | 2/2016 |
| EP | 2475376 B1 | 3/2016 |
| EP | 3031920 A1 | 6/2016 |
| EP | 2421971 B1 | 7/2016 |
| EP | 3067421 A1 | 9/2016 |
| EP | 2027267 B1 | 11/2016 |
| EP | 2623609 B1 | 1/2017 |
| EP | 3192880 A1 | 7/2017 |
| EP | 2736539 B1 | 8/2017 |
| EP | 3202905 A1 | 8/2017 |
| EP | 2457920 B1 | 10/2017 |
| EP | 3238737 A1 | 11/2017 |
| EP | 3271453 A1 | 1/2018 |
| EP | 3315606 A1 | 5/2018 |
| EP | 1988823 B1 | 8/2018 |
| EP | 2499249 B1 | 8/2018 |
| EP | 2922818 B1 | 9/2018 |
| EP | 3386534 A2 | 10/2018 |
| EP | 3436053 A1 | 2/2019 |
| EP | 3436588 A1 | 2/2019 |
| EP | 2889043 B1 | 4/2019 |
| EP | 3473270 A1 | 4/2019 |
| EP | 3489360 A2 | 5/2019 |
| EP | 2457919 B1 | 6/2019 |
| EP | 3510049 A1 | 7/2019 |
| EP | 3075386 B1 | 10/2019 |
| EP | 3560958 A1 | 10/2019 |
| EP | 2825193 B1 | 11/2019 |
| EP | 3565577 A1 | 11/2019 |
| EP | 3624831 A1 | 3/2020 |
| EP | 3135889 B1 | 7/2020 |
| EP | 3684376 A1 | 7/2020 |
| EP | 3691657 A1 | 8/2020 |
| EP | 3720448 A1 | 10/2020 |
| EP | 3735252 A2 | 11/2020 |
| EP | 2806900 B1 | 2/2021 |
| EP | 3018211 B1 | 6/2021 |
| EP | 3898693 A1 | 10/2021 |
| EP | 3959319 A1 | 3/2022 |
| EP | 3980436 A1 | 4/2022 |
| EP | 3980437 A1 | 4/2022 |
| EP | 3608330 B1 | 11/2022 |
| EP | 4121063 A1 | 1/2023 |
| EP | 4126066 A1 | 2/2023 |
| EP | 4146229 A1 | 3/2023 |
| EP | 3563863 B1 | 7/2023 |
| EP | 3597655 B1 | 8/2023 |
| EP | 3201320 B1 | 10/2023 |
| EP | 4291225 A1 | 12/2023 |
| EP | 3628326 B1 | 2/2024 |
| EP | 4314298 A1 | 2/2024 |
| EP | 4122497 B1 | 4/2024 |
| EP | 4401792 A1 | 7/2024 |
| IL | 54795 A | 10/1980 |
| JP | 2002-253259 A | 9/2002 |
| JP | 2007-104971 A | 4/2007 |
| JP | 2010-532168 A | 10/2010 |
| JP | 2013-538560 A | 1/2012 |
| JP | 2015-532264 A | 11/2015 |
| JP | 2015-534996 A | 12/2015 |
| JP | 2016-528258 A | 9/2016 |
| JP | 2018-503357 A | 2/2018 |
| JP | 2019-137675 A | 8/2019 |
| KR | 10-2013-0106811 A | 9/2013 |
| WO | WO 1989/007970 A1 | 9/1989 |
| WO | WO 1991/004753 A1 | 4/1991 |
| WO | WO 2001/083740 A1 | 11/2001 |
| WO | WO 2003/059951 A2 | 7/2003 |
| WO | WO 2003/074654 A2 | 9/2003 |
| WO | WO 2004/048570 A1 | 6/2004 |
| WO | WO 2004/069991 A2 | 8/2004 |
| WO | WO 2005/021064 A2 | 3/2005 |
| WO | WO 2005/023825 A2 | 3/2005 |
| WO | WO 2005/078077 A2 | 8/2005 |
| WO | WO 2006/000057 A1 | 1/2006 |
| WO | WO 2006/022688 A1 | 3/2006 |
| WO | WO 2007/089612 A2 | 8/2007 |
| WO | WO 2007/095056 A2 | 8/2007 |
| WO | WO 2007/135105 A1 | 11/2007 |
| WO | WO 2008/018795 A1 | 2/2008 |
| WO | WO 2008/049085 A1 | 4/2008 |
| WO | WO 2008/089403 A2 | 7/2008 |
| WO | WO 2009/054725 A2 | 4/2009 |
| WO | WO 2009/075815 A1 | 6/2009 |
| WO | WO 2009/144481 A2 | 12/2009 |
| WO | WO 2010/005565 A2 | 1/2010 |
| WO | WO 2010/048586 A1 | 4/2010 |
| WO | WO 2010/050801 A1 | 5/2010 |
| WO | WO 2010/050802 A1 | 5/2010 |
| WO | WO 2010/075010 A2 | 7/2010 |
| WO | WO 2010/096369 A1 | 8/2010 |
| WO | WO 2010/123369 A1 | 10/2010 |
| WO | WO 2010/129861 A1 | 11/2010 |
| WO | WO 2010/148253 A2 | 12/2010 |
| WO | WO 2011/057350 A1 | 5/2011 |
| WO | WO 2011/078797 A2 | 6/2011 |
| WO | WO 2011/136645 A1 | 11/2011 |
| WO | WO 2011/150408 A2 | 12/2011 |
| WO | WO 2011/154427 A1 | 12/2011 |
| WO | WO 2012/012443 A2 | 1/2012 |
| WO | WO 2012/012467 A2 | 1/2012 |
| WO | WO 2012/029986 A1 | 3/2012 |
| WO | WO 2012/075037 A1 | 6/2012 |
| WO | WO 2012/144906 A1 | 10/2012 |
| WO | WO 2013/016352 A1 | 1/2013 |
| WO | WO 2013/019623 A2 | 2/2013 |
| WO | WO 2013/085550 A2 | 6/2013 |
| WO | WO 2013/100190 A1 | 7/2013 |
| WO | WO 2013/112053 A1 | 8/2013 |
| WO | WO 2013/120038 A2 | 8/2013 |
| WO | WO 2013/126746 A2 | 8/2013 |
| WO | WO 2013/136189 A2 | 9/2013 |
| WO | WO 2013/138662 A1 | 9/2013 |
| WO | WO 2013/162363 A1 | 10/2013 |
| WO | WO 2014/007620 A2 | 1/2014 |
| WO | WO 2014/052276 A1 | 4/2014 |
| WO | WO 2014/065661 A1 | 5/2014 |
| WO | WO 2014/144978 A2 | 9/2014 |
| WO | WO 2014/153220 A2 | 9/2014 |
| WO | WO 2014/153240 A2 | 9/2014 |
| WO | WO 2015/021457 A2 | 2/2015 |
| WO | WO 2015/023937 A1 | 2/2015 |
| WO | WO 2015/023939 A1 | 2/2015 |

(56) References Cited

FOREIGN PATENT DOCUMENTS

| | | |
|---|---|---|
| WO | WO 2015/042581 A1 | 3/2015 |
| WO | WO 2015/055859 A1 | 4/2015 |
| WO | WO 2015/070158 A1 | 5/2015 |
| WO | WO 2015/134365 A2 | 9/2015 |
| WO | WO 2015/143062 A1 | 9/2015 |
| WO | WO 2015/179741 A1 | 11/2015 |
| WO | WO 2016/025519 A1 | 2/2016 |
| WO | WO 2016/039796 A2 | 3/2016 |
| WO | WO 2016/054231 A1 | 4/2016 |
| WO | WO 2016/081643 A1 | 5/2016 |
| WO | WO 2016/081670 A2 | 5/2016 |
| WO | WO 2016/094374 A1 | 6/2016 |
| WO | WO 2016/115490 A1 | 7/2016 |
| WO | WO 2016/146760 A1 | 9/2016 |
| WO | WO 2016/187425 A1 | 11/2016 |
| WO | WO 2016/208695 A1 | 12/2016 |
| WO | WO 2017/047707 A1 | 3/2017 |
| WO | WO 2017/049157 A1 | 3/2017 |
| WO | WO 2017/050836 A1 | 3/2017 |
| WO | WO 2017/062835 A2 | 4/2017 |
| WO | WO 2017/062862 A2 | 4/2017 |
| WO | WO 2017/077451 A1 | 5/2017 |
| WO | WO 2017/100467 A2 | 6/2017 |
| WO | WO 2017/106643 A1 | 6/2017 |
| WO | WO 2017/143156 A1 | 8/2017 |
| WO | WO 2017/173059 A1 | 10/2017 |
| WO | WO 2017/173060 A1 | 10/2017 |
| WO | WO 2017/173408 A1 | 10/2017 |
| WO | WO 2017/173411 A1 | 10/2017 |
| WO | WO 2017/184529 A1 | 10/2017 |
| WO | WO 2017/192679 A1 | 11/2017 |
| WO | WO 2017/205191 A1 | 11/2017 |
| WO | WO 2017/221883 A1 | 12/2017 |
| WO | WO 2018/007475 A1 | 1/2018 |
| WO | WO 2018/014042 A1 | 1/2018 |
| WO | WO 2018/017754 A1 | 1/2018 |
| WO | WO 2018/046772 A1 | 3/2018 |
| WO | WO 2018/046774 A1 | 3/2018 |
| WO | WO 2018/046775 A1 | 3/2018 |
| WO | WO 2018/057575 A1 | 3/2018 |
| WO | WO 2018/091544 A1 | 5/2018 |
| WO | WO 2018/098480 A1 | 5/2018 |
| WO | WO 2018/100010 A1 | 6/2018 |
| WO | WO 2018/107003 A1 | 6/2018 |
| WO | WO 2018/118627 A1 | 6/2018 |
| WO | WO 2018/124121 A1 | 7/2018 |
| WO | WO 2018/124277 A1 | 7/2018 |
| WO | WO 2018/129296 A1 | 7/2018 |
| WO | WO 2018/129384 A1 | 7/2018 |
| WO | WO 2018/213340 A1 | 11/2018 |
| WO | WO 2018/226861 A1 | 12/2018 |
| WO | WO 2019/014772 A1 | 1/2019 |
| WO | WO 2019/059973 A1 | 3/2019 |
| WO | WO 2019/060432 A2 | 3/2019 |
| WO | WO 2019/060775 A1 | 3/2019 |
| WO | WO 2019/067975 A1 | 4/2019 |
| WO | WO 2019/070741 A1 | 4/2019 |
| WO | WO 2019/071028 A1 | 4/2019 |
| WO | WO 2019/079637 A2 | 4/2019 |
| WO | WO 2019/092507 A2 | 5/2019 |
| WO | WO 2019/110725 A1 | 6/2019 |
| WO | WO 2019/113393 A1 | 6/2019 |
| WO | WO 2019/126641 A2 | 6/2019 |
| WO | WO 2019/136180 A2 | 7/2019 |
| WO | WO 2019/136216 A1 | 7/2019 |
| WO | WO 2019/151539 A1 | 8/2019 |
| WO | WO 2019/152609 A1 | 8/2019 |
| WO | WO 2019/152820 A1 | 8/2019 |
| WO | WO 2019/157224 A1 | 8/2019 |
| WO | WO 2019/178532 A1 | 9/2019 |
| WO | WO 2019/200185 A1 | 10/2019 |
| WO | WO 2019/209764 A2 | 10/2019 |
| WO | WO 2019/215175 A1 | 11/2019 |
| WO | WO 2019/215333 A1 | 11/2019 |
| WO | WO 2019/217784 A1 | 11/2019 |
| WO | WO 2019/222411 A1 | 11/2019 |
| WO | WO 2019/222663 A1 | 11/2019 |
| WO | WO 2019/229658 A1 | 12/2019 |
| WO | WO 2019/241385 A2 | 12/2019 |
| WO | WO 2019/246480 A1 | 12/2019 |
| WO | WO 2020/028831 A1 | 2/2020 |
| WO | WO 2020/028832 A1 | 2/2020 |
| WO | WO 2020/028836 A1 | 2/2020 |
| WO | WO 2020/028840 A1 | 2/2020 |
| WO | WO 2020/028841 A1 | 2/2020 |
| WO | WO 2020/028842 A1 | 2/2020 |
| WO | WO 2020/028844 A1 | 2/2020 |
| WO | WO 2020/028857 A1 | 2/2020 |
| WO | WO 2020/028861 A1 | 2/2020 |
| WO | WO 2020/028864 A1 | 2/2020 |
| WO | WO 2020/047282 A1 | 3/2020 |
| WO | WO 2020/084488 A1 | 4/2020 |
| WO | WO 2020/094670 A1 | 5/2020 |
| WO | WO 2020/118246 A1 | 6/2020 |
| WO | WO 2020/132584 A1 | 6/2020 |
| WO | WO 2020/163817 A1 | 6/2020 |
| WO | WO 2020/142479 A1 | 7/2020 |
| WO | WO 2020/198268 A1 | 10/2020 |
| WO | WO 2020/209285 A1 | 10/2020 |
| WO | WO 2020/214763 A1 | 10/2020 |
| WO | WO 2020/219820 A1 | 10/2020 |
| WO | WO 2020/247738 A1 | 12/2020 |
| WO | WO 2020/247782 A1 | 12/2020 |
| WO | WO 2020/247818 A1 | 12/2020 |
| WO | WO 2020/257489 A1 | 12/2020 |
| WO | WO 2021/003573 A1 | 1/2021 |
| WO | WO 2021/076856 A1 | 4/2021 |
| WO | WO 2021/108640 A1 | 6/2021 |
| WO | WO 2021/127457 A1 | 6/2021 |
| WO | WO 2021/142217 A1 | 7/2021 |
| WO | WO 2021/142227 A1 | 7/2021 |
| WO | WO 2021/142234 A1 | 7/2021 |
| WO | WO 2021/142260 A1 | 7/2021 |
| WO | WO 2021/142269 A1 | 7/2021 |
| WO | WO 2021/142275 A1 | 7/2021 |
| WO | WO 2021/142307 A1 | 7/2021 |
| WO | WO 2021/142313 A1 | 7/2021 |
| WO | WO 2021/142331 A1 | 7/2021 |
| WO | WO 2021/150382 A1 | 7/2021 |
| WO | WO 2021/154476 A1 | 8/2021 |
| WO | WO 2021/154477 A1 | 8/2021 |
| WO | WO 2021/188390 A1 | 9/2021 |
| WO | WO 2022/020105 A1 | 1/2022 |
| WO | WO 2022/020106 A1 | 1/2022 |
| WO | WO 2022/020107 A1 | 1/2022 |
| WO | WO 2022/020108 A1 | 1/2022 |
| WO | WO 2022/020109 A1 | 1/2022 |
| WO | WO 2022/026152 A1 | 2/2022 |
| WO | WO 2022/051332 A1 | 3/2022 |
| WO | WO 2022/051665 A1 | 3/2022 |
| WO | WO 2022/056266 A2 | 3/2022 |
| WO | WO 2022/115745 A1 | 6/2022 |
| WO | WO 2022/120132 A1 | 6/2022 |
| WO | WO 2022/147207 A1 | 7/2022 |
| WO | WO 2022/147209 A1 | 7/2022 |
| WO | WO 2022/159712 A1 | 7/2022 |
| WO | WO 2022/174037 A1 | 8/2022 |
| WO | WO 2022/212886 A1 | 10/2022 |
| WO | WO 2022/213118 A1 | 10/2022 |
| WO | WO 2022/217366 A1 | 10/2022 |
| WO | WO 2022/232478 A1 | 11/2022 |
| WO | WO 2022/240758 A1 | 11/2022 |
| WO | WO 2022/270585 A1 | 12/2022 |
| WO | WO 2022/271543 A2 | 12/2022 |
| WO | WO 2022/271549 A1 | 12/2022 |
| WO | WO 2023/283531 A2 | 1/2023 |
| WO | WO 2023/283613 A1 | 1/2023 |
| WO | WO 2023/283614 A2 | 1/2023 |
| WO | WO 2023/283615 A1 | 1/2023 |
| WO | WO 2023/283619 A2 | 1/2023 |
| WO | WO 2023/283620 A1 | 1/2023 |
| WO | WO 2023/283623 A1 | 1/2023 |
| WO | WO 2023/283624 A2 | 1/2023 |
| WO | WO 2023/283629 A1 | 1/2023 |

(56) References Cited

FOREIGN PATENT DOCUMENTS

| | | |
|---|---|---|
| WO | WO 2023/022229 A1 | 2/2023 |
| WO | WO 2023/026994 A1 | 3/2023 |
| WO | WO 2023/034818 A1 | 3/2023 |
| WO | WO 2023/043953 A1 | 3/2023 |
| WO | WO 2023/044398 A1 | 3/2023 |
| WO | WO 2023/077120 A1 | 5/2023 |
| WO | WO 2023/086864 A1 | 5/2023 |
| WO | WO 2023/121444 A1 | 6/2023 |
| WO | WO 2023/121445 A1 | 6/2023 |
| WO | WO 2023/121446 A1 | 6/2023 |
| WO | WO 2023/141710 A1 | 8/2023 |
| WO | WO 2023/150623 A2 | 8/2023 |
| WO | WO 2023/154807 A2 | 8/2023 |
| WO | WO 2023/168427 A1 | 9/2023 |
| WO | WO 2023/171820 A1 | 9/2023 |
| WO | WO 2023/178230 A1 | 9/2023 |
| WO | WO 2023/196400 A2 | 10/2023 |
| WO | WO 2023/201318 A1 | 10/2023 |
| WO | WO 2023/201324 A1 | 10/2023 |
| WO | WO 2023/201332 A1 | 10/2023 |
| WO | WO 2024/011135 A1 | 1/2024 |
| WO | WO 2024/011150 A1 | 1/2024 |
| WO | WO 2024/064237 A2 | 3/2024 |
| WO | WO 2024/097644 A1 | 5/2024 |
| WO | WO 2024/112809 A2 | 5/2024 |
| WO | WO 2024/149282 A1 | 7/2024 |
| WO | WO 2024/182358 A1 | 9/2024 |
| WO | WO 2025/076486 A1 | 4/2025 |

OTHER PUBLICATIONS

[No Author Listed], Baliforsen—Ionis Pharmaceuticals Drug Profile. Springer Nature Switzerland AG. Nov. 15, 2016. 9 pages.
[No Author Listed], Building the world's leading muscle disease company. Dyne Company Overview. Jun. 2021. 42 pages.
[No Author Listed], Clinical trial summary NCT000159250 (drisapersen) (Version 2, dated Feb. 19, 2007). 14 pages.
[No Author Listed], Dystrophin—Genomic Sequence. Principle variant—ENST00000357033.9. <https://www.ensembl.org/Homo_sapiens/Transcript/Summary?db=core; g=ENSG0000198947;r=X:31119222-33211549; t=ENST0000357033.> Last accessed Mar. 28, 2023. 1 page.
[No Author Listed], Exondys (eteplirsen): EPAR—Refusal public assessment report and Annex: Scientific conclusions and grounds for refusal. European Medicines Agency. Sep. 20, 2018. 140 pages.
[No Author Listed], FSH Society Facioscapulohumeral Muscular Dystrophy [FSHD] 2010 International Research Consortium & Research Planning Meetings, abstract 8, p. 29.
[No Author Listed], GenBank: AF095738.1. Mus musculus dystrophin gene, exons 22-25 and partial CDs. 2016. Retrieved from the internet Oct. 30, 2019: https://www.ncbi.nlm.nih.gov/nucleotide/AF095738.1?report=genbank&log$=nuclalign&blast_rank=3&RID=VKBMZ9WW014, 5 pages.
[No Author Listed], GenBank: NM_001293798.1. *Homo sapiens* double homeobox 4 (DUX4), transcript variant 2, mRNA. Dec. 31, 2012. Retrieved from the internet May 16, 2024.
[No Author Listed], GenBank: NM_001306068.2. *Homo sapiens* double homeobox 4 (DUX4), transcript variant 1, mRNA. Jul. 1, 2018. Retrieved from the internet Nov. 6, 2024: https://www.ncbi.nlm.nih.gov/nuccore/1030311260?sat=46&satkey=163025297>>. 4 pages.
[No Author Listed], GenBank: NP_001121620. transferrin receptor protein 1 isoform 1 [*Homo sapiens*]. Dec. 28, 2017. Retrieved from the internet Aug. 2, 2023: https://www.ncbi.nlm.nih.gov/protein/NP_001121620.1, 4 pages.
[No Author Listed], Highlights of prescribing information EXONDYS 51. FDA. <accessdata.fda.gov> Sep. 2016. Retrieved May 22, 2021. 11 pages.
[No Author Listed], *Homo sapiens* transferrin receptor (TFRC), transcript variant X1, mRNA. NCBI Reference Sequence XM_011513112.1. Mar. 12, 2025. 2 pages.

[No Author Listed], IRDye® Peptide Labeling Application Guide. <https://licor.com/documents/nmekjs7iez6sw5p8fv7b7005chbrcog7> Published Apr. 2013. Retrieved Oct. 27, 2021. 8 pages.
[No Author Listed], Morpholino History, Production, and Properties. Gene Tools. Retrieved from https://gene-tools.com/history_production_and_properties. Accessed Jan. 9, 2023. 9 pages.
[No Author Listed], NCBI "NM_004006.2(DMD)". Published Oct. 30, 2020. Accessed from ncbi.nlm.nih.gov on May 21, 2021. 2 pages.
[No Author Listed], Transferrin Receptor/CD71 Extracellular Domain (human, recombinant) 2021, retrieved from https://www.caymanchem.com/product/32031/transferrin-receptor-extracellular-domain-(human%2C-recombinant)#:~:text=Cayman's TransferrinReceptor%2FCD71 Extracellular,molecular weight of 103.6 kDa (Year: 2021). 3 pages.
[No Author Listed], UniProtKB/Swiss-Prot P02786. Transferrin receptor protein 1. Jul. 18, 2018. Retrieved from the Internet Oct. 23, 2019: https://www.uniprot.org/uniprot/P02786.txt?version=225, 20 pages.
[No Author Listed], Wikipedia, Dystrophin, Mar. 9, 2018. Retrieved from the internet Nov. 5, 2019: https://en.wikipedia.org/w/index.php?title=Dystrophin&oldid=829543258, 10 pages.
[No Author Listed], Wikipedia, Mannose 6-phosphate receptor, Mar. 2, 20183. Retrieved from the internet Nov. 6, 2019: https://en.wikipedia.org/w/index.php?title=Mannose_6-phosphate_receptor&oldid=832003836, 8 pages.
[No Author Listed], Wikipedia, Myotonic dystrophy, Sep. 8, 2017. Retrieved from the internet Nov. 5, 2019: https://en.wikipedia.org/w/index.php?title=Myotonic_dystrophy&oldid=799605783, 9 pages.
[NO_AUTHOR_LISTED], Dyne Therapeutics Announces Positive Initial Clinical Data from ACHIEVE Trial in DM1 Patients and DELIVER Trial in DMD Patients Demonstrating Promise of the FORCE™ Platform in Developing Therapeutics for Rare Muscle Diseases. Press Release. Jan. 3, 2024. Retrieved on Dec. 23, 2024, from: <<https://investors.dyne-tx.com/news-releases/news-release-details/dyne-therapeutics-announces-positive-initial-clinical-data>>. 4 pages.
Aartsma-Rus et al., Antisense-induced multiexon skipping for Duchenne muscular dystrophy makes more sense. Am J Hum Genet. Jan. 2004;74(1):83-92. Epub Dec. 16, 2003.
Aartsma-Rus et al., Antisense-mediated exon skipping: a versatile tool with therapeutic and research applications. RNA. Oct. 2007;13(10):1609-24. doi: 10.1261/rna.653607. Epub Aug. 7, 2007.
Aartsma-Rus et al., Guidelines for antisense oligonucleotide design and insight into splice-modulating mechanisms. Mol Ther. Mar. 2009; 17(3):548-53. doi: 10.1038/mt.2008.205. Epub Sep. 23, 2008.
Aartsma-Rus et al., Less is more: therapeutic exon skipping for Duchenne muscular dystrophy. Lancet Neurol. Oct. 2009;8(10):873-5. doi: 10.1016/S1474-4422(09)70229-7. Epub Aug. 25, 2009.
Aartsma-Rus et al., Progress in therapeutic antisense applications for neuromuscular disorders. Eur J Hum Genet. Feb. 2010;18(2):146-53. Epub Oct. 7, 2009.
Aartsma-Rus et al., Targeted exon skipping as a potential gene correction therapy for Duchenne muscular dystrophy. Neuromuscul Disord. Oct. 2002;12 Suppl 1:S71-7. doi: 10.1016/s0960-8966(02)00086-x.
Aartsma-Rus, Antisense-mediated modulation of splicing: therapeutic implications for Duchenne muscular dystrophy. RNA Biol. Jul.-Aug. 2010;7(4):453-61. doi: 10.4161/rna.7.4.12264. Epub Jul. 1, 2010.
Adams et al., Antisense oligonucleotide induced exon skipping and the dystrophin gene transcript: cocktails and chemistries. BMC Mol Biol. Jul. 2, 2007;8:57.
Agard et al., A Comparative Study of Bioorthogonal Reactions with Azides. ACS Chem. Biol. 2006;1(10):644-8. Epub Oct. 20, 2006.
Agard et al., A Strain-Promoted [3 + 2] Azide-Alkyne Cycloaddition for Covalent Modification of Biomolecules in Living Systems. J. Am. Chem. Soc. Nov. 2004;126(46):15046-7.
Alter et al., Systemic delivery of morpholino oligonucleotide restores dystrophin expression bodywide and improves dystrophic pathology. Nat Med. Feb. 2006; 12(2):175-7. doi: 10.1038/nm1345. Epub Jan. 29, 2006.

(56) References Cited

OTHER PUBLICATIONS

Altshuler et al., Generation of recombinant antibodies and means for increasing their affinity. Biochemistry (Mosc). Dec. 2010;75(13):1584-605.
Anciaux et al., Transition-metal-catalyzed reactions of diazo compounds. 1. Cyclopropanation of double bonds. The Journal of Organic Chemistry. Feb. 1980;45(4):695-702.
Ansseau et al., Antisense Oligonucleotides Used to Target the DUX4 mRNA as Therapeutic Approaches in FacioScapuloHumeral Muscular Dystrophy (FSHD). Genes (Basel). Mar. 3, 2017;8(3):93. doi: 10.3390/genes8030093.
Ansseau et al., DUX4c is up-regulated in FSHD. It induces the MYF5 protein and human myoblast proliferation. PLoS One. Oct. 15, 2009;4(10):e7482. 11 pages.
Antony-Mayer et al., Bicyclo[6.1.0]nonynes. Chemische Berichte. Nov. 1988;121(11):2013-8.
Aoki et al., Challenges for antisense oligonucleotide-based therapeutics, in particular for exon 51-skipping in Duchenne muscular dystrophy, 2011 Fourth International Conference on Modeling, Simulation and Applied Optimization, 2011, 1-6, doi: 10.1109/ICMSAO.2011.5775520.
Arechavala-Gomeza et al., Comparative analysis of antisense oligonucleotide sequences for targeted skipping of exon 51 during dystrophin pre-mRNA splicing in human muscle. Hum Gene Ther. Sep. 2007;18(9):798-810. doi: 10.1089/hum.2006.061.
Arnett et al., Therapy for neuromuscular disorders. Curr Opin Genet Dev. Jun. 2009;19(3):290-7. doi: 10.1016/j.gde.2009.03.005. Epub May 4, 2009.
Arzumanov et al., A structure-activity study of the inhibition of HIV-1 Tat-dependent trans-activation by mixmer 2'-O-methyl oligoribonucleotides containing locked nucleic acid (LNA), alpha-L-LNA, or 2'-thio-LNA residues. Oligonucleotides. 2003;13(6):435-53. doi: 10.1089/154545703322860762.
Arzumanov et al., Inhibition of HIV-1 Tat-dependent trans activation by steric block chimeric 2'-O-methyl/LNA oligoribonucleotides. Biochemistry. Dec. 4, 2001;40(48):14645-54. doi: 10.1021/bi011279e.
Ast et al., Estergruppenhaltige Polyalkenylene durch Olefin-Metathese. Die Makromolekulare Chemie. May 1976;177(5):1349-55.
Barfield et al., A Novel HER2-targeted Antibody-drug Conjugate Offers the Possibility of Clinical Dosing at Trastuzumab-equivalent Exposure Levels. Mol Cancer Ther. Sep. 2020;19(9):1866-74. Doi: 10.1158/1535-7163.MCT-20-0190. Epub Jul. 10, 2020.
Barrientos et al., Metabolic Catastrophe in Mice Lacking Transferrin Receptor in Muscle. EBioMedicine. Oct. 4, 2015;2(11):1705-17. doi: 10.1016/j.ebiom.2015.09.041. eCollection Nov. 2015.
Baskin et al., Copper-free click chemistry for dynamic in vivo imaging. PNAS. Oct. 2007;104(43):16793-7.
Baskin et al., Copper-free click chemistry: Bioorthogonal Reagents for Tagging Azides. Aldrichimica Acta. 2010;43(1):15-23.
Behlke, Chemical modification of siRNAs for in vivo use. Oligonucleotides. Dec. 2008;18(4):305-19.
Bennett et al., RNA targeting therapeutics: molecular mechanisms of antisense oligonucleotides as a therapeutic platform. Annu Rev Pharmacol Toxicol. 2010;50:259-93. Epub Oct. 19, 2009.
Beskrovnaya, Forcetm platform delivers exon skipping PMO, leads to durable increases in dystrophin protein in mdx mice and is well tolerated NHPs. Presented at Muscle Study Group Annual Scientific Meeting. Oct. 1, 2021. 29 pages.
Bien-Ly et al., Transferrin receptor (TfR) trafficking determines brain uptake of TfR antibody affinity variants. J Exp Med. Feb. 10, 2014;211(2):233-44. Epub Jan. 27, 2014.
Black, 9.13.4.1.1.3.2 Variation 2: C-Alkylation (and Arylation) by Carbenes and Free Radicals. Science of Synthesis. 2001;9:514.
Böhm et al., Mutation spectrum in the large GTPase dynamin 2, and genotype-phenotype correlation in autosomal dominant centronuclear myopathy. Hum Mutat. Jun. 2012;33(6):949-59. doi: 10.1002/humu.22067. Epub Apr. 4, 2012.
Bortolanza et al., AAV6-mediated systemic shRNA delivery reverses disease in a mouse model of facioscapulohumeral muscular dystrophy. Mol Ther. Nov. 2011;19(11):2055-64. doi: 10.1038/mt.2011.153. Epub Aug. 9, 2011.
Bouwman et al., The prospects of targeting DUX4 in facioscapulohumeral muscular dystrophy. Curr Opin Neurol. Oct. 2020;33(5):635-640.
Brown et al., Tolerance to single, but not multiple, amino acid replacements in antibody VH CDR 2: a means of minimizing B cell wastage from somatic hypermutation? J Immunol. May 1, 1996;156(9):3285-91.
Buntz et al., Quantitative fluorescence imaging determines the absolute number of locked nucleic acid oligonucleotides needed for suppression of target gene expression. Nucleic Acids Res. Jan. 25, 2019;47(2):953-969. doi: 10.1093/nar/gky1158.
Bushby et al., MSG/ENMC for DMD Trial Study Group. 145th ENMC International Workshop: planning for an International Trial of Steroid Dosage Regimes in DMD (For DMD), Oct. 22-24, 2006, Naarden, The Netherlands. Neuromuscul Disord. May 2007;17(5):423-8. doi: 10.1016/j.nmd.2007.01.006. Epub Apr. 11, 2007.
Bushby et al., Report on the 124th ENMC International Workshop. Treatment of Duchenne muscular dystrophy; defining the gold standards of management in the use of corticosteroids. Apr. 2-4, 2004, Naarden, The Netherlands. Neuromuscul Disord. Sep. 2004;14(8-9):526-34.
Bushby et al., The multidisciplinary management of Duchenne muscular dystrophy. Curr Paed. 2005; 15: 292-300.
Bushel et al., Blood gene expression signatures predict exposure levels. Proc Natl Acad Sci USA. Nov. 13, 2007;104(46):18211-6. doi: 10.1073/pnas.0706987104. Epub Nov. 2, 2007.
Campbell et al., Deflazacort for the treatment of Duchenne Dystrophy: a systematic review. BMC Neurol. Sep. 8, 2003;3:7. doi: 10.1186/1471-2377-3-7. Epub Sep. 8, 2003.
Campbell et al., NuRD and CAF-1-mediated silencing of the D4Z4 array is modulated by DUX4-induced MBD3L proteins. eLife. May 2018;7:e31023. 27 pages.
Candelaria et al., Antibodies Targeting the Transferrin Receptor 1 (TfR1) as Direct Anti-cancer Agents. Front Immunol. Mar. 17, 2021;12:607692.
Carrell et al., Dmpk gene deletion or antisense knockdown does not compromise cardiac or skeletal muscle function in mice. Hum Mol Genet. Oct. 1, 2016;25(19):4328-4338. doi: 10.1093/hmg/ddw266. Epub Aug. 13, 2016.
Casi et al., Antibody-drug conjugates: basic concepts, examples and future perspectives. J Control Release. Jul. 20, 2012;161(2):422-8. doi: 10.1016/j.jconrel.2012.01.026. Epub Jan. 28, 2012.
Cenik et al., Argonaute proteins. Curr Biol. Jun. 21, 2011;21(12):R446-9.
Chamberlain et al., Validity of RNAi-based therapeutics as a treatment for FSHD as demonstrated in a mouse model of muscular dystrophy. MDA National Scientific Conference—Neuromuscular Therapeutic Strategies: Overcoming the Barriers from Microscope to Marketplace (Book of Abstracts) Mar. 13-16, 2011; p. 40. Abstract.
Chen et al., Morpholino-mediated Knockdown of DUX4 Toward Facioscapulohumeral Muscular Dystrophy Therapeutics. Mol Ther. Aug. 2016;24(8):1405-11. doi: 10.1038/mt.2016.111. Epub Jun. 3, 2016.
Chernikov et al., Current Development of siRNA Bioconjugates: From Research to the Clinic. Front Pharmacol. Apr. 26, 2019;10:444.
Cho et al., Myotonic dystrophy: emerging mechanisms for DM1 and DM2. Biochim Biophys Acta. Feb. 2007;1772(2):195-204. Epub Jun. 20, 2006.
Chothia et al., Canonical structures for the hypervariable regions of immunoglobulins. J Mol Biol. Aug. 20, 1987;196(4):901-17. doi: 10.1016/0022-2836(87)90412-8.
Cirak et al., Exon skipping and dystrophin restoration in patients with Duchenne muscular dystrophy after systemic phosphorodiamidate morpholino oligomer treatment: an open-label, phase 2, dose-escalation study. Lancet. Aug. 13, 2011;378(9791):595-605. doi: 10.1016/S0140-6736(11)60756-3. Epub Jul. 23, 2011.

(56) References Cited

OTHER PUBLICATIONS

Clark et al., Increased brain uptake of targeted nanoparticles by adding an acid-cleavable linkage between transferrin and the nanoparticle core. PNAS. Oct. 2015;112(40):12486-91.

Clayton et al., Antisense Oligonucleotide-mediated Suppression of Muscle Glycogen Synthase 1 Synthesis as an Approach for Substrate Reduction Therapy of Pompe Disease. Mol Ther Nucleic Acids. Oct. 28, 2014;3(10):e206.

Codelli et al., Second-Generation Difluorinated Cyclooctynes for Copper-Free Click Chemistry. J. Am. Chem. Soc. 2008;130(34):11486-11493. Epub Aug. 5, 2008.

Crook et al., Enrichment of early fetal-liver hemopoietic stem cells of the rat using monoclonal antibodies against the transferrin receptor, Thy-1, and MRC-OX82. Dev Immunol. 1996;4(4):235-46. doi: 10.1155/1995/85036.

Crooke et al., Antisense research and applications. 1993. p. 15-35.

Crooke et al., Kinetic characteristics of *Escherichia coli* RNase H1: cleavage of various antisense oligonucleotide-RNA duplexes. Biochem J. Dec. 1, 1995;312(Pt 2):599-608. doi: 10.1042/bj3120599.

Crooke et al., The Effects of 2'-O-Methoxyethyl Oligonucleotides on Renal Function in Humans. Nucleic Acid Ther. Feb. 2018;28(1):10-22. doi: 10.1089/nat.2017.0693. Epub Nov. 29, 2017.

Cuellar et al., Systematic evaluation of antibody-mediated siRNA delivery using an industrial platform of THIOMAB-siRNA conjugates. Nucleic Acids Res. Jan. 2015;43(2):1189-203. Epub Dec. 30, 2014.

Curtius, Ueber die Einwirkung von salpetriger Säure auf salzsauren Glycocolläther. Berichte der deutschen chemischen Gesellschaft. Jul.-Dec. 1883;16(2):2230-1.

Danis et al., Potential therapeutic application of antisense oligonucleotides in the treatment of ocular diseases. Expert Opin Pharmacother. Feb. 2001;2(2):277-91.

Darimont et al., A novel antibody-oligonucleotide conjugate (AOC) platform enables efficient regulation of muscle targets in mice. Abstract. 8-05. J. Cach Sarcopen Musc. 2017; 8: 1065-66.

Davis et al., Improved targeting of miRNA with antisense oligonucleotides. Nucleic Acids Res. May 11, 2006;34(8):2294-304. doi: 10.1093/nar/gkl183. Print 2006.

Daxinger et al., Genetic and epigenetic contributors to FSHD. Current Opinion in Genetics & Development. Aug. 2015;33:56-61. Author manuscript. 11 pages.

De Greef et al., Epigenetic mechanisms of facioscapulohumeral muscular dystrophy. Mutat Res. Dec. 1, 2008;647(1-2):94-102. doi: 10.1016/j.mrfmmm.2008.07.011. Epub Aug. 3, 2008.

De Waele et al., Initial Data from the DELIVER Trial of DYNE-251 in Males with DMD Mutations Amenable to Exon 51 Skipping. 2024 World Muscle Society Annual Meeting P225. Oct. 9, 2024. Poster.

Debets et al., Bioorthogonal labelling of biomolecules: new functional handles and ligation methods. Org Biomol Chem. Oct. 14, 2013;11(38):6439-55. Epub Aug. 23, 2013.

Demonceau et al., Novel Ruthenium-Based Catalyst Systems for the Ring-Opening Metathesis Polymerization of Low-Strain Cyclic Olefins. Macromolecules. 1997;30(11):3127-36. Epub Jun. 2, 1997.

Desguerre et al., Endomysial fibrosis in Duchenne muscular dystrophy: a marker of poor outcome associated with macrophage alternative activation. J Neuropathol Exp Neurol. Jul. 2009;68(7):762-73.

Desjardins et al., Building a FORCETM platform-based DMD franchise for the treatment of individuals with mutations amenable to exon skipping. Neuromusc Dis. Oct. 2022; 32: S101-2. Abstract.

Desjardins et al., Building a ForceTM platform-based DMD franchise for the treatment of individuals with mutations amenable to exon skipping. Presented at 27th Int Hybrid Annual Congress of the World Muscle Society. Oct. 11-15, 2022. Poster. 1 page.

Desjardins et al., Enhanced exon skipping and prolonged dystrophin restoration achieved by TfR1-targeted delivery of antisense oligonucleotide using FORCE conjugation in mdx mice. Nucleic Acids Res. Nov. 11, 2022;50(20):11401-11414.

Desjardins et al., Enhanced exon skipping and prolonged dystrophin restoration achieved by TfR1-targeted delivery of antisense oligonucleotide using FORCE conjugation in mdx mice. Nucleic Acids Res. Nov. 11, 2022;50(20):11401-11414. Supplemental Figures and Figure Legends. 34 pages.

Desjardins et al., Force™ platform achieves robust exon skipping, restores dystrophin at the sarcolemma and halts progression of fibrosis in the severe D2-mdx model of DMD. Abstract. Mar. 2023. 1 page.

Desjardins et al., Force™ platform achieves robust exon skipping, restores dystrophin at the sarcolemma and halts progression of fibrosis in the severe D2-mdx model of DMD. Poster. Presented at The Muscular Dystrophy Association Clinical and Scientific Conference. Mar. 19-22, 2023. 1 page.

Dixit et al., DUX4, a candidate gene of facioscapulohumeral muscular dystrophy, encodes a transcriptional activator of PITX1. Proc Natl Acad Sci U S A. Nov. 13, 2007;104(46):18157-62. doi: 10.1073/pnas.0708659104. Epub Nov. 5, 2007.

Dmitriev et al., Pearls in the junk: dissecting the molecular pathogenesis of facioscapulohumeral muscular dystrophy. Neuromuscul Disord. Jan. 2009;19(1):17-20. doi: 10.1016/j.nmd.2008.09.004. Epub Oct. 29, 2008.

Dommerholt et al., Readily accessible bicyclononynes for bioorthogonal labeling and three-dimensional imaging of living cells. Angew Chem Int Ed. Dec. 3, 2010;49(49):9422-5.

Dommerholt et al., Strain-Promoted 1,3-Dipolar Cycloaddition of Cycloalkynes and Organic Azides. Top Curr Chem. Apr. 2016;374(2):16. doi: 10.1007/s41061-016-0016-4. Epub Mar. 22, 2016.

Doucet et al., Abstract 150—RNA-based gene therapy for myotonic dystrophy type 1 (DM1). The Ottawa Conference on New Directions in Biology & Disease of Skeletal Muscle. Ottawa, CA. May 5-8, 2010:67. 6 pages total.

Douillard-Guilloux et al., Modulation of glycogen synthesis by RNA interference: towards a new therapeutic approach for glycogenosis type II. Hum Mol Genet. Dec. 15, 2008;17(24):3876-86. doi: 10.1093/hmg/ddn290. Epub Sep. 9, 2008.

Dovgan et al., Antibody-Oligonucleotide Conjugates as Therapeutic, Imaging, and Detection Agents. Bioconjug Chem. Oct. 16, 2019;30(10):2483-2501. doi: 10.1021/acs.bioconjchem.9b00306. Epub Jul. 24, 2019.

Echigoya et al., Effects of systemic multiexon skipping with peptide-conjugated morpholinos in the heart of a dog model of Duchenne muscular dystrophy. Proc Natl Acad Sci U S A. Apr. 18, 2017;114(16):4213-4218. doi: 10.1073/pnas.1613203114. Epub Apr. 3, 2017.

Echigoya et al., Exons 45-55 Skipping Using Mutation-Tailored Cocktails of Antisense Morpholinos in the DMD Gene. Mol Ther. Nov. 6, 2019;27(11):2005-2017. doi: 10.1016/j.ymthe.2019.07.012. Epub Jul. 26, 2019.

Echigoya et al., Quantitative Antisense Screening and Optimization for Exon 51 Skipping in Duchenne Muscular Dystrophy. Mol Ther. Nov. 1, 2017;25(11):2561-2572. doi: 10.1016/j.ymthe.2017.07.014. Epub Jul. 28, 2017.

Efferth et al., Enhancement of cytotoxicity of artemisinins toward cancer cells by ferrous iron. Free Radic Biol Med. Oct. 1, 2004;37(7):998-1009. doi: 10.1016/j.freeradbiomed.2004.06.023.

Elangkovan et al., Gene Therapy for Duchenne Muscular Dystrophy. J Neuromuscul Dis. 2021;8(s2):S303-S316.

Flanagan et al., Initial data from the DELIVER trial of DYNE-251 in males with DMD mutations amenable to exon 51 skipping. 2024 MDA Clinical and Scientific Conference. Abstract M156 + Presentation. Mar. 2024. 15 pages.

Flanagan et al., Initial data from the DELIVER trial of DYNE-251 in males with DMD mutations amenable to exon 51 skipping. 2024 MDA Clinical and Scientific Conference. Abstract M156 + Presentation. Mar. 2024. Poster. 3 pages.

Fletcher et al., Morpholino oligomer-mediated exon skipping averts the onset of dystrophic pathology in the mdx mouse. Mol Ther. Sep. 2007;15(9):1587-92. doi: 10.1038/sj.mt.6300245. Epub Jun. 19, 2007.

(56) References Cited

OTHER PUBLICATIONS

Fluiter et al., On the in vitro and in vivo properties of four locked nucleic acid nucleotides incorporated into an anti-H-Ras antisense oligonucleotide. Chembiochem. Jun. 2005;6(6):1104-9. doi: 10.1002/cbic.200400419.

Frazier, Antisense oligonucleotide therapies: the promise and the challenges from a toxicologic pathologist's perspective. Toxicol Pathol. Jan. 2015;43(1):78-89. doi: 10.1177/0192623314551840. Epub Nov. 9, 2014.

Freed et al., Pharmacology Review(s) for Application No. 206488Orig1s000. Center for Drug Evaluation and Research (CDER). Published May 25, 2016. Accessed from accessdata.fda.gov on May 21, 2021. 97 pages.

Friden et al., Anti-transferrin receptor antibody and antibody-drug conjugates cross the blood-brain barrier. Proc Natl Acad Sci U S A. Jun. 1, 1991;88(11):4771-5. doi: 10.1073/pnas.88.11.4771.

Frieden et al., Nuclease stability of LNA oligonucleotides and LNA-DNA chimeras. Nucleosides Nucleotides Nucleic Acids. May-Aug. 2003;22(5-8):1041-3. doi: 10.1081/NCN-120022731.

Furling et al., Abstract R.P.1.01 Therapeutic RNA strategies for myotonic dystrophy with CTG repeats. Neuromuscular Disorders. 2004;14:585. 2 pages total.

Furling et al., Viral vector producing antisense RNA restores myotonic dystrophy myoblast functions. Gene Ther. May 2003;10(9):795-802.

Gagnon et al., RNAi factors are present and active in human cell nuclei. Cell Rep. Jan. 16, 2014;6(1):211-21. Epub Jan. 2, 2014.

Galderisi et al., Myotonic dystrophy: antisense oligonucleotide inhibition of DMPK gene expression in vitro. Biochem Biophys Res Commun. Apr. 25, 1996;221(3):750-4.

Gao et al., Antisense oligonucleotides: rising stars in eliminating RNA toxicity in myotonic dystrophy. Hum Gene Ther. May 2013;24(5):499-507. doi: 10.1089/hum.2012.212. Epub Jan. 30, 2013.

Geary et al., Pharmacokinetics, biodistribution and cell uptake of antisense oligonucleotides. Adv Drug Deliv Rev. Jun. 29, 2015;87:46-51. doi: 10.1016/j.addr.2015.01.008. Epub Feb. 7, 2015.

Gebski et al., Morpholino antisense oligonucleotide induced dystrophin exon 23 skipping in mdx mouse muscle. Hum Mol Genet. Aug. 1, 2003;12(15):1801-11.

Geng et al., DUX4 activates germline genes, retroelements, and immune mediators: implications for facioscapulohumeral dystrophy. Dev Cell. Jan. 17, 2012;22(1):38-51. doi: 10.1016/j.devcel.2011.11.013. Epub Dec. 29, 2011.

Giles et al., Enhanced RNase H activity with methylphosphonodiester/phosphodiester chimeric antisense oligodeoxynucleotides. Anticancer Drug Des. Feb. 1992;7(1):37-48.

Girones et al. Comparison of the kinetics of cycling of the transferrin receptor in the presence or absence of bound diferric transferrin. Biochem J. Nov. 15, 1989;264(1):35-46.

Goemans et al., Systemic administration of PRO051 in Duchenne's muscular dystrophy. N Engl J Med. Apr. 21, 2011;364(16):1513-22. doi: 10.1056/NEJMoa1011367. Epub Mar. 23, 2011. Erratum in: N Engl J Med. Oct. 6, 2011;365(14):1361.

Gong et al., Simple Method To Prepare Oligonucleotide-Conjugated Antibodies and Its Application in Multiplex Protein Detection in Single Cells. Bioconjug Chem. Jan. 20, 2016;27(1):217-25. doi: 10.1021/acs.bioconjchem.5b00613. Epub Jan. 4, 2016.

Gonzalez-Barriga et al., Intracellular Distribution and Nuclear Activity of Antisense Oligonucleotides After Unassisted Uptake in Myoblasts and Differentiated Myotubes In Vitro. Nucleic Acid Ther. Jun. 2017;27(3):144-158. doi: 10.1089/nat.2016.0641. Epub Apr. 4, 2017.

Gray et al., Combinatorial peptide libraries: mining for cell-binding peptides. Chem Rev. Jan. 22, 2014;114(2):1020-81.

Green et al., A small-molecule inhibitor of sarcomere contractility suppresses hypertrophic cardiomyopathy in mice. Science. Feb. 5, 2016;351(6273):617-21.

Griggs et al., Prednisone in Duchenne dystrophy. A randomized, controlled trial defining the time course and dose response. Clinical Investigation of Duchenne Dystrophy Group. Arch Neurol. Apr. 1991;48(4):383-8. doi: 10.1001/archneur.1991.00530160047012.

Guirguis et al., Disease-drug interaction: Reduced response to propranolol despite increased concentration in the rat with inflammation. J Pharm Sci. May 2003;92(5):1077-84. Abstract.

Haack et al., Toxic rise of clozapine plasma concentrations in relation to inflammation. Eur Neuropsychopharmacol. Oct. 2003;13(5):381-5.

Heemskerk et al., Preclinical PK and PD studies on 2'-O-methyl-phosphorothioate RNA antisense oligonucleotides in the mdx mouse model. Mol Ther. Jun. 2010;18(6):1210-7. doi: 10.1038/mt.2010.72. Epub Apr. 20, 2010.

Hein et al., Click chemistry, a powerful tool for pharmaceutical sciences. Pharm Res. Oct. 2008;25(10):2216-30. doi: 10.1007/s11095-008-9616-1. Epub May 29, 2008.

Helguera et al. An antibody recognizing the apical domain of human transferrin receptor 1 efficiently inhibits the entry of all new world hemorrhagic Fever arenaviruses. J Virol. Apr. 2012;86(7):4024-8. doi: 10.1128/JVI.06397-11. Epub Jan. 25, 2012.

Henry et al., Chemically modified oligonucleotides exhibit decreased immune stimulation in mice. J Pharmacol Exp Ther. Feb. 2000;292(2):468-79.

Iwaki et al., Preparation of Chiral Stationary Phase via Activated Carbamate Intermediate for Liquid Chromatographic Optical Resolution. Chromatographia. Oct. 1987;23:727-30.

Jain et al., Current ADC Linker Chemistry. Pharm Res. Nov. 2015;32(11):3526-40. Epub Mar. 11, 2015.

Jauvin et al., Targeting DMPK with Antisense Oligonucleotide Improves Muscle Strength in Myotonic Dystrophy Type 1 Mice. Mol Ther Nucleic Acids. Jun. 16, 2017;7:465-474. Epub May 17, 2017.

Jearawiriyapaisarn et al., Sustained Dystrophin Expression Induced by Peptide-conjugated Morpholino Oligomers in the Muscles of mdx Mice. Mol Ther. Sep. 2008;16(9):1624-9. doi: 10.1038/mt.2008.120. Epub Jun. 10, 2008.

Jepsen et al., Locked nucleic acid: a potent nucleic acid analog in therapeutics and biotechnology. Oligonucleotides. 2004;14(2):130-46. doi: 10.1089/1545457041526317.

Jirka et al., Cyclic Peptides to Improve Delivery and Exon Skipping of Antisense Oligonucleotides in a Mouse Model for Duchenne Muscular Dystrophy. Mol Ther. Jan. 3, 2018;26(1):132-147. doi: 10.1016/j.ymthe.2017.10.004. Epub Oct. 12, 2017.

Juliano, The delivery of therapeutic oligonucleotides. Nucleic Acids Res. Aug. 19, 2016;44(14):6518-48. doi: 10.1093/nar/gkw236. Epub Apr. 15, 2016.

Khan et al., Silencing Myostatin Using Cholesterol-conjugated siRNAs Induces Muscle Growth. Mol Ther Nucleic Acids. Aug. 2, 2016;5(8):e342. doi: 10.1038/mtna.2016.55.

Khan, Corticosteroid therapy in Duchenne muscular dystrophy. J Neurol Sci. Dec. 1, 1993;120(1):8-14.

Kher et al., Antisense Oligonucleotides and RNA Interference. Challenges in Delivery of Therapeutic Genomics and Proteomics. Aug. 2011:325-86.

Kim et al., Strategies for silencing human disease using RNA interference. Nat Rev Genet. Mar. 2007;8(3):173-84. doi: 10.1038/nrg2006.

Kinali et al., Local restoration of dystrophin expression with the morpholino oligomer AVI-4658 in Duchenne muscular dystrophy: a single-blind, placebo-controlled, dose-escalation, proof-of-concept study. Lancet Neurol. Oct. 2009;8(10):918-28. doi: 10.1016/S1474-4422(09)70211-X. Epub Aug. 25, 2009. Erratum in: Lancet Neurol. Dec. 2009;8(12):1083.

Kline et al., Methods to Make Homogenous Antibody Drug Conjugates. Pharm Res. Nov. 2015;32(11):3480-93. Epub Dec. 16, 2014.

Koshelev et al., Abstract 130—Therapeutic application for a cell culture model of myotonic dystrophy. New Directions in Biology & Disease of Skeletal Muscle. New Orleans, LA. Apr. 27-30, 2008:44. 10 pages total.

Koshelev et al., Heart-specific overexpression of CUGBP1 reproduces functional and molecular abnormalities of myotonic dystrophy type 1. Hum Mol Genet. Mar. 15, 2010;19(6):1066-75. Epub Jan. 5, 2010.

(56) References Cited

OTHER PUBLICATIONS

Kumar et al., Antisense RNA: Function and Fate of Duplex RNA in Cells of Higher Eukaryotes. Microbiol Mol Biol Rev. Dec. 1998; 62(4): 1415-34.

Kuran et al., Investigations on the Catalytic Systems Diethylzinc/ Di- and Trihydroxybenzenes in the Copolymerization of Carbon Dioxide with Propylene Oxide. Makromol. Chem. 1976;177:1283-92.

Kurreck et al., Design of antisense oligonucleotides stabilized by locked nucleic acids. Nucleic Acids Res. May 1, 2002;30(9):1911-8. doi: 10.1093/nar/30.9.1911.

Kurreck, Antisense technologies. Improvement through novel chemical modifications. Eur J Biochem. Apr. 2003;270(8):1628-44.

Lai et al., Mechanism of action and spectrum of cell lines sensitive to a doxorubicin-transferrin conjugate. Cancer Chemother Pharmacol. 1998;41(2):155-60. doi: 10.1007/s002800050722.

Lam et al., siRNA Versus miRNA as Therapeutics for Gene Silencing. Mol Ther Nucleic Acids. Sep. 15, 2015;4(9):e252. 20 pages.

Langlois et al., Abstract 831—Ribozyme and Antisense RNA-Based Gene Therapies for Myotonic Dystrophy. Molecular Therapy. May 2003;7(5, Part 2):S320.

Langlois et al., Cytoplasmic and nuclear retained DMPK mRNAs are targets for RNA interference in myotonic dystrophy cells. J Biol Chem. Apr. 29, 2005;280(17):16949-54. Epub Feb. 18, 2005.

Langlois et al., Hammerhead ribozyme-mediated destruction of nuclear foci in myotonic dystrophy myoblasts. Mol Ther. May 2003;7(5 Pt 1):670-80.

Lawrence et al., Crystal structure of the ectodomain of human transferrin receptor. Science. Oct. 22, 1999;286(5440):779-82. doi: 10.1126/science.286.5440.779.

Le Gall et al., Therapeutic Strategies Targeting DUX4 in FSHD. J Clin Med. Sep. 7, 2020;9(9):2886.

Lee et al., Abstract—Targeted Degradation of Toxic RNA in Myotonic Dystrophy. RNA & Oligonucleotide Therapeutics. Cold Spring Harbor Laboratory. Cold Spring Harbor, NY. Apr. 7-10, 2010:35. 19 pages total.

Lee et al., RNase H-mediated degradation of toxic RNA in myotonic dystrophy type 1. Proc Natl Acad Sci U S A. Mar. 13, 2012;109(11):4221-6. doi: 10.1073/pnas.1117019109. Epub Feb. 27, 2012.

Lemmers et al., A unifying genetic model for facioscapulohumeral muscular dystrophy. Science. Sep. 24, 2010;329(5999):1650-3. Epub Aug. 19, 2010.

Lemmers et al., Chromosome 10q-linked FSHD identifies DUX4 as principal disease gene. J Med Genet. Feb. 2022;59(2):180-188. doi: 10.1136/jmedgenet-2020-107041. Epub Jan. 12, 2021.

Lemmers et al., Facioscapulohumeral muscular dystrophy is uniquely associated with one of the two variants of the 4q subtelomere. Nat Genet. Oct. 2002;32(2):235-6.

Lennox et al., Cellular localization of long non-coding RNAs affects silencing by RNAi more than by antisense oligonucleotides. Nucleic Acids Res. Jan. 29, 2016;44(2):863-77. doi: 10.1093/nar/gkv1206. Epub Nov. 17, 2015.

Lesley et al., Selection of cell lines resistant to anti-transferrin receptor antibody: evidence for a mutation in transferrin receptor. Mol Cell Biol. Sep. 1984;4(9):1675-81. doi: 10.1128/mcb.4.9.1675-1681.1984.

Levin, Targeting Therapeutic Oligonucleotides. N Engl J Med. Jan. 5, 2017;376(1):86-88. doi: 10.1056/NEJMcibr1613559.

Li et al., Activation of Frataxin Protein Expression by Antisense Oligonucleotides Targeting the Mutant Expanded Repeat. Nucleic Acid Ther. Feb. 2018;28(1):23-33.

Liang et al., RNase H1-Dependent Antisense Oligonucleotides Are Robustly Active in Directing RNA Cleavage in Both the Cytoplasm and the Nucleus. Mol Ther. Sep. 6, 2017;25(9):2075-2092. Epub Jun. 27, 2017.

Liang et al., Targeted delivery of plasmid DNA to myogenic cells via transferrin-conjugated peptide nucleic acid. Mol Ther. Mar. 2000;1(3):236-43. doi: 10.1006/mthe.2000.0043.

Lim et al., DICER/AGO-dependent epigenetic silencing of D4ZA repeats enhanced by exogenous siRNA suggests mechanisms and therapies for FSHD. Hum Mol Genet. Sep. 1, 2015;24(17):4817-28. doi: 10.1093/hmg/ddv206. Epub Jun. 3, 2015.

Lima et al., Structural requirements at the catalytic site of the heteroduplex substrate for human RNase H1 catalysis. J Biol Chem. Aug. 27, 2004;279(35):36317-26. doi: 10.1074/jbc.M405035200. Epub Jun. 17, 2004.

Lima et al., The positional influence of the helical geometry of the heteroduplex substrate on human RNase H1 catalysis. Mol Pharmacol. Jan. 2007;71(1):73-82. doi: 10.1124/mol.106.025429. Epub Oct. 6, 2006.

Liu et al. Myostatin antisense RNA-mediated muscle growth in normal and cancer cachexia mice. Gene Ther. Feb. 2008;15(3):155-60. doi: 10.1038/sj.gt.3303016. Epub Nov. 22, 2007.

Liu, Exploring cell type-specific internalizing antibodies for targeted delivery of siRNA. Brief Funct Genomic Proteomic. Jun. 2007;6(2):112-9. doi: 10.1093/bfgp/elm015. Epub Jul. 31, 2007.

Lu et al., Functional amounts of dystrophin produced by skipping the mutated exon in the mdx dystrophic mouse. Nat Med. Aug. 2003;9(8):1009-14. Epub Jul. 6, 2003.

Lu et al., Systemic delivery of antisense oligoribonucleotide restores dystrophin expression in body-wide skeletal muscles. Proc Natl Acad Sci U S A. Jan. 4, 2005;102(1):198-203. doi: 10.1073/pnas.0406700102. Epub Dec. 17, 2004.

Luria-Perez et al., Antibody-mediated targeting of the transferrin receptor in cancer cells. Bol Med Hosp Infant Mex. Nov.-Dec. 2016;73(6):372-379. doi: 10.1016/j.bmhimx.2016.11.004. Epub Dec. 13, 2016.

Malek-Adamian et al., Adjusting the Structure of 2'-Modified Nucleosides and Oligonucleotides via C4'-α-F or C4'-α-OMe Substitution: Synthesis and Conformational Analysis. J Org Chem. Sep. 7, 2018;83(17):9839-9849. doi: 10.1021/acs.joc.8b01329. Epub Jul. 17, 2018.

Mann et al., Antisense-induced exon skipping and synthesis of dystrophin in the mdx mouse. Proc Natl Acad Sci U S A. Jan. 2, 2001;98(1):42-7.

Manzur et al., Update on the management of Duchenne muscular dystrophy. Arch Dis Child. Nov. 2008;93(11):986-90. doi: 10.1136/adc.2007.118141. Epub Jul. 30, 2008.

Masters et al., Clinical toxicity of antibody drug conjugates: a meta-analysis of payloads. Invest New Drugs. Feb. 2018;36(1):121-135. doi: 10.1007/s10637-017-0520-6. Epub Oct. 13, 2017.

Meeuwissen et al., Cofactor regeneration in polymersome nanoreactors: Enzymatically catalysed Baeyer-Villiger reactions. Journal of Materials Chemistry. Dec. 2011;21(47):18923-6.

Mignon, Update on Ionis-DMPKRX Program. 2018 MDF Annual Conference. Nashville, TN. Sep. 14-15, 2018:22 pages.

Mojsov et al., A Quantitative Evaluation of Methods for Coupling Asparagine. The Journal of Organic Chemistry. Feb. 1980;45(4):555-60.

Monia et al., Evaluation of 2'-modified oligonucleotides containing 2'-deoxy gaps as antisense inhibitors of gene expression. J Biol Chem. Jul. 5, 1993;268(19):14514-22.

Mulders et al., Abstract S8-06—Chemically modified (CAG)n antisense oligonucleotides as molecular tools to silence toxic, expanded DMPK transcripts. 7th International Myotonic Dystrophy Consortium Meeting (IDMC-7). Wuerzburg, Germany. Sep. 9-12, 2009:421-2. 12 pages total.

Mulders et al., Molecular therapy in myotonic dystrophy: focus on RNA gain-of-function. Human Molecular Genetics. 2010;19(1):R90-7. Epub Apr. 20, 2010.

Mulders et al., Triplet-repeat oligonucleotide-mediated reversal of RNA toxicity in myotonic dystrophy. PNAS. Aug. 18, 2009;106(33):13915-20. Supporting information included. 13 pages.

Nakamura, A. Moving towards successful exon-skipping therapy for Duchenne muscular dystrophy. J Hum Genet. Oct. 2017;62(10):871-876. doi: 10.1038/jhg.2017.57. Epub Jun. 1, 2017.

Natoli et al., The FORCE™ platform achieves robust and durable DUX4 suppression and functional benefit in FSHD mouse models. FHSD International Research Conference, Denver, CO. Jun. 13, 2024. Abstract. 2 pages.

(56) References Cited

OTHER PUBLICATIONS

Natoli et al., The FORCE™ platform achieves robust and durable DUX4 suppression and functional benefit in FSHD mouse models. FHSD International Research Conference, Denver, CO. Jun. 13, 2024. Presentation. 16 pages.
Naylor et al., DELIVER, a randomized, double-blind, placebo controlled, multiple ascending dose study of DYNE-251 in boys with DMD amenable to Exon 51 skipping. Poster. Presented at The Muscular Dystrophy Association Clinical and Scientific Conference. Mar. 19-22, 2023. 1 page.
Naylor et al., DELIVER, a randomized, double-blind, placebo controlled, multiple ascending dose study of DYNE-251 in boys with DMD amenable to Exon 51 skipping. Abstract. Mar. 2023. 1 page.
Neguembor et al., In junk we trust: repetitive DNA, epigenetics and facioscapulohumeral muscular dystrophy. Epigenomics. Apr. 2010;2(2):271-87.
Nguyen et al., Antisense oligonucleotides for the treatment of cardiomyopathy in Duchenne muscular dystrophy. Am J Transl Res. Mar. 15, 2019;11(3):1202-1218.
Novak et al., Myoblasts and macrophages are required for therapeutic morpholino antisense oligonucleotide delivery to dystrophic muscle. Nat Commun. Oct. 16, 2017;8(1):941. doi: 10.1038/s41467-017-00924-7. Erratum in: Nat Commun. Jan. 15, 2018;9(1):208. Erratum in: Nat Commun. Mar. 23, 2018;9(1):1256.
Nowak et al., Duchenne muscular dystrophy and dystrophin: pathogenesis and opportunities for treatment. EMBO Rep. Sep. 2004;5(9):872-6.
Ochala et al., Novel myosin-based therapies for congenital cardiac and skeletal myopathies. J Med Genet. Oct. 2016;53(10):651-4. doi: 10.1136/jmedgenet-2016-103881. Epub Jul. 13, 2016.
Ohrt et al., In situ fluorescence analysis demonstrates active siRNA exclusion from the nucleus by Exportin 5. Nucleic Acids Res. Mar. 6, 2006;34(5):1369-80. doi: 10.1093/nar/gkl001. Print 2006.
Overby et al., RNA-mediated therapies in myotonic dystrophy. Drug Discov Today. Dec. 2018;23(12):2013-2022. Epub Aug. 4, 2018.
Padlan et al., A possible procedure for reducing the immunogenicity of antibody variable domains while preserving their ligand-binding properties. Molecular Immunology. Apr.-May 1991;28(4-5):489-98.
Pandey et al., Identification and characterization of modified antisense oligonucleotides targeting DMPK in mice and nonhuman primates for the treatment of myotonic dystrophy type Pharmacol Exp Ther. Nov. 2015;355(2):329-40. doi: 10.1124/jpet.115.226969. Epub Sep. 1, 2015.
Panowski et al., Site-specific antibody drug conjugates for cancer therapy. MAbs. Jan.-Feb. 2014;6(1):34-45.
Picariello et al., Dyne-101 achieves durable knockdown of toxic human nuclear DMPK RNA and correction of splicing in the hTfR1/DMSXL mouse model of DM1. Presented at The Muscular Dystrophy Association Clinical and Scientific Conference. Mar. 13-16, 2022. 1 page.
Picariello et al., The FORCETM Platform Enables TfR1-mediated Delivery of Enzyme Replacement Therapy to Muscle and Central Nervous System, Resolving Pompe Pathology in Mice. World Muscle Society Annual Meeting. Prague, Czechia. Oct. 9, 2024. Poster.
Picariello et al., The FORCE™ Platform Achieves Robust and Durable DUX4 Suppression and Improves Muscle Function in Facioscapulohumeral Muscular Dystrophy Mouse Model. World Muscle Society Annual Meeting. Prague, Czechia. Oct. 9, 2024. Poster.
Piche-Nicholas et al., Changes in complementarity-determining regions significantly alter IgG binding to the neonatal Fc receptor (FcRn) and pharmacokinetics. MAbs. Jan. 2018;10(1):81-94. Doi: 10.1080/189420862.2017.1389355. Epub Nov. 3, 2017.
Pradeepkumar, Chemically modified oligonucleotides: synthesis, physicochemical and biochemical properties of their duplexes with DNA and RNA. Comprehensive Summaries of Uppsala Disserations from the Faculty of Science and Technology. 2004; 973: 56 pages.
Pradhan et al., Prednisolone in Duchenne muscular dystrophy with imminent loss of ambulation. J Neurol. Oct. 2006;253(10):1309-16. doi: 10.1007/s00415-006-0212-1. Epub Jun. 19, 2006.
Qian et al., Targeted drug delivery via the transferrin receptor-mediated endocytosis pathway. Pharmacol Rev. Dec. 2002;54(4):561-87. doi: 10.1124/pr.54.4.561.
Ramasamy et al., Remarkable enhancement of binding affinity of Heterocycle-modified DNA to DNA and RNA. Synthesis, characterization and biophysical evaluation of N2-imidazolylpropylguanine and N2-imidazolylpropyl-2-aminoadenine modified oligonucleotides. Tetrahedron Let. 1994;35(2):215-18.
Rando et al., Rescue of dystrophin expression in mdx mouse muscle by RNA/DNA oligonucleotides. Proc Natl Acad Sci U S A. May 9, 2000;97(10):5363-8. doi: 10.1073/pnas.97.10.5363.
Richards et al., Facioscapulohumeral muscular dystrophy (FSHD): an enigma unravelled? Hum Genet. Mar. 2012;131(3):325-40. doi: 10.1007/s00439-011-1100-z. Epub Oct. 9, 2011.
Roberts et al., Advances in oligonucleotide drug delivery. Nat Rev Drug Discov. Oct. 2020;19(10):673-694. doi: 10.1038/s41573-020-0075-7. Epub Aug. 11, 2020.
Roberts et al., The Halogenation of Ethylenes. J. Am. Chem. Soc. May 1937;59(5):947-8.
Rodriguez et al. Binding specificity and internalization properties of an antibody-avidin fusion protein targeting the human transferrin receptor. Journal of Controlled Release 124: 35-42. (2007).
Sahenk et al., The muscular dystrophies: distinct pathogenic mechanisms invite novel therapeutic approaches. Curr Rheumatol Rep. Jun. 2011;13(3):199-207.
Saito et al., Antisense PMO found in dystrophic dog model was effective in cells from exon 7-deleted DMD patient. PLoS One. Aug. 18, 2010;5(8):e12239.
Samoylova et al., Elucidation of muscle-binding peptides by phage display screening. Muscle Nerve. Apr. 1999;22(4):460-6.
Sansone et al., Initial data from the ACHIEVE trial of DYNE-101 in adults with myotonic dystrophy type 1 (DM1). 2024 MDA Clinical and Scientific Conference. Mar. 6, 2024. 19 pages.
Sansone et al., Initial data from the ACHIEVE trial of DYNE-101 in adults with myotonic dystrophy type 1 (DM1). 2024 MDA Clinical and Scientific Conference. Mar. 6, 2024. Poster. 3 pages.
Sazani et al., Safety pharmacology and genotoxicity evaluation of AVI-4658. Int J Toxicol. Mar.-Apr. 2010;29(2):143-56. doi: 10.1177/1091581809359206. Epub Jan. 28, 2010.
Sazani et al., Systemically delivered antisense oligomers upregulate gene expression in mouse tissues. Nat Biotechnol. Dec. 2002;20(12):1228-33. doi: 10.1038/nbt759. Epub Nov. 11, 2002.
Scanlon, Anti-genes: siRNA, ribozymes and antisense. Curr Pharm Biotechnol. Oct. 2004;5(5):415-20.
Scherr et al., Detection of antisense and ribozyme accessible sites on native mRNAs: application to NCOA3 mRNA. Mol Ther. Nov. 2001;4(5):454-60.
Schneider et al., Structural features of the cell surface receptor for transferrin that is recognized by the monoclonal antibody OKT9. J Biol Chem. Jul. 25, 1982;257(14):8516-22.
Schnyder et al., Targeting of skeletal muscle in vitro using biotinylated immunoliposomes. Biochem J. Jan. 1, 2004;377(Pt 1):61-7. doi: 10.1042/BJ20031034.
Setten et al., The current state and future directions of RNAi-based therapeutics. Nat Rev Drug Discov. Jun. 2019;18(6):421-446. doi: 10.1038/s41573-019-0017-4.
Shen et al., Activating frataxin expression by single-stranded siRNAs targeting the GAA repeat expansion. Bioorg Med Chem Lett. Sep. 15, 2018;28(17):2850-2855. doi: 10.1016/j.bmcl.2018.07.033. Epub Jul. 21, 2018.
Shen et al., Chemistry, mechanism and clinical status of antisense oligonucleotides and duplex RNAs. Nucleic Acids Res. Feb. 28, 2018;46(4):1584-1600.
Shieh et al., Initial Data from the DELIVER Trial of DYNE-251 in Males with DMD Mutations Amenable to Exon 51 Skipping. American Academy of Neurology (AAN) Annual Meeting. Apr. 15, 2024. Poster.

(56) References Cited

OTHER PUBLICATIONS

Shieh et al., Initial Data from the DELIVER Trial of DYNE-251 in Males with DMD Mutations Amenable to Exon 51 Skipping. American Academy of Neurology (AAN) Annual Meeting. Apr. 15, 2024. Presentation. 11 pages.

Shimizu-Motohashi et al., Exon skipping for Duchenne muscular dystrophy: a systematic review and meta-analysis. Orphanet J Rare Dis. Jun. 15, 2018;13(1):93.

Singh et al., Catalytic Enantioselective Cyclopropanation of Olefins Using Carbenoid Chemistry. Synthesis. Feb. 1997;137-49.

Sklar et al., Methylprednisolone increases dystrophin levels by inhibiting myotube death during myogenesis of normal human muscle in vitro. J Neurol Sci. Jan. 1991;101(1):73-81. doi: 10.1016/0022-510x(91)90019-4.

Snider et al., Facioscapulohumeral dystrophy: incomplete suppression of a retrotransposed gene. PLoS Genet. Oct. 28, 2010;6(10):e1001181. 14 pages.

Snider et al., RNA transcripts, miRNA-sized fragments and proteins produced from D4Z4 units: new candidates for the pathophysiology of facioscapulohumeral dystrophy. Hum Mol Genet. Jul. 1, 2009;18(13):2414-30. Epub Apr. 9, 2009.

Stein, The experimental use of antisense oligonucleotides: a guide for the perplexed. J Clin Invest. Sep. 2001;108(5):641-4.

Stocki et al., Blood-brain barrier transport using a high affinity, brain-selective VNAR antibody targeting transferrin receptor 1. FASEB J. Feb. 2021;35(2):e21172. doi: 10.1096/fj.202001787R. Epub Nov. 25, 2020.

Subramanian et al., Abstract 1074. Targeted delivery of oligonucleotide therapeutics to muscle demonstrates potential to treat duchenne muscular dystrophy. Abstract. Mol Ther. 28 (4S1): 465. (2020) 1 page.

Subramanian, Splice Correction and Reduction of Toxic DMPK RNA In Vitro and In Vivo Utilizing Novel Antibody Targeted Antisense Oligonucleotides. Presented at ASGST Annual Meeting; May 14, 2021. 19 pages.

Sugo et al., Development of antibody-siRNA conjugate targeted to cardiac and skeletal muscles. J Control Release. Sep. 10, 2016;237:1-13. doi: 10.1016/j.jconrel.2016.06.036. Epub Jun. 29, 2016.

Summerton et al., Morpholino antisense oligomers: design, preparation, and properties. Antisense Nucleic Acid Drug Dev. Jun. 1997;7(3):187-95.

Swayze et al., Antisense oligonucleotides containing locked nucleic acid improve potency but cause significant hepatotoxicity in animals. Nucleic Acids Res. 2007;35(2):687-700. doi: 10.1093/nar/gkl1071. Epub Dec. 19, 2006.

Swayze et al., The medicinal chemistry of oligonucleotides. In: Antisense Drug Technology, Second Edition. 2007. Crooke, Ed. Chapter 6: 143-182.

Takeda et al. Exon-Skipping in Duchenne Muscular Dystrophy. J Neuromuscul Dis. 2021;8(s2):S343-S358. doi: 10.3233/JND-210682.

Tasfaout et al., Single Intramuscular Injection of AAV-shRNA Reduces DNM2 and Prevents Myotubular Myopathy in Mice. Mol Ther. Apr. 4, 2018;26(4):1082-1092. doi: 10.1016/j.ymthe.2018.02.008. Epub Feb. 14, 2018.

Tawil et al., Facioscapulohumeral dystrophy: the path to consensus on pathophysiology. Skelet Muscle. Jun. 10, 2014;4:12.

Thomas et al., Myotonic Dystrophy and Developmental Regulation of RNA Processing. Comprehensive Physiology. Apr. 2018;8(2):509-53. Epub Mar. 25, 2018.

Thornton et al., Abstract—Oligonucleotide Therapeutics in Myotonic Dystrophy. RNA & Oligonucleotide Therapeutics. Cold Spring Harbor Laboratory. Cold Spring Harbor, NY. Apr. 7-10, 2010:31. 19 pages total.

Thornton et al., Myotonic dystrophy: approach to therapy. Curr Opin Genet Dev. Jun. 2017;44:135-140. doi: 10.1016/j.gde.2017.03.007. Epub Apr. 1, 2017.

Trollet et al., Gene therapy for muscular dystrophy: current progress and future prospects. Expert Opin Biol Ther. Jul. 2009;9(7):849-66.

Tron et al., Click chemistry reactions in medicinal chemistry: applications of the 1,3-dipolar cycloaddition between azides and alkynes. Med Res Rev. Mar. 2008;28(2):278-308.

Trowbridge et al., Anti-transferrin receptor monoclonal antibody and toxin-antibody conjugates affect growth of human tumour cells. Nature. Nov. 12, 1981;294(5837):171-3. doi: 10.1038/294171a0.

Van Den Bergen et al., Forty-Five Years of Duchenne Muscular Dystrophy in The Netherlands. J Neuromuscul Dis. 2014;1(1):99-109.

Van Der Maarel et al., Facioscapulohumeral muscular dystrophy and DUX4: breaking the silence. Trends Mol Med. May 2011;17(5):252-8. Epub Feb. 1, 2011.

Van Deutekom et al., Local dystrophin restoration with antisense oligonucleotide PRO051. N Engl J Med. Dec. 27, 2007;357(26):2677-86. doi: 10.1056/NEJMoa073108.

Van Deutekom, Abstract—The Development of RNA-Modulating Therapies. RNA & Oligonucleotide Therapeutics. Cold Spring Harbor Laboratory. Cold Spring Harbor, NY. Apr. 7-10, 2010:3. 19 pages total.

Vanderplanck et al., Abstract Keynote 5—Suppression of DUX4 or DUX4C expression by antisense strategies in a therapeutic approach for FSHD. 7th Australian Gene Therapy Society Meeting. The Journal of Gene Medicine. May 2011;13:414.

Vanderplanck et al., Suppression of DUX4 or DUX4c protein expression by antisense strategies in a therapeutic approach for FSHD. MDA National Scientific Conference—Neuromuscular Therapeutic Strategies: Overcoming the Barriers from Microscope to Marketplace (Book of Abstracts) Mar. 13-16, 2011; p. 8. Abstract.

Vickers et al., Efficient reduction of target RNAs by small interfering RNA and RNase H-dependent antisense agents. A comparative analysis. J Biol Chem. Feb. 28, 2003;278(9):7108-18. Epub Dec. 23, 2002.

Wagner et al., Transferrin-polycation conjugates as carriers for DNA uptake into cells. Proc Natl Acad Sci U S A. May 1990;87(9):3410-4. doi: 10.1073/pnas.87.9.3410.

Walder et al., Role of RNase H in hybrid-arrested translation by antisense oligonucleotides. Proc. Natl. Acad. Sci. Jul. 1988;85:5011-5.

Walker et al., Improved cellular delivery of antisense oligonucleotides using transferrin receptor antibody-oligonucleotide conjugates. Pharm Res. Oct. 1995;12(10):1548-53. doi: 10.1023/a:1016260110049.

Wallace et al., Abstract 387—Developing RNAi Therapy for FSHD. Molecular Therapy. May 2009;17(1):S151.

Wallace et al., RNA interference inhibits DUX4-induced muscle toxicity in vivo: implications for a targeted FSHD therapy. Mol Ther. Jul. 2012;20(7):1417-23. doi: 10.1038/mt.2012.68. Epub Apr. 17, 2012.

Walles et al., ADME and Safety Aspects of Non-cleavable Linkers in Drug Discovery and Development. Curr Top Med Chem. 2017;17(32):3463-3475. doi: 10.2174/1568026618666180118153502.

Weeden et al., FORCE platform overcomes barriers of oligonucleotide delivery to muscle and corrects myotonic dystrophy features in preclinical models. Commun Med (Lond). Jan. 18, 2025;5(1):22.

Wei et al., Therapeutic RNAi for dominant muscle disease. Musc Conn Tissue—Antisense and Stem Cells. Abstract. 2009. S200.

Wheeler et al., Reversal of RNA dominance by displacement of protein sequestered on triplet repeat RNA. Science. Jul. 17, 2009;325(5938):336-9.

Wheeler et al., Targeting nuclear RNA for in vivo correction of myotonic dystrophy. Nature. Aug. 2, 2012;488(7409):111-5. doi: 10.1038/nature11362.

Wheeler, Myotonic dystrophy: therapeutic strategies for the future. Neurotherapeutics. Oct. 2008;5(4):592-600.

Wilton et al., Antisense oligonucleotide-induced exon skipping across the human dystrophin gene transcript. Mol Ther. Jul. 2007;15(7):1288-96. doi: 10.1038/sj.mt.6300095. Epub Feb. 6, 2007.

Wilton et al., Antisense oligonucleotides, exon skipping and the dystrophin gene transcript. Acta Myol. Dec. 2005;24(3):222-9.

Wilton et al., Exon skipping and Duchenne muscular dystrophy: hope, hype and how feasible? Neurol India. Jul.-Sep. 2008;56(3):254-62. doi: 10.4103/0028-3886.43443.

(56) References Cited

OTHER PUBLICATIONS

Wolf et al., ACHIEVE trial, a randomized, placebo-controlled, multiple ascending dose study of Dyne-101 in individuals with myotonic dystrophy Type 1 (DM1). Abstract. Mar. 2023. 1 page.
Wolf et al., ACHIEVE trial, a randomized, placebo-controlled, multiple ascending dose study of Dyne-101 in individuals with myotonic dystrophy Type 1 (DM1). Presented at The Muscular Dystrophy Association Clinical and Scientific Conference. Poster. Mar. 19-22, 2023. 1 page.
Wolf et al., Initial Data from the ACHIEVE Trial of DYNE-101 in Adults with Myotonic Dystrophy Type 1 (DM1). 2024 World Muscle Society Annual Meeting P221. Oct. 12-14, 2024. Poster. Prague, Czechia.
Wu et al., Determination of the role of the human RNase H1 in the pharmacology of DNA-like antisense drugs. J Biol Chem. Apr. 23, 2004;279(17):17181-9. Epub Feb. 11, 2004.
Wuebbles et al., Testing the effects of FSHD candidate gene expression in vertebrate muscle development. Int J Clin Exp Pathol. Mar. 28, 2010;3(4):386-400.
Xia et al., Intravenous siRNA of brain cancer with receptor targeting and avidin-biotin technology. Pharm Res. Dec. 2007;24(12):2309-16. doi: 10.1007/s11095-007-9460-8. Epub Oct. 11, 2007.
Yao et al., DUX4-induced gene expression is the major molecular signature in FSHD skeletal muscle. Hum Mol Genet. Oct. 15, 2014; 23(20): 5342-5352. Epub May 26, 2014.
Yao et al., Targeted Delivery of ASOs Demonstrates Potential to Treat Duchenne Muscular Dystrophy. Poster. Presented at ASGCT; May 12, 2020. 1 page.
Ye et al., Generation and functional characterization of the anti-transferrin receptor single-chain antibody-GAL4 (TfRscFv-GAL4) fusion protein. BMC Biotechnol. Nov. 28, 2012;12:91.
Yoshida et al., Evaluation of off-target effects of gapmer antisense oligonucleotides using human cells. Genes Cells. Dec. 2019;24(12):827-835. doi: 10.1111/gtc.12730. Epub Nov. 12, 2019.
Zanotti et al., Abstract 17. Repeat dosing with DYNE-101 is Well Tolerated and Leads to a Sustained Reduction of DMPK RNA expression in key muscles for DM1 pathology in hTfR1/DMSXL mice and NHPs. Abstract. Mol Ther. Apr. 2022; 30(4S1): 9.
Zanotti et al., Abstract 247. The ForceTM platform achieves robust knock down of toxic human nuclear DMPK RNA and foci reduction in DM1 cells and in newly developed hTfR1/DMSXL mouse model. Mol Ther. 29(4S1): 127. Apr. 2021. 1 page.
Zanotti et al., Abstract 82. The ForceTM platform delivers oligonucleotides to the brain in a DM1 mouse model and in NHPs. Mol Ther. Apr. 2023; 31(4S1): 44.
Zanotti et al., Abstract EP.233. The ForceTM platform achieves durable knockdown of toxic human nuclear DMPK RNA and correction of splicing in the hTFR1/DMSXL mouse model. Neuromusc Disord. 2021; 31: S120.
Zanotti et al., DYNE-101 achieves durable knockdown of toxic human nuclear DMPK RNA and correction of splicing in the hTfR1/DMSXL mouse model of DM1. Abstract. Mar. 2022. 1 page.
Zanotti et al., FORCE™ Platform for the Development of Targeted Therapeutics for Rare Muscle Diseases. 2024 New Directions in Biology and Disease of Skeletal Muscle, Ft. Lauderdale, FL. Jun. 23, 2024. Presentation. 22 pages.
Zanotti et al., The Force™ platform achieves durable knockdown of toxic human nuclear DMPK RNA and correction of splicing in the hTFR1/DMSXL mouse model. Presented at WMS Meeting. Sep. 20-24, 2021. 1 page.
Zanotti, Repeat dosing with DYNE-101 is Well Tolerated and Leads to a Sustained Reduction of DMPK RNA expression in key muscles for DM1 pathology in hTfR1/DMSXL mice and NHPs. Presented at American Society of Gene & Cell Therapy Conference. May 16, 2022. 15 pages.
Zanotti, The FORCE™ Platform Achieves Robust Knock Down of Toxic Human Nuclear DMPK RNA and Foci Reduction in DM1 Cells and in Newly Developed hTfR1/DMSXL Mouse Model. Presented at American Society of Gene & Cell Therapy Annual Meeting; May 14, 2021. 13 pages.
Zanotti, The Force™ platform delivers oligonucleotides to the brain in a DM1 mouse model and in NHPs. Presented at American Society of Gene & Cell Therapy Conference. May 17, 2023. 16 pages.
Zeng et al., Specific loss of histone H3 lysine 9 trimethylation and HP1gamma/cohesin binding at D4Z4 repeats is associated with facioscapulohumeral dystrophy (FSHD). PLoS Genet. Jul. 2009;5(7):e1000559. doi: 10.1371/journal.pgen.1000559. Epub Jul. 10, 2009.
Zhang et al., Research progress and application prospects for the treatment of Duchenne muscular dystrophy. Chin J Contemp Neurol Neurosurg. Jul. 2018;18(7):480-93. doi: 10.3969/j.issn.1672-6731. 2018.07.004.

NuPage 4-12% 1mm SDS-PAGE
MES running buffer, 150v 50min

COMPLEXES COMPRISING AN ANTI-TRANSFERRIN RECEPTOR ANTIBODY LINKED TO AN OLIGONICLEOTIDE AND METHOD OF DELIVERING OLIGONUCLEOTIDE TO A SUBJECT

RELATED APPLICATIONS

This application is a continuation of U.S. application Ser. No. 19/066,035, filed Feb. 27, 2025, entitled "MUSCLE TARGETING COMPLEXES AND USES THEREOF FOR TREATING MUSCULAR DYSTROPHY", now U.S. Pat. No. 12,370,264, which is a continuation of U.S. application Ser. No. 18/939,894, filed Nov. 7, 2024, entitled "MUSCLE TARGETING COMPLEXES AND USES THEREOF FOR TREATING MUSCULAR DYSTROPHY", now U.S. Pat. No. 12,319,743, which is a continuation of U.S. application Ser. No. 18/656,654, filed May 7, 2024, entitled "COMPLEXES COMPRISING AN ANTI-TRANSFERRIN RECEPTOR ANTIBODY LINKED TO AN OLIGONUCLEOTIDE", now U.S. Pat. No. 12,173,078, which is a continuation of Ser. No. 18/468,580, filed Sep. 15, 2023, entitled "MUSCLE-TARGETING COMPLEXES COMPRISING AN ANTI-TRANSFERRIN RECEPTOR ANTIBODY LINKED TO AN OLIGONUCLEOTIDE AND METHODS OF DELIVERING OLIGONUCLEOTIDE TO A SUBJECT", now U.S. Pat. No. 12,018,087, which is a Continuation-in-part of U.S. application Ser. No. 18/184,741, filed Mar. 16, 2023, entitled "MUSCLE-TARGETING COMPLEX COMPRISING AN ANTI-TRANSFERRIN RECEPTOR ANTIBODY LINKED TO AN OLIGONUCLEOTIDE", now U.S. Pat. No. 11,795,233, which is a continuation of U.S. application Ser. No. 17/936,483, filed Sep. 29, 2022, entitled "METHODS OF USING MUSCLE TARGETING COMPLEXES TO DELIVER AN OLIGONUCLEOTIDE TO A SUBJECT HAVING FACIOSCAPULOHUMERAL MUSCULAR DYSTROPHY OR A DISEASE ASSOCIATED WITH MUSCLE WEAKNESS", now U.S. Pat. No. 11,787,869, which is a continuation of U.S. application Ser. No. 17/846,738, filed Jun. 22, 2022, entitled "METHODS OF DELIVERING AN OLIGONUCLEOTIDE TO A SUBJECT HAVING FACIOSCAPULOHUMERAL MUSCULAR DYSTROPHY", now U.S. Pat. No. 11,518,816, which is a continuation of U.S. application Ser. No. 17/671,707, filed Feb. 15, 2022, entitled "METHODS OF INTRAVENOUSLY DELIVERING ANTI-TRANSFERRIN ANTIBODY/OLIGONUCLEOTIDE COMPLEXES TO SUBJECTS HAVING MUSCULAR DYSTROPHY", now U.S. Pat. No. 11,390,682, which is a continuation of U.S. application Ser. No. 17/400,295, filed Aug. 12, 2021, entitled "COMPLEX COMPRISING ANTI-TRANSFERRIN RECEPTOR ANTIBODY COVALENTLY LINKED TO AN OLIGONUCLEOTIDE THAT TARGETS DUX4 RNA", now U.S. Pat. No. 11,286,305, which is a continuation of U.S. application Ser. No. 17/205,123, filed Mar. 18, 2021, entitled "A METHOD OF REDUCING EXPRESSION OF DUX4 IN A MUSCLE CELL BY ADMINISTERING AN ANTI-TRANSFERRIN RECEPTOR ANTIBODY LINKED TO AN OLIGONUCLEOTIDE TARGETING DUX4", now U.S. Pat. No. 11,111,309, which is a continuation of U.S. application Ser. No. 17/264,948, filed Feb. 1, 2021, entitled "MUSCLE TARGETING COMPLEXES AND USES THEREOF FOR TREATING FACIOSCAPULOHUMERAL MUSCULAR DYSTROPHY", now abandoned, which is a national stage filing under 35 U.S.C. § 371 of International Patent Application No. PCT/US2019/044990, filed Aug. 2, 2019, entitled "MUSCLE TARGETING COMPLEXES AND USES THEREOF FOR TREATING FACIOSCAPULOHUMERAL MUSCULAR DYSTROPHY", which claims the benefit under 35. U.S.C. § 119(e) of the filing date of U.S. Provisional Application No. 62/713,933, filed Aug. 2, 2018, entitled "MUSCLE TARGETING COMPLEXES AND USES THEREOF FOR TREATING FACIOSCAPULOHUMERAL MUSCULAR DYSTROPHY". U.S. application Ser. No. 18/468,580 is a continuation-in-part of U.S. application Ser. No. 17/264,905, filed Feb. 1, 2021, entitled "MUSCLE TARGETING COMPLEXES AND USES THEREOF FOR TREATING MYOTONIC DYSTROPHY", now abandoned, which is a national stage filing under 35 U.S.C. § 371 of International Patent Application No. PCT/US2019/044987, filed Aug. 2, 2019, entitled "MUSCLE TARGETING COMPLEXES AND USES THEREOF FOR TREATING MYOTONIC DYSTROPHY", which claims the benefit under 35 U.S.C. § 119(e) of the filing date of U.S. Provisional Application No. 62/859,672, filed Jun. 10, 2019, entitled "MUSCLE TARGETING COMPLEXES AND USES THEREOF FOR TREATING MYOTONIC DYSTROPHY", U.S. Provisional Application No. 62/858,888, filed Jun. 7, 2019, entitled "MUSCLE TARGETING COMPLEXES AND USES THEREOF FOR TREATING MYOTONIC DYSTROPHY", of U.S. Provisional Application No. 62/855,761, filed May 31, 2019, entitled "MUSCLE TARGETING COMPLEXES AND USES THEREOF FOR TREATING MYOTONIC DYSTROPHY", of U.S. Provisional Application No. 62/779,161, filed Dec. 13, 2018, entitled "MUSCLE TARGETING COMPLEXES AND USES THEREOF FOR TREATING MYOTONIC DYSTROPHY", and of U.S. Application No. 62/713,914, filed Aug. 2, 2018, entitled "MUSCLE TARGETING COMPLEXES AND USES THEREOF FOR TREATING MYOTONIC DYSTROPHY". U.S. application Ser. No. 18/468,580, now U.S. Pat. No. 12,018,087, is a continuation-in-part of U.S. application Ser. No. 17/265,016, filed Feb. 1, 2021, entitled "MUSCLE TARGETING COMPLEXES AND USES THEREOF FOR TREATING POMPE DISEASE", now abandoned, which is a national stage filing under 35 U.S.C. § 371 of International Patent Application No. PCT/US2019/044960, filed Aug. 2, 2019, entitled "MUSCLE TARGETING COMPLEXES AND USES THEREOF FOR TREATING POMPE DISEASE", which claims the benefit under 35 U.S.C. § 119(e) of the filing date of U.S. Provisional Application No. 62/713,959, filed Aug. 2, 2018, entitled "MUSCLE TARGETING COMPLEXES AND USES THEREOF FOR TREATING POMPE DISEASE". U.S. application Ser. No. 18/468,580, now U.S. Pat. No. 12,018,087, is a continuation-in-part of U.S. application Ser. No. 17/264,998, filed Feb. 1, 2021, entitled "MUSCLE-TARGETING COMPLEXES AND USES THEREOF", now abandoned, which is a national stage filing under 35 U.S.C. § 371 of International Patent Application No. PCT/US2019/044982, filed Aug. 2, 2019, entitled "MUSCLE-TARGETING COMPLEXES AND USES THEREOF", which claims the benefit under 35 U.S.C. § 119(e) of the filing date of U.S. Provisional Application No. 62/859,694, filed Jun. 10, 2019, entitled "MUSCLE-TARGETING COMPLEXES AND USES THEREOF", of U.S. Provisional Application No. 62/858,925, filed Jun. 7, 2019, entitled "MUSCLE-TARGETING COMPLEXES AND USES THEREOF", of U.S. Provisional Application No. 62/855,781, filed May 31, 2019, entitled "MUSCLE-TARGETING COMPLEXES AND USES THEREOF", of U.S. Provisional Application No.

62/779,173, filed Dec. 13, 2018, entitled "MUSCLE-TARGETING COMPLEXES AND USES THEREOF", and of U.S. Provisional Application No. 62/714,010, filed Aug. 2, 2018, entitled "MUSCLE-TARGETING COMPLEXES AND USES THEREOF". U.S. application Ser. No. 18/468,580, now U.S. Pat. No. 12,018,087, is a continuation-in-part of U.S. application Ser. No. 17/265,044, filed Feb. 1, 2021, entitled "MUSCLE-TARGETING COMPLEXES AND USES THEREOF IN TREATING MUSCLE ATROPHY", now abandoned, which is a national stage filing under 35 U.S.C. § 371 of International Patent Application No. PCT/US2019/044955, filed Aug. 2, 2019, entitled "MUSCLE-TARGETING COMPLEXES AND USES THEREOF IN TREATING MUSCLE ATROPHY", which claims the benefit under 35 U.S.C. § 119(e) of the filing date of U.S. Provisional Application No. 62/714,025, filed Aug. 2, 2018, entitled "MUSCLE-TARGETING COMPLEXES FOR TREATING MUSCLE ATROPHY". U.S. application Ser. No. 18/468,580, now U.S. Pat. No. 12,018,087, is a continuation-in-part of U.S. application Ser. No. 17/265,024, filed Feb. 1, 2021, entitled "MUSCLE TARGETING COMPLEXES AND USES THEREOF FOR TREATING DYSTROPHINOPATHIES", now abandoned, which is a national stage filing under 35 U.S.C. § 371 of International Patent Application No. PCT/US2019/044949, filed Aug. 2, 2019, entitled "MUSCLE TARGETING COMPLEXES AND USES THEREOF FOR TREATING DYSTROPHINOPATHIES", which claims the benefit under 35 U.S.C. § 119(e) of the filing date of U.S. Provisional Application No. 62/855,766, filed May 31, 2019, entitled "MUSCLE TARGETING COMPLEXES AND USES THEREOF FOR TREATING DYSTROPHINOPATHIES", and of U.S. Provisional Application No. 62/714,031, filed Aug. 2, 2018, entitled "MUSCLE TARGETING COMPLEXES AND USES THEREOF FOR TREATING DYSTROPHINOPATHIES". U.S. application Ser. No. 18/468,580, now U.S. Pat. No. 12,018,087, is a continuation-in-part of U.S. application Ser. No. 17/265,019, filed Feb. 1, 2021, entitled "MUSCLE TARGETING COMPLEXES AND USES THEREOF FOR TREATING FRIEDREICH'S ATAXIA", now abandoned, which is a national stage filing under 35 U.S.C. § 371 of International Patent Application No. PCT/US2019/044959, filed Aug. 2, 2019, entitled "MUSCLE TARGETING COMPLEXES AND USES THEREOF FOR TREATING FRIEDREICH'S ATAXIA", which claims the benefit under 35 U.S.C. 119(e) of the filing date of U.S. Provisional Application No. 62/714,035, filed Aug. 2, 2018, entitled "MUSCLE TARGETING COMPLEXES AND USES THEREOF FOR TREATING FRIEDREICH'S ATAXIA". U.S. application Ser. No. 18/468,580, now U.S. Pat. No. 12,018,087, is a continuation-in-part of U.S. application Ser. No. 17/264,972, filed Feb. 1, 2021, entitled "MUSCLE TARGETING COMPLEXES AND USES THEREOF FOR TREATING HYPERTROPHIC CARDIOMYOPATHY", now abandoned, which is a national stage filing under 35 U.S.C. § 371 of International Patent Application No. PCT/US2019/044961, filed Aug. 2, 2019, entitled "MUSCLE TARGETING COMPLEXES AND USES THEREOF FOR TREATING HYPERTROPHIC CARDIOMYOPATHY", which claims the benefit under 35 U.S.C. 119(e) of the filing date of U.S. Provisional Application No. 62/714,034, filed Aug. 2, 2018, entitled "MUSCLE TARGETING COMPLEXES AND USES THEREOF FOR TREATING HYPERTROPHIC CARDIOMYOPATHY". The contents of each of these applications are incorporated herein by reference in their entirety.

FIELD OF THE INVENTION

The present application relates to targeting complexes for delivering molecular payloads (e.g., oligonucleotides) to cells and uses thereof, particularly uses relating to treatment of disease.

REFERENCE TO THE SEQUENCE LISTING

The content of the electronic sequence listing (D082470001US19-SEQ-ZJG.xml; Size: 1,174,452 bytes; and Date of Creation: May 16, 2025) is herein incorporated by reference in its entirety.

BACKGROUND OF INVENTION

Muscle diseases are often associated with muscle weakness and/or muscle dysfunction that lead to life-threatening complications. Many examples of such diseases have been characterized, including various forms of muscular dystrophy (e.g., Duchenne, facioscapulohumeral, myotonic, and oculopharyngeal), Pompe disease, centronuclear myopathy, familial hypertrophic cardiomyopathy, Laing distal myopathy, Fibrodysplasia Ossificans Progressiva, Friedereich's ataxia, myofibrilar myopathy, and others. These conditions are generally hereditary, but can arise spontaneously. These conditions are often congenital but can arise later in life. Many rare muscle disease are single gene disorders associated with gain-of-function or loss-of-function mutations, which may have dominant or recessive phenotypes. For example, activating mutations have been identified in genes encoding ion channels, structural proteins, metabolic proteins, and signaling proteins that contribute to muscle disease. Despite advances in understanding the genetic etiology of muscle disease, effective treatment options remain limited.

SUMMARY OF INVENTION

According to some aspects, the disclosure provides complexes that target muscle cells for purposes of delivering molecular payloads to those cells. In some embodiments, the complexes of the present disclosure facilitate muscle-specific delivery of molecular payloads that target muscle disease alleles. For example, in some embodiments, complexes provided herein are particularly useful for delivering molecular payloads that modulate the expression or activity of a gene in a subject having or suspected of having a muscle disease associated with the gene (e.g., a gene/disease of Table 1). In some embodiments, complexes provided herein comprise muscle-targeting agents (e.g., muscle targeting antibodies) that specifically bind to receptors on the surface of muscle cells for purposes of delivering molecular payloads to the muscle cells. In some embodiments, the complexes are taken up into the cells via a receptor (e.g., transferrin receptor) mediated internalization, following which the molecular payload may be released to perform a function inside the cells. For example, complexes engineered to deliver oligonucleotides may release the oligonucleotides such that the oligonucleotides can modulate expression or activity of a muscle disease allele. In some embodiments, the oligonucleotides are released by endosomal cleavage of covalent linkers connecting oligonucleotides and muscle-targeting agents of the complexes.

In some embodiments, methods are provided for treating a subject diagnosed as having a muscle disease associated with a disease allele (e.g., a gain-of-function disease allele).

In some embodiments, the methods involve administering to the subject a complex comprising a muscle-targeting agent covalently linked to a molecular payload configured to inhibit expression or activity of the disease allele. In some embodiments, the muscle-targeting agent specifically binds to an internalizing cell surface receptor on muscle cells of the subject. In some embodiments, the muscle disease is hereditary, and may exhibit increased severity in sequential family generations of the subject. In some embodiments, the subject has been diagnosed as having the muscle disease based on a genetic analysis of the disease allele. In some embodiments, the subject exhibits progressive muscle weakness and/or sarcopenia prior to the administration. In some embodiments, the subject exhibits myotonia prior to the administration.

According to some aspects, a method for treating a subject diagnosed as having a muscle disease (e.g., associated with a gain-of-function disease allele) is provided. In some embodiments, the methods comprise administering to the subject a complex comprising a muscle-targeting agent covalently linked to a molecular payload configured to inhibit expression or activity of the disease allele. In some embodiments, the muscle-targeting agent specifically binds to an internalizing cell surface receptor on muscle cells of the subject.

In some embodiments, the muscle disease is hereditary. In some embodiments, the muscle disease exhibits increased severity in sequential family generations of the subject. In some embodiments, the subject was diagnosed as having the muscle disease based on a genetic analysis of a disease allele. In some embodiments, the subject exhibits progressive muscle weakness and/or sarcopenia prior to the administration. In some embodiments, the subject exhibits myotonia, e.g., measurable with electromyography, prior to the administration.

In some embodiments, the muscle-targeting agent is a muscle-targeting antibody. In some embodiments, the muscle-targeting antibody specifically binds to an extracellular epitope of a transferrin receptor. In some embodiments, the extracellular epitope of the transferrin receptor comprises an epitope of the apical domain of the transferrin receptor. In some embodiments, the muscle-targeting antibody specifically binds to an epitope of a sequence in the range of C89 to F760 of SEQ ID NO: 1-3. In some embodiments, the equilibrium dissociation constant (Kd) of binding of the muscle-targeting antibody to the transferrin receptor is in a range from $10^{-11}$ M to $10^{-6}$ M. In some embodiments, the muscle-targeting antibody competes for specific binding to an epitope of a transferrin receptor with an antibody listed in Table 2.

In some embodiments, the muscle-targeting antibody competes for specific binding to an epitope of a transferrin receptor with a Kd of less than or equal to $10^{-6}$ M. In some embodiments, the Kd is in a range of $10^{-11}$ M to $10^{-6}$ M.

In some embodiments, the muscle-targeting antibody does not specifically bind to the transferrin binding site of the transferrin receptor and/or the muscle-targeting antibody does not inhibit binding of transferrin to the transferrin receptor. In some embodiments, the muscle-targeting antibody is cross-reactive with extracellular epitopes of two or more of a human, non-human primate and rodent transferrin receptor. In some embodiments, the method is configured to promote transferrin receptor mediated internalization of the molecular payload into a muscle cell.

In some embodiments, the muscle-targeting antibody is a chimeric antibody, optionally wherein the chimeric antibody is a humanized monoclonal antibody. In some embodiments, the muscle-targeting antibody is in the form of a ScFv, a Fab fragment, Fab' fragment, F(ab')$_2$ fragment, or Fv fragment.

In some embodiments, the molecular payload is an oligonucleotide. In some embodiments, the oligonucleotide comprises a region of complementarity to gene listed in Table 1 or mRNA encoded therefrom. In some embodiments, the oligonucleotide is a gapmer oligonucleotide, a mixmer oligonucleotide, an antisense oligonucleotide, a RNAi oligonucleotide, a messenger RNA (mRNA), or a guide sequence.

In some embodiments, the complex is administered to the subject by extramuscular parenteral administration. In some embodiments, the complex is administered to the subject by intravenous administration. In some embodiments, the complex is administered to the subject by subcutaneous administration of the complex.

In some aspects, a complex is provided that comprises a muscle-targeting agent linked to a single-stranded oligonucleotide. In some embodiments, the muscle-targeting agent specifically binds to an internalizing cell surface receptor on muscle cells, and wherein the oligonucleotide comprises a region of complementarity to a muscle disease gene.

In some embodiments, a composition is provided that comprises a plurality of complexes, each complex comprising a muscle-targeting agent covalently linked to at two, at least three or more (e.g., 2 to 6) oligonucleotides. In some embodiments, the muscle-targeting agent specifically binds to an internalizing cell surface receptor on muscle cells of a subject, and each oligonucleotide comprises a region of complementarity to a muscle disease gene.

In some aspects, a complex is provided that comprises a muscle-targeting agent covalently linked to a molecular payload configured to modulate expression or activity of a muscle disease gene that encodes a non-secreted product that functions within muscle cells. In some embodiments, the muscle-targeting agent specifically binds to an internalizing cell surface receptor on muscle cells.

In some embodiments, the muscle-targeting agent is a muscle-targeting antibody. In some embodiments, the muscle-targeting antibody specifically binds to an extracellular epitope of a transferrin receptor. In some embodiments, the extracellular epitope of the transferrin receptor comprises an epitope of the apical domain of the transferrin receptor. In some embodiments, the muscle-targeting antibody specifically binds to an epitope of a sequence within amino acids C89 to F760 of SEQ ID NO: 1-3. In some embodiments, the equilibrium dissociation constant (Kd) of binding of the muscle-targeting antibody to the transferrin receptor is in a range from $10^{-11}$ M to $10^{-6}$ M. In some embodiments, the muscle-targeting antibody competes for specific binding to an epitope of a transferrin receptor with an antibody listed in Table 2. In some embodiments, the muscle-targeting antibody competes for specific binding to an epitope of a transferrin receptor with a Kd of less than or equal to $10^{-6}$ M. In some embodiments, the Kd is in a range of $10^{-11}$ M to $10^{-6}$ M.

In some embodiments, the muscle-targeting antibody does not specifically bind to the transferrin binding site of the transferrin receptor and/or wherein the muscle-targeting antibody does not inhibit binding of transferrin to the transferrin receptor. In some embodiments, the muscle-targeting antibody is cross-reactive with extracellular epitopes of two or more of a human, non-human primate and rodent transferrin receptor.

In some embodiments, the complex is configured to promote transferrin receptor mediated internalization of the molecular payload into a muscle cell. In some embodiments, the muscle-targeting antibody is a chimeric antibody. In some embodiments, the chimeric antibody is a humanized monoclonal antibody.

In some embodiments, the muscle-targeting antibody is in the form of a ScFv, a Fab fragment, Fab' fragment, F(ab')$_2$ fragment, or Fv fragment.

In some embodiments, the molecular payload is an oligonucleotide. In some embodiments, the oligonucleotide comprises a region of complementarity to a muscle disease gene having a gain-of-function disease allele.

In some embodiments, the molecular payload is an polypeptide. In some embodiments, the polypeptide is an E3 ubiquitin ligase inhibitor peptide.

In some embodiments, the oligonucleotide comprises at least one modified internucleotide linkage. In some embodiments, the the at least one modified internucleotide linkage is a phosphorothioate linkage. In some embodiments, the oligonucleotide comprises phosphorothioate linkages in the Rp stereochemical conformation and/or in the Sp stereochemical conformation. In some embodiments, the oligonucleotide comprises phosphorothioate linkages that are all in the Rp stereochemical conformation or that are all in the Sp stereochemical conformation.

In some embodiments, the oligonucleotide comprises one or more modified nucleotides. In some embodiments, the one or more modified nucleotides are 2'-modified nucleotides.

In some embodiments, the oligonucleotide is a gapmer oligonucleotide that directs RNAse H-mediated cleavage of an mRNA transcript encoded by the muscle disease gene in a cell. In some embodiments, the gapmer oligonucleotide comprises a central portion of 5 to 15 deoxyribonucleotides flanked by wings of 2 to 8 modified nucleotides.

In some embodiments, the modified nucleotides of the wings are 2'-modified nucleotides. In some embodiments, the oligonucleotide is a mixmer oligonucleotide.

In some embodiments, the mixmer oligonucleotide comprises two or more different 2' modified nucleotides. In some embodiments, the oligonucleotide is an RNAi oligonucleotide that promotes RNAi-mediated cleavage of a mRNA transcript encoded by the muscle disease gene.

In some embodiments, the oligonucleotide is a double-stranded oligonucleotide of 19 to 25 nucleotides in length. In some embodiments, the RNAi oligonucleotide comprises at least one 2' modified nucleotide. In some embodiments, each 2' modified nucleotide is selected from the group consisting of: 2'-O-methyl, 2'-fluoro (2'-F), 2'-O-methoxyethyl (2'-MOE), and 2', 4'-bridged nucleotides.

In some embodiments, the one or more modified nucleotides are bridged nucleotides. In some embodiments, at least one 2' modified nucleotide is a 2',4'-bridged nucleotide selected from: 2',4'-constrained 2'-O-ethyl (cEt) and locked nucleic acid (LNA) nucleotides.

In some embodiments, the oligonucleotide comprises a guide sequence for a genome editing nuclease.

In some embodiments, the oligonucleotide is phosphorodiamidite morpholino oligomer. In some embodiments, the muscle-targeting agent is covalently linked to the molecular payload via a cleavable linker.

In some embodiments, the cleavable linker is selected from: a protease-sensitive linker, pH-sensitive linker, and glutathione-sensitive linker. In some embodiments, the cleavable linker is a protease-sensitive linker. In some embodiments, the protease-sensitive linker comprises a sequence cleavable by a lysosomal protease and/or an endosomal protease. In some embodiments, the protease-sensitive linker comprises a valine-citrulline dipeptide sequence. In some embodiments, the linker is a pH-sensitive linker that is cleaved at a pH in a range of 4 to 6.

In some embodiments, the muscle-targeting agent is covalently linked to the molecular payload via a non-cleavable linker. In some embodiments, the non-cleavable linker is an alkane linker.

In some embodiments, the muscle-targeting antibody comprises a non-natural amino acid to which the oligonucleotide is covalently linked. In some embodiments, the muscle-targeting antibody is covalently linked to the oligonucleotide via conjugation to a lysine residue or a cysteine residue of the antibody. In some embodiments, the muscle-targeting antibody is conjugated to the cysteine via a maleimide-containing linker, optionally wherein the maleimide-containing linker comprises a maleimidocaproyl or maleimidomethyl cyclohexane-1-carboxylate group.

In some embodiments, the muscle-targeting antibody is a glycosylated antibody that comprises at least one sugar moiety to which the oligonucleotide is covalently linked. In some embodiments, the sugar moiety is a branched mannose. In some embodiments, the muscle-targeting antibody is a glycosylated antibody that comprises one to four sugar moieties each of which is covalently linked to a separate oligonucleotide.

In some embodiments, the muscle-targeting antibody is a fully-glycosylated antibody. In some embodiments, the muscle-targeting antibody is a partially-glycosylated antibody. In some embodiments, the partially-glycosylated antibody is produced via chemical or enzymatic means. In some embodiments, the partially-glycosylated antibody is produced in a cell, cell that is deficient for an enzyme in the N- or O-glycosylation pathway.

According to some aspects, methods of delivering a molecular payload to a cell expressing transferrin receptor are provided. In some embodiments, the methods comprise contacting the cell with a complex provided herein.

According to some aspects, methods of inhibiting expression or activity of muscle disease gene in a cell are provided. In some embodiments, the methods comprise contacting the cell with a complex provided herein in an amount effective for promoting internalization of the molecular payload to the cell. In some embodiments, the cell is in vitro. In some embodiments, the cell is in a subject. In some embodiments, the subject is a human.

According to some aspects, methods of treating a subject having a muscle disease are provided. In some embodiments, the methods comprise administering to the subject an effective amount of a complex provided herein. In some embodiments, the muscle disease is a disease listed in Table 1. In some embodiments, the muscle disease is a disease selected from the group consisting of: Adult Pompe Disease, Centronuclear myopathy (CNM), Duchenne Muscular Dystrophy, Facioscapulohumeral Muscular Dystrophy (FSHD), Familial Hypertrophic Cardiomyopathy, Fibrodysplasia Ossificans Progressiva (FOP), Friedreich's Ataxia (FRDA), Inclusion Body Myopathy 2, Laing Distal Myopathy, Myofibrillar Myopathy, Myotonia Congenita (autosomal dominant form, Thomsen Disease), Myotonic Dystrophy Type I, Myotonic Dystrophy Type II, Myotubular Myopathy, Oculopharyngeal Muscular Dystrophy, and Paramyotonia Congenita.

DETAILED DESCRIPTION OF INVENTION

Figure 1:
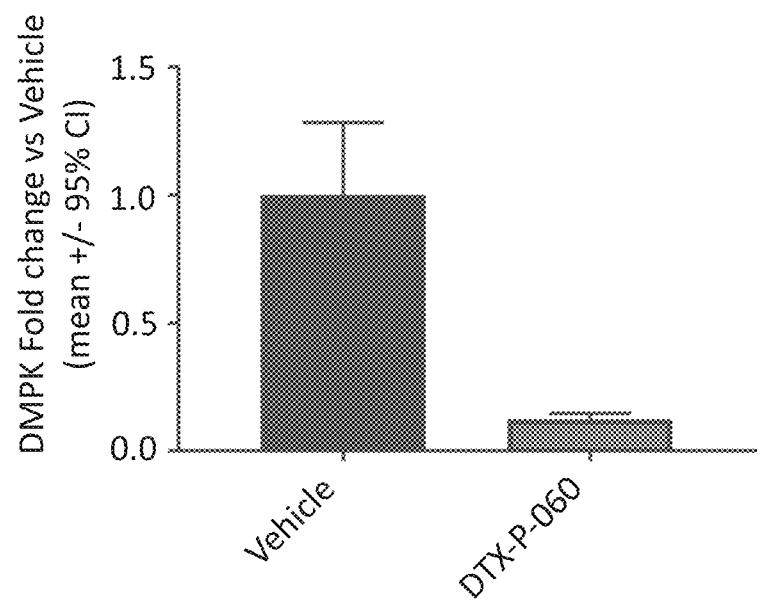
FIG. 1 depicts a non-limiting schematic showing the effect of transfecting Hepa 1-6 cells with an antisense oligonucleotide that targets DMPK (DTX-P-060) on expression levels of DMPK relative to a vehicle transfection.

Aspects of the disclosure relate to a recognition that while certain molecular payloads (e.g., oligonucleotides, peptides, small molecules) can have beneficial effects in muscle cells, it has proven challenging to effectively target such cells. As described herein, the present disclosure provides complexes comprising muscle-targeting agents covalently linked to molecular payloads in order to overcome such challenges. In some embodiments, the complexes are particularly useful for delivering molecular payloads that modulate expression or activity of target genes in muscle cells, e.g., in a subject having or suspected of having a muscle disease. For example, in some embodiments, complexes are useful for treating subjects having rare muscle diseases, including Pompe disease, Centronuclear myopathy, Fibrodysplasia Ossificans Progressiva, Friedreich's ataxia, or Duchenne muscular dystrophy. In some embodiments, depending on the condition to be treated, different molecular payloads may be used in such complexes. For example, if the underlying mutation gives rise to a splicing defect, then an oligonucleotide or other payload may be used to correct the splicing defect (e.g., an oligonucleotide that inhibits exon skipping or promotes alternative splicing). If the underlying mutation results in a gain-of-function allele, then an oligonucleotide (e.g., RNAi, PMO, ASO-gapmer) may be used to inhibit the expression or activity of the allele. In some embodiments, e.g., when the mutation results in a loss-of-function allele, the payload may comprise an expression construct, e.g., for expressing a wild-type version of the allele. In some embodiments, the payload may comprise machinery (e.g., a guide nucleic acid, expression construct encoding a gene editing enzyme) for correcting the underlying defect, e.g., by gene editing.

Further aspects of the disclosure, including a description of defined terms, are provided below.

I. Definitions

Administering: As used herein, the terms "administering" or "administration" means to provide a complex to a subject in a manner that is physiologically and/or pharmacologically useful (e.g., to treat a condition in the subject).

Approximately: As used herein, the term "approximately" or "about," as applied to one or more values of interest, refers to a value that is similar to a stated reference value. In certain embodiments, the term "approximately" or "about" refers to a range of values that fall within 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Antibody: As used herein, the term "antibody" refers to a polypeptide that includes at least one immunoglobulin variable domain or at least one antigenic determinant, e.g., paratope that specifically binds to an antigen. In some embodiments, an antibody is a full-length antibody. In some embodiments, an antibody is a chimeric antibody. In some embodiments, an antibody is a humanized antibody. However, in some embodiments, an antibody is a Fab fragment, a F(ab')2 fragment, a Fv fragment or a scFv fragment. In some embodiments, an antibody is a nanobody derived from a camelid antibody or a nanobody derived from shark antibody. In some embodiments, an antibody is a diabody. In some embodiments, an antibody comprises a framework having a human germline sequence. In another embodiment, an antibody comprises a heavy chain constant domain selected from the group consisting of IgG, IgG1, IgG2, IgG2A, IgG2B, IgG2C, IgG3, IgG4, IgA1, IgA2, IgD, IgM, and IgE constant domains. In some embodiments, an antibody comprises a heavy (H) chain variable region (abbreviated herein as VH), and/or a light (L) chain variable region (abbreviated herein as VL). In some embodiments, an antibody comprises a constant domain, e.g., an Fc region. An immunoglobulin constant domain refers to a heavy or light chain constant domain. Human IgG heavy chain and light chain constant domain amino acid sequences and their functional variations are known. With respect to the heavy chain, in some embodiments, the heavy chain of an antibody described herein can be an alpha (α), delta (Δ), epsilon (ε), gamma (γ) or mu (μ) heavy chain. In some embodiments, the heavy chain of an antibody described herein can comprise a human alpha (α), delta (Δ), epsilon (ε), gamma (γ) or mu (μ) heavy chain. In a particular embodiment, an antibody described herein comprises a human gamma 1 CH1, CH2, and/or CH3 domain. In some embodiments, the amino acid sequence of the VH domain comprises the amino acid sequence of a human gamma (γ) heavy chain constant region, such as any known in the art. Non-limiting examples of human constant region sequences have been described in the art, e.g., see U.S. Pat. No. 5,693,780 and Kabat E A et al., (1991) supra. In some embodiments, the VH domain comprises an amino acid sequence that is at least 70%, 75%, 80%, 85%, 90%, 95%, 98%, or at least 99% identical to any of the variable chain constant regions provided herein. In some embodiments, an antibody is modified, e.g., modified via glycosylation, phosphorylation, sumoylation, and/or methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or phosphoglycosylation. In some embodiments, the one or more sugar or carbohydrate molecule are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, an antibody is a construct that comprises a polypeptide comprising one or more antigen binding fragments of the disclosure linked to a linker polypeptide or an immunoglobulin constant domain. Linker polypeptides comprise two or more amino acid residues joined by peptide bonds and are used to link one or more antigen binding portions. Examples of linker polypeptides have been reported (see e.g., Holliger, P., et al. (1993) Proc. Natl. Acad. Sci. USA 90:6444-6448; Poljak, R. J., et al. (1994) Structure 2:1121-1123). Still further, an antibody may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058).

CDR: As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Sub-portions of CDRs may be designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

CDR-grafted antibody: The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

Chimeric antibody: The term "chimeric antibody" refers to antibodies which comprise heavy and light chain variable region sequences from one species and constant region sequences from another species, such as antibodies having murine heavy and light chain variable regions linked to human constant regions.

Complementary: As used herein, the term "complementary" refers to the capacity for precise pairing between two nucleotides or two sets of nucleotides. In particular, complementary is a term that characterizes an extent of hydrogen bond pairing that brings about binding between two nucleotides or two sets of nucleotides. For example, if a base at one position of an oligonucleotide is capable of hydrogen bonding with a base at the corresponding position of a target nucleic acid (e.g., an mRNA), then the bases are considered to be complementary to each other at that position. Base pairings may include both canonical Watson-Crick base pairing and non-Watson-Crick base pairing (e.g., Wobble base pairing and Hoogsteen base pairing). For example, in some embodiments, for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroindole can hybridize to and are considered complementary to any A, C, U, or T. Inosine (I) has also been considered in the art to be a universal base and is considered complementary to any A, C, U or T.

Conservative amino acid substitution: As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Fourth Edition, Cold Spring Harbor Laboratory Press, Cold Spring Harbor, New York, 2012, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Covalently linked: As used herein, the term "covalently linked" refers to a characteristic of two or more molecules being linked together via at least one covalent bond. In some embodiments, two molecules can be covalently linked together by a single bond, e.g., a disulfide bond or disulfide bridge, that serves as a linker between the molecules. However, in some embodiments, two or more molecules can be covalently linked together via a molecule that serves as a linker that joins the two or more molecules together through multiple covalent bonds. In some embodiments, a linker may be a cleavable linker. However, in some embodiments, a linker may be a non-cleavable linker.

Cross-reactive: As used herein and in the context of a targeting agent (e.g., antibody), the term "cross-reactive," refers to a property of the agent being capable of specifically binding to more than one antigen of a similar type or class (e.g., antigens of multiple homologs, paralogs, or orthologs) with similar affinity or avidity. For example, in some embodiments, an antibody that is cross-reactive against human and non-human primate antigens of a similar type or class (e.g., a human transferrin receptor and non-human primate transferring receptor) is capable of binding to the human antigen and non-human primate antigens with a similar affinity or avidity. In some embodiments, an antibody is cross-reactive against a human antigen and a rodent antigen of a similar type or class. In some embodiments, an antibody is cross-reactive against a rodent antigen and a non-human primate antigen of a similar type or class. In some embodiments, an antibody is cross-reactive against a human antigen, a non-human primate antigen, and a rodent antigen of a similar type or class.

Disease allele: As used herein, the term "disease allele" refers to any one of alternative forms (e.g., mutant forms) of a gene for which the allele is correlated with and/or directly or indirectly contributes to, or causes, disease. A disease allele may comprise gene alterations including, but not limited to, insertions (e.g., disease-associated repeats described below), deletions, missense mutations, nonsense mutations and splice-site mutations relative to a wild-type (non-disease) allele. In some embodiments, a disease allele has a loss-of-function mutation. In some embodiments, a disease allele has a gain-of-function mutation. In some embodiments, a disease allele encodes an activating mutation (e.g., encodes a protein that is constitutively active). In some embodiments, a disease allele is a recessive allele having a recessive phenotype. In some embodiments, a disease allele is a dominant allele having a dominant phenotype.

Disease-associated-repeat: As used herein, the term "disease-associated-repeat" refers to a repeated nucleotide sequence at a genomic location for which the number of units of the repeated nucleotide sequence is correlated with and/or directly or indirectly contributes to, or causes, genetic disease. Each repeating unit of a disease associated repeat may be 2, 3, 4, 5 or more nucleotides in length. For example, in some embodiments, a disease associated repeat is a dinucleotide repeat. In some embodiments, a disease associated repeat is a trinucleotide repeat. In some embodiments, a disease associated repeat is a tetranucleotide repeat. In some embodiments, a disease associated repeat is a pentanucleotide repeat. In some embodiments, embodiments, the disease-associated-repeat comprises CAG repeats, CTG repeats, CUG repeats, CGG repeats, CCTG repeats, or a nucleotide complement of any thereof. In some embodiments, a disease-associated-repeat is in a non-coding portion of a gene. However, in some embodiments, a disease-associated-repeat is in a coding region of a gene. In some embodiments, a disease-associated-repeat is expanded from a normal state to a length that directly or indirectly contributes to, or causes, genetic disease. In some embodiments, a disease-associated-repeat is in RNA (e.g., an RNA transcript). In some embodiments, a disease-associated-repeat is in DNA (e.g., a chromosome, a plasmid). In some embodiments, a disease-associated-repeat is expanded in a chromosome of a germline cell. In some embodiments, a disease-associated-repeat is expanded in a chromosome of a somatic cell. In some embodiments, a disease-associated-repeat is expanded to a number of repeating units that is associated with congenital onset of disease. In some embodiments, a disease-associated-repeat is expanded to a number of repeating units that is associated with childhood onset of disease. In some embodiments, a disease-associated-repeat is expanded to a number of repeating units that is associated with adult onset of disease.

Framework: As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region. Human heavy chain and light chain acceptor sequences are known in the art. In one embodiment, the acceptor sequences known in the art may be used in the antibodies disclosed herein.

Human antibody: The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

Humanized antibody: The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. In one embodiment, humanized anti-transferrin receptor antibodies and antigen binding portions are provided. Such antibodies may be generated by obtaining murine anti-transferrin receptor monoclonal antibodies using traditional hybridoma technology followed by humanization using in vitro genetic engineering, such as those disclosed in Kasaian et al PCT publication No. WO 2005/123126 A2.

Internalizing cell surface receptor: As used herein, the term, "internalizing cell surface receptor" refers to a cell surface receptor that is internalized by cells, e.g., upon external stimulation, e.g., ligand binding to the receptor. In some embodiments, an internalizing cell surface receptor is internalized by endocytosis. In some embodiments, an internalizing cell surface receptor is internalized by clathrin-mediated endocytosis. However, in some embodiments, an internalizing cell surface receptor is internalized by a clathrin-independent pathway, such as, for example, phagocytosis, macropinocytosis, caveolae- and raft-mediated uptake or constitutive clathrin-independent endocytosis. In some embodiments, the internalizing cell surface receptor comprises an intracellular domain, a transmembrane domain, and/or an extracellular domain, which may optionally further comprise a ligand-binding domain. In some embodiments, a cell surface receptor becomes internalized by a cell after ligand binding. In some embodiments, a ligand may be a muscle-targeting agent or a muscle-targeting antibody. In some embodiments, an internalizing cell surface receptor is a transferrin receptor.

Isolated antibody: An "isolated antibody", as used herein, is intended to refer to an antibody that is substantially free of other antibodies having different antigenic specificities (e.g., an isolated antibody that specifically binds transferrin receptor is substantially free of antibodies that specifically bind antigens other than transferrin receptor). An isolated antibody that specifically binds transferrin receptor complex may, however, have cross-reactivity to other antigens, such as transferrin receptor molecules from other species. Moreover, an isolated antibody may be substantially free of other cellular material and/or chemicals.

Kabat numbering: The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

Molecular payload: As used herein, the term "molecular payload" refers to a molecule or species that functions to modulate a biological outcome. In some embodiments, a molecular payload is linked to, or otherwise associated with a muscle-targeting agent. In some embodiments, the molecular payload is a small molecule, a protein, a peptide, a nucleic acid, or an oligonucleotide. In some embodiments, the molecular payload functions to modulate the transcription of a DNA sequence, to modulate the expression of a protein, or to modulate the activity of a protein. In some embodiments, the molecular payload is an oligonucleotide that comprises a strand having a region of complementarity to a target gene.

Muscle Disease Gene: As used herein, the term "muscle disease gene" refers to a gene having a least one disease allele correlated with and/or directly or indirectly contributing to, or causing, a muscle disease. In some embodiments, the muscle disease is a rare disease, e.g., as defined by the Genetic and Rare Diseases Information Center (GARD), which is a program of the National Center for Advancing Translational Sciences (NCATS). In some embodiments, the muscle disease is a rare disease that is characterized as affecting fewer than 200,000 people. In some embodiments, the muscle disease is a single-gene disease. In some embodiments, a muscle disease gene is a gene listed in Table 1.

Muscle-targeting agent: As used herein, the term, "muscle-targeting agent," refers to a molecule that specifically binds to an antigen expressed on muscle cells. The antigen in or on muscle cells may be a membrane protein, for example an integral membrane protein or a peripheral membrane protein. Typically, a muscle-targeting agent specifically binds to an antigen on muscle cells that facilitates internalization of the muscle-targeting agent (and any associated molecular payload) into the muscle cells. In some embodiments, a muscle-targeting agent specifically binds to an internalizing, cell surface receptor on muscles and is capable of being internalized into muscle cells through receptor mediated internalization. In some embodiments, the muscle-targeting agent is a small molecule, a protein, a peptide, a nucleic acid (e.g., an aptamer), or an antibody. In some embodiments, the muscle-targeting agent is linked to a molecular payload.

Muscle-targeting antibody: As used herein, the term, "muscle-targeting antibody," refers to a muscle-targeting agent that is an antibody that specifically binds to an antigen found in or on muscle cells. In some embodiments, a muscle-targeting antibody specifically binds to an antigen on muscle cells that facilitates internalization of the muscle-targeting antibody (and any associated molecular payment) into the muscle cells. In some embodiments, the muscle-targeting antibody specifically binds to an internalizing, cell surface receptor present on muscle cells. In some embodiments, the muscle-targeting antibody is an antibody that specifically binds to a transferrin receptor.

Oligonucleotide: As used herein, the term "oligonucleotide" refers to an oligomeric nucleic acid compound of up to 200 nucleotides in length. Examples of oligonucleotides include, but are not limited to, RNAi oligonucleotides (e.g., siRNAs, shRNAs), microRNAs, gapmers, mixmers, phosphorodiamidite morpholinos, peptide nucleic acids, aptamers, guide nucleic acids (e.g., Cas9 guide RNAs), etc. Oligonucleotides may be single-stranded or double-stranded. In some embodiments, an oligonucleotide may comprise one or more modified nucleotides (e.g. 2'-O-methyl sugar modifications, purine or pyrimidine modifications). In some embodiments, an oligonucleotide may comprise one or more modified internucleotide linkage. In some embodiments, an oligonucleotide may comprise one or more phosphorothioate linkages, which may be in the Rp or Sp stereochemical conformation.

Recombinant antibody: The term "recombinant human antibody", as used herein, is intended to include all human antibodies that are prepared, expressed, created or isolated by recombinant means, such as antibodies expressed using a recombinant expression vector transfected into a host cell (described in more details in this disclosure), antibodies isolated from a recombinant, combinatorial human antibody library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597; Little M. et al (2000) Immunology Today 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. One embodiment of the disclosure provides fully human antibodies capable of binding human transferrin receptor which can be generated using techniques well known in the art, such as, but not limited to, using human Ig phage libraries such as those disclosed in Jermutus et al., PCT publication No. WO 2005/007699 A2.

Region of complementarity: As used herein, the term "region of complementarity" refers to a nucleotide sequence, e.g., of a oligonucleotide, that is sufficiently complementary to a cognate nucleotide sequence, e.g., of a target nucleic acid, such that the two nucleotide sequences are capable of annealing to one another under physiological conditions (e.g., in a cell). In some embodiments, a region of complementarity is fully complementary to a cognate nucleotide sequence of target nucleic acid. However, in some embodiments, a region of complementarity is partially complementary to a cognate nucleotide sequence of target nucleic acid (e.g., at least 80%, 90%, 95% or 99% complementarity). In some embodiments, a region of complementarity contains 1, 2, 3, or 4 mismatches compared with a cognate nucleotide sequence of a target nucleic acid.

Specifically binds: As used herein, the term "specifically binds" refers to the ability of a molecule to bind to a binding partner with a degree of affinity or avidity that enables the molecule to be used to distinguish the binding partner from an appropriate control in a binding assay or other binding context. With respect to an antibody, the term, "specifically binds", refers to the ability of the antibody to bind to a specific antigen with a degree of affinity or avidity, compared with an appropriate reference antigen or antigens, that enables the antibody to be used to distinguish the specific antigen from others, e.g., to an extent that permits preferential targeting to certain cells, e.g., muscle cells, through binding to the antigen, as described herein. In some embodiments, an antibody specifically binds to a target if the antibody has a $K_D$ for binding the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. In some embodiments, an antibody specifically binds to the transferrin receptor, e.g., an epitope of the apical domain of transferrin receptor.

Subject: As used herein, the term "subject" refers to a mammal. In some embodiments, a subject is non-human primate, or rodent. In some embodiments, a subject is a human. In some embodiments, a subject is a patient, e.g., a human patient that has or is suspected of having a disease. In some embodiments, the subject is a human patient who has or is suspected of having a muscle disease (e.g., any of the diseases provided in Table 1).

Transferrin receptor: As used herein, the term, "transferrin receptor" (also known as TFRC, CD71, p90, or TFR1) refers to an internalizing cell surface receptor that binds transferrin to facilitate iron uptake by endocytosis. In some embodiments, a transferrin receptor may be of human (NCBI Gene ID 7037), non-human primate (e.g., NCBI Gene ID 711568 or NCBI Gene ID 102136007), or rodent (e.g., NCBI Gene ID 22042) origin. In addition, multiple human transcript variants have been characterized that encoded different isoforms of the receptor (e.g., as annotated under GenBank RefSeq Accession Numbers: NP_001121620.1, NP_003225.2, NP_001300894.1, and NP_001300895.1).

II. Complexes

Provided herein are complexes that comprise a targeting agent, e.g. an antibody, covalently linked to a molecular payload. In some embodiments, a complex comprises a muscle-targeting antibody covalently linked to an oligonucleotide. A complex may comprise an antibody that specifically binds a single antigenic site or that binds to at least two antigenic sites that may exist on the same or different antigens. A complex may be used to modulate the activity or function of at least one gene, protein, and/or nucleic acid. In some embodiments, the molecular payload present with a complex is responsible for the modulation of a gene, protein, and/or nucleic acids. A molecular payload may be a small molecule, protein, nucleic acid, oligonucleotide, or any molecular entity capable of modulating the activity or function of a gene, protein, and/or nucleic acid in a cell. In some embodiments, a molecular payload is an oligonucleotide that targets a muscle disease allele in muscle cells.

In some embodiments, a complex comprises a muscle-targeting agent, e.g. an anti-transferrin receptor antibody, covalently linked to a molecular payload, e.g. an antisense oligonucleotide that targets a muscle disease allele.

In some embodiments, a complex is useful for treating a muscle disease, in which a molecular payload affects the activity of the corresponding gene provided in Table 1. For example, depending on the condition, a molecular payload may modulate (e.g., decrease, increase) transcription or expression of the gene, modulate the expression of a protein encoded by the gene, or to modulate the activity of the encoded protein. In some embodiments, the molecular payload is an oligonucleotide that comprises a strand having a region of complementarity to a target gene provided in Table 1.

TABLE 1

List of muscle diseases and corresponding genes.

| Disease | Gene Symbol | GenBank Accession No. |
|---|---|---|
| Adult Pompe | GAA | NM_000152; NM_001079803; NM_001079804 |
| Adult Pompe | GYS1 | NM_001161587; NM_002103 |
| Centronuclear myopathy (CNM) | DNM2 | NM_001190716; NM_004945; NM_001005362; NM_001005360; NM_001005361; NM_007871 |
| Duchenne muscular dystrophy | DMD | NM_004023; NM_004020; NM_004018; NM_004012 |
| Facioscapulohumeral muscular dystrophy (FSHD) | DUX4 | NM_001306068; NM_001363820; NM_001205218; NM_001293798 |
| Familial hypertrophic cardiomyopathy | MYBPC3 | NM_000256 |
| Familial hypertrophic cardiomyopathy | MYH6 | NM_002471; NM_001164171; NM_010856 |
| Familial hypertrophic cardiomyopathy | MYH7 | NM_000257; NM_080728 |
| Familial hypertrophic cardiomyopathy | TNNI3 | NM_000363 |
| Familial hypertrophic cardiomyopathy | TNNT2 | NM_001001432; NM_001001431; NM_000364; NM_001001430; NM_001276347; NM_001276346; NM_001276345 |
| Fibrodysplasia Ossificans Progressiva (FOP) | ACVR1 | NM_001105; NM_001347663; NM_001347664; NM_001347665; NM_001347666; NM_001347667; NM_001111067 |
| Friedreich's ataxia (FRDA) | FXN | NM_001161706; NM_181425; NM_000144 |
| Inclusion body myopathy 2 | GNE | NM_001190383; NM_001190384; NM_001128227; NM_005476; NM_001190388 |
| Laing distal myopathy | MYH7 | NM_000257; NM_080728 |
| Myofibrillar myopathy | BAG3 | NM_004281 |
| Myofibrillar myopathy | CRYAB | NM_001885; NM_001330379; NM_001289807; NM_001289808 |
| Myofibrillar myopathy | DES | NM_001927 |
| Myofibrillar myopathy | DNAJB6 | NM_005494; NM_058246 |
| Myofibrillar myopathy | FHL1 | NM_001159701; NM_001159699; NM_001159702; NM_001159703; NM_001159704; NM_001159700; NM_001167819; NM_001330659; NM_001449; NM_001077362 |
| Myofibrillar myopathy | FLNC | NM_001458; NM_001127487 |
| Myofibrillar myopathy | LDB3 | NM_007078; NM_001171611; NM_001171610; NM_001080114; NM_001080115; NM_001080116 |
| Myofibrillar myopathy | MYOT | NM_001300911; NM_006790; NM_001135940 |
| Myofibrillar myopathy | PLEC | NM_201378; NM_201379; NM_201380; NM_201381; NM_201382; NM_201383; NM_201384; NM_000445 |
| Myofibrillar myopathy | TTN | NM_133432; NM_133379; NM_133437; NM_003319; NM_001256850; NM_001267550; NM_133378 |
| Myotonia congenita (autosomal dominant form, Thomsen Disease) | CLCN1 | NM_000083; NM_013491 |
| Myotonic dystrophy type I | DMPK | NM_001081563; NM_004409; NM_001081560; NM_001081562; NM_001288764; NM_001288765; NM_001288766 |
| Myotonic dystrophy type II | CNBP | NM_001127192; NM_001127193; NM_001127194; |

TABLE 1-continued

List of muscle diseases and corresponding genes.

| Disease | Gene Symbol | GenBank Accession No. |
|---|---|---|
|  |  | NM_001127195; NM_001127196; NM_003418 |
| Myotubular myopathy | MTM1 | NM_000252 |
| Oculopharyngeal muscular dystrophy | PABPN1 | NM_004643 |
| Paramyotonia congenita | SCN4A | NM_000334 |

A. Muscle-Targeting Agents

Some aspects of the disclosure provide muscle-targeting agents, e.g., for delivering a molecular payload to a muscle cell. In some embodiments, such muscle-targeting agents are capable of binding to a muscle cell, e.g., via specifically binding to an antigen on the muscle cell, and delivering an associated molecular payload to the muscle cell. In some embodiments, the molecular payload is bound (e.g., covalently bound) to the muscle targeting agent and is internalized into the muscle cell upon binding of the muscle targeting agent to an antigen on the muscle cell, e.g., via endocytosis. It should be appreciated that various types of muscle-targeting agents may be used in accordance with the disclosure. For example, the muscle-targeting agent may comprise, or consist of, a nucleic acid (e.g., DNA or RNA), a peptide (e.g., an antibody), a lipid (e.g., a microvesicle), or a sugar moiety (e.g., a polysaccharide). Exemplary muscle-targeting agents are described in further detail herein, however, it should be appreciated that the exemplary muscle-targeting agents provided herein are not meant to be limiting.

Some aspects of the disclosure provide muscle-targeting agents that specifically bind to an antigen on muscle, such as skeletal muscle, smooth muscle, or cardiac muscle. In some embodiments, any of the muscle-targeting agents provided herein bind to (e.g., specifically bind to) an antigen on a skeletal muscle cell, a smooth muscle cell, and/or a cardiac muscle cell.

By interacting with muscle-specific cell surface recognition elements (e.g., cell membrane proteins), both tissue localization and selective uptake into muscle cells can be achieved. In some embodiments, molecules that are substrates for muscle uptake transporters are useful for delivering a molecular payload into muscle tissue. Binding to muscle surface recognition elements followed by endocytosis can allow even large molecules such as antibodies to enter muscle cells. As another example molecular payloads conjugated to transferrin or anti-transferrin receptor antibodies can be taken up by muscle cells via binding to transferrin receptor, which may then be endocytosed, e.g., via clathrin-mediated endocytosis.

The use of muscle-targeting agents may be useful for concentrating a molecular payload (e.g., oligonucleotide) in muscle while reducing toxicity associated with effects in other tissues. In some embodiments, the muscle-targeting agent concentrates a bound molecular payload in muscle cells as compared to another cell type within a subject. In some embodiments, the muscle-targeting agent concentrates a bound molecular payload in muscle cells (e.g., skeletal, smooth, or cardiac muscle cells) in an amount that is at least 1, 2, 3, 4, 5, 6, 7, 8, 9, 10, 15, 20, 30, 40, 50, 60, 70, 80, 90, or 100 times greater than an amount in non-muscle cells (e.g., liver, neuronal, blood, or fat cells). In some embodiments, a toxicity of the molecular payload in a subject is reduced by at least 1%, 2%, 3%, 4%, 5%, 10%, 15%, 20%, 25%, 30%, 35%, 40%, 45%, 50%, 55%, 60%, 65%, 70%, 75%, 80%, 90%, or 95% when it is delivered to the subject when bound to the muscle-targeting agent.

In some embodiments, to achieve muscle selectivity, a muscle recognition element (e.g., a muscle cell antigen) may be required. As one example, a muscle-targeting agent may be a small molecule that is a substrate for a muscle-specific uptake transporter. As another example, a muscle-targeting agent may be an antibody that enters a muscle cell via transporter-mediated endocytosis. As another example, a muscle targeting agent may be a ligand that binds to cell surface receptor on a muscle cell. It should be appreciated that while transporter-based approaches provide a direct path for cellular entry, receptor-based targeting may involve stimulated endocytosis to reach the desired site of action.

Muscle cells encompassed by the present disclosure include, but are not limited to, skeletal muscle cells, smooth muscle cells, cardiac muscle cells, myoblasts and myocytes.

i. Muscle-Targeting Antibodies

In some embodiments, the muscle-targeting agent is an antibody. Generally, the high specificity of antibodies for their target antigen provides the potential for selectively targeting muscle cells (e.g., skeletal, smooth, and/or cardiac muscle cells). This specificity may also limit off-target toxicity. Examples of antibodies that are capable of targeting a surface antigen of muscle cells have been reported and are within the scope of the disclosure. For example, antibodies that target the surface of muscle cells are described in Arahata K., et al. "Immunostaining of skeletal and cardiac muscle surface membrane with antibody against Duchenne muscular dystrophy peptide" *Nature* 1988; 333: 861-3; Song K. S., et al. "Expression of caveolin-3 in skeletal, cardiac, and smooth muscle cells. Caveolin-3 is a component of the sarcolemma and co-fractionates with dystrophin and dystrophin-associated glycoproteins" *J Biol Chem* 1996; 271: 15160-5; and Weisbart R. H. et al., "Cell type specific targeted intracellular delivery into muscle of a monoclonal antibody that binds myosin IIb" *Mol Immunol*. 2003 March, 39(13):78309; the entire contents of each of which are incorporated herein by reference.

a. Anti-Transferrin Receptor Antibodies

Some aspects of the disclosure are based on the recognition that agents binding to transferrin receptor, e.g., anti-transferrin-receptor antibodies, are capable of targeting muscle cell. Transferrin receptors are internalizing cell surface receptors that transport transferrin across the cellular membrane and participate in the regulation and homeostasis of intracellular iron levels. Some aspects of the disclosure provide transferrin receptor binding proteins, which are capable of binding to transferrin receptor. Accordingly, aspects of the disclosure provide binding proteins (e.g., antibodies) that bind to transferrin receptor. In some embodiments, binding proteins that bind to transferrin receptor are internalized, along with any bound molecular payload, into a muscle cell. As used herein, an antibody that binds to a transferrin receptor may be referred to as an anti-transferrin receptor antibody. Antibodies that bind, e.g. specifically bind, to a transferrin receptor may be internalized into the cell, e.g. through receptor-mediated endocytosis, upon binding to a transferrin receptor.

It should be appreciated that anti-transferrin receptor antibodies may be produced, synthesized, and/or derivatized using several known methodologies, e.g. library design using phage display. Exemplary methodologies have been characterized in the art and are incorporated by reference (Diez, P. et al. "High-throughput phage-display screening in array format", Enzyme and microbial technology, 2015, 79, 34-41.; Christoph M. H. and Stanley, J. R. "Antibody Phage Display: Technique and Applications" J Invest Dermatol. 2014, 134:2.; Engleman, Edgar (Ed.) "Human Hybridomas and Monoclonal Antibodies." 1985, Springer.). In other embodiments, an anti-transferrin antibody has been previously characterized or disclosed. Antibodies that specifically bind to transferrin receptor are known in the art (see, e.g. U.S. Pat. No. 4,364,934, filed Dec. 4, 1979, "Monoclonal antibody to a human early thymocyte antigen and methods for preparing same"; U.S. Pat. No. 8,409,573, filed Jun. 14, 2006, "Anti-CD71 monoclonal antibodies and uses thereof for treating malignant tumor cells"; U.S. Pat. No. 9,708,406, filed May 20, 2014, "Anti-transferrin receptor antibodies and methods of use"; U.S. Pat. No. 9,611,323, filed Dec. 19, 2014, "Low affinity blood brain barrier receptor antibodies and uses therefor"; WO 2015/098989, filed Dec. 24, 2014, "Novel anti-Transferrin receptor antibody that passes through blood-brain barrier"; Schneider C. et al. "Structural features of the cell surface receptor for transferrin that is recognized by the monoclonal antibody OKT9." J Biol Chem. 1982, 257:14, 8516-8522.; Lee et al. "Targeting Rat Anti-Mouse Transferrin Receptor Monoclonal Antibodies through Blood-Brain Barrier in Mouse" 2000, J Pharmacol. Exp. Ther., 292: 1048-1052.).

Any appropriate anti-transferrin receptor antibodies may be used in the complexes disclosed herein. Examples of anti-transferrin receptor antibodies, including associated references and binding epitopes, are listed in Table 2. In some embodiments, the anti-transferrin receptor antibody comprises the complementarity determining regions (CDR-H1, CDR-H2, CDR-H3, CDR-L1, CDR-L2, and CDR-L3) of any of the anti-transferrin receptor antibodies provided herein, e.g., anti-transferrin receptor antibodies listed in Table 2.

TABLE 2

List of anti-transferrin receptor antibody clones, including associated references and binding epitope information.

| Antibody Clone Name | Reference(s) | Epitope/Notes |
|---|---|---|
| OKT9 | U.S. Pat. No. 4,364,934, filed Dec. 4, 1979, entitled "MONOCLONAL ANTIBODY TO A HUMAN EARLY THYMOCYTE ANTIGEN AND METHODS FOR PREPARING SAME" Schneider C. et al. "Structural features of the cell surface receptor for transferrin that is recognized by the monoclonal antibody OKT9." J Biol Chem. 1982, 257:14, 8516-8522. | Apical domain of TfR (residues 305-366 of human TfR sequence XM_052730.3, available in GenBank) |
| (From JCR) Clone M11 Clone M23 Clone M27 Clone B84 | WO 2015/098989, filed Dec. 24, 2014, "Novel anti-Transferrin receptor antibody that passes through blood-brain barrier" U.S. Pat. No. 9,994,641, filed Dec. 24, 2014, "Novel anti-Transferrin receptor antibody that passes through blood-brain barrier" | Apical domain (residues 230-244 and 326-347 of TfR) and protease-like domain (residues 461-473) |
| (From Genentech) 7A4, 8A2, 15D2, 10D11, 7B10, 15G11, 16G5, 13C3, 16G4, 16F6, 7G7, 4C2, 1B12, and 13D4 | WO 2016/081643, filed May 26, 2016, entitled "ANTI-TRANSFERRIN RECEPTOR ANTIBODIES AND METHODS OF USE" U.S. Pat. No. 9,708,406, filed May 20, 2014, "Anti-transferrin receptor antibodies and methods of use" | Apical domain and non-apical regions |
| (From Armagen) 8D3 | Lee et al. "Targeting Rat Anti-Mouse Transferrin Receptor Monoclonal Antibodies through Blood-Brain Barrier in Mouse" 2000, J Pharmacol. Exp. Ther., 292: 1048-1052. U.S. Pat. App. 2010/077498, filed Sep. 11, 2008, entitled "COMPOSITIONS AND METHODS FOR BLOOD-BRAIN BARRIER DELIVERY IN THE MOUSE" | |
| OX26 | Haobam, B. et al. 2014. Rab17-mediated recycling endosomes contribute to autophagosome formation in response to Group A *Streptococcus* invasion. Cellular microbiology. 16: 1806-21. | |

TABLE 2-continued

List of anti-transferrin receptor antibody clones, including associated references and binding epitope information.

| Antibody Clone Name | Reference(s) | Epitope/Notes |
|---|---|---|
| DF1513 | Ortiz-Zapater E et al. Trafficking of the human transferrin receptor in plant cells: effects of tyrphostin A23 and brefeldin A. Plant J 48:757-70 (2006). | |
| 1A1B2, 66IG10, MEM-189, JF0956, 29806, 1A1B2, TFRC/1818, 1E6, 66Ig10, TFRC/1059, Q1/71, 23D10, 13E4, TFRC/1149, ER-MP21, YTA74.4, BU54, 2B6, RI7 217 | Commercially available anti-transferrin receptor antibodies. | Novus Biologicals 8100 Southpark Way, A-8 Littleton CO 80120 |
| (From INSERM) BA120g | U.S. Pat. App. 2011/0311544A1, filed Jun. 15, 2005, entitled "ANTI-CD71 MONOCLONAL ANTIBODIES AND USES THEREOF FOR TREATING MALIGNANT TUMOR CELLS" | Does not compete with OKT9 |
| LUCA31 | U.S. Pat. No. 7,572,895, filed Jun. 7, 2004, entitled "TRANSFERRIN RECEPTOR ANTIBODIES" | "LUCA31 epitope" |
| (Salk Institute) B3/25 T58/30 | Trowbridge, I.S. et al. "Anti-transferrin receptor monoclonal antibody and toxin-antibody conjugates affect growth of human tumour cells." Nature, 1981, volume 294, pages 171-173 | |
| R17 217.1.3, 5E9C11, OKT9 BE0023 clone) | Commercially available anti-transferrin receptor antibodies. | BioXcell 10 Technology Dr., Suite 2B West Lebanon, NH 03784-1671 USA |
| BK19.9, B3/25, T56/14 and T58/1 | Gatter, K.C. et al. "Transferrin receptors in human tissues: their distribution and possible clinical relevance." J Clin Pathol. 1983 May; 36(5):539-45. | |

In some embodiments, the muscle-targeting agent is an anti-transferrin receptor antibody. In some embodiment, an anti-transferrin receptor antibody specifically binds to a transferrin protein having an amino acid sequence as disclosed herein. In some embodiments, an anti-transferrin receptor antibody may specifically bind to any extracellular epitope of a transferrin receptor or an epitope that becomes exposed to an antibody, including the apical domain, the transferrin binding domain, and the protease-like domain. In some embodiments, an anti-transferrin receptor antibody binds to an amino acid segment of a human or non-human primate transferrin receptor, as provided in SEQ ID Nos. 1-3 in the range of amino acids C89 to F760. In some embodiments, an anti-transferrin receptor antibody specifically binds with binding affinity of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. Anti-transferrin receptor antibodies used herein may be capable of competing for binding with other anti-transferrin receptor antibodies, e.g. OKT9, 8D3, that bind to transferrin receptor with $10^{-3}$ M, $10^{-4}$ M, $10^{-5}$ M, $10^{-6}$ M, $10^{-7}$ M, or less.

An example human transferrin receptor amino acid sequence, corresponding to NCBI sequence NP_003225.2 (transferrin receptor protein 1 isoform 1, Homo sapiens) is as follows:

(SEQ ID NO: 1)
MMDQARSAFSNLFGGEPLSYTRFSLARQVDGDNSHVEMKLAVDEEENADN

NTKANVTKPKRCSGSICYGTIAVIVFFLIGFMIGYLGYCKGVEPKTECER

LAGTESPVREEPGEDFPAARRLYWDDLKRKLSEKLDSTDFTGTIKLLNEN

SYVPREAGSQKDENLALYVENQFREFKLSKVWRDQHFVKIQVKDSAQNSV

IIVDKNGRLVYLVENPGGYVAYSKAATVTGKLVHANFGTKKDFEDLYTPV

NGSIVIVRAGKITFAEKVANAESLNAIGVLIYMDQTKFPIVNAELSFFGH

AHLGTGDPYTPGFPSFNHTQFPPSRSSGLPNIPVQTISRAAAEKLFGNME

GDCPSDWKTDSTCRMVTSESKNVKLTVSNVLKEIKILNIFGVIKGFVEPD

HYVVVGAQRDAWGPGAAKSGVGTALLLKLAQMFSDMVLKDGFQPSRSIIF

ASWSAGDFGSVGATEWLEGYLSSLHLKAFTYINLDKAVLGTSNFKVSASP

LLYTLIEKTMQNVKHPVTGQFLYQDSNWASKVEKLTLDNAAFPFLAYSGI

PAVSFCFCEDTDYPYLGTTMDTYKELIERIPELNKVARAAAEVAGQFVIK

LTHDVELNLDYERYNSQLLSFVRDLNQYRADIKEMGLSLOWLYSARGDFF

RATSRLTTDFGNAEKTDRFVMKKLNDRVMRVEYHFLSPYVSPKESPFRHV

FWGSGSHTLPALLENLKLRKQNNGAFNETLFRNQLALATWTIQGAANALS

GDVWDIDNEF

An example non-human primate transferrin receptor amino acid sequence, corresponding to NCBI sequence NP_001244232.1 (transferrin receptor protein 1, *Macaca mulatta*) is as follows:

(SEQ ID NO: 2)
MMDQARSAFSNLFGGEPLSYTRFSLARQVDGDNSHVEMKLGVDEEENTDN

NTKPNGTKPKRCGGNICYGTIAVIIFFLIGFMIGYLGYCKGVEPKTECER

LAGTESPAREEPEEDFPAAPRLYWDDLKRKLSEKLDTTDFTSTIKLLNEN

LYVPREAGSQKDENLALYIENQFREFKLSKVWRDQHFVKIQVKDSAQNSV

IIVDKNGGLVYLVENPGGYVAYSKAATVTGKLVHANFGTKKDFEDLDSPV

NGSIVIVRAGKITFAEKVANAESLNAIGVLIYMDQTKFPIVKADLSFFGH

AHLGTGDPYTPGFPSFNHTQFPPSQSSGLPNIPVQTISRAAAEKLFGNME

GDCPSDWKTDSTCKMVTSENKSVKLTVSNVLKETKILNIFGVIKGFVEPD

HYVVVGAQRDAWGPGAAKSSVGTALLLKLAQMFSDMVLKDGFQPSRSIIF

ASWSAGDFGSVGATEWLEGYLSSLHLKAFTYINLDKAVLGTSNFKVSASP

LLYTLIEKTMQDVKHPVTGRSLYQDSNWASKVEKLTLDNAAFPFLAYSGI

PAVSFCFCEDTDYPYLGTTMDTYKELVERIPELNKVARAAAEVAGQFVIK

LTHDTELNLDYERYNSQLLLFLRDLNQYRADVKEMGLSLOWLYSARGDFF

RATSRLTTDFRNAEKRDKFVMKKLNDRVMRVEYYFLSPYVSPKESPFRHV

FWGSGSHTLSALLESLKLRRQNNSAFNETLFRNQLALATWTIQGAANALS

GDVWDIDNEF

An example non-human primate transferrin receptor amino acid sequence, corresponding to NCBI sequence XP_005545315.1 (transferrin receptor protein 1, *Macaca fascicularis*) is as follows:

(SEQ ID NO: 3)
MMDQARSAFSNLFGGEPLSYTRFSLARQVDGDNSHVEMKLGVDEEENTDN

NTKANGTKPKRCGGNICYGTIAVIIFFLIGFMIGYLGYCKGVEPKTECER

LAGTESPAREEPEEDFPAAPRLYWDDLKRKLSEKLDTTDFTSTIKLLNEN

LYVPREAGSQKDENLALYIENQFREFKLSKVWRDQHFVKIQVKDSAQNSV

IIVDKNGGLVYLVENPGGYVAYSKAATVTGKLVHANFGTKKDFEDLDSPV

NGSIVIVRAGKITFAEKVANAESLNAIGVLIYMDQTKFPIVKADLSFFGH

AHLGTGDPYTPGFPSFNHTQFPPSQSSGLPNIPVQTISRAAAEKLFGNME

GDCPSDWKTDSTCKMVTSENKSVKLTVSNVLKETKILNIFGVIKGFVEPD

HYVVVGAQRDAWGPGAAKSSVGTALLLKLAQMFSDMVLKDGFQPSRSIIF

ASWSAGDFGSVGATEWLEGYLSSLHLKAFTYINLDKAVLGTSNFKVSASP

LLYTLIEKTMQDVKHPVTGRSLYQDSNWASKVEKLTLDNAAFPFLAYSGI

PAVSFCFCEDTDYPYLGTTMDTYKELVERIPELNKVARAAAEVAGQFVIK

LTHDTELNLDYERYNSQLLLFLRDLNQYRADVKEMGLSLOWLYSARGDFF

RATSRLTTDFRNAEKRDKFVMKKLNDRVMRVEYYFLSPYVSPKESPFRHV

FWGSGSHTLSALLESLKLRRQNNSAFNETLFRNQLALATWTIQGAANALS

GDVWDIDNEF.

An example mouse transferrin receptor amino acid sequence, corresponding to NCBI sequence NP_001344227.1 (transferrin receptor protein 1, *Mus musculus*) is as follows:

(SEQ ID NO: 4)
MMDQARSAFSNLFGGEPLSYTRFSLARQVDGDNSHVEMKLAADEEENADN

NMKASVRKPKRFNGRLCFAAIALVIFFLIGFMSGYLGYCKRVEQKEECVK

LAETEETDKSETMETEDVPTSSRLYWADLKTLLSEKLNSIEFADTIKQLS

QNTYTPREAGSQKDESLAYYIENQFHEFKFSKVWRDEHYVKIQVKSSIGQ

NMVTIVQSNGNLDPVESPEGYVAFSKPTEVSGKLVHANFGTKKDFEELSY

SVNGSLVIVRAGEITFAEKVANAQSFNAIGVLIYMDKNKFPVVEADLALF

GHAHLGTGDPYTPGFPSFNHTQFPPSQSSGLPNIPVQTISRAAAEKLFGK

MEGSCPARWNIDSSCKLELSQNQNVKLIVKNVLKERRILNIFGVIKGYEE

PDRYVVVGAQRDALGAGVAAKSSVGTGLLLKLAQVFSDMISKDGFRPSRS

IIFASWTAGDFGAVGATEWLEGYLSSLHLKAFTYINLDKVVLGTSNFKVS

ASPLLYTLMGKIMQDVKHPVDGKSLYRDSNWISKVEKLSFDNAAYPFLAY

SGIPAVSFCFCEDADYPYLGTRLDTYEALTQKVPQLNOMVRTAAEVAGQL

IIKLTHDVELNLDYEMYNSKLLSFMKDLNQFKTDIRDMGLSLOWLYSARG

DYFRATSRLTTDFHNAEKTNRFVMREINDRIMKVEYHFLSPYVSPRESPF

RHIFWGSGSHTLSALVENLKLRQKNITAFNETLFRNQLALATWTIQGVAN

ALSGDIWNIDNEF

In some embodiments, an anti-transferrin receptor antibody binds to an amino acid segment of the receptor as follows: FVKIQVKDSAQNSVIIVDKNGRLVYLVENPG-GYVAYSKAATVTGKLVHANFGTKKDFE DLYTPVNG-SIVIVRAGKITFAEKVANAESLN-AIGVLIYMDQTKFPIVNAELSFFGHAHLG TGDPYTPGFPSFNHTQFPPSRSSGLPNIPVQTIS-RAAAEKLFGNMEGDCPSDWKTDSTCR MVTS-ESKNVKLTVSNVLKE (SEQ ID NO: 5) and does not inhibit the binding interactions between transferrin receptors and transferrin and/or human hemochromatosis protein (also known as HFE).

Appropriate methodologies may be used to obtain and/or produce antibodies, antibody fragments, or antigen-binding agents, e.g., through the use of recombinant DNA protocols. In some embodiments, an antibody may also be produced through the generation of hybridomas (see, e.g., Kohler, G and Milstein, C. "Continuous cultures of fused cells secreting antibody of predefined specificity" Nature, 1975, 256: 495-497). The antigen-of-interest may be used as the immunogen in any form or entity, e.g., recombinant or a naturally occurring form or entity. Hybridomas are screened using standard methods, e.g. ELISA screening, to find at least one hybridoma that produces an antibody that targets a particular antigen. Antibodies may also be produced through screening of protein expression libraries that express antibodies, e.g., phage display libraries. Phage display library design may also be used, in some embodiments, (see, e.g. U.S. Pat. No. 5,223,409, filed Mar. 1, 1991, "Directed evolution of novel binding proteins"; WO 1992/18619, filed Apr. 10, 1992, "Heterodimeric receptor libraries using phagemids"; WO 1991/17271, filed May 1, 1991, "Recombinant library screening methods"; WO 1992/20791, filed May 15, 1992, "Methods for producing members of specific binding pairs"; WO 1992/15679, filed Feb. 28, 1992, and "Improved epitope displaying phage"). In some embodiments, an antigen-of-interest may be used to immunize a non-human animal, e.g., a rodent or a goat. In some embodiments, an antibody is then obtained from the non-human animal, and may be optionally modified using a number of methodologies, e.g., using recombinant DNA techniques. Additional examples of antibody production and methodologies are known in the art (see, e.g. Harlow et al. "Antibodies: A Laboratory Manual", Cold Spring Harbor Laboratory, 1988.).

In some embodiments, an antibody is modified, e.g., modified via glycosylation, phosphorylation, sumoylation, and/or methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or phosphoglycosylation. In some embodiments, the one or more sugar or carbohydrate molecules are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, there are about 1-10, about 1-5, about 5-10, about 1-4, about 1-3, or about 2 sugar molecules. In some embodiments, a glycosylated antibody is fully or partially glycosylated. In some embodiments, an antibody is glycosylated by chemical reactions or by enzymatic means. In some embodiments, an antibody is glycosylated in vitro or inside a cell, which may optionally be deficient in an enzyme in the N- or O-glycosylation pathway, e.g. a glycosyltransferase. In some embodiments, an antibody is functionalized with sugar or carbohydrate molecules as described in International Patent Application Publication WO2014065661, published on May 1, 2014, entitled, *"Modified antibody, antibody-conjugate and process for the preparation thereof"*.

Some aspects of the disclosure provide proteins that bind to transferrin receptor (e.g., an extracellular portion of the transferrin receptor). In some embodiments, transferrin receptor antibodies provided herein bind specifically to transferrin receptor (e.g., human transferrin receptor). Transferrin receptors are internalizing cell surface receptors that transport transferrin across the cellular membrane and participate in the regulation and homeostasis of intracellular iron levels. In some embodiments, transferrin receptor antibodies provided herein bind specifically to transferrin receptor from human, non-human primates, mouse, rat, etc. In some embodiments, transferrin receptor antibodies provided herein bind to human transferrin receptor. In some embodiments, transferrin receptor antibodies provided herein specifically bind to human transferrin receptor. In some embodiments, transferrin receptor antibodies provided herein bind to an apical domain of human transferrin receptor. In some embodiments, transferrin receptor antibodies provided herein specifically bind to an apical domain of human transferrin receptor.

In some embodiments, transferrin receptor antibodies of the present disclosure include one or more of the CDR-H (e.g., CDR-H1, CDR-H2, and CDR-H3) amino acid sequences from any one of the anti-transferrin receptor antibodies selected from Table 2. In some embodiments, transferrin receptor antibodies include the CDR-H1, CDR-H2, and CDR-H3 as provided for any one of the anti-transferrin receptor antibodies selected from Table 2. In some embodiments, anti-transferrin receptor antibodies include the CDR-L1, CDR-L2, and CDR-L3 as provided for any one of the anti-transferrin receptor antibodies selected from Table 2. In some embodiments, anti-transferrin antibodies include the CDR-H1, CDR-H2, CDR-H3, CDR-L1, CDR-L2, and CDR-L3 as provided for any one of the anti-transferrin receptor antibodies selected from Table 2. The disclosure also includes any nucleic acid sequence that encodes a molecule comprising a CDR-H1, CDR-H2, CDR-H3, CDR-L1, CDR-L2, or CDR-L3 as provided for any one of the anti-transferrin receptor antibodies selected from Table 2. In some embodiments, antibody heavy and light chain CDR3 domains may play a particularly important role in the binding specificity/affinity of an antibody for an antigen. Accordingly, anti-transferrin receptor antibodies of the disclosure may include at least the heavy and/or light chain CDR3s of any one of the anti-transferrin receptor antibodies selected from Table 2.

In some examples, any of the anti-transferrin receptor antibodies of the disclosure have one or more CDR (e.g., CDR-H or CDR-L) sequences substantially similar to any of the CDR-H1, CDR-H2, CDR-H3, CDR-L1, CDR-L2, and/or CDR-L3 sequences from one of the anti-transferrin receptor antibodies selected from Table 2. In some embodiments, the position of one or more CDRs along the VH (e.g., CDR-H1, CDR-H2, or CDR-H3) and/or VL (e.g., CDR-L1, CDR-L2, or CDR-L3) region of an antibody described herein can vary by one, two, three, four, five, or six amino acid positions so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived). For example, in some embodiments, the position defining a CDR of any antibody described herein can vary by shifting the N-terminal and/or C-terminal boundary of the CDR by one, two, three, four, five, or six amino acids, relative to the CDR position of any one of the antibodies described herein, so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived). In another embodiment, the length of one or more CDRs along the VH (e.g., CDR-H1, CDR-H2, or CDR-H3) and/or VL (e.g., CDR-L1, CDR-L2, or CDR-L3) region of an antibody described herein can vary (e.g., be shorter or longer) by one, two, three, four, five, or more amino acids, so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived).

Accordingly, in some embodiments, a CDR-L1, CDR-L2, CDR-L3, CDR-H1, CDR-H2, and/or CDR-H3 described herein may be one, two, three, four, five or more amino acids shorter than one or more of the CDRs described herein (e.g., CDRS from any of the anti-transferrin receptor antibodies selected from Table 2) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, a CDR-L1, CDR-L2, CDR-L3, CDR-H1, CDR-H2, and/or CDR-H3 described herein may be one, two, three, four, five or more amino acids longer than one or more of the CDRs described herein (e.g., CDRS from any of the anti-transferrin receptor antibodies selected from Table 2) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the amino portion of a CDR-L1, CDR-L2, CDR-L3, CDR-H1, CDR-H2, and/or CDR-H3 described herein can be extended by one, two, three, four, five or more amino acids compared to one or more of the CDRs described herein (e.g., CDRS from any of the anti-transferrin receptor antibodies selected from Table 2) so long as immunospecific binding to transferrin receptor (e.g., human transferrin receptor is maintained (e.g., substantially maintained, for example, at least 50%, at least 60%, at least 70%, at least 80%, at least 90%, at least 95% relative to the binding of the original antibody from which it is derived). In some embodiments, the carboxy portion of a CDR-L1, CDR-L2, CDR-L3, CDR-H1, CDR-H2, and/or CDR-H3 described herein can be extended by one, two, three, four, five or more amino acids compared to one or more of the CDRs described herein (e.g., CDRS from any of the anti-transferrin receptor antibodies selected from Table 2) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the amino portion of a CDR-L1, CDR-L2, CDR-L3, CDR-H1, CDR-H2, and/or CDR-H3 described herein can be shortened by one, two, three, four, five or more amino acids compared to one or more of the CDRs described herein (e.g., CDRS from any of the anti-transferrin receptor antibodies selected from Table 2) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the carboxy portion of a CDR-L1, CDR-L2, CDR-L3, CDR-H1, CDR-H2, and/or CDR-H3 described herein can be shortened by one, two, three, four, five or more amino acids compared to one or more of the CDRs described herein (e.g., CDRS from any of the anti-transferrin receptor antibodies selected from Table 2) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). Any method can be used to ascertain whether immunospecific binding to transferrin receptor (e.g., human transferrin receptor) is maintained, for example, using binding assays and conditions described in the art.

In some examples, any of the anti-transferrin receptor antibodies of the disclosure have one or more CDR (e.g., CDR-H or CDR-L) sequences substantially similar to any one of the anti-transferrin receptor antibodies selected from Table 2. For example, the antibodies may include one or more CDR sequence(s) from any of the anti-transferrin receptor antibodies selected from Table 2 containing up to 5, 4, 3, 2, or 1 amino acid residue variations as compared to the corresponding CDR region in any one of the CDRs provided herein (e.g., CDRs from any of the anti-transferrin receptor antibodies selected from Table 2) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, any of the amino acid variations in any of the CDRs provided herein may be conservative variations. Conservative variations can be introduced into the CDRs at positions where the residues are not likely to be involved in interacting with a transferrin receptor protein (e.g., a human transferrin receptor protein), for example, as determined based on a crystal structure. Some aspects of the disclosure provide transferrin receptor antibodies that comprise one or more of the heavy chain variable (VH) and/or light chain variable (VL) domains provided herein. In some embodiments, any of the VH domains provided herein include one or more of the CDR-H sequences (e.g., CDR-H1, CDR-H2, and CDR-H3) provided herein, for example, any of the CDR-H sequences provided in any one of the anti-transferrin receptor antibodies selected from Table 2. In some embodiments, any of the VL domains provided herein include one or more of the CDR-L sequences (e.g., CDR-L1, CDR-L2, and CDR-L3) provided herein, for example, any of the CDR-L sequences provided in any one of the anti-transferrin receptor antibodies selected from Table 2.

In some embodiments, anti-transferrin receptor antibodies of the disclosure include any antibody that includes a heavy chain variable domain and/or a light chain variable domain of any anti-transferrin receptor antibody, such as any one of the anti-transferrin receptor antibodies selected from Table 2. In some embodiments, anti-transferrin receptor antibodies of the disclosure include any antibody that includes the heavy chain variable and light chain variable pairs of any anti-transferrin receptor antibody, such as any one of the anti-transferrin receptor antibodies selected from Table 2.

Aspects of the disclosure provide anti-transferrin receptor antibodies having a heavy chain variable (VH) and/or a light chain variable (VL) domain amino acid sequence homologous to any of those described herein. In some embodiments, the anti-transferrin receptor antibody comprises a heavy chain variable sequence or a light chain variable sequence that is at least 75% (e.g., 80%, 85%, 90%, 95%, 98%, or 99%) identical to the heavy chain variable sequence and/or any light chain variable sequence of any anti-transferrin receptor antibody, such as any one of the anti-transferrin receptor antibodies selected from Table 2. In some embodiments, the homologous heavy chain variable and/or a light chain variable amino acid sequences do not vary within any of the CDR sequences provided herein. For example, in some embodiments, the degree of sequence variation (e.g., 75%, 80%, 85%, 90%, 95%, 98%, or 99%) may occur within a heavy chain variable and/or a light chain variable sequence excluding any of the CDR sequences provided herein. In some embodiments, any of the anti-transferrin receptor antibodies provided herein comprise a heavy chain variable sequence and a light chain variable sequence that comprises a framework sequence that is at least 75%, 80%, 85%, 90%, 95%, 98%, or 99% identical to the framework sequence of any anti-transferrin receptor antibody, such as any one of the anti-transferrin receptor antibodies selected from Table 2.

In some embodiments, an anti-transferrin receptor antibody, which specifically binds to transferrin receptor (e.g., human transferrin receptor), comprises a light chain variable VL domain comprising any of the CDR-L domains (CDR-L1, CDR-L2, and CDR-L3), or CDR-L domain variants provided herein, of any of the anti-transferrin receptor antibodies selected from Table 2. In some embodiments, an anti-transferrin receptor antibody, which specifically binds to transferrin receptor (e.g., human transferrin receptor), comprises a light chain variable VL domain comprising the CDR-L1, the CDR-L2, and the CDR-L3 of any anti-transferrin receptor antibody, such as any one of the anti-transferrin receptor antibodies selected from Table 2. In some embodiments, the anti-transferrin receptor antibody comprises a light chain variable (VL) region sequence comprising one, two, three or four of the framework regions of the light chain variable region sequence of any anti-transferrin receptor antibody, such as any one of the anti-transferrin receptor antibodies selected from Table 2. In some embodiments, the anti-transferrin receptor antibody comprises one, two, three or four of the framework regions of a light chain variable region sequence which is at least 75%, 80%, 85%, 90%, 95%, or 100% identical to one, two, three or four of the framework regions of the light chain variable region sequence of any anti-transferrin receptor antibody, such as any one of the anti-transferrin receptor antibodies selected from Table 2. In some embodiments, the light chain variable framework region that is derived from said amino acid sequence consists of said amino acid sequence but for the presence of up to 10 amino acid substitutions, deletions, and/or insertions, preferably up to 10 amino acid substitutions. In some embodiments, the light chain variable framework region that is derived from said amino acid sequence consists of said amino acid sequence with 1, 2, 3, 4, 5, 6, 7, 8, 9 or 10 amino acid residues being substituted for an amino acid found in an analogous position in a corresponding non-human, primate, or human light chain variable framework region.

In some embodiments, an anti-transferrin receptor antibody that specifically binds to transferrin receptor comprises the CDR-L1, the CDR-L2, and the CDR-L3 of any anti-transferrin receptor antibody, such as any one of the anti-transferrin receptor antibodies selected from Table 2. In some embodiments, the antibody further comprises one, two, three or all four VL framework regions derived from the VL of a human or primate antibody. The primate or human light chain framework region of the antibody selected for use with the light chain CDR sequences described herein, can have, for example, at least 70% (e.g., at least 75%, 80%, 85%, 90%, 95%, 98%, or at least 99%) identity with a light chain framework region of a non-human parent antibody. The primate or human antibody selected can have the same or substantially the same number of amino acids in its light chain complementarity determining regions to that of the light chain complementarity determining regions of any of the antibodies provided herein, e.g., any of the anti-transferrin receptor antibodies selected from Table 2. In some embodiments, the primate or human light chain framework region amino acid residues are from a natural primate or human antibody light chain framework region having at least 75% identity, at least 80% identity, at least 85% identity, at least 90% identity, at least 95% identity, at least 98% identity, at least 99% (or more) identity with the light chain framework regions of any anti-transferrin receptor antibody, such as any one of the anti-transferrin receptor antibodies selected from Table 2. In some embodiments, an anti-transferrin receptor antibody further comprises one, two, three or all four VL framework regions derived from a human light chain variable kappa subfamily. In some embodiments, an anti-transferrin receptor antibody further comprises one, two, three or all four VL framework regions derived from a human light chain variable lambda subfamily.

In some embodiments, any of the anti-transferrin receptor antibodies provided herein comprise a light chain variable domain that further comprises a light chain constant region. In some embodiments, the light chain constant region is a kappa, or a lambda light chain constant region. In some embodiments, the kappa or lambda light chain constant region is from a mammal, e.g., from a human, monkey, rat, or mouse. In some embodiments, the light chain constant region is a human kappa light chain constant region. In some embodiments, the light chain constant region is a human lambda light chain constant region. It should be appreciated that any of the light chain constant regions provided herein may be variants of any of the light chain constant regions provided herein. In some embodiments, the light chain constant region comprises an amino acid sequence that is at least 75%, 80%, 85%, 90%, 95%, 98%, or 99% identical to any of the light chain constant regions of any anti-transferrin receptor antibody, such as any one of the anti-transferrin receptor antibodies selected from Table 2.

In some embodiments, the anti-transferrin receptor antibody is any anti-transferrin receptor antibody, such as any one of the anti-transferrin receptor antibodies selected from Table 2.

In some embodiments, an anti-transferrin receptor antibody comprises a VL domain comprising the amino acid sequence of any anti-transferrin receptor antibody, such as any one of the anti-transferrin receptor antibodies selected from Table 2, and wherein the constant regions comprise the amino acid sequences of the constant regions of an IgG, IgE, IgM, IgD, IgA or IgY immunoglobulin molecule, or a human IgG, IgE, IgM, IgD, IgA or IgY immunoglobulin molecule. In some embodiments, an anti-transferrin receptor antibody comprises any of the VL domains, or VL domain variants, and any of the VH domains, or VH domain variants, wherein the VL and VH domains, or variants thereof, are from the same antibody clone, and wherein the constant regions comprise the amino acid sequences of the constant regions of an IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule. Non-limiting examples of human constant regions are described in the art, e.g., see Kabat E A et al., (1991) supra.

In some embodiments, an antibody of the disclosure can bind to a target antigen (e.g., transferrin receptor) with relatively high affinity, e.g., with a $K_D$ less than $10^{-6}$ M, $10^{-7}$ M, $10^{-8}$ M, $10^{-9}$ M, $10^{-10}$ M, $10^{-11}$ M or lower. For example, anti-transferrin receptor antibodies can bind to a transferrin receptor protein (e.g., human transferrin receptor) with an affinity between 5 pM and 500 nM, e.g., between 50 pM and 100 nM, e.g., between 500 pM and 50 nM. The disclosure also includes antibodies that compete with any of the antibodies described herein for binding to a transferrin receptor protein (e.g., human transferrin receptor) and that have an affinity of 50 nM or lower (e.g., 20 nM or lower, 10 nM or lower, 500 pM or lower, 50 pM or lower, or 5 pM or lower). The affinity and binding kinetics of the anti-transferrin receptor antibody can be tested using any suitable method including but not limited to biosensor technology (e.g., OCTET® or BIACORE®).

In some embodiments, an antibody of the disclosure can bind to a target antigen (e.g., transferrin receptor) with relatively high affinity, e.g., with a $K_D$ less than $10^{-6}$ M, $10^{-7}$ M, $10^{-8}$ M, $10^{-9}$ M, $10^{-10}$ M, $10^{-11}$ M or lower. For example, anti-transferrin receptor antibodies can bind to a transferrin receptor protein (e.g., human transferrin receptor) with an affinity between 5 pM and 500 nM, e.g., between 50 pM and 100 nM, e.g., between 500 pM and 50 nM. The disclosure also includes antibodies that compete with any of the antibodies described herein for binding to a transferrin receptor protein (e.g., human transferrin receptor) and that have an affinity of 50 nM or lower (e.g., 20 nM or lower, 10 nM or lower, 500 pM or lower, 50 pM or lower, or 5 pM or lower). The affinity and binding kinetics of the anti-transferrin receptor antibody can be tested using any suitable method including but not limited to biosensor technology (e.g., OCTET® or BIACORE®).

In some embodiments, the muscle-targeting agent is a transferrin receptor antibody (e.g., the antibody and variants thereof as described in International Application Publication WO 2016/081643, incorporated herein by reference).

The heavy chain and light chain CDRs of the antibody according to different definition systems are provided in Table 1.1. The different definition systems, e.g., the Kabat definition, the Chothia definition, and/or the contact definition have been described. See, e.g., (e.g., Kabat, E. A., et al. (1991) Sequences of Proteins of Immunological Interest, Fifth Edition, U.S. Department of Health and Human Services, NIH Publication No. 91-3242, Chothia et al., (1989) Nature 342:877; Chothia, C. et al. (1987) J. Mol. Biol. 196:901-917, Al-lazikani et al (1997) J. Molec. Biol. 273: 927-948; and Almagro, J. Mol. Recognit. 17:132-143 (2004). See also hgmp.mrc.ac.uk and bioinf.org.uk/abs).

TABLE 1.1

Heavy chain and light chain CDRs of a transferrin receptor antibody

| CDRs | Kabat | Chothia | Contact |
|---|---|---|---|
| CDR-H1 | SYWMH (SEQ ID NO: 17) | GYTFTSY (SEQ ID NO: 23) | TSYWMH (SEQ ID NO: 25) |
| CDR-H2 | EINPTNGRTNY IEKFKS (SEQ ID NO: 18) | NPTNGR (SEQ ID NO: 24) | WIGEINPTNGRTN (SEQ ID NO: 26) |
| CDR-H3 | GTRAYHY (SEQ ID NO: 19) | GTRAYHY (SEQ ID NO: 19) | ARGTRA (SEQ ID NO: 27) |
| CDR-L1 | RASDNLYSNLA (SEQ ID NO: 20) | RASDNLYSNLA (SEQ ID NO: 20) | YSNLAWY (SEQ ID NO: 28) |
| CDR-L2 | DATNLAD (SEQ ID NO: 21) | DATNLAD (SEQ ID NO: 21) | LLVYDATNLA (SEQ ID NO: 29) |
| CDR-L3 | QHFWGTPLT (SEQ ID NO: 22) | QHFWGTPLT (SEQ ID NO: 22) | QHFWGTPL (SEQ ID NO: 30) |

The heavy chain variable domain (VH) and light chain variable domain sequences are also provided:

VH
(SEQ ID NO: 33)
QVQLQQPGAELVKPGASVKLSCKASGYTFTSYWMHWVKQRPGQGLEWIGE
INPTNGRTNYIEKFKSKATLTVDKSSSTAYMQLSSLTSEDSAVYYCARGT
RAYHYWGQGTSVTVSS

VL
(SEQ ID NO: 34)
DIQMTQSPASLSVSVGETVTITCRASDNLYSNLAWYQQKQGKSPQLLVYD
ATNLADGVPSRFSGSGSGTQYSLKINSLQSEDFGTYYCQHFWGTPLTFGA
GTKLELK

In some embodiments, the transferrin receptor antibody of the present disclosure comprises a CDR-H1, a CDR-H2, and a CDR-H3 that are the same as the CDR-H1, CDR-H2, and CDR-H3 shown in Table 1.1. Alternatively or in addition, the transferrin receptor antibody of the present disclosure comprises a CDR-L1, a CDR-L2, and a CDR-L3 that are the same as the CDR-L1, CDR-L2, and CDR-L3 shown in Table 1.1.

In some embodiments, the transferrin receptor antibody of the present disclosure comprises a CDR-H1, a CDR-H2, and a CDR-H3, which collectively contains no more than 5 amino acid variations (e.g., no more than 5, 4, 3, 2, or 1 amino acid variation) as compared with the CDR-H1, CDR-H2, and CDR-H3 as shown in Table 1.1. "Collectively" means that the total number of amino acid variations in all of the three heavy chain CDRs is within the defined range. Alternatively or in addition, the transferrin receptor antibody of the present disclosure may comprise a CDR-L1, a CDR-L2, and a CDR-L3, which collectively contains no more than 5 amino acid variations (e.g., no more than 5, 4, 3, 2 or 1 amino acid variation) as compared with the CDR-L1, CDR-L2, and CDR-L3 as shown in Table 1.1.

In some embodiments, the transferrin receptor antibody of the present disclosure comprises a CDR-H1, a CDR-H2, and a CDR-H3, at least one of which contains no more than 3 amino acid variations (e.g., no more than 3, 2, or 1 amino acid variation) as compared with the counterpart heavy chain CDR as shown in Table 1.1. Alternatively or in addition, the transferrin receptor antibody of the present disclosure may comprise CDR-L1, a CDR-L2, and a CDR-L3, at least one of which contains no more than 3 amino acid variations (e.g., no more than 3, 2, or 1 amino acid variation) as compared with the counterpart light chain CDR as shown in Table 1.1.

In some embodiments, the transferrin receptor antibody of the present disclosure comprises a CDR-L3, which contains no more than 3 amino acid variations (e.g., no more than 3, 2, or 1 amino acid variation) as compared with the CDR-L3 as shown in Table 1.1. In some embodiments, the transferrin receptor antibody of the present disclosure comprises a CDR-L3 containing one amino acid variation as compared with the CDR-L3 as shown in Table 1.1. In some embodiments, the transferrin receptor antibody of the present disclosure comprises a CDR-L3 of QHFAGTPLT (SEQ ID NO: 31 according to the Kabat and Chothia definition system) or QHFAGTPL (SEQ ID NO: 32 according to the Contact definition system). In some embodiments, the transferrin receptor antibody of the present disclosure comprises a CDR-H1, a CDR-H2, a CDR-H3, a CDR-L1 and a CDR-L2 that are the same as the CDR-H1, CDR-H2, and CDR-H3 shown in Table 1.1, and comprises a CDR-L3 of QHFAGTPLT (SEQ ID NO: 31 according to the Kabat and Chothia definition system) or QHFAGTPL (SEQ ID NO: 32 according to the Contact definition system).

In some embodiments, the transferrin receptor antibody of the present disclosure comprises heavy chain CDRs that collectively are at least 80% (e.g., 80%, 85%, 90%, 95%, or 98%) identical to the heavy chain CDRs as shown in Table 1.1. Alternatively or in addition, the transferrin receptor antibody of the present disclosure comprises light chain CDRs that collectively are at least 80% (e.g., 80%, 85%, 90%, 95%, or 98%) identical to the light chain CDRs as shown in Table 1.1.

In some embodiments, the transferrin receptor antibody of the present disclosure comprises a VH comprising the amino acid sequence of SEQ ID NO: 33. Alternatively or in addition, the transferrin receptor antibody of the present disclosure comprises a VL comprising the amino acid sequence of SEQ ID NO: 34.

In some embodiments, the transferrin receptor antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 33. Alternatively or in addition, the transferrin receptor antibody of the present disclosure comprises a VL containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 34.

In some embodiments, the transferrin receptor antibody of the present disclosure comprises a VH comprising an amino acid sequence that is at least 80% (e.g., 80%, 85%, 90%, 95%, or 98%) identical to the VH as set forth in SEQ ID NO: 33. Alternatively or in addition, the transferrin receptor antibody of the present disclosure comprises a VL comprising an amino acid sequence that is at least 80% (e.g., 80%, 85%, 90%, 95%, or 98%) identical to the VL as set forth in SEQ ID NO: 34.

In some embodiments, the transferrin receptor antibody of the present disclosure is a humanized antibody (e.g., a humanized variant of an antibody). In some embodiments, the transferrin receptor antibody of the present disclosure comprises a CDR-H1, a CDR-H2, a CDR-H3, a CDR-L1, a CDR-L2, and a CDR-L3 that are the same as the CDR-H1, CDR-H2, and CDR-H3 shown in Table 1.1, and comprises a humanized heavy chain variable region and/or a humanized light chain variable region.

Humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some embodiments, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs derived from one or more CDRs from the original antibody. Humanized antibodies may also involve affinity maturation.

In some embodiments, humanization is achieved by grafting the CDRs (e.g., as shown in Table 1.1) into the IGKV1-NL1*01 and IGHV1-3*01 human variable domains. In some embodiments, the transferrin receptor antibody of the present disclosure is a humanized variant comprising one or more amino acid substitutions at positions 9, 13, 17, 18, 40, 45, and 70 as compared with the VL as set forth in SEQ ID NO: 34, and/or one or more amino acid substitutions at positions 1, 5, 7, 11, 12, 20, 38, 40, 44, 66, 75, 81, 83, 87, and 108 as compared with the VH as set forth in SEQ ID NO: 33. In some embodiments, the transferrin receptor antibody of the present disclosure is a humanized variant comprising amino acid substitutions at all of positions 9, 13, 17, 18, 40, 45, and 70 as compared with the VL as set forth in SEQ ID NO: 34, and/or amino acid substitutions at all of positions 1, 5, 7, 11, 12, 20, 38, 40, 44, 66, 75, 81, 83, 87, and 108 as compared with the VH as set forth in SEQ ID NO: 33.

In some embodiments, the transferrin receptor antibody of the present disclosure is a humanized antibody and contains the residues at positions 43 and 48 of the VL as set forth in SEQ ID NO: 34. Alternatively or in addition, the transferrin receptor antibody of the present disclosure is a humanized antibody and contains the residues at positions 48, 67, 69, 71, and 73 of the VH as set forth in SEQ ID NO: 33.

The VH and VL amino acid sequences of an example humanized antibody that may be used in accordance with the present disclosure are provided:

Humanized VH
(SEQ ID NO: 35)
EVQLVQSGAEVKKPGASVKVSCKASGYTFTSYWMHWVRQAPGQRLEWIGE
INPTNGRTNYIEKFKSRATLTVDKSASTAYMELSSLRSEDTAVYYCARGT
RAYHYWGQGTMVTVSS Humanized VL
(SEQ ID NO: 36)
DIQMTQSPSSLSASVGDRVTITCRASDNLYSNLAWYQQKPGKSPKLLVYD
ATNLADGVPSRFSGSGSGTDYSLKINSLQSEDFGTYYCQHFWGTPLTFGA
GTKLELK In some embodiments, the transferrin receptor antibody of the present disclosure comprises a VH comprising the amino acid sequence of SEQ ID NO: 35. Alternatively or in addition, the transferrin receptor antibody of the present disclosure comprises a VL comprising the amino acid sequence of SEQ ID NO: 36.

In some embodiments, the transferrin receptor antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 35. Alternatively or in addition, the transferrin receptor antibody of the present disclosure comprises a VL containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 36.

In some embodiments, the transferrin receptor antibody of the present disclosure comprises a VH comprising an amino acid sequence that is at least 80% (e.g., 80%, 85%, 90%, 95%, or 98%) identical to the VH as set forth in SEQ ID NO:

35. Alternatively or in addition, the transferrin receptor antibody of the present disclosure comprises a VL comprising an amino acid sequence that is at least 80% (e.g., 80%, 85%, 90%, 95%, or 98%) identical to the VL as set forth in SEQ ID NO: 36.

In some embodiments, the transferrin receptor antibody of the present disclosure is a humanized variant comprising amino acid substitutions at one or more of positions 43 and 48 as compared with the VL as set forth in SEQ ID NO: 34, and/or amino acid substitutions at one or more of positions 48, 67, 69, 71, and 73 as compared with the VH as set forth in SEQ ID NO: 33. In some embodiments, the transferrin receptor antibody of the present disclosure is a humanized variant comprising a S43A and/or a V48L mutation as compared with the VL as set forth in SEQ ID NO: 34, and/or one or more of A67V, L69I, V71R, and K73T mutations as compared with the VH as set forth in SEQ ID NO: 33

In some embodiments, the transferrin receptor antibody of the present disclosure is a humanized variant comprising amino acid substitutions at one or more of positions 9, 13, 17, 18, 40, 43, 48, 45, and 70 as compared with the VL as set forth in SEQ ID NO: 34, and/or amino acid substitutions at one or more of positions 1, 5, 7, 11, 12, 20, 38, 40, 44, 48, 66, 67, 69, 71, 73, 75, 81, 83, 87, and 108 as compared with the VH as set forth in SEQ ID NO: 33.

In some embodiments, the transferrin receptor antibody of the present disclosure is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the transferrin receptor antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the heavy chain of any of the transferrin receptor antibodies as described herein may comprises a heavy chain constant region (CH) or a portion thereof (e.g., CH1, CH2, CH3, or a combination thereof). The heavy chain constant region can of any suitable origin, e.g., human, mouse, rat, or rabbit. In one specific example, the heavy chain constant region is from a human IgG (a gamma heavy chain), e.g., IgG1, IgG2, or IgG4. An exemplary human IgG1 constant region is given below:

```
                                            (SEQ ID NO: 37)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

In some embodiments, the light chain of any of the transferrin receptor antibodies described herein may further comprise a light chain constant region (CL), which can be any CL known in the art. In some examples, the CL is a kappa light chain. In other examples, the CL is a lambda light chain. In some embodiments, the CL is a kappa light chain, the sequence of which is provided below:

```
                                            (SEQ ID NO: 38)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCP
```

Other antibody heavy and light chain constant regions are well known in the art, e.g., those provided in the IMGT database (imgt.org) or at vbase2.org/vbstat.php., both of which are incorporated by reference herein.

Exemplary heavy chain and light chain amino acid sequences of the transferrin receptor antibodies described are provided below:

```
Heavy Chain (VH + human IgG1 constant region)
                                            (SEQ ID NO: 39)
QVQLQQPGAELVKPGASVKLSCKASGYTFTSYWMHWVKQRPGQGLEWIGE
INPTNGRTNYIEKFKSKATLTVDKSSSTAYMQLSSLTSEDSAVYYCARGT
RAYHYWGQGTSVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK Light Chain (VL + kappa light chain)
                                            (SEQ ID NO: 40)
QVQLQQPGAELVKPGASVKLSCKASGYTFTSYWMHWVKQRPGQGLEWIGE
INPTNGRTNYIEKFKSKATLTVDKSSSTAYMQLSSLTSEDSAVYYCARGT
RAYHYWGQGTSVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCP Heavy Chain (humanized VH + human IgG1 constant
region)
                                            (SEQ ID NO: 41)
EVQLVQSGAEVKKPGASVKVSCKASGYTFTSYWMHWVRQAPGQRLEWIGE
INPTNGRTNYIEKFKSRATLTVDKSASTAYMELSSLRSEDTAVYYCARGT
RAYHYWGQGTMVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK Light Chain (humanized VL + kappa light chain)
                                            (SEQ ID NO: 42)
DIQMTQSPSSLSASVGDRVTITCRASDNLYSNLAWYQQKPGKSPKLLVYD
ATNLADGVPSRFSGSGSGTDYSLKINSLQSEDFGTYYCQHFWGTPLTFGA
```

-continued
GTKLELKASTKGPSVFPLAPSSKSTSGGTAALGCLVKDYFPEPVTVSWNS
GALTSGVHTFPAVLQSSGLYSLSSVVTVPSSSLGTQTYICNVNHKPSNTK
VDKKVEPKSCDKTHTCP In some embodiments, the transferrin receptor antibody described herein comprises a heavy chain comprising an amino acid sequence that is at least 80% (e.g., 80%, 85%, 90%, 95%, or 98%) identical to SEQ ID NO: 39. Alternatively or in addition, the transferrin receptor antibody described herein comprises a light chain comprising an amino acid sequence that is at least 80% (e.g., 80%, 85%, 90%, 95%, or 98%) identical to SEQ ID NO: 40. In some embodiments, the transferrin receptor antibody described herein comprises a heavy chain comprising the amino acid sequence of SEQ ID NO: 39. Alternatively or in addition, the transferrin receptor antibody described herein comprises a light chain comprising the amino acid sequence of SEQ ID NO: 40.

In some embodiments, the transferrin receptor antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in SEQ ID NO: 39. Alternatively or in addition, the transferrin receptor antibody of the present disclosure comprises a light chain containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in SEQ ID NO: 40.

In some embodiments, the transferrin receptor antibody described herein comprises a heavy chain comprising an amino acid sequence that is at least 80% (e.g., 80%, 85%, 90%, 95%, or 98%) identical to SEQ ID NO: 41. Alternatively or in addition, the transferrin receptor antibody described herein comprises a light chain comprising an amino acid sequence that is at least 80% (e.g., 80%, 85%, 90%, 95%, or 98%) identical to SEQ ID NO: 42. In some embodiments, the transferrin receptor antibody described herein comprises a heavy chain comprising the amino acid sequence of SEQ ID NO: 41. Alternatively or in addition, the transferrin receptor antibody described herein comprises a light chain comprising the amino acid sequence of SEQ ID NO: 42.

In some embodiments, the transferrin receptor antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain of humanized antibody as set forth in SEQ ID NO: 39. Alternatively or in addition, the transferrin receptor antibody of the present disclosure comprises a light chain containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the light chain of humanized antibody as set forth in SEQ ID NO: 40.

In some embodiments, the transferrin receptor antibody is an antigen binding fragment (FAB) of an intact antibody (full-length antibody). Antigen binding fragment of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments. Exemplary FABs amino acid sequences of the transferrin receptor antibodies described herein are provided below:

Heavy Chain FAB (VH + a portion of human IgG1 constant region)
(SEQ ID NO: 43)
QVQLQQPGAELVKPGASVKLSCKASGYTFTSYWMHWVKQRPGQGLEWIGE
INPTNGRTNYIEKFKSKATLTVDKSSSTAYMQLSSLTSEDSAVYYCARGT
RAYHYWGQGTSVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCP Heavy Chain FAB (humanized VH + a portion of human IgG1 constant region)
(SEQ ID NO: 44)
EVQLVQSGAEVKKPGASVKVSCKASGYTFTSYWMHWVRQAPGQRLEWIGE
INPTNGRTNYIEKFKSRATLTVDKSASTAYMELSSLRSEDTAVYYCARGT
RAYHYWGQGTMVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCP The transferrin receptor antibodies described herein can be in any antibody form, including, but not limited to, intact (i.e., full-length) antibodies, antigen-binding fragments thereof (such as Fab, Fab', F(ab')2, Fv), single chain antibodies, bi-specific antibodies, or nanobodies. In some embodiments, the transferrin receptor antibody described herein is a scFv. In some embodiments, the transferrin receptor antibody described herein is a scFv-Fab (e.g., scFv fused to a portion of a constant region). In some embodiments, the transferrin receptor antibody described herein is a scFv fused to a constant region (e.g., human IgG1 constant region as set forth in SEQ ID NO: 39).

b. Other Muscle-Targeting Antibodies

In some embodiments, the muscle-targeting antibody is an antibody that specifically binds hemojuvelin, caveolin-3, Duchenne muscular dystrophy peptide, myosin Jib or CD63. In some embodiments, the muscle-targeting antibody is an antibody that specifically binds a myogenic precursor protein. Exemplary myogenic precursor proteins include, without limitation, ABCG2, M-Cadherin/Cadherin-15, Caveolin-1, CD34, FoxK1, Integrin alpha 7, Integrin alpha 7 beta 1, MYF-5, MyoD, Myogenin, NCAM-1/CD56, Pax3, Pax7, and Pax9. In some embodiments, the muscle-targeting antibody is an antibody that specifically binds a skeletal muscle protein. Exemplary skeletal muscle proteins include, without limitation, alpha-Sarcoglycan, beta-Sarcoglycan, Calpain Inhibitors, Creatine Kinase MM/CKMM, eIF5A, Enolase 2/Neuron-specific Enolase, epsilon-Sarcoglycan, FABP3/H-FABP, GDF-8/Myostatin, GDF-11/GDF-8, Integrin alpha 7, Integrin alpha 7 beta 1, Integrin beta 1/CD29, MCAM/CD146, MyoD, Myogenin, Myosin Light Chain Kinase Inhibitors, NCAM-1/CD56, and Troponin I. In some embodiments, the muscle-targeting antibody is an antibody that specifically binds a smooth muscle protein. Exemplary smooth muscle proteins include, without limitation, alpha-Smooth Muscle Actin, VE-Cadherin, Caldesmon/CALD1, Calponin 1, Desmin, Histamine H2 R, Motilin R/GPR38, Transgelin/TAGLN, and Vimentin. However, it should be appreciated that antibodies to additional targets are within the scope of this disclosure and the exemplary lists of targets provided herein are not meant to be limiting.

c. Antibody Features/Alterations

In some embodiments, conservative mutations can be introduced into antibody sequences (e.g., CDRs or framework sequences) at positions where the residues are not likely to be involved in interacting with a target antigen (e.g., transferrin receptor), for example, as determined based on a crystal structure. In some embodiments, one, two or more mutations (e.g., amino acid substitutions) are introduced into the Fc region of a muscle-targeting antibody described herein (e.g., in a CH2 domain (residues 231-340 of human IgG1) and/or CH3 domain (residues 341-447 of human IgG1) and/or the hinge region, with numbering according to the Kabat numbering system (e.g., the EU index in Kabat)) to alter one or more functional properties of the antibody, such as serum half-life, complement fixation, Fc receptor binding and/or antigen-dependent cellular cytotoxicity.

In some embodiments, one, two or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain can be altered to, e.g., facilitate assembly of the light and heavy chains, or to alter (e.g., increase or decrease) the stability of the antibody or to facilitate linker conjugation.

In some embodiments, one, two or more mutations (e.g., amino acid substitutions) are introduced into the Fc region of a muscle-targeting antibody described herein (e.g., in a CH2 domain (residues 231-340 of human IgG1) and/or CH3 domain (residues 341-447 of human IgG1) and/or the hinge region, with numbering according to the Kabat numbering system (e.g., the EU index in Kabat)) to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745 for examples of mutations that will alter (e.g., decrease or increase) the half-life of an antibody in vivo.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to decrease the half-life of the anti-transferrin receptor antibody in vivo. In some embodiments, one, two or more amino acid mutations (i.e., substitutions, insertions or deletions) are introduced into an IgG constant domain, or FcRn-binding fragment thereof (preferably an Fc or hinge-Fc domain fragment) to increase the half-life of the antibody in vivo. In some embodiments, the antibodies can have one or more amino acid mutations (e.g., substitutions) in the second constant (CH2) domain (residues 231-340 of human IgG1) and/or the third constant (CH3) domain (residues 341-447 of human IgG1), with numbering according to the EU index in Kabat (Kabat E A et al., (1991) supra). In some embodiments, the constant region of the IgG1 of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU index as in Kabat. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In some embodiments, an antibody comprises an IgG constant domain comprising one, two, three or more amino acid substitutions of amino acid residues at positions 251-257, 285-290, 308-314, 385-389, and 428-436, numbered according to the EU index as in Kabat.

In some embodiments, one, two or more amino acid substitutions are introduced into an IgG constant domain Fc region to alter the effector function(s) of the anti-transferrin receptor antibody. The effector ligand to which affinity is altered can be, for example, an Fc receptor or the C1 component of complement. This approach is described in further detail in U.S. Pat. Nos. 5,624,821 and 5,648,260. In some embodiments, the deletion or inactivation (through point mutations or other means) of a constant region domain can reduce Fc receptor binding of the circulating antibody thereby increasing tumor localization. See, e.g., U.S. Pat. Nos. 5,585,097 and 8,591,886 for a description of mutations that delete or inactivate the constant domain and thereby increase tumor localization. In some embodiments, one or more amino acid substitutions may be introduced into the Fc region of an antibody described herein to remove potential glycosylation sites on Fc region, which may reduce Fc receptor binding (see, e.g., Shields R L et al., (2001) J Biol Chem 276: 6591-604).

In some embodiments, one or more amino in the constant region of a muscle-targeting antibody described herein can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al). In some embodiments, one or more amino acid residues in the N-terminal region of the CH2 domain of an antibody described herein are altered to thereby alter the ability of the antibody to fix complement. This approach is described further in International Publication No. WO 94/29351. In some embodiments, the Fc region of an antibody described herein is modified to increase the ability of the antibody to mediate antibody dependent cellular cytotoxicity (ADCC) and/or to increase the affinity of the antibody for an Fc7 receptor. This approach is described further in International Publication No. WO 00/42072.

In some embodiments, the heavy and/or light chain variable domain(s) sequence(s) of the antibodies provided herein can be used to generate, for example, CDR-grafted, chimeric, humanized, or composite human antibodies or antigen-binding fragments, as described elsewhere herein. As understood by one of ordinary skill in the art, any variant, CDR-grafted, chimeric, humanized, or composite antibodies derived from any of the antibodies provided herein may be useful in the compositions and methods described herein and will maintain the ability to specifically bind transferrin receptor, such that the variant, CDR-grafted, chimeric, humanized, or composite antibody has at least 50%, at least 60%, at least 70%, at least 80%, at least 90%, at least 95% or more binding to transferrin receptor relative to the original antibody from which it is derived.

In some embodiments, the antibodies provided herein comprise mutations that confer desirable properties to the antibodies. For example, to avoid potential complications due to Fab-arm exchange, which is known to occur with native IgG4 mAbs, the antibodies provided herein may comprise a stabilizing 'Adair' mutation (Angal S., et al., "A single amino acid substitution abolishes the heterogeneity of chimeric mouse/human (IgG4) antibody," Mol Immunol 30, 105-108; 1993), where serine 228 (EU numbering; residue 241 Kabat numbering) is converted to proline resulting in an IgG1-like hinge sequence. Accordingly, any of the antibodies may include a stabilizing 'Adair' mutation.

As provided herein, antibodies of this disclosure may optionally comprise constant regions or parts thereof. For example, a VL domain may be attached at its C-terminal end to a light chain constant domain like Cκ or Cλ. Similarly, a VH domain or portion thereof may be attached to all or part of a heavy chain like IgA, IgD, IgE, IgG, and IgM, and any isotype subclass. Antibodies may include suitable constant regions (see, for example, Kabat et al., Sequences of Proteins of Immunological Interest, No. 91-3242, National Institutes of Health Publications, Bethesda, Md. (1991)). Therefore, antibodies within the scope of this may disclosure include VH and VL domains, or an antigen binding portion thereof, combined with any suitable constant regions.

ii. Muscle-Targeting Peptides

Some aspects of the disclosure provide muscle-targeting peptides as muscle-targeting agents. Short peptide sequences (e.g., peptide sequences of 5-20 amino acids in length) that bind to specific cell types have been described. For example, cell-targeting peptides have been described in Vines e., et al., A. "Cell-penetrating and cell-targeting peptides in drug delivery" Biochim Biophys Acta 2008, 1786: 126-38; Jarver P., et al., "In vivo biodistribution and efficacy of peptide mediated delivery" *Trends Pharmacol Sci* 2010; 31: 528-35; Samoylova T. I., et al., "Elucidation of muscle-binding peptides by phage display screening" *Muscle Nerve* 1999; 22: 460-6; U.S. Pat. No. 6,329,501, issued on Dec. 11, 2001, entitled "METHODS AND COMPOSITIONS FOR TARGETING COMPOUNDS TO MUSCLE"; and Samoylov A. M., et al., "Recognition of cell-specific binding of phage display derived peptides using an acoustic wave sensor." *Biomol Eng* 2002; 18: 269-72; the entire contents of each of which are incorporated herein by reference. By designing peptides to interact with specific cell surface antigens (e.g., receptors), selectivity for a desired tissue, e.g., muscle, can be achieved. Skeletal muscle-targeting has been investigated and a range of molecular payloads are able to be delivered. These approaches may have high selectivity for muscle tissue without many of the practical disadvantages of a large antibody or viral particle. Accordingly, in some embodiments, the muscle-targeting agent is a muscle-targeting peptide that is from 4 to 50 amino acids in length. In some embodiments, the muscle-targeting peptide is 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. Muscle-targeting peptides can be generated using any of several methods, such as phage display.

In some embodiments, a muscle-targeting peptide may bind to an internalizing cell surface receptor that is overexpressed or relatively highly expressed in muscle cells, e.g. a transferrin receptor, compared with certain other cells. In some embodiments, a muscle-targeting peptide may target, e.g., bind to, a transferrin receptor. In some embodiments, a peptide that targets a transferrin receptor may comprise a segment of a naturally occurring ligand, e.g., transferrin. In some embodiments, a peptide that targets a transferrin receptor is as described in U.S. Pat. No. 6,743,893, filed Nov. 30, 2000, "RECEPTOR-MEDIATED UPTAKE OF PEPTIDES THAT BIND THE HUMAN TRANSFERRIN RECEPTOR". In some embodiments, a peptide that targets a transferrin receptor is as described in Kawamoto, M. et al, "A novel transferrin receptor-targeted hybrid peptide disintegrates cancer cell membrane to induce rapid killing of cancer cells." BMC Cancer. 2011 Aug. 18; 11:359. In some embodiments, a peptide that targets a transferrin receptor is as described in U.S. Pat. No. 8,399,653, filed May 20, 2011, "TRANSFERRIN/TRANSFERRIN RECEPTOR-MEDIATED SIRNA DELIVERY".

As discussed above, examples of muscle targeting peptides have been reported. For example, muscle-specific peptides were identified using phage display library presenting surface heptapeptides. As one example a peptide having the amino acid sequence ASSLNIA (SEQ ID NO: 6) bound to C2C12 murine myotubes in vitro, and bound to mouse muscle tissue in vivo. Accordingly, in some embodiments, the muscle-targeting agent comprises the amino acid sequence ASSLNIA (SEQ ID NO: 6). This peptide displayed improved specificity for binding to heart and skeletal muscle tissue after intravenous injection in mice with reduced binding to liver, kidney, and brain. Additional muscle-specific peptides have been identified using phage display. For example, a 12 amino acid peptide was identified by phage display library for muscle targeting in the context of treatment for DMD. See, Yoshida D., et al., "Targeting of salicylate to skin and muscle following topical injections in rats." Int J Pharm 2002; 231: 177-84; the entire contents of which are hereby incorporated by reference. Here, a 12 amino acid peptide having the sequence SKTFNTHPQSTP (SEQ ID NO: 7) was identified and this muscle-targeting peptide showed improved binding to C2C12 cells relative to the ASSLNIA (SEQ ID NO: 6) peptide.

An additional method for identifying peptides selective for muscle (e.g., skeletal muscle) over other cell types includes in vitro selection, which has been described in Ghosh D., et al., "Selection of muscle-binding peptides from context-specific peptide-presenting phage libraries for adenoviral vector targeting" J Virol 2005; 79: 13667-72; the entire contents of which are incorporated herein by reference. By pre-incubating a random 12-mer peptide phage display library with a mixture of non-muscle cell types, non-specific cell binders were selected out. Following rounds of selection the 12 amino acid peptide TARGEHKEEELI (SEQ ID NO: 8) appeared most frequently. Accordingly, in some embodiments, the muscle-targeting agent comprises the amino acid sequence TARGEHKEEELI (SEQ ID NO: 8).

A muscle-targeting agent may an amino acid-containing molecule or peptide. A muscle-targeting peptide may correspond to a sequence of a protein that preferentially binds to a protein receptor found in muscle cells. In some embodiments, a muscle-targeting peptide contains a high propensity of hydrophobic amino acids, e.g. valine, such that the peptide preferentially targets muscle cells. In some embodiments, a muscle-targeting peptide has not been previously characterized or disclosed. These peptides may be conceived of, produced, synthesized, and/or derivatized using any of several methodologies, e.g. phage displayed peptide libraries, one-bead one-compound peptide libraries, or positional scanning synthetic peptide combinatorial libraries. Exemplary methodologies have been characterized in the art and are incorporated by reference (Gray, B. P. and Brown, K. C. "Combinatorial Peptide Libraries: Mining for Cell-Binding Peptides" Chem Rev. 2014, 114:2, 1020-1081.; Samoylova, T. I. and Smith, B. F. "Elucidation of muscle-binding peptides by phage display screening." Muscle Nerve, 1999, 22:4. 460-6.). In some embodiments, a muscle-targeting peptide has been previously disclosed (see, e.g. Writer M. J.

et al. "Targeted gene delivery to human airway epithelial cells with synthetic vectors incorporating novel targeting peptides selected by phage display." J. Drug Targeting. 2004; 12:185; Cai, D. "BDNF-mediated enhancement of inflammation and injury in the aging heart." Physiol Genomics. 2006, 24:3, 191-7.; Zhang, L. "Molecular profiling of heart endothelial cells." Circulation, 2005, 112:11, 1601-11.; McGuire, M. J. et al. "In vitro selection of a peptide with high selectivity for cardiomyocytes in vivo." J Mol Biol. 2004, 342:1, 171-82.). Exemplary muscle-targeting peptides comprise an amino acid sequence of the following group: CQAQGQLVC (SEQ ID NO: 9), CSERSMNFC (SEQ ID NO: 10), CPKTRRVPC (SEQ ID NO: 11), WLSEA-GPVVTVRALRGTGSW (SEQ ID NO: 12), ASSLNIA (SEQ ID NO: 6), CMQHSMRVC (SEQ ID NO: 13), and DDTRHWG (SEQ ID NO: 14). In some embodiments, a muscle-targeting peptide may comprise about 2-25 amino acids, about 2-20 amino acids, about 2-15 amino acids, about 2-10 amino acids, or about 2-5 amino acids. Muscle-targeting peptides may comprise naturally-occurring amino acids, e.g. cysteine, alanine, or non-naturally-occurring or modified amino acids. Non-naturally occurring amino acids include 3-amino acids, homo-amino acids, proline derivatives, 3-substituted alanine derivatives, linear core amino acids, N-methyl amino acids, and others known in the art. In some embodiments, a muscle-targeting peptide may be linear; in other embodiments, a muscle-targeting peptide may be cyclic, e.g. bicyclic (see, e.g. Silvana, M. G. et al. Mol. Therapy, 2018, 26:1, 132-147.).

iii. Muscle-Targeting Receptor Ligands

A muscle-targeting agent may be a ligand, e.g. a ligand that binds to a receptor protein. A muscle-targeting ligand may be a protein, e.g. transferrin, which binds to an internalizing cell surface receptor expressed by a muscle cell. Accordingly, in some embodiments, the muscle-targeting agent is transferrin, or a derivative thereof that binds to a transferrin receptor. A muscle-targeting ligand may alternatively be a small molecule, e.g. a lipophilic small molecule that preferentially targets muscle cells relative to other cell types. Exemplary lipophilic small molecules that may target muscle cells include compounds comprising cholesterol, cholesteryl, stearic acid, palmitic acid, oleic acid, oleyl, linolene, linoleic acid, myristic acid, sterols, dihydrotestosterone, testosterone derivatives, glycerine, alkyl chains, trityl groups, and alkoxy acids.

iv. Muscle-Targeting Aptamers

A muscle-targeting agent may be an aptamer, e.g. an RNA aptamer, which preferentially targets muscle cells relative to other cell types. In some embodiments, a muscle-targeting aptamer has not been previously characterized or disclosed. These aptamers may be conceived of, produced, synthesized, and/or derivatized using any of several methodologies, e.g. Systematic Evolution of Ligands by Exponential Enrichment. Exemplary methodologies have been characterized in the art and are incorporated by reference (Yan, A. C. and Levy, M. "Aptamers and aptamer targeted delivery" RNA biology, 2009, 6:3, 316-20.; Germer, K. et al. "RNA aptamers and their therapeutic and diagnostic applications." Int. J. Biochem. Mol. Biol. 2013; 4: 27-40.). In some embodiments, a muscle-targeting aptamer has been previously disclosed (see, e.g. Phillippou, S. et al. "Selection and Identification of Skeletal-Muscle-Targeted RNA Aptamers." Mol Ther Nucleic Acids. 2018, 10:199-214.; Thiel, W. H. et al. "Smooth Muscle Cell-targeted RNA Aptamer Inhibits Neointimal Formation." Mol Ther. 2016, 24:4, 779-87.). Exemplary muscle-targeting aptamers include the A01B RNA aptamer and RNA Apt 14. In some embodiments, an aptamer is a nucleic acid-based aptamer, an oligonucleotide aptamer or a peptide aptamer. In some embodiments, an aptamer may be about 5-15 kDa, about 5-10 kDa, about $10^{-15}$ kDa, about 1-5 Da, about 1-3 kDa, or smaller.

v. Other Muscle-Targeting Agents

One strategy for targeting a muscle cell (e.g., a skeletal muscle cell) is to use a substrate of a muscle transporter protein, such as a transporter protein expressed on the sarcolemma. In some embodiments, the muscle-targeting agent is a substrate of an influx transporter that is specific to muscle tissue. In some embodiments, the influx transporter is specific to skeletal muscle tissue. Two main classes of transporters are expressed on the skeletal muscle sarcolemma, (1) the adenosine triphosphate (ATP) binding cassette (ABC) superfamily, which facilitate efflux from skeletal muscle tissue and (2) the solute carrier (SLC) superfamily, which can facilitate the influx of substrates into skeletal muscle. In some embodiments, the muscle-targeting agent is a substrate that binds to an ABC superfamily or an SLC superfamily of transporters. In some embodiments, the substrate that binds to the ABC or SLC superfamily of transporters is a naturally-occurring substrate. In some embodiments, the substrate that binds to the ABC or SLC superfamily of transporters is a non-naturally occurring substrate, for example, a synthetic derivative thereof that binds to the ABC or SLC superfamily of transporters.

In some embodiments, the muscle-targeting agent is a substrate of an SLC superfamily of transporters. SLC transporters are either equilibrative or use proton or sodium ion gradients created across the membrane to drive transport of substrates. Exemplary SLC transporters that have high skeletal muscle expression include, without limitation, the SATT transporter (ASCT1; SLC1A4), GLUT4 transporter (SLC2A4), GLUT7 transporter (GLUT7; SLC2A7), ATRC2 transporter (CAT-2; SLC7A2), LAT3 transporter (KIAA0245; SLC7A6), PHT1 transporter (PTR4; SLC15A4), OATP-J transporter (OATP5A1; SLC21A15), OCT3 transporter (EMT; SLC22A3), OCTN2 transporter (FLJ46769; SLC22A5), ENT transporters (ENT1; SLC29A1 and ENT2; SLC29A2), PAT2 transporter (SLC36A2), and SAT2 transporter (KIAA1382; SLC38A2). These transporters can facilitate the influx of substrates into skeletal muscle, providing opportunities for muscle targeting.

In some embodiments, the muscle-targeting agent is a substrate of an equilibrative nucleoside transporter 2 (ENT2) transporter. Relative to other transporters, ENT2 has one of the highest mRNA expressions in skeletal muscle. While human ENT2 (hENT2) is expressed in most body organs such as brain, heart, placenta, thymus, pancreas, prostate, and kidney, it is especially abundant in skeletal muscle. Human ENT2 facilitates the uptake of its substrates depending on their concentration gradient. ENT2 plays a role in maintaining nucleoside homeostasis by transporting a wide range of purine and pyrimidine nucleobases. The hENT2 transporter has a low affinity for all nucleosides (adenosine, guanosine, uridine, thymidine, and cytidine) except for inosine. Accordingly, in some embodiments, the muscle-targeting agent is an ENT2 substrate. Exemplary ENT2 substrates include, without limitation, inosine, 2',3'-dideoxyinosine, and calofarabine. In some embodiments, any of the muscle-targeting agents provided herein are associated with a molecular payload (e.g., oligonucleotide payload). In some embodiments, the muscle-targeting agent is covalently linked to the molecular payload. In some embodiments, the muscle-targeting agent is non-covalently linked to the molecular payload.

In some embodiments, the muscle-targeting agent is a substrate of an organic cation/carnitine transporter (OCTN2), which is a sodium ion-dependent, high affinity carnitine transporter. In some embodiments, the muscle-targeting agent is carnitine, mildronate, acetylcarnitine, or any derivative thereof that binds to OCTN2. In some embodiments, the carnitine, mildronate, acetylcarnitine, or derivative thereof is covalently linked to the molecular payload (e.g., oligonucleotide payload).

A muscle-targeting agent may be a protein that is protein that exists in at least one soluble form that targets muscle cells. In some embodiments, a muscle-targeting protein may be hemojuvelin (also known as repulsive guidance molecule C or hemochromatosis type 2 protein), a protein involved in iron overload and homeostasis. In some embodiments, hemojuvelin may be full length or a fragment, or a mutant with at least 75%, at least 80%, at least 85%, at least 90%, at least 95%, at least 98% or at least 99% sequence identity to a functional hemojuvelin protein. In some embodiments, a hemojuvelin mutant may be a soluble fragment, may lack a N-terminal signaling, and/or lack a C-terminal anchoring domain. In some embodiments, hemojuvelin may be annotated under GenBank RefSeq Accession Numbers NM_001316767.1, NM_145277.4, NM_202004.3, NM_213652.3, or NM_213653.3. It should be appreciated that a hemojuvelin may be of human, non-human primate, or rodent origin.

B. Molecular Payloads

Some aspects of the disclosure provide molecular payloads, e.g., for modulating a biological outcome, e.g., the transcription of a DNA sequence, the expression of a protein, or the activity of a protein. In some embodiments, a molecular payload is linked to, or otherwise associated with a muscle-targeting agent. In some embodiments, such molecular payloads are capable of targeting to a muscle cell, e.g., via specifically binding to a nucleic acid or protein in the muscle cell following delivery to the muscle cell by an associated muscle-targeting agent. It should be appreciated that various types of muscle-targeting agents may be used in accordance with the disclosure. For example, the molecular payload may comprise, or consist of, an oligonucleotide (e.g., antisense oligonucleotide), a peptide (e.g., a peptide that binds a nucleic acid or protein associated with disease in a muscle cell), a protein (e.g., a protein that binds a nucleic acid or protein associated with disease in a muscle cell), or a small molecule (e.g., a small molecule that modulates the function of a nucleic acid or protein associated with disease in a muscle cell). In some embodiments, the molecular payload is an oligonucleotide that comprises a strand having a region of complementarity to a gene provided in Table 1. Exemplary molecular payloads are described in further detail herein, however, it should be appreciated that the exemplary molecular payloads provided herein are not meant to be limiting.

In some embodiments at least one (e.g., at least 2, at least 3, at least 4, at least 5, at least 10) molecular payload (e.g., oligonucleotides) is linked to a muscle-targeting agent. In some embodiments, all molecular payloads attached to a muscle-targeting agent are the same, e.g. target the same gene. In some embodiments, all molecular payloads attached to a muscle-targeting agent are different, for example the molecular payloads may target different portions of the same target gene, or the molecular payloads may target at least two different target genes. In some embodiments, a muscle-targeting agent may be attached to some molecular payloads that are the same and some molecular payloads that are different.

The present disclosure also provides a composition comprising a plurality of complexes, for which at least 80% (e.g., at least 85%, at least 90%, at least 91%, at least 92%, at least 93%, at least 94%, at least 95%, at least 96%, at least 97%, at least 98%, or at least 99%) of the complexes comprise a muscle-targeting agent linked to the same number of molecular payloads (e.g., oligonucleotides).

i. Oligonucleotides

Any suitable oligonucleotide may be used as a molecular payload, as described herein. In some embodiments, the oligonucleotide may be designed to cause degradation of an mRNA (e.g., the oligonucleotide may be a gapmer, an siRNA, a ribozyme or an aptamer that causes degradation). In some embodiments, the oligonucleotide may be designed to block translation of an mRNA (e.g., the oligonucleotide may be a mixmer, an siRNA or an aptamer that blocks translation). In some embodiments, an oligonucleotide may be designed to caused degradation and block translation of an mRNA. In some embodiments, an oligonucleotide may be a guide nucleic acid (e.g., guide RNA) for directing activity of an enzyme (e.g., a gene editing enzyme). Other examples of oligonucleotides are provided herein. It should be appreciated that, in some embodiments, oligonucleotides in one format (e.g., antisense oligonucleotides) may be suitably adapted to another format (e.g., siRNA oligonucleotides) by incorporating functional sequences (e.g., antisense strand sequences) from one format to the other format.

In some embodiments, an oligonucleotide may comprise a region of complementarity to a target gene provided in Table 1. Further non-limiting examples are provided below for selected genes of Table 1.

DMPK/DM1

In some embodiments, examples of oligonucleotides useful for targeting DMPK, e.g., for the treatment of DM1, are provided in US Patent Application Publication 20100016215A1, published on Jan. 1, 2010, entitled *Compound And Method For Treating Myotonic Dystrophy*; US Patent Application Publication 20130237585A1, published Jul. 19, 2010, *Modulation Of Dystrophia Myotonica-Protein Kinase (DMPK) Expression*; US Patent Application Publication 20150064181A1, published on Mar. 5, 2015, entitled "*Antisense Conjugates For Decreasing Expression Of Dmpk*"; US Patent Application Publication 20150238627A1, published on Aug. 27, 2015, entitled "*Peptide-Linked Morpholino Antisense Oligonucleotides For Treatment Of Myotonic Dystrophy*"; Pandey, S. K. et al. "*Identification and Characterization of Modified Antisense Oligonucleotides Targeting DMPK in Mice and Nonhuman Primates for the Treatment of Myotonic Dystrophy Type 1*" J. of Pharmacol Exp Ther, 2015, 355:329-340.; Langlois, M. et al. "*Cytoplasmic and Nuclear Retained DMPK mRNAs Are Targets for RNA Interference in Myotonic Dystrophy Cells*" J. Biological Chemistry, 2005, 280:17, 16949-16954.; Jauvin, D. et al. "*Targeting DMPK with Antisense Oligonucleotide Improves Muscle Strength in Myotonic Dystrophy Type 1 Mice*", Mol. Ther: Nucleic Acids, 2017, 7:465-474.; Mulders, S. A. et al. "*Triplet-repeat oligonucleotide-mediated reversal of RNA toxicity in myotonic dystrophy*" PNAS, 2009, 106:33, 13915-13920.; Wheeler, T. M. et al., "*Targeting nuclear RNA for in vivo correction of myotonic dystrophy*" Nature, 2012, 488(7409):111-115.; and US Patent Application Publication 20160304877A1, published on Oct. 20, 2016, entitled "*Compounds And Methods For Modulation Of Dystrophia Myotonica-Protein Kinase (Dmpk) Expression*," the contents of each of which are incorporated herein by reference in their entireties.

Examples of oligonucleotides for promoting DMPK gene editing include US Patent Application Publication 20170088819A1, published on Mar. 3, 2017, entitled "*Genetic Correction Of Myotonic Dystrophy Type* 1"; and International Patent Application Publication WO18002812A1, published on Apr. 1, 2018, entitled "*Materials And Methods For Treatment Of Myotonic Dystrophy Type* 1 (*DM*1) *And Other Related Disorders*," the contents of each of which are incorporated herein by reference in their entireties.

In some embodiments, the oligonucleotide may have region of complementarity to a mutant form of DMPK, for example, a mutant form as reported in Botta A. et al. "The CTG repeat expansion size correlates with the splicing defects observed in muscles from myotonic dystrophy type 1 patients." *J Med Genet.* 2008 October; 45(10):639-46.; and Machuca-Tzili L. et al. "Clinical and molecular aspects of the myotonic dystrophies: a review." Muscle Nerve. 2005 July; 32(1):1-18.; the contents of each of which are incorporated herein by reference in their entireties.

In some embodiments, an oligonucleotide provided herein is an antisense oligonucleotide targeting DMPK. In some embodiments, the oligonucleotide targeting is any one of the antisense oligonucleotides (e.g., a Gapmer) targeting DMPK as described in US Patent Application Publication US20160304877A1, published on Oct. 20, 2016, entitled "*Compounds And Methods For Modulation Of Dystrophia Myotonica-Protein Kinase* (*DMPK*) *Expression*," incorporated herein by reference. In some embodiments, the DMPK targeting oligonucleotide targets a region of the DMPK gene sequence as set forth in Genbank accession No. NM 001081560.2 or as set forth in Genbank accession No. NG 009784.1.

In some embodiments, the DMPK targeting oligonucleotide comprises a nucleotide sequence comprising a region complementary to a target region that is at least 10 continuous nucleotides (e.g., at least 10, at least 12, at least 14, at least 16, or more continuous nucleotides) in Genbank accession No. NM_001081560.2.

In some embodiments, the DMPK targeting oligonucleotide comprise a gapmer motif. "Gapmer" means a chimeric antisense compound in which an internal region having a plurality of nucleotides that support RNase H cleavage is positioned between external regions having one or more nucleotides, wherein the nucleotides comprising the internal region are chemically distinct from the nucleotide or nucleotides comprising the external regions. The internal region can be referred to as a "gap segment" and the external regions can be referred to as "wing segments." In some embodiments, the DMPK targeting oligonucleotide comprises one or more modified nucleotides, and/or one or more modified internucleotide linkages. In some embodiments, the internucleotide linkage is a phosphorothioate linkage. In some embodiments, the oligonucleotide comprises a full phosphorothioate backbone. In some embodiments, the oligonucleotide is a DNA gapmer with cET ends (e.g., 3-10-3; cET-DNA-cET). In some embodiments, the DMPK targeting oligonucleotide comprises one or more 6'-(S)-CH$_3$ bicyclic nucleotides, one or more β-D-2'-deoxyribonucleotides, and/or one or more 5-methylcytosine nucleotides.

DUX4/FSHD

In some embodiments, examples of oligonucleotides useful for targeting DUX4, e.g., for the treatment of FSHD, are provided in U.S. Pat. No. 9,988,628, published on Feb. 2, 2017, entitled "AGENTS USEFUL IN TREATING FACIOSCAPULOHUMERAL MUSCULAR DYSTROPHY"; U.S. Pat. No. 9,469,851, published Oct. 30, 2014, entitled "RECOMBINANT VIRUS PRODUCTS AND METHODS FOR INHIBITING EXPRESSION OF DUX4"; US Patent Application Publication 20120225034, published on Sep. 6, 2012, entitled "AGENTS USEFUL IN TREATING FACIOSCAPULOHUMERAL MUSCULAR DYSTROPHY"; PCT Patent Application Publication Number WO 2013/120038, published on Aug. 15, 2013, entitled "MORPHOLINO TARGETING DUX4 FOR TREATING FSHD"; Chen et al., "Morpholino-mediated Knockdown of DUX4 Toward Facioscapulohumeral Muscular Dystrophy Therapeutics," Molecular Therapy, 2016, 24:8, 1405-1411.; and Ansseau et al., "Antisense Oligonucleotides Used to Target the DUX4 mRNA as Therapeutic Approaches in Facioscapulohumeral Muscular Dystrophy (FSHD)," Genes, 2017, 8, 93.; the contents of each of which are incorporated herein in their entireties. In some embodiments, the oligonucleotide is an antisense oligonucleotide, a morpholino, a siRNA, a shRNA, or another nucleotide which hybridizes with the target DUX4 gene or mRNA.

In some embodiments, e.g., for the treatment of FSHD, oligonucleotides may have a region of complementarity to a hypomethylated, contracted D4Z4 repeat, as in Daxinger, et al., "Genetic and Epigenetic Contributors to FSHD," published in Curr Opin Genet Dev in 2015, Lim J-W, et al., DICER/AGO-dependent epigenetic silencing of D4Z4 repeats enhanced by exogenous siRNA suggests mechanisms and therapies for FSHD Hum Mol Genet. 2015 Sep. 1; 24(17): 4817-4828, the contents of each of which are incorporated in their entireties.

DNM2/CNM

In some embodiments, examples of oligonucleotides useful for targeting DNM2, e.g., for the treatment of CNM, are provided in US Patent Application Publication Number 20180142008, published on May 24, 2018, entitled "DYNAMIN 2 INHIBITOR FOR THE TREATMENT OF DUCHENNE'S MUSCULAR DYSTROPHY", and in PCT Application Publication Number WO 2018/100010A1, published on Jun. 7, 2018, entitled "ALLELE-SPECIFIC SILENCING THERAPY FOR DYNAMIN 2-RELATED DISEASES". For example, in some embodiments, the oligonucleotide is a RNAi, an antisense nucleic acid, a siRNA, or a ribozyme that interferes specifically with DNM2 expression. Other examples of oligonucleotides useful for targeting DNM2 are provided in Tasfaout, et al., "Single Intramuscular Injection of AAV-shRNA Reduces DNM2 and Prevents Myotubular Myopathy in Mice," published in Mol. Ther. on Apr. 4, 2018, and in Tasfaout, et al., "Antisense oligonucleotide-mediated Dnm2 knockdown prevents and reverts myotubular myopathy in mice," Nature Communications volume 8, Article number: 15661 (2017). In some embodiments, the oligonucleotide is a shRNA or a morpholino that efficiently targets DNM2 mRNA. In some embodiments, the oligonucleotide encodes wild-type DNM2 which is resistant to miR-133 activity, as in Todaka, et al. "Overexpression of NF90-NF45 Represses Myogenic MicroRNA Biogenesis, Resulting in Development of Skeletal Muscle Atrophy and Centronuclear Muscle Fibers," published in Mol. Cell Biol. in July 2015 Further examples of oligonucleotides useful for targeting DNM2 are provided in Gibbs, et al., "Two Dynamin-2 Genes are Required for Normal Zebrafish Development" published in PLoS One in 2013, the contents of each of which are incorporated herein in their entirety.

In some embodiments, e.g., for the treatment of CNM, the oligonucleotide may have a region of complementarity to a mutant in DNM2 associated with CNM, as in Bohm et al, "Mutation Spectrum in the Large GTPase Dynamin 2, and Genotype-Phenotype Correlation in Autosomal Dominant Centronuclear Myopathy," as published in Hum. Mutat. in 2012, the contents of which are incorporated herein in its entirety.

Pompe Disease

In some embodiments, e.g., for the treatment of Pompe disease, an oligonucleotide mediates exon 2 inclusion in a GAA disease allele as in van der Wal, et al., "GAA Deficiency in Pompe Disease is Alleviated by Exon Inclusion in iPSC-Derived Skeletal Muscle Cells," Mol Ther Nucleic Acids. 2017 Jun. 16; 7: 101-115, the contents of which are incorporated herein by reference. Accordingly, in some embodiments, the oligonucleotide may have a region of complementarity to a GAA disease allele.

In some embodiments, e.g., for the treatment of Pompe disease, an oligonucleotide, such as an RNAi or antisense oligonucleotide, is utilized to suppress expression of wild-type GYS1 in muscle cells, as reported, for example, in Clayton, et al., "Antisense Oligonucleotide-mediated Suppression of Muscle Glycogen Synthase 1 Synthesis as an Approach for Substrate Reduction Therapy of Pompe Disease," published in Mol Ther Nucleic Acids in 2017, or US Patent Application Publication Number 2017182189, published on Jun. 29, 2017, entitled "INHIBITING OR DOWN-REGULATING GLYCOGEN SYNTHASE BY CREATING PREMATURE STOP CODONS USING ANTISENSE OLIGONUCLEOTIDES", the contents of which are incorporated herein by reference. Accordingly, in some embodiments, oligonucleotides may have an antisense strand having a region of complementarity to a sequence a human GYS1 sequence, corresponding to RefSeq number NM_002103.4 and/or a mouse GYS1 sequence, corresponding to RefSeq number NM_030678.3.

ACVR1/FOP

In some embodiments, examples of oligonucleotides useful for targeting ACVR1, e.g., for the treatment of FOP, are provided in US Patent Application 2009/0253132, published Oct. 8, 2009, "Mutated ACVR1 for diagnosis and treatment of fibrodyplasia ossificans progressiva (FOP)"; WO 2015/152183, published Oct. 8, 2015, "Prophylactic agent and therapeutic agent for fibrodysplasia ossificans progressive"; Lowery, J. W. et al, "Allele-specific RNA Interference in FOP-Silencing the FOP gene", GENE THERAPY, vol. 19, 2012, pages 701-762; Takahashi, M. et al. "Disease-causing allele-specific silencing against the ALK2 mutants, R206H and G356D, in fibrodysplasia ossificans progressiva" Gene Therapy (2012) 19, 781-785; Shi, S. et al. "Antisense-Oligonucleotide Mediated Exon Skipping in Activin-Receptor-Like Kinase 2: Inhibiting the Receptor That Is Overactive in Fibrodysplasia Ossificans Progressiva" Plos One, July 2013, Vol 8:7, e69096.; US Patent Application 2017/0159056, published Jun. 8, 2017, "Antisense oligonucleotides and methods of use thereof"; U.S. Pat. No. 8,859,752, issued Oct. 4, 2014, "SIRNA-based therapy of Fibrodysplasia Ossificans Progressiva (FOP)"; WO 2004/094636, published Nov. 4, 2004, "Effective sirna knock-down constructs", the contents of each of which are incorporated herein in their entireties.

FXN/Friedreich's Ataxia

In some embodiments, examples of oligonucleotides useful for targeting FXN and/or otherwise compensating for frataxin deficiency, e.g., for the treatment of Freidrich Ataxia, are provided in Li, L. et al "Activating frataxin expression by repeat-targeted nucleic acids" Nat. Comm. 2016, 7:10606.; WO 2016/094374, published Jun. 16, 2016, "Compositions and methods for treatment of friedreich's ataxia."; WO 2015/020993, published Feb. 12, 2015, "RNAi COMPOSITIONS AND METHODS FOR TREATMENT OF FRIEDREICH'S ATAXIA"; WO 2017/186815, published Nov. 2, 2017, "Antisense oligonucleotides for enhanced expression of frataxin"; WO 2008/018795, published Feb. 14, 2008, "Methods and means for treating dna repeat instability associated genetic disorders"; US Patent Application 2018/0028557, published Feb. 1, 2018, "Hybrid oligonucleotides and uses thereof"; WO 2015/023975, published Feb. 19, 2015, "Compositions and methods for modulating RNA"; WO 2015/023939, published Feb. 19, 2015, "Compositions and methods for modulating expression of frataxin"; US Patent Application 2017/0281643, published Oct. 5, 2017, "Compounds and methods for modulating frataxin expression"; Li L. et al., "Activating frataxin expression by repeat-targeted nucleic acids" Nature Communications, Published 4 Feb. 2016; and Li L. et al. "Activation of Frataxin Protein Expression by Antisense Oligonucleotides Targeting the Mutant Expanded Repeat" Nucleic Acid Ther. 2018 February; 28(1):23-33., the contents of each of which are incorporated herein in their entireties.

In some embodiments, an oligonucleotide payload is configured (e.g., as a gapmer or RNAi oligonucleotide) for inhibiting expression of a natural antisense transcript that inhibits FXN expression, e.g., as disclosed in U.S. Pat. No. 9,593,330, filed Jun. 9, 2011, "Treatment of frataxin (FXN) related diseases by inhibition of natural antisense transcript to FXN", the contents of which are incorporated herein by reference in its entirety.

Examples of oligonucleotides for promoting FXN gene editing include WO 2016/094845, published Jun. 16, 2016, "Compositions and methods for editing nucleic acids in cells utilizing oligonucleotides"; WO 2015/089354, published Jun. 18, 2015, "Compositions and methods of use of CRISPR-Cas systems in nucleotide repeat disorders"; WO 2015/139139, published Sep. 24, 2015, "CRISPR-based methods and products for increasing frataxin levels and uses thereof"; and WO 2018/002783, published Jan. 4, 2018, "Materials and methods for treatment of Friedreich ataxia and other related disorders", the contents of each of which are incorporated herein in their entireties.

Examples of oligonucleotides for promoting FXN gene expression through targeting of non-FXN genes, e.g. epigenetic regulators of FXN, include WO 2015/023938, published Feb. 19, 2015, "Epigenetic regulators of frataxin", the contents of which are incorporated herein in its entirety.

In some embodiments, oligonucleotides may have a region of complementarity to a sequence set forth as: a FXN gene from humans (Gene ID 2395; NC_000009.12) and/or a FXN gene from mice (Gene ID 14297; NC_000085.6). In some embodiments, the oligonucleotide may have region of complementarity to a mutant form of FXN, for example as reported in e.g., Montermini, L. et al. "The Friedreich ataxia GAA triplet repeat: premutation and normal alleles." Hum. Molec. Genet., 1997, 6: 1261-1266.; Filla, A. et al. "The relationship between trinucleotide (GAA) repeat length and clinical features in Friedreich ataxia." Am. J. Hum. Genet. 1996, 59: 554-560.; Pandolfo, M. Friedreich ataxia: the clinical picture. J. Neurol. 2009, 256, 3-8.; the contents of each of which are incorporated herein by reference in their entireties.

DMD/Dystrophinopathies

Examples of oligonucleotides useful for targeting DMD are provided in U.S. Patent Application Publication US20100130591A1, published on May 27, 2010, entitled "MULTIPLE EXON SKIPPING COMPOSITIONS FOR DMD"; U.S. Pat. No. 8,361,979, issued Jan. 29, 2013, entitled "MEANS AND METHOD FOR INDUCING EXON-SKIPPING"; U.S. Patent Application Publication 20120059042, published Mar. 8, 2012, entitled "METHOD FOR EFFICIENT EXON (44) SKIPPING IN DUCHENNE MUSCULAR DYSTROPHY AND ASSOCIATED MEANS; U.S. Patent Application Publication 20140329881, published Nov. 6, 2014, entitled "EXON SKIPPING COMPOSITIONS FOR TREATING MUSCULAR DYSTROPHY"; U.S. Pat. No. 8,232,384, issued Jul. 31, 2012, entitled "ANTISENSE OLIGONUCLEOTIDES FOR INDUCING EXON SKIPPING AND METHODS OF USE THEREOF"; U.S. Patent Application Publication 20120022134A1, published Jan. 26, 2012, entitled "METHODS AND MEANS FOR EFFICIENT SKIPPING OF EXON 45 IN DUCHENNE MUSCULAR DYSTROPHY PRE-MRNA; U.S. Patent Application Publication 20120077860, published Mar. 29, 2012, entitled "ADENO-ASSOCIATED VIRAL VECTOR FOR EXON SKIPPING IN A GENE ENCODING A DISPENSABLE DOMAN PROTEIN"; U.S. Pat. No. 8,324,371, issued Dec. 4, 2012, entitled "OLIGOMERS"; U.S. Pat. No. 9,078,911, issued Jul. 14, 2015, entitled "ANTISENSE OLIGONUCLEOTIDES"; U.S. Pat. No. 9,079,934, issued Jul. 14, 2015, entitled "ANTISENSE NUCLEIC ACIDS"; U.S. Pat. No. 9,034,838, issued May 19, 2015, entitled "MIR-31 IN DUCHENNE MUSCULAR DYSTROPHY THERAPY"; and International Patent Publication WO2017062862A3, published Apr. 13, 2017, entitled "OLIGONUCLEOTIDE COMPOSITIONS AND METHODS THEREOF"; the contents of each of which are incorporated herein in their entireties.

Examples of oligonucleotides for promoting DMD gene editing include International Patent Publication WO2018053632A1, published Mar. 29, 2018, entitled "METHODS OF MODIFYING THE DYSTROPHIN GENE AND RESTORING DYSTROPHIN EXPRESSION AND USES THEREOF"; International Patent Publication WO2017049407A1, published Mar. 30, 2017, entitled "MODIFICATION OF THE DYSTROPHIN GENE AND USES THEREOF"; International Patent Publication WO2016161380A1, published Oct. 6, 2016, entitled "CRISPR/CAS-RELATED METHODS AND COMPOSITIONS FOR TREATING DUCHENNE MUSCULAR DYSTROPHY AND BECKER MUSCULAR DYSTROPHY"; International Patent Publication WO2017095967, published Jun. 8, 2017, entitled "THERAPEUTIC TARGETS FOR THE CORRECTION OF THE HUMAN DYSTROPHIN GENE BY GENE EDITING AND METHODS OF USE"; International Patent Publication WO2017072590A1, published May 4, 2017, entitled "MATERIALS AND METHODS FOR TREATMENT OF DUCHENNE MUSCULAR DYSTROPHY"; International Patent Publication WO2018098480A1, published May 31, 2018, entitled "PREVENTION OF MUSCULAR DYSTROPHY BY CRISPR/CPF1-MEDIATED GENE EDITING"; US Patent Application Publication US20170266320A1, published Sep. 21, 2017, entitled "RNA-Guided Systems for In Vivo Gene Editing"; International Patent Publication WO2016025469A1, published Feb. 18, 2016, entitled "PREVENTION OF MUSCULAR DYSTROPHY BY CRISPR/CAS9-MEDIATED GENE EDITING"; U.S. Patent Application Publication 2016/0201089, published Jul. 14, 2016, entitled "RNA-GUIDED GENE EDITING AND GENE REGULATION"; and U.S. Patent Application Publication 2013/0145487, published Jun. 6, 2013, entitled "MEGANUCLEASE VARIANTS CLEAVING A DNA TARGET SEQUENCE FROM THE DYSTROPHN GENE AND USES THEREOF", the contents of each of which are incorporated herein in their entireties. In some embodiments, an oligonucleotide may have a region of complementarity to DMD gene sequences of multiple species, e.g., selected from human, mouse and non-human species.

In some embodiments, the oligonucleotide may have region of complementarity to a mutant DMD allele, for example, a DMD allele with at least one mutation in any of exons 1-79 of DMD in humans that leads to a frameshift and improper RNA splicing/processing.

MYH7/Hypertrophic Cardiomyopathy

Examples of oligonucleotides useful as payloads, e.g., for targeting MYH7, are provided in US Patent Application Publication 20180094262, published on Apr. 5, 2018, entitled *Inhibitors of MYH7B and Uses Thereof*; US Patent Application Publication 20160348103, published on Dec. 1, 2016, entitled *Oligonucleotides and Methods for Treatment of Cardiomyopathy Using RNA Interference*; US Patent Application Publication 20160237430, published on Aug. 18, 2016, entitled *"Allele-specific RNA Silencing for the Treatment of Hypertrophic Cardiomyopathy"*; US Patent Application Publication 20160032286, published on Feb. 4, 2016, entitled *"Inhibitors of MYH7B and Uses Thereof"*; US Patent Application Publication 20140187603, published on Jul. 3, 2014, entitled *"MicroRNA Inhibitors Comprising Locked Nucleotides"*; US Patent Application Publication 20140179764, published on Jun. 26, 2014, entitled *"Dual Targeting of miR-208 and miR-499 in the Treatment of Cardiac Disorders"*; US Patent Application Publication 20120114744, published on May 10, 2012, entitled *"Compositions and Methods to Treat Muscular and Cardiovascular Disorders"*; the contents of each of which are incorporated herein in their entireties.

In some embodiments, the oligonucleotide may target lncRNA or mRNA, e.g., for degradation. In some embodiments, the oligonucleotide may target, e.g., for degradation, a nucleic acid encoding a protein involved in a mismatch repair pathway, e.g., MSH2, MutLalpha, MutSbeta, MutLalpha. Non-limiting examples of proteins involved in mismatch repair pathways, for which mRNAs encoding such proteins may be targeted by oligonucleotides described herein, are described in Iyer, R. R. et al., *"DNA triplet repeat expansion and mismatch repair"* Annu Rev Biochem. 2015; 84:199-226.; and Schmidt M. H. and Pearson C. E., "Disease-associated repeat instability and mismatch repair" DNA Repair (Amst). 2016 February; 38:117-26.

a. Oligonucleotide Size/Sequence

Oligonucleotides may be of a variety of different lengths, e.g., depending on the format. In some embodiments, an oligonucleotide is 7, 8, 9, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In a some embodiments, the oligonucleotide is 8 to 50 nucleotides in length, 8 to 40 nucleotides in length, 8 to 30 nucleotides in length, 10 to 15 nucleotides in length, 10 to 20 nucleotides in length, 15 to 25 nucleotides in length, 21 to 23 nucleotides in lengths, etc.

In some embodiments, a complementary nucleic acid sequence of an oligonucleotide for purposes of the present disclosure is specifically hybridizable or specific for the target nucleic acid when binding of the sequence to the target molecule (e.g., mRNA) interferes with the normal function of the target (e.g., mRNA) to cause a loss of activity (e.g., inhibiting translation) or expression (e.g., degrading a target mRNA) and there is a sufficient degree of complementarity to avoid non-specific binding of the sequence to non-target sequences under conditions in which avoidance of non-specific binding is desired, e.g., under physiological conditions in the case of in vivo assays or therapeutic treatment, and in the case of in vitro assays, under conditions in which the assays are performed under suitable conditions of stringency. Thus, in some embodiments, an oligonucleotide may be at least 80%, at least 85%, at least 90%, at least 91%, at least 92%, at least 93%, at least 94%, at least 95%, at least 96%, at least 97%, at least 98%, at least 99% or 100% complementary to the consecutive nucleotides of an target nucleic acid. In some embodiments a complementary nucleotide sequence need not be 100% complementary to that of its target to be specifically hybridizable or specific for a target nucleic acid.

In some embodiments, an oligonucleotide comprises region of complementarity to a target nucleic acid that is in the range of 8 to 15, 8 to 30, 8 to 40, or 10 to 50, or 5 to 50, or 5 to 40 nucleotides in length. In some embodiments, a region of complementarity of an oligonucleotide to a target nucleic acid is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the region of complementarity is complementary with at least 8 consecutive nucleotides of a target nucleic acid. In some embodiments, an oligonucleotide may contain 1, 2 or 3 base mismatches compared to the portion of the consecutive nucleotides of target nucleic acid. In some embodiments the oligonucleotide may have up to 3 mismatches over 15 bases, or up to 2 mismatches over 10 bases.

b. Oligonucleotide Modifications:

The oligonucleotides described herein may be modified, e.g., comprise a modified sugar moiety, a modified internucleoside linkage, a modified nucleotide and/or combinations thereof. In addition, in some embodiments, oligonucleotides may exhibit one or more of the following properties: do not mediate alternative splicing; are not immune stimulatory; are nuclease resistant; have improved cell uptake compared to unmodified oligonucleotides; are not toxic to cells or mammals; have improved endosomal exit internally in a cell; minimizes TLR stimulation; or avoid pattern recognition receptors. Any of the modified chemistries or formats of oligonucleotides described herein can be combined with each other. For example, one, two, three, four, five, or more different types of modifications can be included within the same oligonucleotide.

In some embodiments, certain nucleotide modifications may be used that make an oligonucleotide into which they are incorporated more resistant to nuclease digestion than the native oligodeoxynucleotide or oligoribonucleotide molecules; these modified oligonucleotides survive intact for a longer time than unmodified oligonucleotides. Specific examples of modified oligonucleotides include those comprising modified backbones, for example, modified internucleoside linkages such as phosphorothioates, phosphotriesters, methyl phosphonates, short chain alkyl or cycloalkyl intersugar linkages or short chain heteroatomic or heterocyclic intersugar linkages. Accordingly, oligonucleotides of the disclosure can be stabilized against nucleolytic degradation such as by the incorporation of a modification, e.g., a nucleotide modification.

In some embodiments, an oligonucleotide may be of up to 50 or up to 100 nucleotides in length in which 2 to 10, 2 to 15, 2 to 16, 2 to 17, 2 to 18, 2 to 19, 2 to 20, 2 to 25, 2 to 30, 2 to 40, 2 to 45, or more nucleotides of the oligonucleotide are modified nucleotides. The oligonucleotide may be of 8 to 30 nucleotides in length in which 2 to 10, 2 to 15, 2 to 16, 2 to 17, 2 to 18, 2 to 19, 2 to 20, 2 to 25, 2 to 30 nucleotides of the oligonucleotide are modified nucleotides. The oligonucleotide may be of 8 to 15 nucleotides in length in which 2 to 4, 2 to 5, 2 to 6, 2 to 7, 2 to 8, 2 to 9, 2 to 10, 2 to 11, 2 to 12, 2 to 13, 2 to 14 nucleotides of the oligonucleotide are modified nucleotides. Optionally, the oligonucleotides may have every nucleotide except 1, 2, 3, 4, 5, 6, 7, 8, 9, or 10 nucleotides modified. Oligonucleotide modifications are described further herein.

c. Modified Nucleotides

In some embodiments, an oligonucleotide include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O-N-methylacetamido (2'-O-NMA).

In some embodiments, an oligonucleotide can include at least one 2'-O-methyl-modified nucleotide, and in some embodiments, all of the nucleotides include a 2'-O-methyl modification. In some embodiments, an oligonucleotide comprises modified nucleotides in which the ribose ring comprises a bridge moiety connecting two atoms in the ring, e.g., connecting the 2'-O atom to the 4'-C atom. In some embodiments, the oligonucleotides are "locked," e.g., comprise modified nucleotides in which the ribose ring is "locked" by a methylene bridge connecting the 2'-O atom and the 4'-C atom. Examples of LNAs are described in International Patent Application Publication WO/2008/043753, published on Apr. 17, 2008, and entitled "*RNA Antagonist Compounds For The Modulation Of PCSK9*", the contents of which are incorporated herein by reference in its entirety.

Other modifications that may be used in the oligonucleotides disclosed herein include ethylene-bridged nucleic acids (ENAs). ENAs include, but are not limited to, 2'-0,4'-C-ethylene-bridged nucleic acids. Examples of ENAs are provided in International Patent Publication No. WO 2005/042777, published on May 12, 2005, and entitled "APP/ENA Antisense"; Morita et al., Nucleic Acid Res., Suppl 1:241-242, 2001; Surono et al., Hum. Gene Ther., 15:749-757, 2004; Koizumi, Curr. Opin. Mol. Ther., 8:144-149, 2006 and Horie et al., Nucleic Acids Symp. Ser (Oxf), 49:171-172, 2005; the disclosures of which are incorporated herein by reference in their entireties.

In some embodiments, the oligonucleotide may comprise a bridged nucleotide, such as a locked nucleic acid (LNA) nucleotide, a constrained ethyl (cEt) nucleotide, or an ethylene bridged nucleic acid (ENA) nucleotide. In some embodiments, the oligonucleotide comprises a modified nucleotide disclosed in one of the following United States Patent or Patent Application Publications: U.S. Pat. No. 7,399,845, issued on Jul. 15, 2008, and entitled "6-*Modified Bicyclic Nucleic Acid Analogs*"; U.S. Pat. No. 7,741,457, issued on Jun. 22, 2010, and entitled "6-*Modified Bicyclic Nucleic Acid Analogs*"; U.S. Pat. No. 8,022,193, issued on Sep. 20, 2011, and entitled "6-*Modified Bicyclic Nucleic Acid Analogs*"; U.S. Pat. No. 7,569,686, issued on Aug. 4, 2009, and entitled "*Compounds And Methods For Synthesis Of Bicyclic Nucleic Acid Analogs*"; U.S. Pat. No. 7,335,765, issued on Feb. 26, 2008, and entitled "*Novel Nucleoside And Oligonucleotide Analogues*"; U.S. Pat. No. 7,314,923, issued on Jan. 1, 2008, and entitled "*Novel Nucleoside And Oligonucleotide Analogues*"; U.S. Pat. No. 7,816,333, issued on Oct. 19, 2010, and entitled "*Oligonucleotide Analogues And Methods Utilizing The Same*" and US Publication Number 2011/0009471 now U.S. Pat. No. 8,957, 201, issued on Feb. 17, 2015, and entitled "*Oligonucleotide*

*Analogues And Methods Utilizing The Same*", the entire contents of each of which are incorporated herein by reference for all purposes.

In some embodiments, the oligonucleotide comprises at least one nucleotide modified at the 2' position of the sugar, preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA.

In some embodiments, the oligonucleotide may have at least one modified nucleotide that results in an increase in Tm of the oligonucleotide in a range of 1° C., 2° C., 3° C., 4° C., or 5° C. compared with an oligonucleotide that does not have the at least one modified nucleotide. The oligonucleotide may have a plurality of modified nucleotides that result in a total increase in Tm of the oligonucleotide in a range of 2° C., 3° C., 4° C., 5° C., 6° C., 7° C., 8° C., 9° C., 10° C., 15° C., 20° C., 25° C., 30° C., 35° C., 40° C., 45° C. or more compared with an oligonucleotide that does not have the modified nucleotide.

The oligonucleotide may comprise alternating nucleotides of different kinds. For example, an oligonucleotide may comprise alternating deoxyribonucleotides or ribonucleotides and 2'-fluoro-deoxyribonucleotides. An oligonucleotide may comprise alternating deoxyribonucleotides or ribonucleotides and 2'-O-methyl nucleotides. An oligonucleotide may comprise alternating 2'-fluoro nucleotides and 2'-O-methyl nucleotides. An oligonucleotide may comprise alternating bridged nucleotides and 2'-fluoro or 2'-O-methyl nucleotides.

d. Internucleotide Linkages/Backbones

In some embodiments, oligonucleotide may contain a phosphorothioate or other modified internucleotide linkage. In some embodiments, the oligonucleotide comprises phosphorothioate internucleoside linkages. In some embodiments, the oligonucleotide comprises phosphorothioate internucleoside linkages between at least two nucleotides. In some embodiments, the oligonucleotide comprises phosphorothioate internucleoside linkages between all nucleotides. For example, in some embodiments, oligonucleotides comprise modified internucleotide linkages at the first, second, and/or third internucleoside linkage at the 5' or 3' end of the nucleotide sequence.

Phosphorus-containing linkages that may be used include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563, 253; 5,571,799; 5,587,361; and 5,625,050.

In some embodiments, oligonucleotides may have heteroatom backbones, such as methylene(methylimino) or MMI backbones; amide backbones (see De Mesmaeker et al. Ace. Chem. Res. 1995, 28:366-374); morpholino backbones (see Summerton and Weller, U.S. Pat. No. 5,034,506); or peptide nucleic acid (PNA) backbones (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497).

e. Stereospecific Oligonucleotides

In some embodiments, internucleotidic phosphorus atoms of oligonucleotides are chiral, and the properties of the oligonucleotides are adjusted based on the configuration of the chiral phosphorus atoms. In some embodiments, appropriate methods may be used to synthesize P-chiral oligonucleotide analogs in a stereocontrolled manner (e.g., as described in Oka N, Wada T, Stereocontrolled synthesis of oligonucleotide analogs containing chiral internucleotidic phosphorus atoms. Chem Soc Rev. 2011 December; 40(12): 5829-43.) In some embodiments, phosphorothioate containing oligonucleotides are provided that comprise nucleoside units that are joined together by either substantially all Sp or substantially all Rp phosphorothioate intersugar linkages. In some embodiments, such phosphorothioate oligonucleotides having substantially chirally pure intersugar linkages are prepared by enzymatic or chemical synthesis, as described, for example, in U.S. Pat. No. 5,587,261, issued on Dec. 12, 1996, the contents of which are incorporated herein by reference in their entirety. In some embodiments, chirally controlled oligonucleotides provide selective cleavage patterns of a target nucleic acid. For example, in some embodiments, a chirally controlled oligonucleotide provides single site cleavage within a complementary sequence of a nucleic acid, as described, for example, in US Patent Application Publication 20170037399 A1, published on Feb. 2, 2017, entitled "CHIRAL DESIGN", the contents of which are incorporated herein by reference in their entirety.

f. Morpholinos

In some embodiments, the oligonucleotide may be a morpholino-based compounds. Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010; the disclosures of which are incorporated herein by reference in their entireties).

g. Peptide Nucleic Acids (PNAs)

In some embodiments, both a sugar and an internucleoside linkage (the backbone) of the nucleotide units of an oligonucleotide are replaced with novel groups. In some embodiments, the base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative publication that report the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

h. Gapmers

In some embodiments, the oligonucleotide is a gapmer. A gapmer oligonucleotide generally has the formula 5'-X—Y—Z-3', with X and Z as flanking regions around a gap region Y. In some embodiments, the Y region is a contiguous stretch of nucleotides, e.g., a region of at least 6 DNA nucleotides, which are capable of recruiting an RNAse, such as RNAse H. In some embodiments, the gapmer binds to the target nucleic acid, at which point an RNAse is recruited and can then cleave the target nucleic acid. In some embodiments, the Y region is flanked both 5' and 3' by regions X and Z comprising high-affinity modified nucleotides, e.g., one to six modified nucleotides. Examples of modified nucleotides include, but are not limited to, 2' MOE or 2'OMe or Locked Nucleic Acid bases (LNA). The flanking sequences X and Z may be of one to twenty nucleotides, one to eight nucleotides or one to five nucleotides in length, in some embodiments. The flanking sequences X and Z may be of similar length or of dissimilar lengths. The gap-segment Y may be a nucleotide sequence of five to twenty nucleotides, size to twelve nucleotides or six to ten nucleotides in length, in some embodiments.

In some embodiments, the gap region of the gapmer oligonucleotides may contain modified nucleotides known to be acceptable for efficient RNase H action in addition to DNA nucleotides, such as C4'-substituted nucleotides, acyclic nucleotides, and arabino-configured nucleotides. In some embodiments, the gap region comprises one or more unmodified internucleosides. In some embodiments, one or both flanking regions each independently comprise one or more phosphorothioate internucleoside linkages (e.g., phosphorothioate internucleoside linkages or other linkages) between at least two, at least three, at least four, at least five or more nucleotides. In some embodiments, the gap region and two flanking regions each independently comprise modified internucleoside linkages (e.g., phosphorothioate internucleoside linkages or other linkages) between at least two, at least three, at least four, at least five or more nucleotides.

A gapmer may be produced using appropriate methods. Representative U.S. patents, U.S. patent publications, and PCT publications that teach the preparation of gapmers include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; 5,898,031; 7,432,250; and 7,683,036; U.S. patent publication Nos. US20090286969, US20100197762, and US20110112170; and PCT publication Nos. WO2008049085 and WO2009090182, each of which is herein incorporated by reference in its entirety.

i. Mixmers

In some embodiments, an oligonucleotide described herein may be a mixmer or comprise a mixmer sequence pattern. In general, mixmers are oligonucleotides that comprise both naturally and non-naturally occurring nucleotides or comprise two different types of non-naturally occurring nucleotides typically in an alternating pattern. Mixmers generally have higher binding affinity than unmodified oligonucleotides and may be used to specifically bind a target molecule, e.g., to block a binding site on the target molecule. Generally, mixmers do not recruit an RNAse to the target molecule and thus do not promote cleavage of the target molecule. Such oligonucleotides that are incapable of recruiting RNAse H have been described, for example, see WO2007/112754 or WO2007/112753.

In some embodiments, the mixmer comprises or consists of a repeating pattern of nucleotide analogues and naturally occurring nucleotides, or one type of nucleotide analogue and a second type of nucleotide analogue. However, a mixmer need not comprise a repeating pattern and may instead comprise any arrangement of modified nucleotides and naturally occurring nucleotides or any arrangement of one type of modified nucleotide and a second type of modified nucleotide. The repeating pattern, may, for instance be every second or every third nucleotide is a modified nucleotide, such as LNA, and the remaining nucleotides are naturally occurring nucleotides, such as DNA, or are a 2' substituted nucleotide analogue such as 2'MOE or 2' fluoro analogues, or any other modified nucleotide described herein. It is recognized that the repeating pattern of modified nucleotide, such as LNA units, may be combined with modified nucleotide at fixed positions—e.g. at the 5' or 3' termini.

In some embodiments, a mixmer does not comprise a region of more than 5, more than 4, more than 3, or more than 2 consecutive naturally occurring nucleotides, such as DNA nucleotides. In some embodiments, the mixmer comprises at least a region consisting of at least two consecutive modified nucleotide, such as at least two consecutive LNAs. In some embodiments, the mixmer comprises at least a region consisting of at least three consecutive modified nucleotide units, such as at least three consecutive LNAs.

In some embodiments, the mixmer does not comprise a region of more than 7, more than 6, more than 5, more than 4, more than 3, or more than 2 consecutive nucleotide analogues, such as LNAs. In some embodiments, LNA units may be replaced with other nucleotide analogues, such as those referred to herein.

Mixmers may be designed to comprise a mixture of affinity enhancing modified nucleotides, such as in non-limiting example LNA nucleotides and 2'-O-methyl nucleotides. In some embodiments, a mixmer comprises modified internucleoside linkages (e.g., phosphorothioate internucleoside linkages or other linkages) between at least two, at least three, at least four, at least five or more nucleotides.

A mixmer may be produced using any suitable method. Representative U.S. patents, U.S. patent publications, and PCT publications that teach the preparation of mixmers include U.S. patent publication Nos. US20060128646, US20090209748, US20090298916, US20110077288, and US20120322851, and U.S. Pat. No. 7,687,617.

In some embodiments, a mixmer comprises one or more morpholino nucleotides. For example, in some embodiments, a mixmer may comprise morpholino nucleotides mixed (e.g., in an alternating manner) with one or more other nucleotides (e.g., DNA, RNA nucleotides) or modified nucleotides (e.g., LNA, 2'-O-Methyl nucleotides).

In some embodiments, mixmers are useful for splice correcting or exon skipping, for example, as reported in Touznik A., et al., *LNA/DNA mixmer-based antisense oligonucleotides correct alternative splicing of the SMN2 gene and restore SMN protein expression in type* 1 *SMA fibroblasts* Scientific Reports, volume 7, Article number: 3672 (2017), Chen S. et al., *Synthesis of a Morpholino Nucleic Acid (MNA)-Uridine Phosphoramidite, and Exon Skipping Using MNA/2'-O-Methyl Mixmer Antisense Oligonucleotide*, Molecules 2016, 21, 1582, the contents of each which are incorporated herein by reference.

j. RNA Interference (RNAi)

In some embodiments, oligonucleotides provided herein may be in the form of small interfering RNAs (siRNA), also known as short interfering RNA or silencing RNA. SiRNA, is a class of double-stranded RNA molecules, typically about 20-25 base pairs in length that target nucleic acids (e.g., mRNAs) for degradation via the RNA interference (RNAi) pathway in cells. Specificity of siRNA molecules may be determined by the binding of the antisense strand of the molecule to its target RNA. Effective siRNA molecules are generally less than 30 to 35 base pairs in length to prevent the triggering of non-specific RNA interference pathways in the cell via the interferon response, although longer siRNA can also be effective.

Following selection of an appropriate target RNA sequence, siRNA molecules that comprise a nucleotide sequence complementary to all or a portion of the target sequence, i.e. an antisense sequence, can be designed and prepared using appropriate methods (see, e.g., PCT Publication Number WO 2004/016735; and U.S. Patent Publication Nos. 2004/0077574 and 2008/0081791).

The siRNA molecule can be double stranded (i.e. a dsRNA molecule comprising an antisense strand and a complementary sense strand) or single-stranded (i.e. a ssRNA molecule comprising just an antisense strand). The siRNA molecules can comprise a duplex, asymmetric duplex, hairpin or asymmetric hairpin secondary structure, having self-complementary sense and antisense strands.

Double-stranded siRNA may comprise RNA strands that are the same length or different lengths. Double-stranded siRNA molecules can also be assembled from a single oligonucleotide in a stem-loop structure, wherein self-complementary sense and antisense regions of the siRNA molecule are linked by means of a nucleic acid based or non-nucleic acid-based linker(s), as well as circular single-stranded RNA having two or more loop structures and a stem comprising self-complementary sense and antisense strands, wherein the circular RNA can be processed either in vivo or in vitro to generate an active siRNA molecule capable of mediating RNAi. Small hairpin RNA (shRNA) molecules thus are also contemplated herein. These molecules comprise a specific antisense sequence in addition to the reverse complement (sense) sequence, typically separated by a spacer or loop sequence. Cleavage of the spacer or loop provides a single-stranded RNA molecule and its reverse complement, such that they may anneal to form a dsRNA molecule (optionally with additional processing steps that may result in addition or removal of one, two, three or more nucleotides from the 3' end and/or the 5' end of either or both strands). A spacer can be of a sufficient length to permit the antisense and sense sequences to anneal and form a double-stranded structure (or stem) prior to cleavage of the spacer (and, optionally, subsequent processing steps that may result in addition or removal of one, two, three, four, or more nucleotides from the 3' end and/or the 5' end of either or both strands). A spacer sequence is may be an unrelated nucleotide sequence that is situated between two complementary nucleotide sequence regions which, when annealed into a double-stranded nucleic acid, comprise a shRNA.

The overall length of the siRNA molecules can vary from about 14 to about 100 nucleotides depending on the type of siRNA molecule being designed. Generally between about 14 and about 50 of these nucleotides are complementary to the RNA target sequence, i.e. constitute the specific antisense sequence of the siRNA molecule. For example, when the siRNA is a double- or single-stranded siRNA, the length can vary from about 14 to about 50 nucleotides, whereas when the siRNA is a shRNA or circular molecule, the length can vary from about 40 nucleotides to about 100 nucleotides.

An siRNA molecule may comprise a 3' overhang at one end of the molecule, The other end may be blunt-ended or have also an overhang (5' or 3'). When the siRNA molecule comprises an overhang at both ends of the molecule, the length of the overhangs may be the same or different. In one embodiment, the siRNA molecule of the present disclosure comprises 3' overhangs of about 1 to about 3 nucleotides on both ends of the molecule.

k. microRNA (miRNAs)

In some embodiments, an oligonucleotide may be a microRNA (miRNA). MicroRNAs (referred to as "miRNAs") are small non-coding RNAs, belonging to a class of regulatory molecules that control gene expression by binding to complementary sites on a target RNA transcript. Typically, miRNAs are generated from large RNA precursors (termed pri-miRNAs) that are processed in the nucleus into approximately 70 nucleotide pre-miRNAs, which fold into imperfect stem-loop structures. These pre-miRNAs typically undergo an additional processing step within the cytoplasm where mature miRNAs of 18-25 nucleotides in length are excised from one side of the pre-miRNA hairpin by an RNase III enzyme, Dicer.

As used herein, miRNAs including pri-miRNA, pre-miRNA, mature miRNA or fragments of variants thereof that retain the biological activity of mature miRNA. In one embodiment, the size range of the miRNA can be from 21 nucleotides to 170 nucleotides. In one embodiment the size range of the miRNA is from 70 to 170 nucleotides in length. In another embodiment, mature miRNAs of from 21 to 25 nucleotides in length can be used.

l. Aptamers

In some embodiments, oligonucleotides provided herein may be in the form of aptamers. Generally, in the context of molecular payloads, aptamer is any nucleic acid that binds specifically to a target, such as a small molecule, protein, nucleic acid in a cell. In some embodiments, the aptamer is a DNA aptamer or an RNA aptamer. In some embodiments, a nucleic acid aptamer is a single-stranded DNA or RNA (ssDNA or ssRNA). It is to be understood that a single-stranded nucleic acid aptamer may form helices and/or loop structures. The nucleic acid that forms the nucleic acid aptamer may comprise naturally occurring nucleotides, modified nucleotides, naturally occurring nucleotides with hydrocarbon linkers (e.g., an alkylene) or a polyether linker (e.g., a PEG linker) inserted between one or more nucleotides, modified nucleotides with hydrocarbon or PEG linkers inserted between one or more nucleotides, or a combination of thereof. Exemplary publications and patents describing aptamers and method of producing aptamers include, e.g., Lorsch and Szostak, 1996; Jayasena, 1999; U.S. Pat. Nos. 5,270,163; 5,567,588; 5,650,275; 5,670,637; 5,683,867; 5,696,249; 5,789,157; 5,843,653; 5,864,026; 5,989,823; 6,569,630; 8,318,438 and PCT application WO 99/31275, each incorporated herein by reference.

m. Ribozymes

In some embodiments, oligonucleotides provided herein may be in the form of a ribozyme. A ribozyme (ribonucleic acid enzyme) is a molecule, typically an RNA molecule, that is capable of performing specific biochemical reactions, similar to the action of protein enzymes. Ribozymes are molecules with catalytic activities including the ability to cleave at specific phosphodiester linkages in RNA molecules to which they have hybridized, such as mRNAs, RNA-containing substrates, lncRNAs, and ribozymes, themselves.

Ribozymes may assume one of several physical structures, one of which is called a "hammerhead." A hammerhead ribozyme is composed of a catalytic core containing nine conserved bases, a double-stranded stem and loop structure (stem-loop II), and two regions complementary to the target RNA flanking regions the catalytic core. The flanking regions enable the ribozyme to bind to the target RNA specifically by forming double-stranded stems I and III. Cleavage occurs in cis (i.e., cleavage of the same RNA molecule that containing the hammerhead motif) or in trans (cleavage of an RNA substrate other than that containing the ribozyme) next to a specific ribonucleotide triplet by a transesterification reaction from a 3', 5'-phosphate diester to a 2', 3'-cyclic phosphate diester. Without wishing to be bound by theory, it is believed that this catalytic activity requires the presence of specific, highly conserved sequences in the catalytic region of the ribozyme.

Modifications in ribozyme structure have also included the substitution or replacement of various non-core portions of the molecule with non-nucleotidic molecules. For example, Benseler et al. (J. Am. Chem. Soc. (1993) 115: 8483-8484) disclosed hammerhead-like molecules in which two of the base pairs of stem II, and all four of the nucleotides of loop II were replaced with non-nucleoside linkers based on hexaethylene glycol, propanediol, bis(triethylene glycol) phosphate, tris(propanediol)bisphosphate, or bis(propanediol) phosphate. Ma et al. (Biochem. (1993) 32:1751-1758; Nucleic Acids Res. (1993) 21:2585-2589) replaced the six nucleotide loop of the TAR ribozyme hairpin with non-nucleotidic, ethylene glycol-related linkers. Thomson et al. (Nucleic Acids Res. (1993) 21:5600-5603) replaced loop II with linear, non-nucleotidic linkers of 13, 17, and 19 atoms in length.

Ribozyme oligonucleotides can be prepared using well known methods (see, e.g., PCT Publications WO9118624; WO9413688; WO9201806; and WO 92/07065; and U.S. Pat. Nos. 5,436,143 and 5,650,502) or can be purchased from commercial sources (e.g., US Biochemicals) and, if desired, can incorporate nucleotide analogs to increase the resistance of the oligonucleotide to degradation by nucleases in a cell. The ribozyme may be synthesized in any known manner, e.g., by use of a commercially available synthesizer produced, e.g., by Applied Biosystems Inc. or Milligen. The ribozyme may also be produced in recombinant vectors by conventional means. See, Molecular Cloning: A Laboratory Manual, Cold Spring Harbor Laboratory (Current edition). The ribozyme RNA sequences maybe synthesized conventionally, for example, by using RNA polymerases such as T7 or SP6.

n. Guide Nucleic Acids

In some embodiments, oligonucleotides are guide nucleic acid, e.g., guide RNA (gRNA) molecules. Generally, a guide RNA is a short synthetic RNA composed of (1) a scaffold sequence that binds to a nucleic acid programmable DNA binding protein (napDNAbp), such as Cas9, and (2) a nucleotide spacer portion that defines the DNA target sequence (e.g., genomic DNA target) to which the gRNA binds in order to bring the nucleic acid programmable DNA binding protein in proximity to the DNA target sequence. In some embodiments, the napDNAbp is a nucleic acid-programmable protein that forms a complex with (e.g., binds or associates with) one or more RNA(s) that targets the nucleic acid-programmable protein to a target DNA sequence (e.g., a target genomic DNA sequence). In some embodiments, a nucleic acid-programmable nuclease, when in a complex with an RNA, may be referred to as a nuclease:RNA complex. Guide RNAs can exist as a complex of two or more RNAs, or as a single RNA molecule.

Guide RNAs (gRNAs) that exist as a single RNA molecule may be referred to as single-guide RNAs (sgRNAs), though gRNA is also used to refer to guide RNAs that exist as either single molecules or as a complex of two or more molecules. Typically, gRNAs that exist as a single RNA species comprise two domains: (1) a domain that shares homology to a target nucleic acid (i.e., directs binding of a Cas9 complex to the target); and (2) a domain that binds a Cas9 protein. In some embodiments, domain (2) corresponds to a sequence known as a tracrRNA and comprises a stem-loop structure. In some embodiments, domain (2) is identical or homologous to a tracrRNA as provided in Jinek et al., Science 337:816-821 (2012), the entire contents of which is incorporated herein by reference.

In some embodiments, a gRNA comprises two or more of domains (1) and (2), and may be referred to as an extended gRNA. For example, an extended gRNA will bind two or more Cas9 proteins and bind a target nucleic acid at two or more distinct regions, as described herein. The gRNA comprises a nucleotide sequence that complements a target site, which mediates binding of the nuclease/RNA complex to said target site, providing the sequence specificity of the nuclease:RNA complex. In some embodiments, the RNA-programmable nuclease is the (CRISPR-associated system) Cas9 endonuclease, for example, Cas9 (Csn1) from Streptococcus pyogenes (see, e.g., "Complete genome sequence of an M1 strain of Streptococcus pyogenes." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663 (2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607 (2011); and "A programmable dual-RNA-guided DNA endonuclease in adaptive bacterial immunity." Jinek M., Chylinski K., Fonfara I., Hauer M., Doudna J. A., Charpentier E. Science 337:816-821 (2012), the entire contents of each of which are incorporated herein by reference.

o. Splice Altering Oligonucleotides

In some embodiments, a oligonucleotide (e.g., an antisense oligonucleotide including a morpholino) of the present disclosure target splicing. In some embodiments, the oligonucleotide targets splicing by inducing exon skipping and restoring the reading frame within a gene. As a non-limiting example, the oligonucleotide may induce skipping of an exon encoding a frameshift mutation and/or an exon that encodes a premature stop codon. In some embodiments, an oligonucleotide may induce exon skipping by blocking spliceosome recognition of a splice site. In some embodiments, exon skipping results in a truncated but functional protein compared to the reference protein (e.g., truncated but functional DMD protein as described below). In some embodiments, the oligonucleotide promotes inclusion of a particular exon (e.g., exon 7 of the SMN2 gene described below). In some embodiments, an oligonucleotide may induce inclusion of an exon by targeting a splice site inhibitory sequence. RNA splicing has been implicated in muscle diseases, including Duchenne muscular dystrophy (DMD) and spinal muscular atrophy (SMA).

Alterations (e.g., deletions, point mutations, and duplications) in the gene encoding dystrophin (DMD) cause DMD. These alterations can lead to frameshift mutations and/or nonsense mutations. In some embodiments, an oligonucleotide of the present disclosure promotes skipping of one or more DMD exons (e.g., exon 8, exon 43, exon 44, exon 45, exon 50, exon 51, exon 52, exon 53, and/or exon 55) and results in a functional truncated protein. See, e.g., U.S. Pat. No. 8,486,907 published on Jul. 16, 2013 and U.S. 20140275212 published on Sep. 18, 2014.

In SMA, there is loss of functional SMN1. Although the SMN2 gene is a paralog to SMN1, alternative splicing of the SMN2 gene predominantly leads to skipping of exon 7 and subsequent production of a truncated SMN protein that cannot compensate for SMN1 loss. In some embodiments, an oligonucleotide of the present disclosure promotes inclusion of SMN2 exon 7. In some embodiments, an oligonucleotide is an antisense oligonucleotide that targets SMN2 splice site inhibitory sequences (see, e.g., U.S. Pat. No. 7,838,657, which was published on Nov. 23, 2010).

p. Multimers

In some embodiments, molecular payloads may comprise multimers (e.g., concatemers) of 2 or more oligonucleotides connected by a linker. In this way, in some embodiments, the oligonucleotide loading of a complex/conjugate can be increased beyond the available linking sites on a targeting agent (e.g., available thiol sites on an antibody) or otherwise tuned to achieve a particular payload loading content. Oligonucleotides in a multimer can be the same or different (e.g., targeting different genes or different sites on the same gene or products thereof).

In some embodiments, multimers comprise 2 or more oligonucleotides linked together by a cleavable linker. However, in some embodiments, multimers comprise 2 or more oligonucleotides linked together by a non-cleavable linker. In some embodiments, a multimer comprises 2, 3, 4, 5, 6, 7, 8, 9, 10 or more oligonucleotides linked together. In some embodiments, a multimer comprises 2 to 5, 2 to 10 or 4 to 20 oligonucleotides linked together.

In some embodiments, a multimer comprises 2 or more oligonucleotides linked end-to-end (in a linear arrangement). In some embodiments, a multimer comprises 2 or more oligonucleotides linked end-to-end via a oligonucleotide based linker (e.g., poly-dT linker, an abasic linker). In some embodiments, a multimer comprises a 5' end of one oligonucleotide linked to a 3' end of another oligonucleotide. In some embodiments, a multimer comprises a 3' end of one oligonucleotide linked to a 3' end of another oligonucleotide. In some embodiments, a multimer comprises a 5' end of one oligonucleotide linked to a 5' end of another oligonucleotide. Still, in some embodiments, multimers can comprise a branched structure comprising multiple oligonucleotides linked together by a branching linker.

Further examples of multimers that may be used in the complexes provided herein are disclosed, for example, in US Patent Application Number 2015/0315588 A1, entitled *Methods of delivering multiple targeting oligonucleotides to a cell using cleavable linkers*, which was published on Nov. 5, 2015; US Patent Application Number 2015/0247141 A1, entitled *Multimeric Oligonucleotide Compounds*, which was published on Sep. 3, 2015, US Patent Application Number US 2011/0158937 A1, entitled *Immunostimulatory Oligonucleotide Multimers*, which was published on Jun. 30, 2011; and U.S. Pat. No. 5,693,773, entitled *Triplex-Forming Antisense Oligonucleotides Having Abasic Linkers Targeting Nucleic Acids Comprising Mixed Sequences Of Purines And Pyrimidines*, which issued on Dec. 2, 1997, the contents of each of which are incorporated herein by reference in their entireties.

ii. Small Molecules:

Any suitable small molecule may be used as a molecular payload, as described herein. Non-limiting examples are provided below for selected genes of Table 1.

DMPK/DM1

In some embodiments, e.g., for the treatment of DM, the small molecule is as described in US Patent Application Publication 2016052914A1, published on Feb. 25, 2016, entitled "*Compounds And Methods For Myotonic Dystrophy Therapy*". Further examples of small molecule payloads are provided in Lopez-Morato M, et al., Small Molecules Which Improve Pathogenesis of Myotonic Dystrophy Type 1, (Review) Front. Neurol., 18 May 2018. For example, in some embodiments, the small molecule is an MBNL1 upregulator such as phenylbuthazone, ketoprofen, ISOX, or vorinostat. In some embodiments, the small molecule is an H-Ras pathway inhibitor such as manumycin A. In some embodiments, the small molecule is a protein kinase modulator such as Ro-318220, C16, C51, Metformin, AICAR, lithium chloride, TDZD-8 or Bio. In some embodiments, the small molecule is a plant alkaloid such as harmine. In some embodiments, the small molecule is a transcription inhibitor such as pentamidine, propamidine, heptamidiine or actinomycin D. In some embodiments, the small molecule is an inhibitor of Glycogen synthase kinase 3 beta (GSK3B), for example, as disclosed in Jones K, et al., GSK30 mediates muscle pathology in myotonic dystrophy. J Clin Invest. 2012 December; 122(12):4461-72; and Wei C, et al., GSK30 is a new therapeutic target for myotonic dystrophy type 1. Rare Dis. 2013; 1: e26555; and Palomo V, et al., Subtly Modulating Glycogen Synthase Kinase 3 β: Allosteric Inhibitor Development and Their Potential for the Treatment of Chronic Diseases. J Med Chem. 2017 Jun. 22; 60(12):4983-5001, the contents of each of which are incorporated herein by reference in their entireties. In some embodiments, the small molecule is a substituted pyrido[2,3-d]pyrimidines and pentamidine-like compound, as disclosed in Gonzalez A L, et al., In silico discovery of substituted pyrido[2,3-d] pyrimidines and pentamidine-like compounds with biological activity in myotonic dystrophy models. PLoS One. 2017 Jun. 5; 12(6):e0178931, the contents of which are incorporated herein by reference in its entirety. In some embodiments, the small molecule is an MBNL1 modulator, for example, as disclosed in: Zhange F, et al., A flow cytometry-based screen identifies MBNL1 modulators that rescue splicing defects in myotonic dystrophy type I. Hum Mol Genet. 2017 Aug. 15; 26(16):3056-3068, the contents of which are incorporated herein by reference in its entirety.

DUX4/FSHD

In some embodiments, e.g., for the treatment of FSHD, the small molecule payload is as described in US Patent Application Publication 20170340606, published on Nov. 30, 2017, entitled "METHODS OF TREATING MUSCULAR DYSTROPHY" or as described in US Patent Application Publication 20180050043, published on Feb. 22, 2018, entitled "INHIBITION OF DUX4 EXPRESSION USING BROMODOMAIN AND EXTRA-TERMINAL DOMAIN PROTEIN INHIBITORS (BETi). Further examples of small molecule payloads are provided in Bosnakovski, D., et al., High-throughput screening identifies inhibitors of DUX4-induced myoblast toxicity, Skelet Muscle, February 2014, and Choi. S., et al., "Transcriptional Inhibitors Identified in a 160,000-Compound Small-Molecule DUX4 Viability Screen," Journal of Biomolecular Screening, 2016. For example, in some embodiments, the small molecule is a transcriptional inhibitor, such as SHC351, SHC540, SHC572. In some embodiments, the small molecule is STR00316 increases production or activity of another protein, such as integrin. In some embodiments, the small molecule is a bromodomain inhibitor (BETi), such as JQ1, PF1-1, I-BET-762, I-BET-151, RVX-208, or CPI-0610.

DNM/CNM

In some embodiments, e.g., for the treatment of CNM, the small molecule, for the treatment of CNM, is as described in US Patent Application Publication Number 20160264976, published on Sep. 15, 2016, entitled "DYNAMIN 2 INHIBITOR FOR TREATMENT OF CENTRONUCLEAR MYOPATHIES". For example, in some embodiments, the small molecule is selected from a group consisting of 3-Hydroxynaphthalene-2-carboxylic acid (3,4-dihydroxybenzylidene) hydrazide, 3-Hydroxy-N'-[(2,4,5-trihydroxyphenyl)methylidene]naphthalene-2-carbohydr-azide. In some embodiments, the small molecule is as described in US Patent Application Publication Number 20180000762, published Jan. 4, 2018, entitled "COMPOSITION AND METHOD FOR MUSCLE REPAIR AND REGENERATION". In some embodiments, the small molecule is a retinoic receptor agonist, such as 4-[(E)-2-[5,6,7,8-Tetrahydro-5,5,8,8-tetramethyl-3-(1H-pyrazol-1-ylmethyl-)-2-naphthalenyl]-ethenyl]-benzoic acid. In some embodiments, the small molecule is as described in US Patent Application Publication Number 20170119748, published May 4, 2017, entitled "METHODS, COMPOUNDS, AND COMPOSITIONS FOR THE TREATMENT OF MUSCULOSKELETAL DISEASES." The contents of each of these publications listed above are incorporated herein in their entirety.

Pompe Disease

In some embodiments, e.g., for the treatment of Pompe disease, the small molecule is a 1-deoxynojirimycin (DNJ) derivative, such as N-butyl-DNJ, N-methyl-DNJ, or N-cyclopropylmethyl-DNJ as described in US Patent Application Publication Number 20160051528, published on Feb. 25, 2016, entitled "METHOD FOR TREATMENT OF POMPE DISEASE USING 1-DEOXYNOJIRIMYCIN DERIVATIVES". In some embodiments, the small molecule DNJ derivative is used as a molecular chaperone to increase the activity of a GAA. In some embodiments, the non-inhibitory acid alpha glucosidase chaperone ML247 small molecule is utilized as in Marugan, et al., "Discovery, SAR, and Biological Evaluation of a Non-Inhibitory Chaperone for Acid Alpha Glucosidase," published in Probe Reports from NIH Molecular Libraries in December 2011. For example, the small molecule chaperone ML247 is utilized to increase the activity of a PD-associated GAA allele or a wild-type GAA allele. The contents of each of these publications listed above are incorporated herein in their entirety.

FXN/Friedreich's Ataxia

In some embodiments, e.g., for the treatment of Friedreich's Ataxia, the small molecule is as described in Herman D. et al. "Histone deacetylase inhibitors reverse gene silencing in Friedreich's ataxia." Nat Chem Biol. 2006; 2:551-558. In some embodiments, the small molecule is as described in Rai, M. et al. "HDAC inhibitors correct frataxin deficiency in a Friedreich ataxia mouse model." PLoS One. 2008 Apr. 9; 3(4):e1958. Further examples of small molecule payloads are provided in Richardson, T. E. et al, "Therapeutic strategies in Friedreich's Ataxia", Brain Res. 2013 Jun. 13; 1514: 91-97; Zeier Z et al. "Bromodomain inhibitors regulate the C90RF72 locus in ALS" Exp Neurol. 2015 September; 271:241-50.; and Gottesfeld J. M. "Small molecules affecting transcription in Friedreich ataxia." Pharmacol Ther. 2007 November; 116(2):236-48. For example, in some embodiments, the small molecule is an inhibitor of a histone deacetylase, e.g., BML-210 and compound 106. In some embodiments, the small molecule is 17β-Estradiol or methylene blue. In some embodiments, the small molecule targets, e.g., binds to, a disease-associated-repeat and/or R-loop. In some embodiments, the small molecule is as described in WO 2004/003565, published Jan. 8, 2004, "A screening method and compounds for treating friedreich ataxia". In some embodiments, the small molecule is a Glutathione peroxidase mimetic.

DMD/Dystrophinopathies

In some embodiments, the small molecule enhances exon skipping of an mRNA expression from a mutant DMD allele. In some embodiments, the small molecule is as described in US Patent Application Publication US20140080896A1, published Mar. 20, 2014, entitled "IDENTIFICATION OF SMALL MOLECULES THAT FACILITATE THERAPEUTIC EXON SKIPPING". Further examples of small molecule payloads are provided in U.S. Pat. No. 9,982,260, issued May 29, 2018, entitled "Identification of structurally similar small molecules that enhance therapeutic exon skipping". For example, in some embodiments, the small molecule is an enhancer of exon skipping such as perphenazine, flupentixol, zuclopenthixol or corynanthine. In some embodiments, a small molecule enhancer of exon skipping inhibits the ryanodine receptor or calmodulin. In some embodiments, the small molecule is an H-Ras pathway inhibitor such as manumycin A. In some embodiments, the small molecule is a suppressor of stop codons and desensitizes ribosomes to premature stop codons. In some embodiments, the small molecule is ataluren, as described in McElroy S. P. et al. "A Lack of Premature Termination Codon Read Through Efficacy of PTC124 (Ataluren) in a Diverse Array of Reporter Assays." PLOS Biology, published Jun. 25, 2013. In some embodiments, the small molecule is a corticosteroid, e.g., as described in Manzur, A. Y. et al. "Glucocorticoid corticosteroids for Duchenne muscular dystrophy". Cochrane Database Syst Rev. 2004; (2):CD003725. In some embodiments, the small molecule upregulates the expression and/or activity of genes that can replace the function of dystrophin, such as utrophin. In some embodiments, a utrophin modulator is as described in International Publication No. WO2007091106, published Aug. 16, 2007, entitled "TREATMENT OF DUCHENNE MUSCULAR DYSTROPHY" and/or International Publication No. WO/2017/168151, published Oct. 5, 2017, entitled "COMPOSITION FOR THE TREATMENT OF DUCHENNE MUSCULAR DYSTROPHY".

MYH7/Hypertrophic Cardiomyopathy

In some embodiments, the small molecule is a hypomethylating agent, such as 5-Azacytidine or 5-Aza-2'-Deoxycytidine, which modulates the expression of the MYH7 gene, such as in US Patent Application Publication 20160106771, published on Apr. 21, 2016, entitled *Therapies for Cardiomyopathy*; in some embodiments, the small molecule is a JAK-STAT inhibitor such as nifuroxazide, ketoprofen, sulfasalazine, 5,15-diphenylporphyrin, or AG490, such as in US Patent Application Publication 20180185478, published on Jul. 5, 2018, entitled *Treatment for Myopathy*; in some embodiments the small molecule is para-Nitroblebbistatin, which reduces the force of myosin contraction while not changing the dissociation of ADP, as in Tang, W., et al. "Modulating Beta-Cardiac Myosin Function at the Molecular and Tissue Levels," *Front. Physiol.* 2016 (7): 659, the contents of any of which are incorporated herein by reference in their entirety.

iii. Peptides/Proteins

Any suitable peptide or protein may be used as a molecular payload, as described herein. In some embodiments, a protein is an enzyme (e.g., an acid alpha-glucosidase, e.g., as encoded by the GAA gene). These peptides or proteins may be produced, synthesized, and/or derivatized using several methodologies, e.g. phage displayed peptide libraries, one-bead one-compound peptide libraries, or positional scanning synthetic peptide combinatorial libraries. Exemplary methodologies have been characterized in the art and are incorporated by reference (Gray, B. P. and Brown, K. C. "Combinatorial Peptide Libraries: Mining for Cell-Binding Peptides" Chem Rev. 2014, 114:2, 1020-1081.; Samoylova, T. I. and Smith, B. F. "Elucidation of muscle-binding peptides by phage display screening." Muscle Nerve, 1999, 22:4. 460-6.).

Non-limiting examples are provided below for selected genes of Table 1.

DMPK/DM1

A peptide or protein payload, e.g., for the treatment of DM1, may correspond to a sequence of a protein that preferentially binds to a nucleic acid, e.g. a disease-associated repeat, or a protein, e.g. MBNL1, found in muscle cells. In some embodiments, the peptide is as described in US Patent Application 2018/0021449, published on Jan. 25, 2018, "Antisense conjugates for decreasing expression of DMPK". In some embodiments, the peptide is as described in Garcia-Lopez et al., "In vivo discovery of a peptide that prevents CUG-RNA hairpin formation and reverses RNA toxicity in myotonic dystrophy models", *PNAS* Jul. 19, 2011. 108 (29) 11866-11871. In some embodiments, the peptide or protein may target, e.g., bind to, a disease-associated repeat, e.g. a RNA CUG repeat expansion.

In some embodiments, e.g., for the treatment of DM1, the peptide or protein comprises a fragment of an MBNL protein, e.g., MBNL1. In some embodiments, the peptide or protein comprises at least one zinc finger. In some embodiments, the peptide or protein may comprise about 2-25 amino acids, about 2-20 amino acids, about 2-15 amino acids, about 2-10 amino acids, or about 2-5 amino acids. The peptide or protein may comprise naturally-occurring amino acids, e.g. cysteine, alanine, or non-naturally-occurring or modified amino acids. Non-naturally occurring amino acids include β-amino acids, homo-amino acids, proline derivatives, β-substituted alanine derivatives, linear core amino acids, N-methyl amino acids, and others known in the art. In some embodiments, the peptide may be linear; in other embodiments, the peptide may be cyclic, e.g. bicyclic.

DUX4/FSHD

In some embodiments, e.g., for the treatment of FSHD, the peptide or protein may bind a DME1 or DME2 enhancer to inhibit DUX4 expression, e.g., by blocking binding of an activator.

DNM2/CNM

In some embodiments, e.g., for the treatment of CNM, the peptide is a dynamin inhibitor peptide with amino acid sequence QVPSRPNRAP, as described in US Patent Application Publication Number 20160264976, published on Sep. 15, 2016, entitled "DYNAMIN 2 INHIBITOR FOR TREATMENT OF CENTRONUCLEAR MYOPATHIES".

Pompe Disease

In some embodiments, e.g., for the treatment of Pompe disease, the molecular payload is a protein or enzyme such as an acid alpha-glucosidase or wild-type GAA protein or an active fragment thereof as in US Patent Application Publication Number 20160346363, published on Dec. 1, 2016, entitled "METHODS AND ORAL FORMULATIONS FOR ENZYME REPLACEMENT THERAPY OF HUMAN LYSOSOMAL AND METABOLIC DISEASES," US Patent Application Publication Number 20160279254, published Sep. 29, 2016, entitled "METHODS AND MATERIALS FOR TREATMENT OF POMPE'S DISEASE", or US Patent Application Publication Number 20130243746, published on Sep. 19, 2013, entitled "METHODS AND MATERIALS FOR TREATMENT OF POMPE'S DISEASE". In some embodiments, the acid alpha-glucosidase or wild-type GAA protein increases the GAA activity of a subject. In some embodiments, the acid alpha-glucosidase or wild-type GAA protein is encoded by the GAA gene.

ACVR1/FOP

In some embodiments, e.g., for the treatment of FOP, the peptide or protein is a BMP inhibitor such as regulatory SMAD 6 and 7 or fragment thereof. Additional examples of peptides or proteins are included in Cappato, S. et al. "The Horizon of a Therapy for Rare Genetic Diseases: A "Druggable" Future for Fibrodysplasia Ossificans Progressiva" Int. J. Mol. Sci. 2018, 19(4), 989. The contents of each of the foregoing are incorporated herein by reference in their entireties.

FXN/Freidrich Ataxia

In some embodiments, e.g., for the treatment of Friedreich's Ataxia, the peptide is as described in U.S. Pat. No. 8,815,230, filed Aug. 30, 2010, "Methods for treating Friedreich's ataxia with interferon gamma". In some embodiments, the peptide is as described in Britti, E. et al. "Frataxin-deficient neurons and mice models of Friedreich ataxia are improved by TAT-MTScs-FXN treatment." J Cell Mol Med. 2018 February; 22(2):834-848. In some embodiments, the peptide is as described in Zhao, H. et al., "Peptide SS-31 upregulates frataxin expression and improves the quality of mitochondria: implications in the treatment of Friedreich ataxia", Sci Rep. 2017 Aug. 29; 7(1):9840. In some embodiments, the peptide is as described in Vyas, P. M. et al. "A TAT-frataxin fusion protein increases lifespan and cardiac function in a conditional Friedreich's ataxia mouse model", Hum Mol Genet. 2012 Mar. 15; 21(6):1230-47. In some embodiments, the peptide or protein may target, e.g., bind to, a disease-associated repeat, e.g. a GAA repeat expansion.

DMD/Dystrophinopathies

In some embodiments, e.g., for the treatment of dystrophinopathies, such as Duchenne muscular dystrophy, a peptide may facilitate exon skipping in an mRNA expressed from a mutant DMD allele. In some embodiments, a peptide may promote the expression of functional dystrophin and/or the expression of a protein capable of functioning in place of dystrophin. In some embodiments, payload is a protein that is a functional fragment of dystrophin, e.g. an amino acid segment of a functional dytrophin protein.

iv. Nucleic Acid Constructs

Any suitable gene expression construct may be used as a molecular payload, as described herein. In some embodiments, a gene expression construct may be a vector or a cDNA fragment. In some embodiments, a gene expression construct may be messenger RNA (mRNA). In some embodiments, a mRNA used herein may be a modified mRNA, e.g., as described in U.S. Pat. No. 8,710,200, issued on Apr. 24, 2014, entitled "*Engineered nucleic acids encoding a modified erythropoietin and their expression*". In some embodiments, a mRNA may comprise a 5' methyl cap. In some embodiments, a mRNA may comprise a polyA tail, optionally of up to 160 nucleotides in length. A gene expression construct may encode a sequence of a protein that is deficient in a muscle disease. In some embodiments, the gene expression construct may be expressed, e.g., overexpressed, within the nucleus of a muscle cell. In some embodiments, the gene expression construct encodes a gene that is deficient in a muscle disease. In some embodiments, the gene expression constructs encodes a protein that comprises at least one zinc finger. In some embodiments, the gene expression construct encodes a protein that binds to a gene in Table 1. In some embodiments, the gene expression construct encodes a protein that leads to a reduction in the expression of a protein (e.g., mutant protein) encoded by a gene in Table 1. In some embodiments, the gene expression construct encodes a gene editing enzyme. Additional examples of nucleic acid constructs that may be used as molecular payloads are provided in International Patent Application Publication WO2017152149A1, published on Sep. 19, 2017, entitled, "CLOSED-ENDED LINEAR DUPLEX DNA FOR NON-VIRAL GENE TRANSFER"; U.S. Pat. No. 8,853,377B2, issued on Oct. 7, 2014, entitled, "MRNA FOR USE IN TREATMENT OF HUMAN GENETIC DISEASES"; and US Patent U.S. Pat. No. 8,822,663B2, issued on Sep. 2, 2014, ENGINEERED NUCLEIC ACIDS AND METHODS OF USE THEREOF," the contents of each of which are incorporated herein by reference in their entireties.

Further non-limiting examples are provided below for selected genes/disease of Table 1.

DMPK/DM1

In some embodiments, e.g., for the treatment of DM, the gene expression construct encodes a MBNL protein, e.g., MBNL1.

DUX4/FSHD

In some embodiments, e.g., for the treatment of FSHD, the gene expression construct encodes a oligonucleotide (e.g., an shRNA targeting DUX4) or a protein that downregulates the expression of DUX4 (e.g., a peptide or protein that binds to DME1 or DME2 enhancer to inhibit DUX4 expression, e.g., by blocking binding of an activator).

DNM2/CNM

In some embodiments, e.g., for the treatment of CNM1, a gene expression construct may encode a sequence of a protein that downregulates the expression of a mutant DNM2 protein, or which expresses wild-type DNM2. In some embodiments, a gene expression construct encodes an oligonucleotide (e.g., an shRNA) that inhibits expression of DNM2. However, in some embodiments, an expression construct encodes Spliceosome-Mediated RNA Trans-splicing components that may be used to reprogram mutated DNM2-mRNA, as disclosed in Trochet D., et al., Reprogramming the Dynamin 2 mRNA by Spliceosome-mediated RNA Trans-splicing Mol Ther Nucleic Acids. 2016 September; 5(9): e362, the contents of which are incorporated herein by reference.

Pompe Disease

In some embodiments, e.g., for the treatment of Pompe disease, the gene expression construct encodes a wild-type GAA protein. A gene expression construct may encode a sequence of a protein that leads to decreased expression of ACVR1 gene or decreased activity of GYS1 protein. In some embodiments, e.g., for the treatment of Pompe disease, the gene expression construct encodes and oligonucleotide (e.g., shRNA) that inhibits expression of GYS1.

ACVR1/FOP

A gene expression construct may encode a sequence of a protein that leads to decreased expression of ACVR1 gene or decreased activity of ACVR1 protein. In some embodiments, the gene expression construct encodes a protein that leads to a reduction in the expression of a epigenetic regulators that negatively regulate the expression of ACVR1, e.g. histone deactylases. In some embodiments, the gene expression construct encodes an oligonucleotide (e.g., shRNA) that inhibits expression of ACVR1.

FXN/Friedreich's Ataxia

A gene expression construct may encode a sequence of a protein that leads to increased expression of frataxin. In some embodiments, the gene expression construct may be expressed, e.g., overexpressed, within the nucleus of a muscle cell. In some embodiments, the gene expression construct encodes frataxin. In some embodiments, the gene expression constructs encodes a protein that inhibit the function of epigenetic regulators that negatively regulate the expression of FXN, e.g. histone deactylases. In some embodiments, the gene expression construct encodes a protein that binds to a disease-associated-repeat expansion of a GAA trinucleotide. In some embodiments, the gene expression construct encodes a protein that leads to a reduction in the expression of a epigenetic regulators that negatively regulate the expression of FXN, e.g. histone deactylases. In some embodiments, the gene expression construct encodes a gene editing enzyme. In some embodiments, the gene expression construct encodes erythropoietin (see, e.g. Miller, J. L. et al, "Erythropoietin and small molecule agonists of the tissue-protective erythropoietin receptor increase FXN expression in neuronal cells in vitro and in FXN-deficient KIKO mice in vivo", Neuropharmacology. 2017 Sep. 1; 123:34-45.). In some embodiments, the gene expression construct encodes interferon gamma (see, e.g. U.S. Pat. No. 8,815,230, filed Aug. 30, 2010, "Methods for treating Friedreich's ataxia with interferon gamma").

DMD/Dystrophinopathies

A gene expression construct may encode a sequence of a dystrophin protein, a dystrophin fragment, a mini-dystrophin, a utrophin protein, or any protein that shares a common function with dystrophin. In some embodiments, the gene expression construct may be expressed, e.g., overexpressed, within the nucleus of a muscle cell. In some embodiments, the gene expression constructs encodes a protein that comprises at least one zinc finger. In some embodiments, the gene expression construct encodes a protein that promotes the expression of dystrophin or a protein that shares function with dystrophin, e.g., utrophin. In some embodiments, the gene expression construct encodes a gene editing enzyme. In some embodiments, the gene expression construct is as described in U.S. Patent Application Publication US20170368198A1, published Dec. 28, 2017, entitled "Optimized mini-dystrophin genes and expression cassettes and their use"; Duan D. "Myodys, a full-length dystrophin plasmid vector for Duchenne and Becker muscular dystrophy gene therapy." Curr Opin Mol Ther 2008; 10:86-94; and expression cassettes disclosed in Tang, Y. et al., "AAV-directed muscular dystrophy gene therapy" Expert Opin Biol Ther. 2010 March; 10(3):395-408; the contents of each of which are incorporated herein by reference in their entireties.

C. Linkers

Complexes described herein generally comprise a linker that connects a muscle-targeting agent to a molecular payload. A linker comprises at least one covalent bond. In some embodiments, a linker may be a single bond, e.g., a disulfide bond or disulfide bridge, that connects a muscle-targeting agent to a molecular payload. However, in some embodiments, a linker may connect a muscle-targeting agent to a molecular payload through multiple covalent bonds. In some embodiments, a linker may be a cleavable linker. However, in some embodiments, a linker may be a non-cleavable linker. A linker is generally stable in vitro and in vivo, and may be stable in certain cellular environments. Additionally, generally a linker does not negatively impact the functional properties of either the muscle-targeting agent or the molecular payload. Examples and methods of synthesis of linkers are known in the art (see, e.g. Kline, T. et al. "Methods to Make Homogenous Antibody Drug Conjugates." Pharmaceutical Research, 2015, 32:11, 3480-3493.; Jain, N. et al. "Current ADC Linker Chemistry" Pharm Res. 2015, 32:11, 3526-3540.; McCombs, J. R. and Owen, S. C.

"Antibody Drug Conjugates: Design and Selection of Linker, Payload and Conjugation Chemistry" AAPS J. 2015, 17:2, 339-351.).

A precursor to a linker typically will contain two different reactive species that allow for attachment to both the muscle-targeting agent and a molecular payload. In some embodiments, the two different reactive species may be a nucleophile and/or an electrophile. In some embodiments, a linker is connected to a muscle-targeting agent via conjugation to a lysine residue or a cysteine residue of the muscle-targeting agent. In some embodiments, a linker is connected to a cysteine residue of a muscle-targeting agent via a maleimide-containing linker, wherein optionally the maleimide-containing linker comprises a maleimidocaproyl or maleimidomethyl cyclohexane-1-carboxylate group. In some embodiments, a linker is connected to a cysteine residue of a muscle-targeting agent or thiol functionalized molecular payload via a 3-arylpropionitrile functional group. In some embodiments, a linker is connected to a muscle-targeting agent and/or a molecular payload via an amide bond, a hydrazide, a triazole, a thioether, or a disulfide bond.

i. Cleavable Linkers

A cleavable linker may be a protease-sensitive linker, a pH-sensitive linker, or a glutathione-sensitive linker. These linkers are generally cleavable only intracellularly and are preferably stable in extracellular environments, e.g. extracellular to a muscle cell.

Protease-sensitive linkers are cleavable by protease enzymatic activity. These linkers typically comprise peptide sequences and may be 2-10 amino acids, about 2-5 amino acids, about 5-10 amino acids, about 10 amino acids, about 5 amino acids, about 3 amino acids, or about 2 amino acids in length. In some embodiments, a peptide sequence may comprise naturally-occurring amino acids, e.g. cysteine, alanine, or non-naturally-occurring or modified amino acids. Non-naturally occurring amino acids include j-amino acids, homo-amino acids, proline derivatives, β-substituted alanine derivatives, linear core amino acids, N-methyl amino acids, and others known in the art. In some embodiments, a protease-sensitive linker comprises a valine-citrulline or alanine-citrulline dipeptide sequence. In some embodiments, a protease-sensitive linker can be cleaved by a lysosomal protease, e.g. cathepsin B, and/or an endosomal protease.

A pH-sensitive linker is a covalent linkage that readily degrades in high or low pH environments. In some embodiments, a pH-sensitive linker may be cleaved at a pH in a range of 4 to 6. In some embodiments, a pH-sensitive linker comprises a hydrazone or cyclic acetal. In some embodiments, a pH-sensitive linker is cleaved within an endosome or a lysosome.

In some embodiments, a glutathione-sensitive linker comprises a disulfide moiety. In some embodiments, a glutathione-sensitive linker is cleaved by an disulfide exchange reaction with a glutathione species inside a cell. In some embodiments, the disulfide moiety further comprises at least one amino acid, e.g. a cysteine residue.

In some embodiments, the linker is a Val-cit linker (e.g., as described in U.S. Pat. No. 6,214,345, incorporated herein by reference). In some embodiments, before conjugation, the val-cit linker has a structure of:

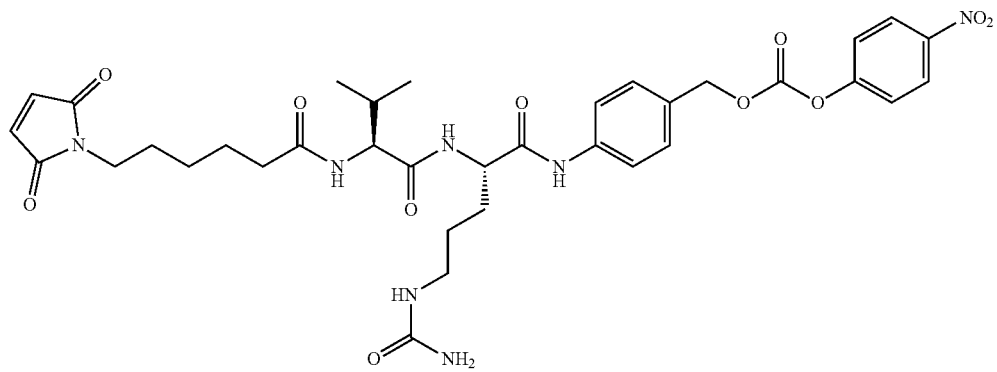 [SMILES: CC(C)[C@H](NC(=O)CCCCCN1C(=O)C=CC1=O)C(=O)N[C@@H](CCCNC(N)=O)C(=O)Nc1ccc(COC(=O)Oc2ccc([N+](=O)[O-])cc2)cc1]

In some embodiments, after conjugation, the val-cit linker has a structure of:

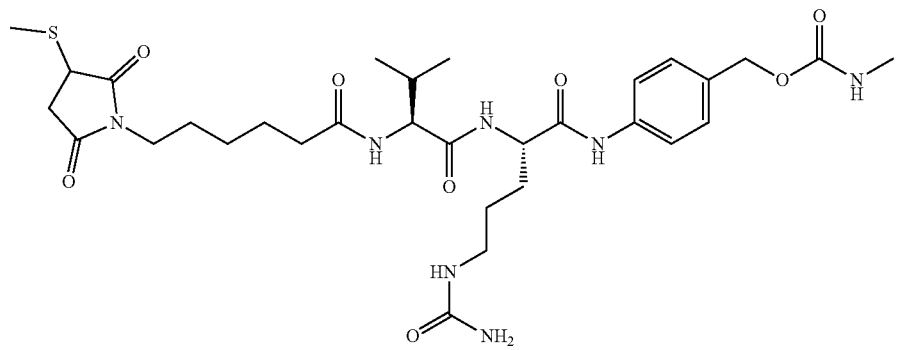

ii. Non-Cleavable Linkers

In some embodiments, non-cleavable linkers may be used. Generally, a non-cleavable linker cannot be readily degraded in a cellular or physiological environment. In some embodiments, a non-cleavable linker comprises an optionally substituted alkyl group, wherein the substitutions may include halogens, hydroxyl groups, oxygen species, and other common substitutions. In some embodiments, a linker may comprise an optionally substituted alkyl, an optionally substituted alkylene, an optionally substituted arylene, a heteroarylene, a peptide sequence comprising at least one non-natural amino acid, a truncated glycan, a sugar or sugars that cannot be enzymatically degraded, an azide, an alkyne-azide, a peptide sequence comprising a LPXT sequence, a thioether, a biotin, a biphenyl, repeating units of polyethylene glycol or equivalent compounds, acid esters, acid amides, sulfamides, and/or an alkoxy-amine linker. In some embodiments, sortase-mediated ligation will be utilized to covalently link a muscle-targeting agent comprising a LPXT sequence to a molecular payload comprising a $(G)_n$ sequence (see, e.g. Proft T. Sortase-mediated protein ligation: an emerging biotechnology tool for protein modification and immobilization. Biotechnol Lett. 2010, 32(1):1-10.). In some embodiments, a linker comprises a LPXTG sequence (SEQ ID NO: 16), where X is any amino acid.

In some embodiments, a linker may comprise a substituted alkylene, an optionally substituted alkenylene, an optionally substituted alkynylene, an optionally substituted cycloalkylene, an optionally substituted cycloalkenylene, an optionally substituted arylene, an optionally substituted heteroarylene further comprising at least one heteroatom selected from N, O, and S; an optionally substituted heterocyclylene further comprising at least one heteroatom selected from N, O, and S; an imino, an optionally substituted nitrogen species, an optionally substituted oxygen species O, an optionally substituted sulfur species, or a poly(alkylene oxide), e.g. polyethylene oxide or polypropylene oxide.

Iii. Linker Conjugation

In some embodiments, a linker is connected to a muscle-targeting agent and/or molecular payload via a phosphate, thioether, ether, carbon-carbon, or amide bond. In some embodiments, a linker is connected to an oligonucleotide through a phosphate or phosphorothioate group, e.g. a terminal phosphate of an oligonucleotide backbone. In some embodiments, a linker is connected to an muscle-targeting agent, e.g. an antibody, through a lysine or cysteine residue present on the muscle-targeting agent In some embodiments, a linker is connected to a muscle-targeting agent and/or molecular payload by a cycloaddition reaction between an azide and an alkyne to form a triazole, wherein the azide and the alkyne may be located on the muscle-targeting agent, molecular payload, or the linker. In some embodiments, an alkyne may be a cyclic alkyne, e.g., a cyclooctyne. In some embodiments, an alkyne may be bicyclononyne (also known as bicyclo[6.1.0]nonyne or BCN) or substituted bicyclononyne. In some embodiments, a cyclooctane is as described in International Patent Application Publication WO2011136645, published on Nov. 3, 2011, entitled, "*Fused Cyclooctyne Compounds And Their Use In Metal-free Click Reactions*". In some embodiments, an azide may be a sugar or carbohydrate molecule that comprises an azide. In some embodiments, an azide may be 6-azido-6-deoxygalactose or 6-azido-N-acetylgalactosamine. In some embodiments, a sugar or carbohydrate molecule that comprises an azide is as described in International Patent Application Publication WO2016170186, published on Oct. 27, 2016, entitled, "*Process For The Modification Of A Glycoprotein Using A Glycosyltransferase That Is Or Is Derived From A β(1,4)-N-Acetylgalactosaminyltransferase*". In some embodiments, a cycloaddition reaction between an azide and an alkyne to form a triazole, wherein the azide and the alkyne may be located on the muscle-targeting agent, molecular payload, or the linker is as described in International Patent Application Publication WO2014065661, published on May 1, 2014, entitled, "*Modified antibody, antibody-conjugate and process for the preparation thereof*"; or International Patent Application Publication WO2016170186, published on Oct. 27, 2016, entitled, "*Process For The Modification Of A Glycoprotein Using A Glycosyltransferase That Is Or Is Derived From A β(1,4)-N-Acetylgalactosaminyltransferase*".

In some embodiments, a linker further comprises a spacer, e.g., a polyethylene glycol spacer or an acyl/carbomoyl sulfamide spacer, e.g., a HYDRASPACE™ spacer. In some embodiments, a spacer is as described in Verkade, J. M. M. et al., "*A Polar Sulfamide Spacer Significantly Enhances the Manufacturability, Stability, and Therapeutic Index of Antibody—Drug Conjugates*", Antibodies, 2018, 7, 12.

In some embodiments, a linker is connected to a muscle-targeting agent and/or molecular payload by the Diels-Alder reaction between a dienophile and a diene/hetero-diene, wherein the dienophile and the diene/hetero-diene may be located on the muscle-targeting agent, molecular payload, or the linker. In some embodiments a linker is connected to a muscle-targeting agent and/or molecular payload by other pericyclic reactions, e.g. ene reaction. In some embodiments, a linker is connected to a muscle-targeting agent and/or molecular payload by an amide, thioamide, or sulfonamide bond reaction. In some embodiments, a linker is connected to a muscle-targeting agent and/or molecular payload by a condensation reaction to form an oxime, hydrazone, or semicarbazide group existing between the linker and the muscle-targeting agent and/or molecular payload.

In some embodiments, a linker is connected to a muscle-targeting agent and/or molecular payload by a conjugate addition reactions between a nucleophile, e.g. an amine or a hydroxyl group, and an electrophile, e.g. a carboxylic acid or an aldehyde. In some embodiments, a nucleophile may exist on a linker and an electrophile may exist on a muscle-targeting agent or molecular payload prior to a reaction between a linker and a muscle-targeting agent or molecular payload. In some embodiments, an electrophile may exist on a linker and a nucleophile may exist on a muscle-targeting agent or molecular payload prior to a reaction between a linker and a muscle-targeting agent or molecular payload. In some embodiments, an electrophile may be an azide, a silicon centers, a carbonyl, a carboxylic acid, an anhydride, an isocyanate, a thioisocyanate, a succinimidyl ester, a sulfosuccinimidyl ester, a maleimide, an alkyl halide, an alkyl pseudohalide, an epoxide, an episulfide, an aziridine, an aryl, an activated phosphorus center, and/or an activated sulfur center. In some embodiments, a nucleophile may be an optionally substituted alkene, an optionally substituted alkyne, an optionally substituted aryl, an optionally substituted heterocyclyl, a hydroxyl group, an amino group, an alkylamino group, an anilido group, or a thiol group.

D. Examples of Antibody-Molecular Payload Complexes

Other aspects of the present disclosure provide complexes comprising any one the muscle targeting agent (e.g., a transferrin receptor antibodies) described herein covalently linked to any of the molecular payloads (e.g., an oligonucleotide) described herein. In some embodiments, the muscle targeting agent (e.g., a transferrin receptor antibody) is covalently linked to a molecular payload (e.g., an oligonucleotide) via a linker. Any of the linkers described herein may be used. In some embodiments, the linker is linked to the 5' end, the 3' end, or internally of the oligonucleotide. In some embodiments, the linker is linked to the antibody via a thiol-reactive linkage (e.g., via a cysteine in the antibody).

An exemplary structure of a complex comprising a transferrin receptor antibody covalently linked to an oligonucleotide via a Val-cit linker is provided below:

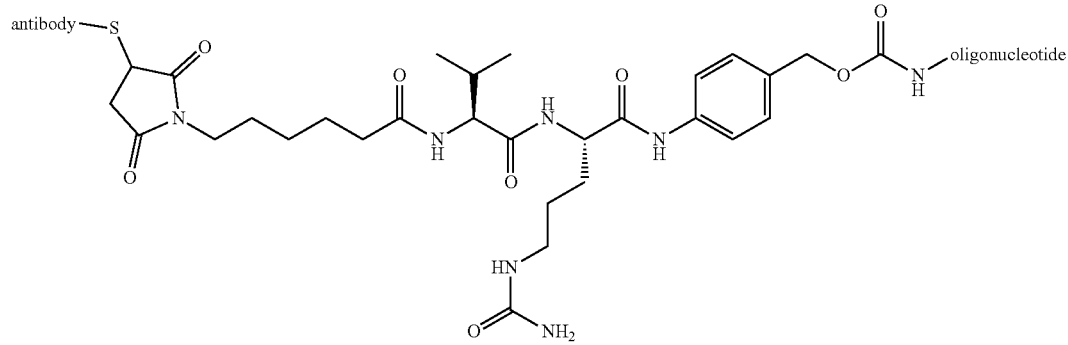

wherein the linker is linked to the 5' end, the 3' end, or internally of the oligonucleotide, and wherein the linker is linked to the antibody via a thiol-reactive linkage (e.g., via a cysteine in the antibody).

It should be appreciated that antibodies can be linked to oligonucleotides with different stochiometries, a property that may be referred to as a drug to antibody ratios (DAR) with the "drug" being the oligonucleotide. In some embodiments, one oligonucleotide is linked to an antibody (DAR=1). In some embodiments, two oligonucleotides are linked to an antibody (DAR=2). In some embodiments, three oligonucleotides are linked to an antibody (DAR=3). In some embodiments, four oligonucleotides are linked to an antibody (DAR=4). In some embodiments, a mixture of different complexes, each having a different DAR, is provided. In some embodiments, an average DAR of complexes in such a mixture may be in a range of 1 to 3, 1 to 4, 1 to 5 or more. DAR may be increased by conjugating oligonucleotides to different sites on an antibody and/or by conjugating multimers to one or more sites on antibody. For example, a DAR of 2 may be achieved by conjugating a single oligonucleotide to two different sites on an antibody or by conjugating a dimer oligonucleotide to a single site of an antibody.

In some embodiments, the complex described herein comprises a transferrin receptor antibody (e.g., an antibody or any variant thereof as described herein) covalently linked to an oligonucleotide. In some embodiments, the complex described herein comprises a transferrin receptor antibody (e.g., an antibody or any variant thereof as described herein) covalently linked to an oligonucleotide via a linker (e.g., a Val-cit linker). In some embodiments, the linker (e.g., a Val-cit linker) is linked to the 5' end, the 3' end, or internally of the oligonucleotide. In some embodiments, the linker (e.g., a Val-cit linker) is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to an oligonucleotide, wherein the transferrin receptor antibody comprises a CDR-H1, a CDR-H2, and a CDR-H3 that are the same as the CDR-H1, CDR-H2, and CDR-H3 shown in Table 1.1; and a CDR-L1, a CDR-L2, and a CDR-L3 that are the same as the CDR-L1, CDR-L2, and CDR-L3 shown in Table 1.1.

In some embodiments, the complex described herein comprises a transferrin receptor antibody covalently linked to an oligonucleotide, wherein the transferrin receptor antibody comprises a VH having the amino acid sequence of SEQ ID NO: 33 and a VL having the amino acid sequence of SEQ ID NO: 34. In some embodiments, the complex described herein comprises a transferrin receptor antibody covalently linked to an oligonucleotide, wherein the transferrin receptor antibody comprises a VH having the amino acid sequence of SEQ ID NO: 35 and a VL having the amino acid sequence of SEQ ID NO: 36.

In some embodiments, the complex described herein comprises a transferrin receptor antibody covalently linked to an oligonucleotide, wherein the transferrin receptor antibody comprises a heavy chain having the amino acid sequence of SEQ ID NO: 39 and a light chain having the amino acid sequence of SEQ ID NO: 40. In some embodiments, the complex described herein comprises a transferrin receptor antibody covalently linked to an oligonucleotide, wherein the transferrin receptor antibody comprises a heavy chain having the amino acid sequence of SEQ ID NO: 41 and a light chain having the amino acid sequence of SEQ ID NO: 42.

In some embodiments, the complex described herein comprises a transferrin receptor antibody covalently linked to an oligonucleotide via a linker (e.g., a Val-cit linker), wherein the transferrin receptor antibody comprises a CDR-H1, a CDR-H2, and a CDR-H3 that are the same as the CDR-H1, CDR-H2, and CDR-H3 shown in Table 1.1; and a CDR-L1, a CDR-L2, and a CDR-L3 that are the same as the CDR-L1, CDR-L2, and CDR-L3 shown in Table 1.1.

In some embodiments, the complex described herein comprises a transferrin receptor antibody covalently linked to an oligonucleotide via a linker (e.g., a Val-cit linker), wherein the transferrin receptor antibody comprises a VH having the amino acid sequence of SEQ ID NO: 33 and a VL having the amino acid sequence of SEQ ID NO: 34. In some embodiments, the complex described herein comprises a transferrin receptor antibody covalently linked to an oligonucleotide via a linker (e.g., a Val-cit linker), wherein the transferrin receptor antibody comprises a VH having the amino acid sequence of SEQ ID NO: 35 and a VL having the amino acid sequence of SEQ ID NO: 36.

In some embodiments, the complex described herein comprises a transferrin receptor antibody covalently linked to an oligonucleotide via a linker (e.g., a Val-cit linker), wherein the transferrin receptor antibody comprises a heavy chain having the amino acid sequence of SEQ ID NO: 39 and a light chain having the amino acid sequence of SEQ ID NO: 40. In some embodiments, the complex described herein comprises a transferrin receptor antibody covalently linked to an oligonucleotide via a linker (e.g., a Val-cit linker), wherein the transferrin receptor antibody comprises a heavy chain having the amino acid sequence of SEQ ID NO: 41 and a light chain having the amino acid sequence of SEQ ID NO: 42.

In some embodiments, the complex described herein comprises a transferrin receptor antibody covalently linked to an oligonucleotide via a Val-cit linker, wherein the transferrin receptor antibody comprises a CDR-H1, a CDR-H2, and a CDR-H3 that are the same as the CDR-H1, CDR-H2, and CDR-H3 shown in Table 1.1; and a CDR-L1, a CDR-L2, and a CDR-L3 that are the same as the CDR-L1, CDR-L2, and CDR-L3 shown in Table 1.1, and wherein the complex comprises the structure of:

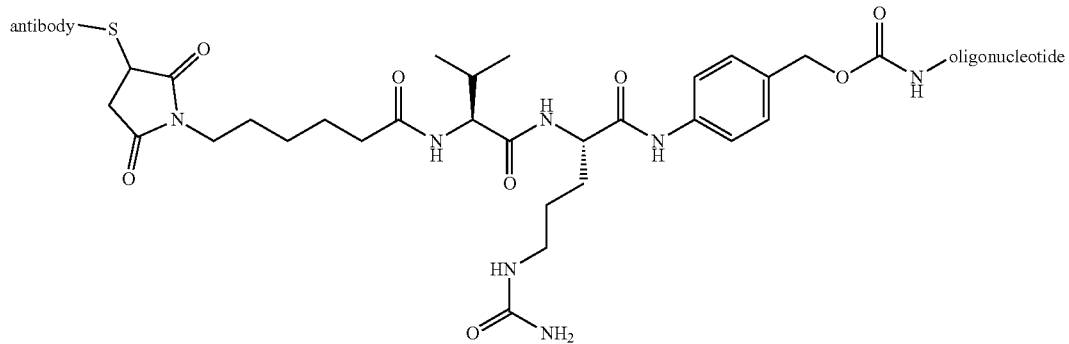

wherein the linker Val-cit linker is linked to the 5' end, the 3' end, or internally of the oligonucleotide, and wherein the Val-cit linker is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to an oligonucleotide via a Val-cit linker, wherein the transferrin receptor antibody comprises a VH having the amino acid sequence of SEQ ID NO: 33 and a VL having the amino acid sequence of SEQ ID NO: 34, and wherein the complex comprises the structure of:

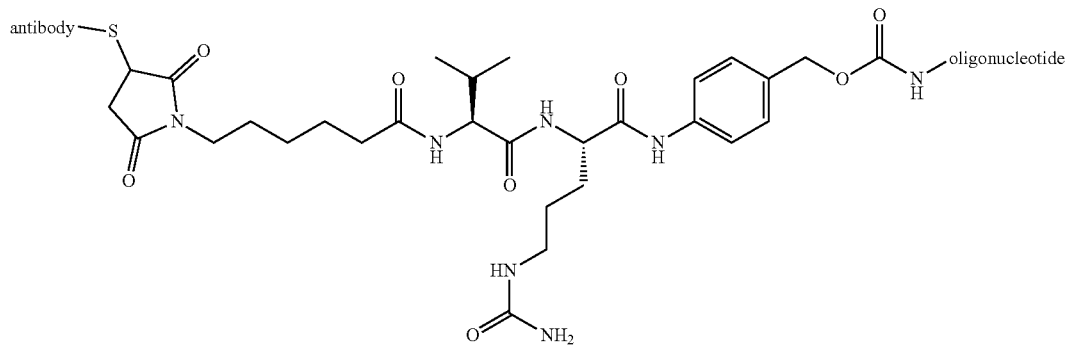

wherein the linker Val-cit linker is linked to the 5' end, the 3' end, or internally of the oligonucleotide, and wherein the Val-cit linker is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to an oligonucleotide via a Val-cit linker, wherein the transferrin receptor antibody comprises a VH having the amino acid sequence of SEQ ID NO: 35 and a VL having the amino acid sequence of SEQ ID NO: 36, and wherein the complex comprises the structure of:

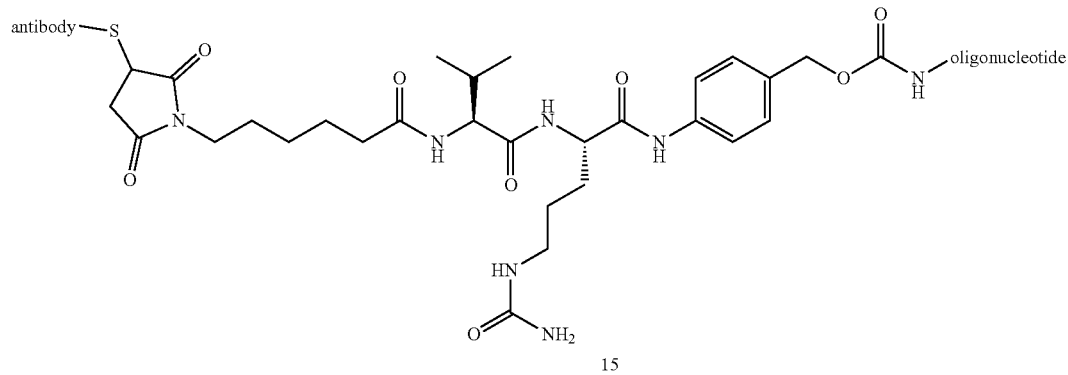

wherein the linker Val-cit linker is linked to the 5' end, the 3' end, or internally of the oligonucleotide, and wherein the Val-cit linker is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to an oligonucleotide via a Val-cit linker, wherein the transferrin receptor antibody comprises a heavy chain having the amino acid sequence of SEQ ID NO: 39 and a light chain having the amino acid sequence of SEQ ID NO: 40, and wherein the complex comprises the structure of:

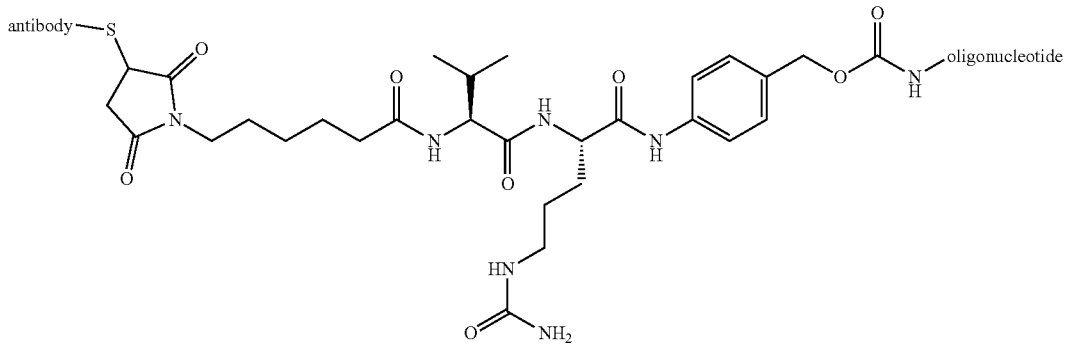

wherein the linker Val-cit linker is linked to the 5' end, the 3' end, or internally of an oligonucleotide, and wherein the Val-cit linker is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to an oligonucleotide via a Val-cit linker, wherein the transferrin receptor antibody comprises a heavy chain having the amino acid sequence of SEQ ID NO: 41 and a light chain having the amino acid sequence of SEQ ID NO: 42, and wherein the complex comprises the structure of:

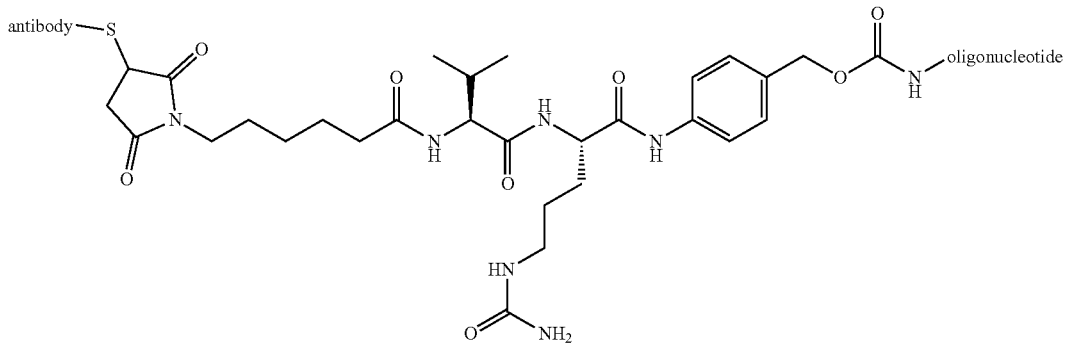

wherein the linker Val-cit linker is linked to the 5' end, the 3' end, or internally of an oligonucleotide, and wherein the Val-cit linker is linked to the antibody (e.g., an antibody or any variant thereof as described herein) via a thiol-reactive linkage (e.g., via a cysteine in the antibody).

Further examples of complexes and molecular payloads (e.g., oligonucleotides useful for targeting muscle genes) are provided in US Patent Application Publication US20210308272, published on Oct. 7, 2021, entitled, "MUSCLE TARGETING COMPLEXES AND USES THEREOF FOR TREATING MYOTONIC DYSTROPHY"; US Patent Application Publication US20210317226, published on Oct. 14, 2021, entitled, "MUSCLE TARGETING COMPLEXES AND USES THEREOF FOR TREATING POMPE DISEASE"; US Patent Application Publication US20210308274, published on Oct. 7, 2021, 2020, entitled, "MUSCLE TARGETING COMPLEXES AND USES THEREOF FOR TREATING FRIEDREICH'S ATAXIA"; US Patent Application Publication US20210261680, published on Aug. 26, 2021, entitled, "MUSCLE-TARGETING COMPLEXES AND USES THEREOF"; US Patent Application Publication US20220378934, published on Dec. 1, 2022, entitled, "MUSCLE-TARGETING COMPLEXES AND USES THEREOF IN TREATING MUSCLE ATROPHY"; US Patent Application Publication US20210308273, published on Oct. 7, 2021, entitled, "MUSCLE TARGETING COMPLEXES AND USES THEREOF FOR TREATING DYSTROPHINOPATHIES"; US Patent Application Publication US20210324101, published on Oct. 21, 2021, entitled, "MUSCLE TARGETING COMPLEXES AND USES THEREOF FOR TREATING HYPERTROPHIC CARDIOMYOPATHY"; US Patent Application Publication US20220193250, published on Jun. 23, 2022, entitled, "MUSCLE TARGETING COMPLEXES AND USES THEREOF FOR TREATING FACIOSCAPULOHUMERAL MUSCULAR DYSTROPHY"; the entire contents of each of which are incorporated herein by reference.

III. Formulations

Complexes provided herein may be formulated in any suitable manner. Generally, complexes provided herein are formulated in a manner suitable for pharmaceutical use. For example, complexes can be delivered to a subject using a formulation that minimizes degradation, facilitates delivery and/or uptake, or provides another beneficial property to the complexes in the formulation. In some embodiments, provided herein are compositions comprising complexes and pharmaceutically acceptable carriers. Such compositions can be suitably formulated such that when administered to a subject, either into the immediate environment of a target cell or systemically, a sufficient amount of the complexes enter target muscle cells. In some embodiments, complexes are formulated in buffer solutions such as phosphate-buffered saline solutions, liposomes, micellar structures, and capsids.

It should be appreciated that, in some embodiments, compositions may include separately one or more components of complexes provided herein (e.g., muscle-targeting agents, linkers, molecular payloads, or precursor molecules of any one of them).

In some embodiments, complexes are formulated in water or in an aqueous solution (e.g., water with pH adjustments). In some embodiments, complexes are formulated in basic buffered aqueous solutions (e.g., PBS). In some embodiments, formulations as disclosed herein comprise an excipient. In some embodiments, an excipient confers to a composition improved stability, improved absorption, improved solubility and/or therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethyl sulfoxide, or mineral oil).

In some embodiments, a complex or component thereof (e.g., oligonucleotide or antibody) is lyophilized for extending its shelf-life and then made into a solution before use (e.g., administration to a subject). Accordingly, an excipient in a composition comprising a complex, or component thereof, described herein may be a lyoprotectant (e.g., mannitol, lactose, polyethylene glycol, or polyvinyl pyrolidone), or a collapse temperature modifier (e.g., dextran, ficoll, or gelatin).

In some embodiments, a pharmaceutical composition is formulated to be compatible with its intended route of administration. Examples of routes of administration include parenteral, e.g., intravenous, intradermal, subcutaneous, administration. Typically, the route of administration is intravenous or subcutaneous. In some embodiments, the route of administration is extramuscular parenteral administration.

Pharmaceutical compositions suitable for injectable use include sterile aqueous solutions (where water soluble) or dispersions and sterile powders for the extemporaneous preparation of sterile injectable solutions or dispersions. The carrier can be a solvent or dispersion medium containing, for example, water, ethanol, polyol (for example, glycerol, propylene glycol, and liquid polyethylene glycol, and the like), and suitable mixtures thereof. In some embodiments, formulations include isotonic agents, for example, sugars, polyalcohols such as mannitol, sorbitol, and sodium chloride in the composition. Sterile injectable solutions can be prepared by incorporating the complexes in a required amount in a selected solvent with one or a combination of ingredients enumerated above, as required, followed by filtered sterilization.

In some embodiments, a composition may contain at least about 0.1% of the a complex, or component thereof, or more, although the percentage of the active ingredient(s) may be between about 1% and about 80% or more of the weight or volume of the total composition. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

IV. Methods of Use/Treatment

Complexes comprising a muscle-targeting agent covalently to a molecular payload as described herein are effective in treating a muscle disease (e.g., a rare muscle disease). In some embodiments, complexes are effective in treating a muscle disease provided in Table 1. In some embodiments, a muscle disease is associated with a disease allele, for example, a disease allele for a particular muscle disease may comprise a genetic alteration in a corresponding gene listed in Table 1.

In some embodiments, a subject may be a human subject, a non-human primate subject, a rodent subject, or any suitable mammalian subject. In some embodiments, a subject may have a muscle disease provided in Table 1.

An aspect of the disclosure includes a methods involving administering to a subject an effective amount of a complex as described herein. In some embodiments, an effective amount of a pharmaceutical composition that comprises a complex comprising a muscle-targeting agent covalently to a molecular payload can be administered to a subject in need of treatment. In some embodiments, a pharmaceutical composition comprising a complex as described herein may be administered by a suitable route, which may include intravenous administration, e.g., as a bolus or by continuous infusion over a period of time. In some embodiments, intravenous administration may be performed by intramuscular, intraperitoneal, intracerebrospinal, subcutaneous, intra-articular, intrasynovial, or intrathecal routes. In some embodiments, a pharmaceutical composition may be in solid form, aqueous form, or a liquid form. In some embodiments, an aqueous or liquid form may be nebulized or lyophilized. In some embodiments, a nebulized or lyophilized form may be reconstituted with an aqueous or liquid solution.

Compositions for intravenous administration may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In some embodiments, a pharmaceutical composition that comprises a complex comprising a muscle-targeting agent covalently to a molecular payload is administered via site-specific or local delivery techniques. Examples of these techniques include implantable depot sources of the complex, local delivery catheters, site specific carriers, direct injection, or direct application.

In some embodiments, a pharmaceutical composition that comprises a complex comprising a muscle-targeting agent covalently to a molecular payload is administered at an effective concentration that confers therapeutic effect on a subject. Effective amounts vary, as recognized by those skilled in the art, depending on the severity of the disease, unique characteristics of the subject being treated, e.g. age, physical conditions, health, or weight, the duration of the treatment, the nature of any concurrent therapies, the route of administration and related factors. These related factors are known to those in the art and may be addressed with no more than routine experimentation. In some embodiments, an effective concentration is the maximum dose that is considered to be safe for the patient. In some embodiments, an effective concentration will be the lowest possible concentration that provides maximum efficacy.

Empirical considerations, e.g. the half-life of the complex in a subject, generally will contribute to determination of the concentration of pharmaceutical composition that is used for treatment. The frequency of administration may be empirically determined and adjusted to maximize the efficacy of the treatment.

Generally, for administration of any of the complexes described herein, an initial candidate dosage may be about 1 to 100 mg/kg, or more, depending on the factors described above, e.g. safety or efficacy. In some embodiments, a treatment will be administered once. In some embodiments, a treatment will be administered daily, biweekly, weekly, bimonthly, monthly, or at any time interval that provide maximum efficacy while minimizing safety risks to the subject. Generally, the efficacy and the treatment and safety risks may be monitored throughout the course of treatment The efficacy of treatment may be assessed using any suitable methods. In some embodiments, the efficacy of treatment may be assessed by evaluation of observation of symptoms associated with a muscle disease.

In some embodiments, a pharmaceutical composition that comprises a complex comprising a muscle-targeting agent covalently to a molecular payload described herein is administered to a subject at an effective concentration sufficient to inhibit activity or expression of a target gene by at least 10%, at least 20%, at least 30%, at least 40%, at least 50%, at least 60%, at least 70%, at least 80%, at least 90% or at least 95% relative to a control, e.g. baseline level of gene expression prior to treatment.

In some embodiments, a single dose or administration of a pharmaceutical composition that comprises a complex comprising a muscle-targeting agent covalently to a molecular payload described herein to a subject is sufficient to inhibit activity or expression of a target gene for at least 1-5, 1-10, 5-15, 10-20, 15-30, 20-40, 25-50, or more days. In some embodiments, a single dose or administration of a pharmaceutical composition that comprises a complex comprising a muscle-targeting agent covalently to a molecular payload described herein to a subject is sufficient to inhibit activity or expression of a target gene for at least 1, 2, 3, 4, 5, 6, 7, 8, 9, 10, 11, or 12 weeks. In some embodiments, a single dose or administration of a pharmaceutical composition that comprises a complex comprising a muscle-targeting agent covalently to a molecular payload described herein to a subject is sufficient to inhibit activity or expression of a target gene for at least 1, 2, 3, 4, 5, or 6 months.

In some embodiments, a pharmaceutical composition may comprises more than one complex comprising a muscle-targeting agent covalently to a molecular payload. In some embodiments, a pharmaceutical composition may further comprise any other suitable therapeutic agent for treatment of a subject, e.g. a human subject having a muscle disease (e.g., a muscle disease provided in Table 1). In some embodiments, the other therapeutic agents may enhance or supplement the effectiveness of the complexes described herein. In some embodiments, the other therapeutic agents may function to treat a different symptom or disease than the complexes described herein.

EXAMPLES

Example 1: Targeting DMPK with Transfected Antisense Oligonucleotides

A gapmer antisense oligonucleotide that targets both wild-type and mutant alleles of DMPK (DTX-P-060) was tested in vitro for its ability to reduce expression levels of DMPK in an immortalized cell line. Briefly, Hepa 1-6 cells were transfected with the DTX-P-060 (100 nM) formulated with LIPOFECTAMINE™ 2000. DMPK expression levels were evaluated 72 hours following transfection. A control experiment was also performed in which vehicle (phosphate-buffered saline) was delivered to Hepa 1-6 cells in culture and the cells were maintained for 72 hours. As shown in FIG. 1, it was found that the DTX-P-060 reduced DMPK expression levels by ~90% compared with controls.

Example 2: Targeting DMPK with a Muscle-Targeting Complex

A muscle-targeting complex was generated comprising the DMPK ASO used in Example 1 (DTX-P-060) covalently linked, via a cathepsin cleavable linker, to DTX-A-002 (RI7 217 (Fab)), an anti-transferrin receptor antibody.

Briefly, a maleimidocaproyl-L-valine-L-citrulline-p-aminobenzyl alcohol p-nitrophenyl carbonate (MC-Val-Cit-PABC-PNP) linker molecule was coupled to $NH_2$—$C_6$-DTX-β-060 using an amide coupling reaction. Excess linker and organic solvents were removed by gel permeation chromatography. The purified Val-Cit-linker-DTX-P-060 was then coupled to a thiol-reactive anti-transferrin receptor antibody (DTX-A-002).

Figure 2A:
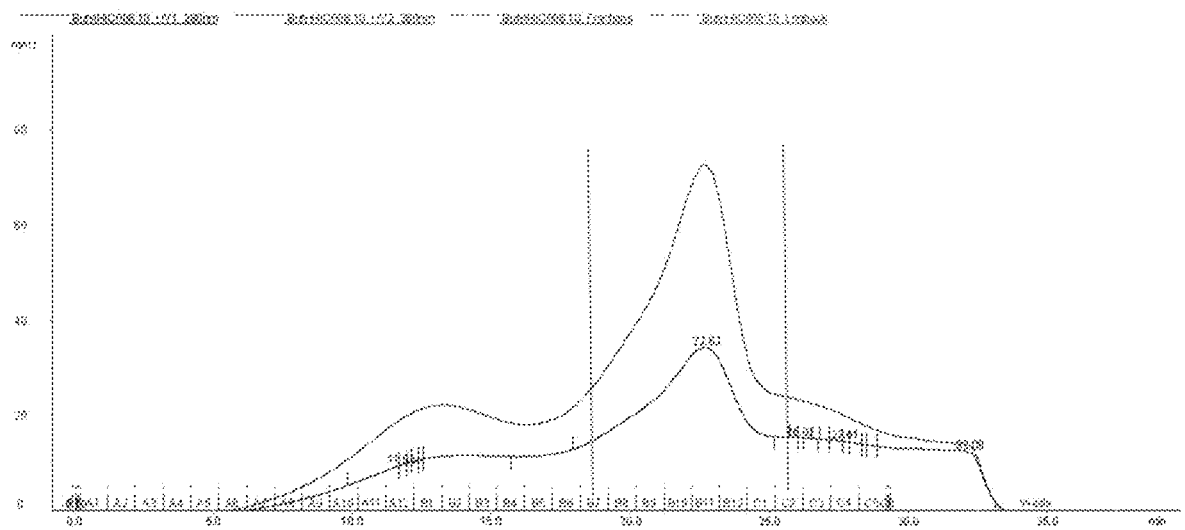
FIG. 2A depicts a non-limiting schematic showing an HIL-HPLC trace obtained during purification of a muscle targeting complex comprising an anti-transferrin receptor antibody covalently linked to a DMPK antisense oligonucleotide.
Figure 2B:
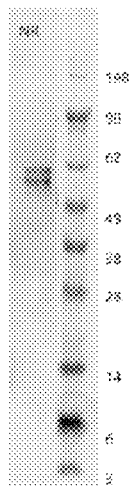
FIG. 2B depicts a non-limiting image of an SDS-PAGE analysis of a muscle targeting complex.

The product of the antibody coupling reaction was subjected to hydrophobic interaction chromatography (HIC-HPLC). FIG. 2A shows a resulting HIC-HPLC trace, in which fractions B7-C2 of the trace (denoted by vertical lines) contained ASO to antibody ratio of 1 or 2 as determined by SDS-PAGE. These fractions were pooled to arrive at the final muscle-targeting complex, referred to as DTX-C-008. Densitometry confirmed that DTX-C-008 had an average ASO to antibody ratio of 1.48, and SDS-PAGE revealed a purity of 86.4% (FIG. 2B).

Using the same approach, a control complex was generated comprising the DMPK ASO used in Example 1 (DTX-P-060) covalently linked via a Val-Cit linker to an IgG2a (Fab) antibody (DTX-C-007).

Figure 3:
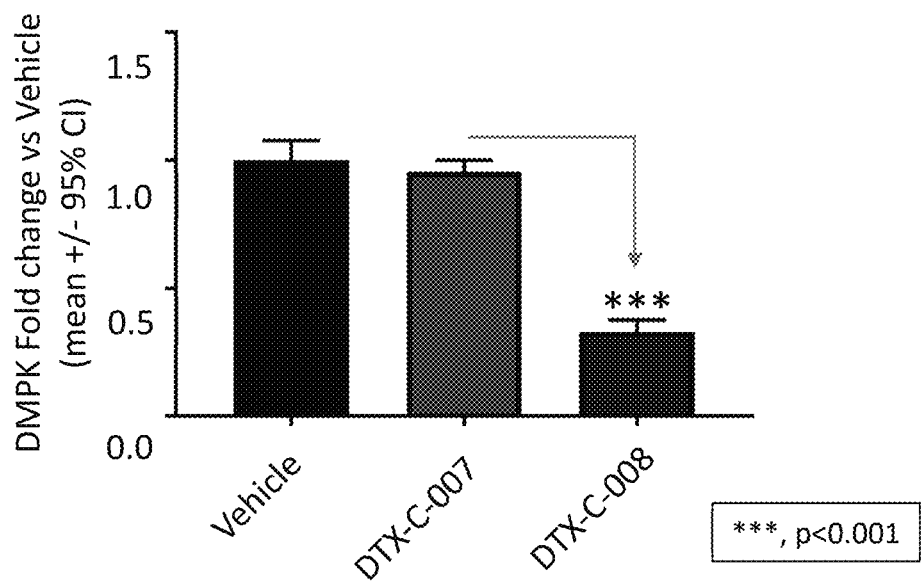
FIG. 3 depicts a non-limiting schematic showing the ability of a muscle targeting complex (DTX-C-008) comprising DTX-P-060 to reduce expression levels of DMPK.
Figure 4A:
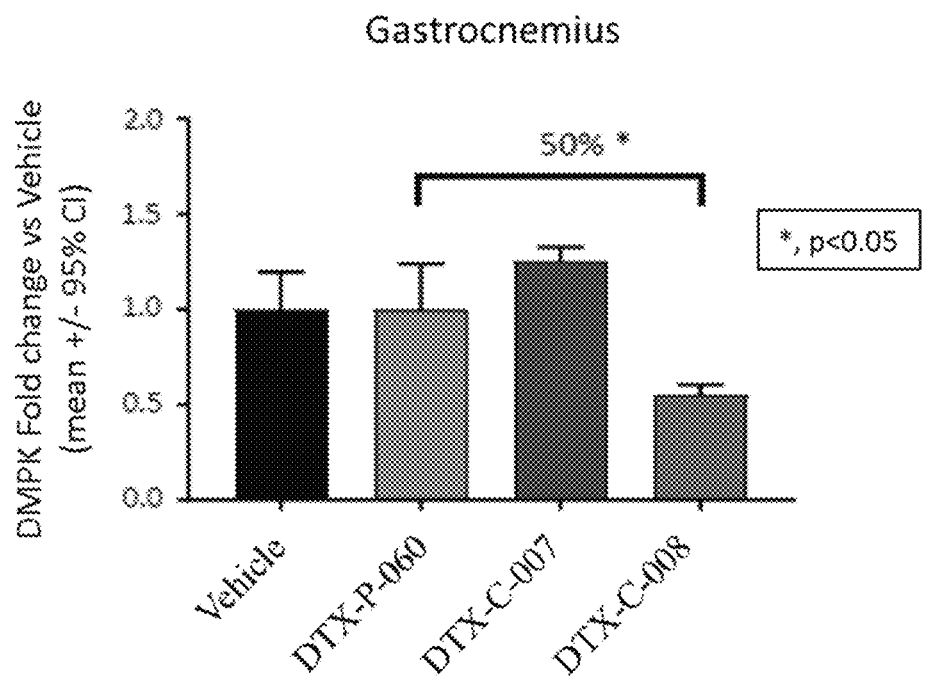
FIGS. 4A-4E depict non-limiting schematics showing the ability of a muscle targeting complex (DTX-C-008) comprising DTX-P-060 to reduce expression levels of DMPK in mouse muscle tissues in vivo, relative to a vehicle experiment. (N=3 C57Bl/6 WT mice)
Figure 4B:
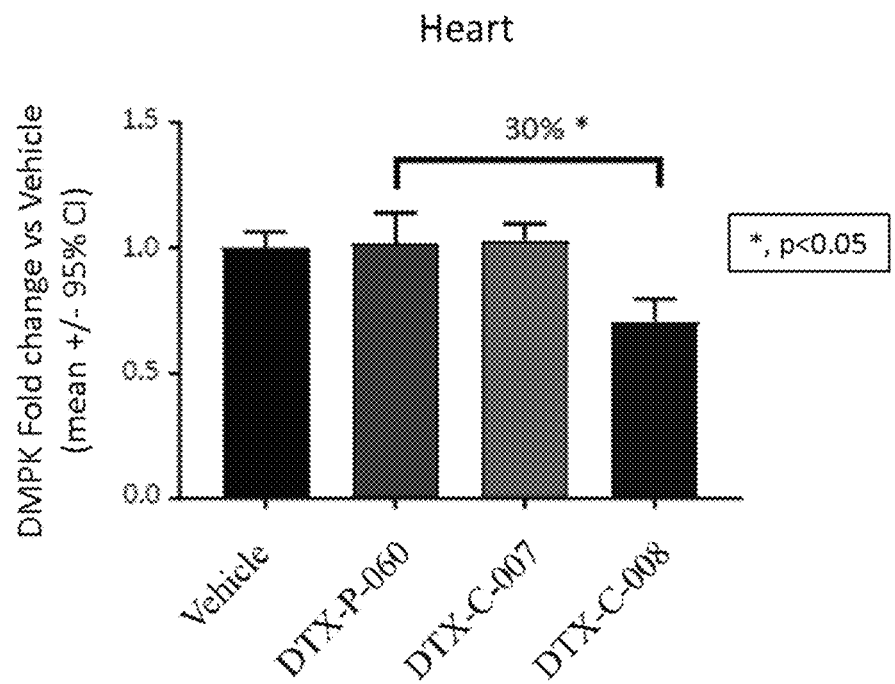
Figure 4C:
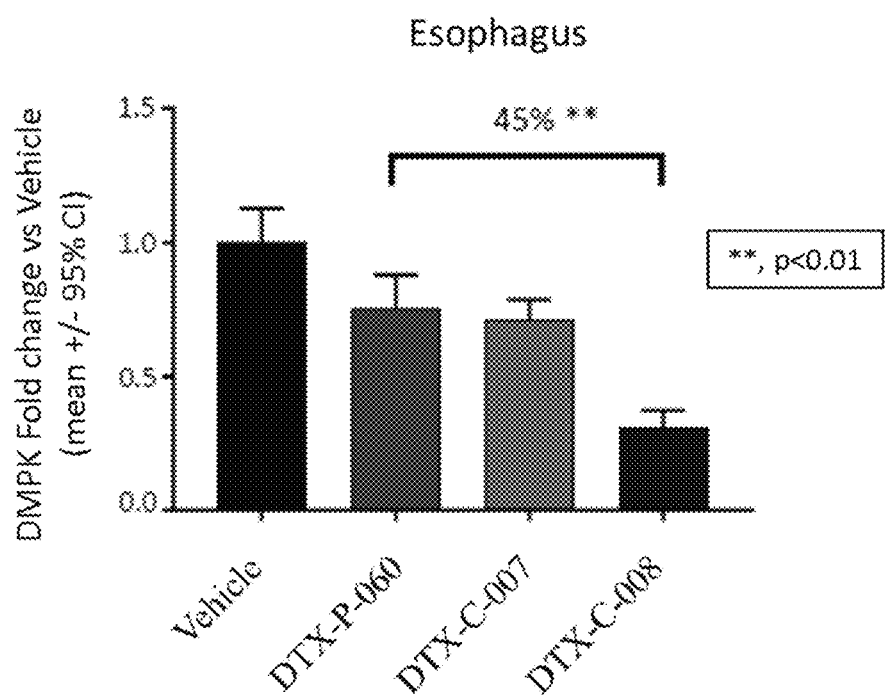
Figure 4D:
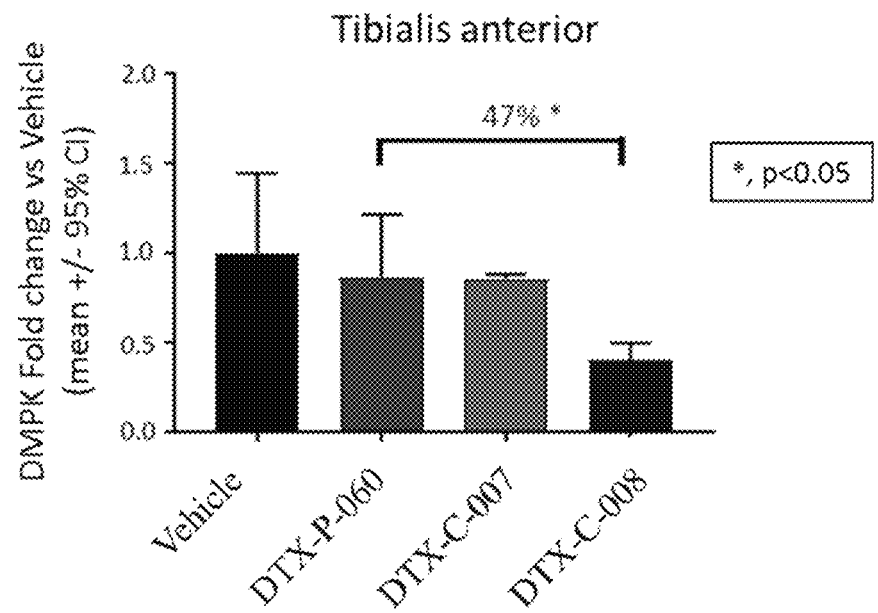
Figure 4E:
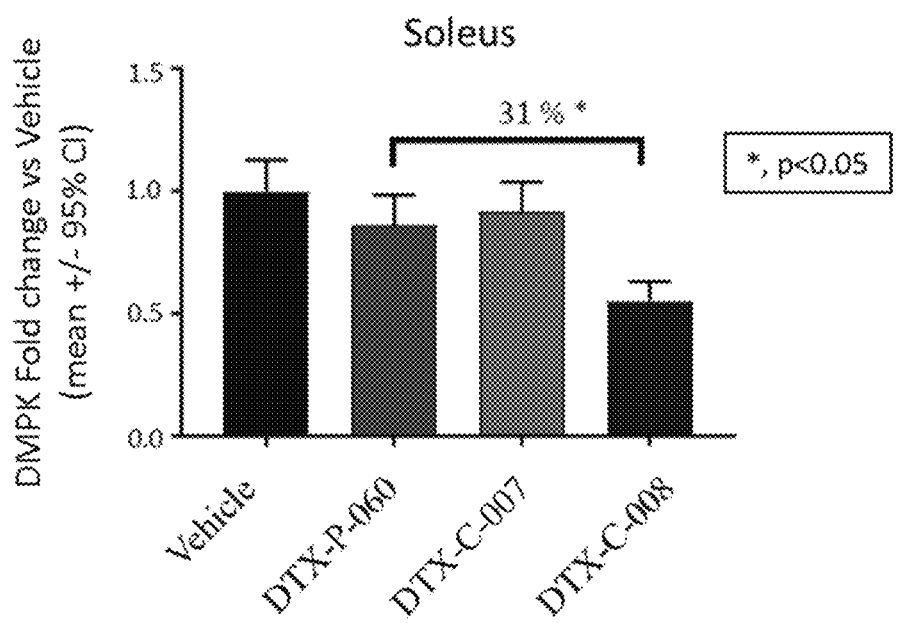

The purified DTX-C-008 was then tested for cellular internalization and inhibition of DMPK. Hepa 1-6 cells, which have relatively high expression levels of transferrin receptor, were incubated in the presence of vehicle control, DTX-C-008 (100 nM), or DTX-C-007 (100 nM) for 72 hours. After the 72 hour incubation, the cells were isolated and assayed for expression levels of DMPK (FIG. 3). Cells treated with the DTX-C-008 demonstrated a reduction in DMPK expression by ~65% relative to the cells treated with the vehicle control. Meanwhile, cells treated with the DTX-C-007 had DMPK expression levels comparable to the vehicle control (no reduction in DMPK expression). These data indicate that the anti-transferrin receptor antibody of the DTX-C-008 enabled cellular internalization of the complex, thereby allowing the DMPK ASO to inhibit expression of DMPK.

Example 3: Targeting DMPK in Mouse Muscle Tissues with a Muscle-Targeting Complex The muscle-targeting complex described in Example 2, DTX-C-008, was tested for inhibition of DMPK in mouse tissues. C57BL/6 wild-type mice were intravenously injected with a single dose of a vehicle control, DMPK-1 (3 mg/kg of RNA), DTX-C-008 (3 mg/kg of RNA, corresponding to 20 mg/kg antibody conjugate), or DTX-C-007 (3 mg/kg of RNA, corresponding to 20 mg/kg antibody conjugate). DTX-P-060, the DMPK ASO as described in Example 1, was used as a control. Each experimental condition was replicated in three individual C57BL/6 wild-type mice. Following a seven-day period after injection, the mice were euthanized and segmented into isolated tissue types. Individual tissue samples were subsequently assayed for expression levels of DMPK (FIGS. 4A-4E and 5A-5B).

Mice treated with the DTX-C-008 complex demonstrated a reduction in DMPK expression in a variety of skeletal, cardiac, and smooth muscle tissues. For example, as shown in FIGS. 4A-4E, DMPK expression levels were significantly reduced in gastrocnemius (50% reduction), heart (30% reduction), esophagus (45% reduction), tibialis anterior (47% reduction), and soleus (31% reduction) tissues, relative to the mice treated with the vehicle control. Meanwhile, mice treated with the DTX-C-007 complex had DMPK expression levels comparable to the vehicle control (no reduction in DMPK expression) for all assayed muscle tissue types.

Figure 5A:
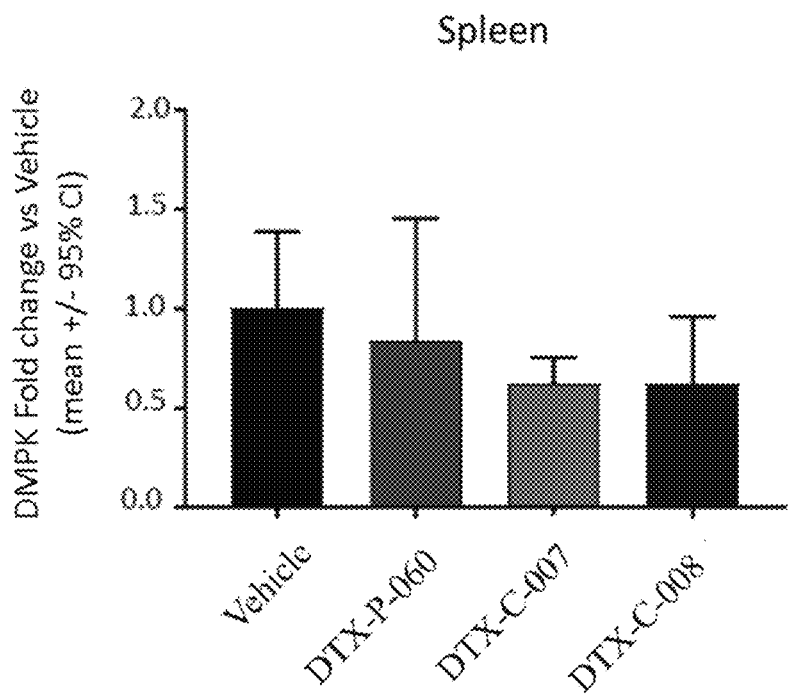
FIGS. 5A-5B depict non-limiting schematics showing the tissue selectivity of a muscle targeting complex (DTX-C-008) comprising DTX-P-060. The muscle targeting complex (DTX-C-008) comprising DTX-P-060 does not reduce expression levels of DMPK in mouse brain or spleen tissues in vivo, relative to a vehicle experiment. (N=3 C57Bl/6 WT mice)
Figure 5B:
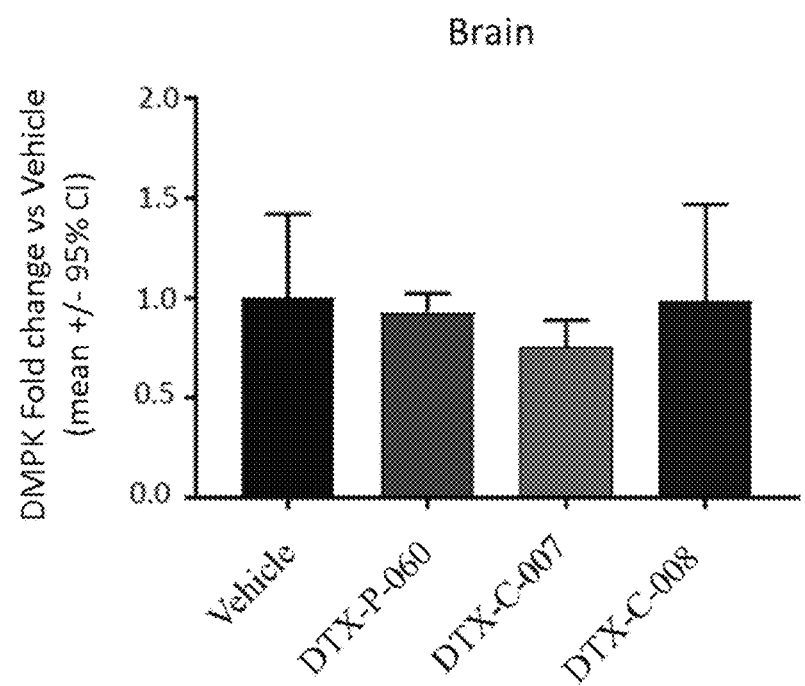
Figure 6A:
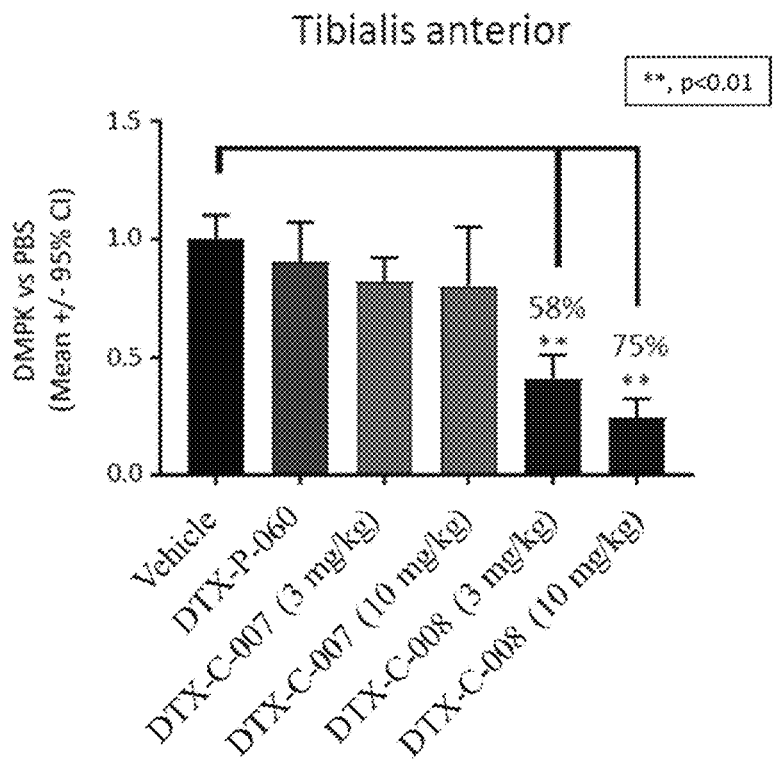
FIGS. 6A-6F depict non-limiting schematics showing the ability of a muscle targeting complex (DTX-C-008) comprising DTX-P-060 to reduce expression levels of DMPK in mouse muscle tissues in vivo, relative to a vehicle experiment. (N=5 C57Bl/6 WT mice)
Figure 6B:
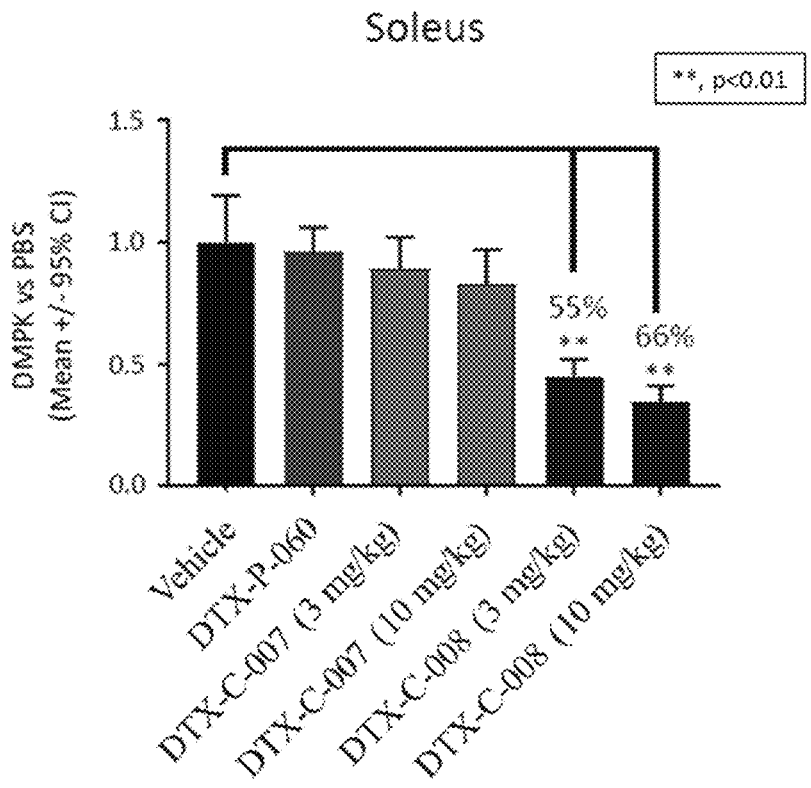
Figure 6C:
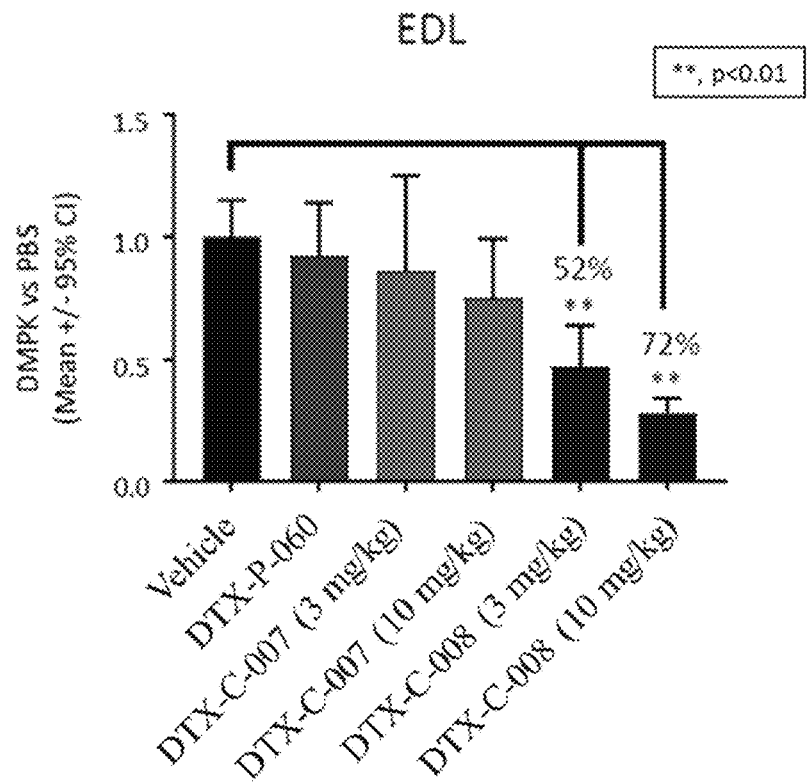
Figure 6D:
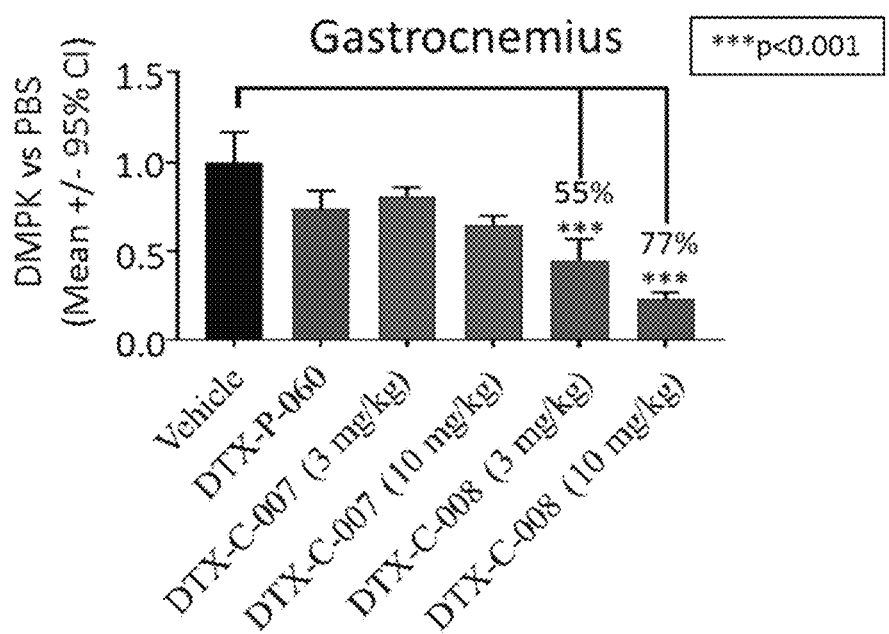
Figure 6E:
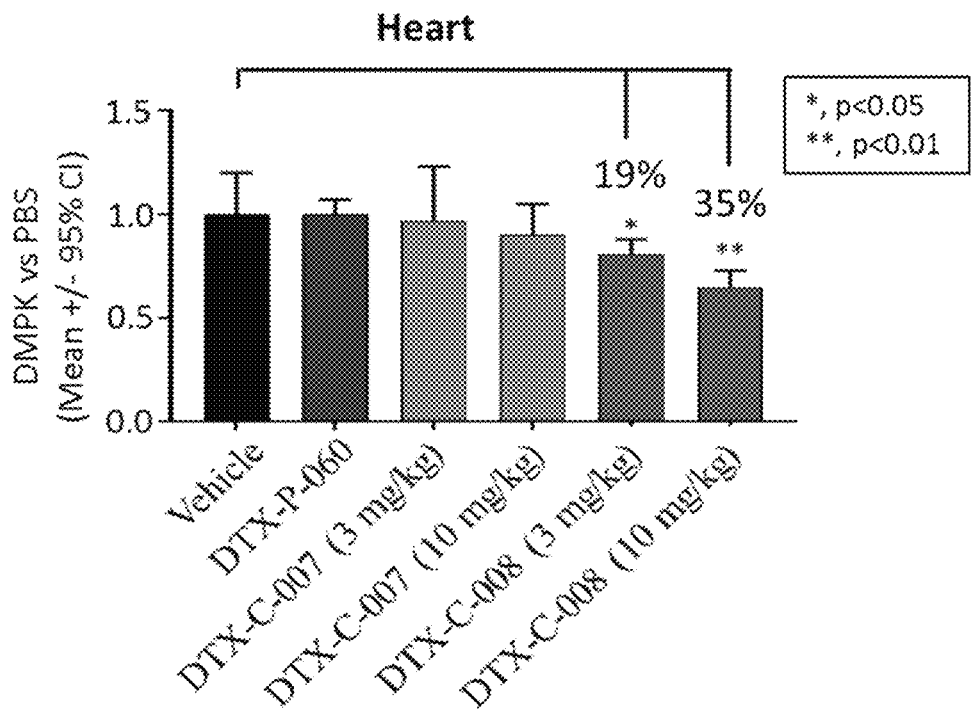
Figure 6F:
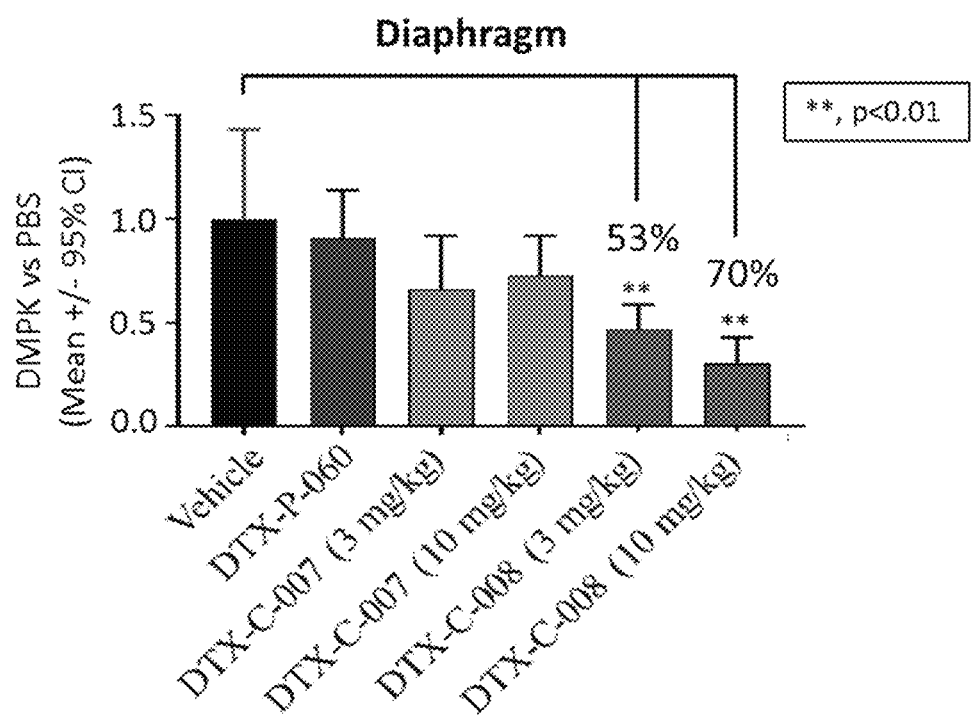

Mice treated with the DTX-C-008 complex demonstrated no change in DMPK expression in non-muscle tissues such as spleen and brain tissues (FIGS. 5A and 5B).

These data indicate that the anti-transferrin receptor antibody of the DTX-C-008 enabled cellular internalization of the complex into muscle-specific tissues in an in vivo mouse model, thereby allowing the DMPK ASO to inhibit expression of DMPK. These data further demonstrate that the DTX-C-008 complex is capable of specifically targeting muscle tissues.

Example 4: Targeting DMPK in Mouse Muscle Tissues with a Muscle-Targeting Complex The muscle-targeting complex described in Example 2, DTX-C-008, was tested for dose-dependent inhibition of DMPK in mouse tissues. C57BL/6 wild-type mice were intravenously injected with a single dose of a vehicle control (phosphate-buffered saline, PBS), DTX-P-060 (10 mg/kg of RNA), DTX-C-008 (3 mg/kg or 10 mg/kg of RNA, wherein 3 mg/kg corresponds to 20 mg/kg antibody conjugate), or DTX-C-007 (3 mg/kg or 10 mg/kg of RNA, wherein 3 mg/kg corresponds to 20 mg/kg antibody conjugate). DTX-P-060, the DMPK ASO as described in Example 1, was used as a control. Each experimental condition was replicated in five individual C57BL/6 wild-type mice. Following a seven-day period after injection, the mice were euthanized and segmented into isolated tissue types. Individual tissue samples were subsequently assayed for expression levels of DMPK (FIGS. 6A-6F).

Mice treated with the DTX-C-008 complex demonstrated a reduction in DMPK expression in a variety of skeletal muscle tissues. As shown in FIGS. 6A-6F, DMPK expression levels were significantly reduced in tibialis anterior (58% and 75% reduction for 3 mg/kg and 10 mg/kg DTX-C-008, respectively), soleus (55% and 66% reduction for 3 mg/kg and 10 mg/kg DTX-C-008, respectively), extensor digitorum longus (EDL) (52% and 72% reduction for 3 mg/kg and 10 mg/kg DTX-C-008, respectively), gastrocnemius (55% and 77% reduction for 3 mg/kg and 10 mg/kg DTX-C-008, respectively), heart (19% and 35% reduction for 3 mg/kg and 10 mg/kg DTX-C-008, respectively), and diaphragm (53% and 70% reduction for 3 mg/kg and 10 mg/kg DTX-C-008, respectively) tissues, relative to the mice treated with the vehicle control. Notably, all assayed muscle tissue types experienced dose-dependent inhibition of DMPK, with greater reduction in DMPK levels at 10 mg/kg antibody conjugate relative to 3 mg/kg antibody conjugate.

Meanwhile, mice treated with the control DTX-C-007 complex had DMPK expression levels comparable to the vehicle control (no reduction in DMPK expression) for all assayed muscle tissue types.

These data indicate that the anti-transferrin receptor antibody of the DTX-C-008 enabled cellular internalization of the complex into muscle-specific tissues in an in vivo mouse model, thereby allowing the DMPK ASO to inhibit expression of DMPK. These data further demonstrate that the DTX-C-008 complex is capable of specifically targeting muscle tissues for dose-dependent inhibition of DMPK.

Example 5: Targeting DMPK in Cynomolgus Monkey Muscle Tissues with a Muscle-Targeting Complex A muscle-targeting complex comprising DTX-P-060 (DTX-C-012), was generated and purified using methods described in Example 2. DTX-C-012 is a complex comprising a human anti-transferrin antibody covalently linked, via a cathepsin cleavable Val-Cit linker, to DTX-P-060, an antisense oligonucleotide that targets DMPK. Following HIC-HPLC purification, densitometry confirmed that DTX-C-012 had an average ASO to antibody ratio of 1.32, and SDS-PAGE revealed a purity of 92.3%.

DTX-C-012 was tested for dose-dependent inhibition of DMPK in male cynomolgus monkey tissues. Male cynomolgus monkeys (19-31 months; 2-3 kg) were intravenously injected with a single dose of a saline control, DTX-P-060 (naked DMPK ASO) (10 mg/kg of RNA), or DTX-C-012 (10 mg/kg of RNA) on Day 0. Each experimental condition was replicated in three individual male cynomolgus monkeys. On Day 7 after injection, tissue biopsies (including muscle tissues) were collected. DMPK mRNA expression levels, ASO detection assays, serum clinical chemistries, tissue histology, clinical observations, and body weights were analyzed. The monkeys were euthanized on Day 14.

Figure 7A:
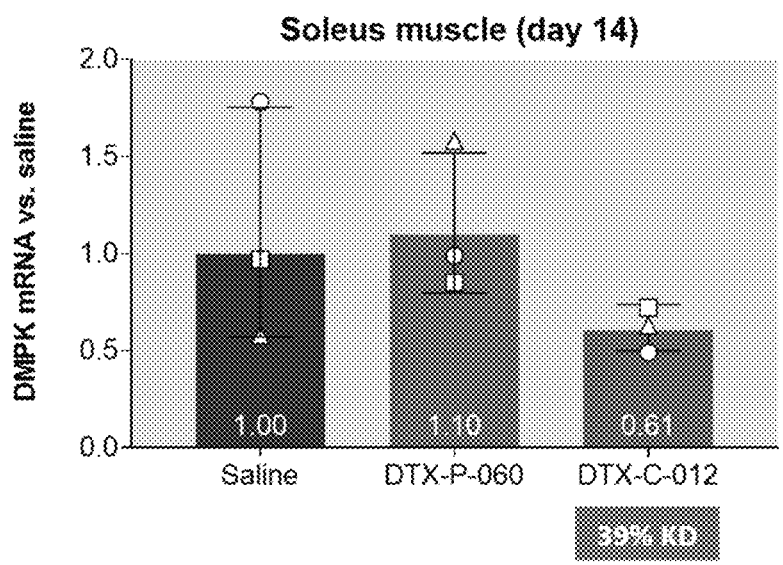
FIGS. 7A-7L depict non-limiting schematics showing the ability of a muscle targeting complex (DTX-C-012) comprising DTX-P-060 to reduce expression levels of DMPK in cynomolgus monkey muscle tissues in vivo, relative to a vehicle experiment and compared to a naked DMPK ASO (DTX-P-060). (N=3 male cynomolgus monkeys)
Figure 7B:
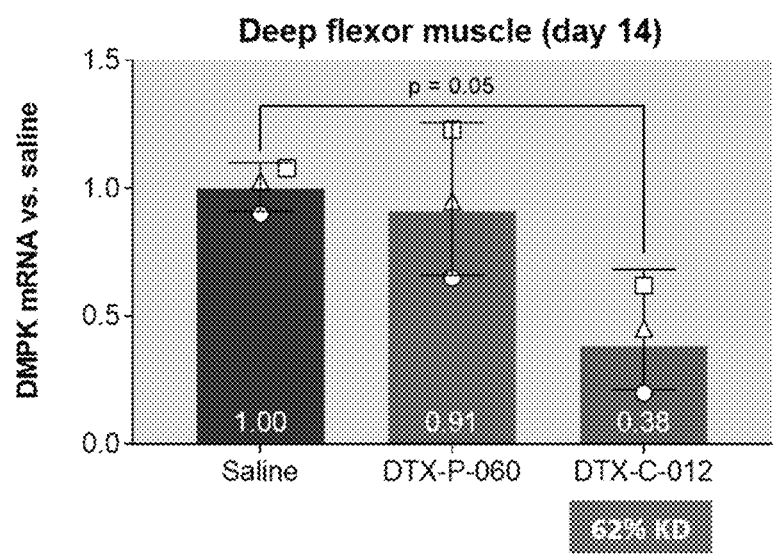
Figure 7C:
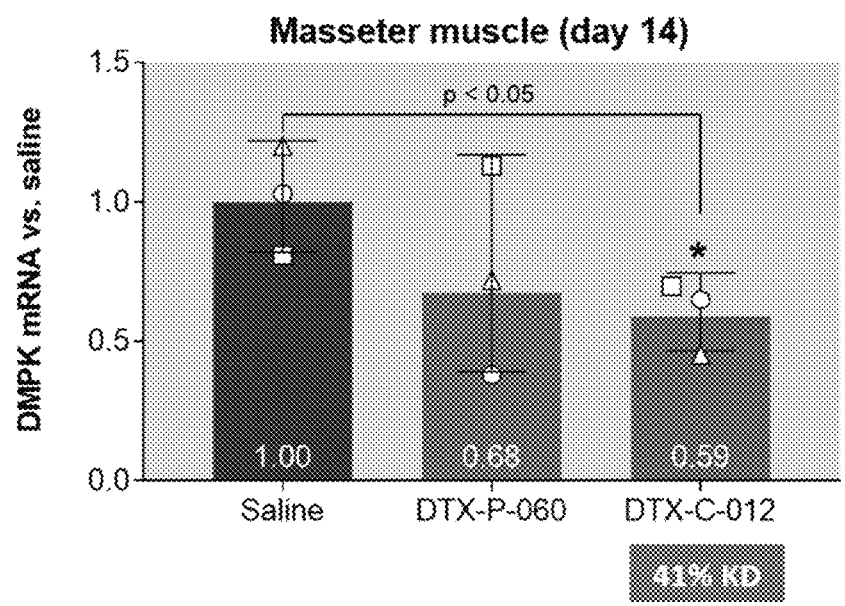
Figure 7D:
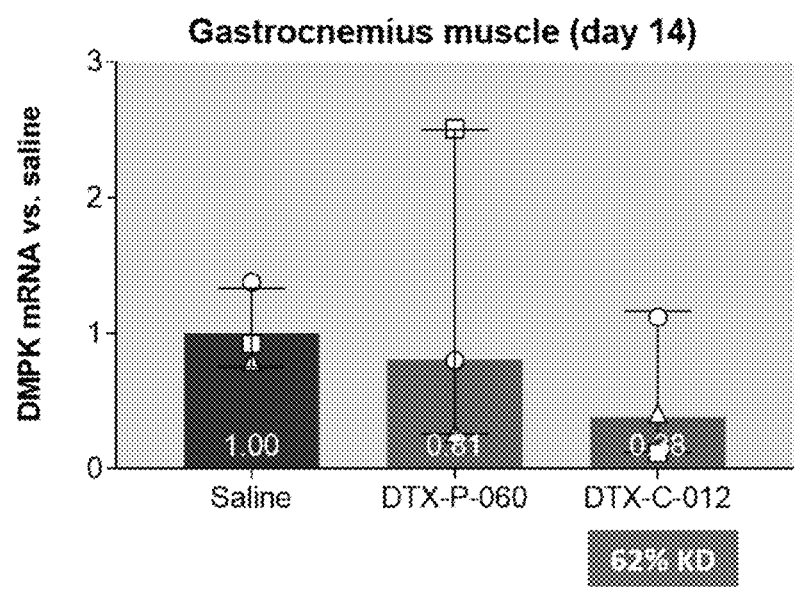
Figure 7E:
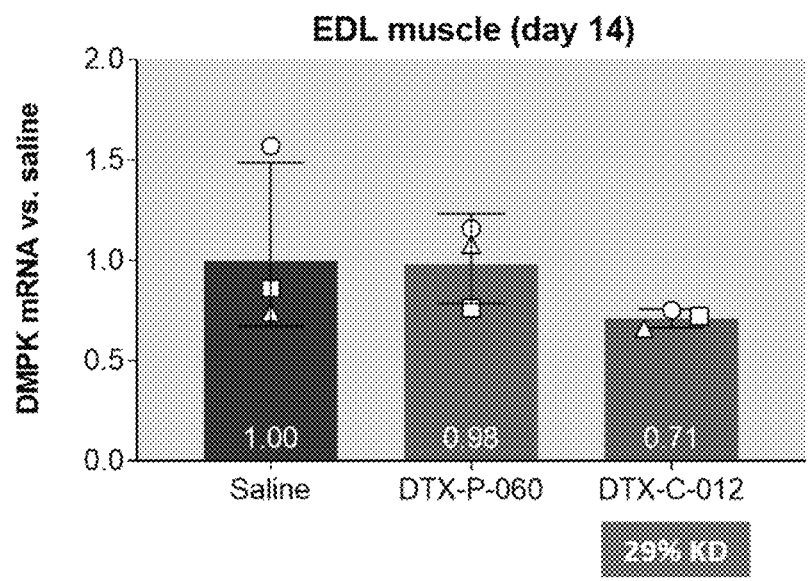
Figure 7F:
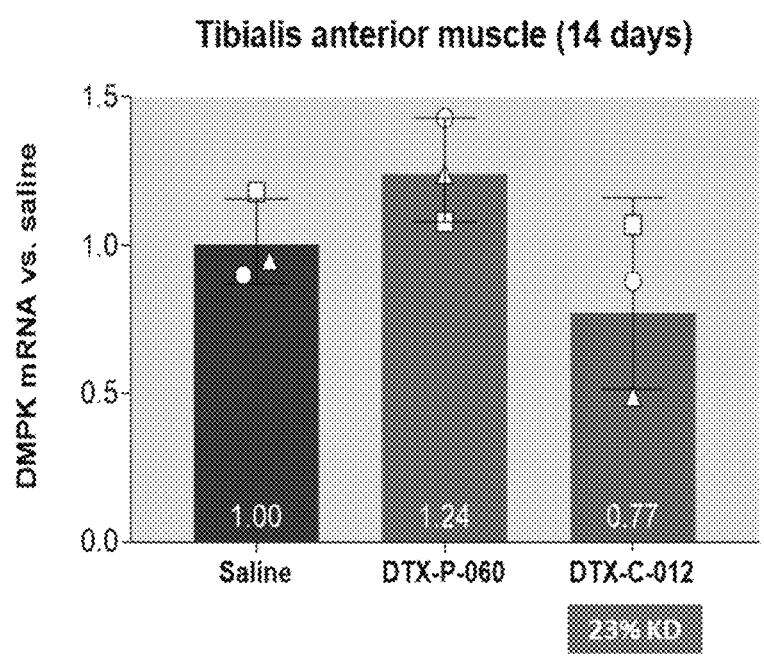
Figure 7G:
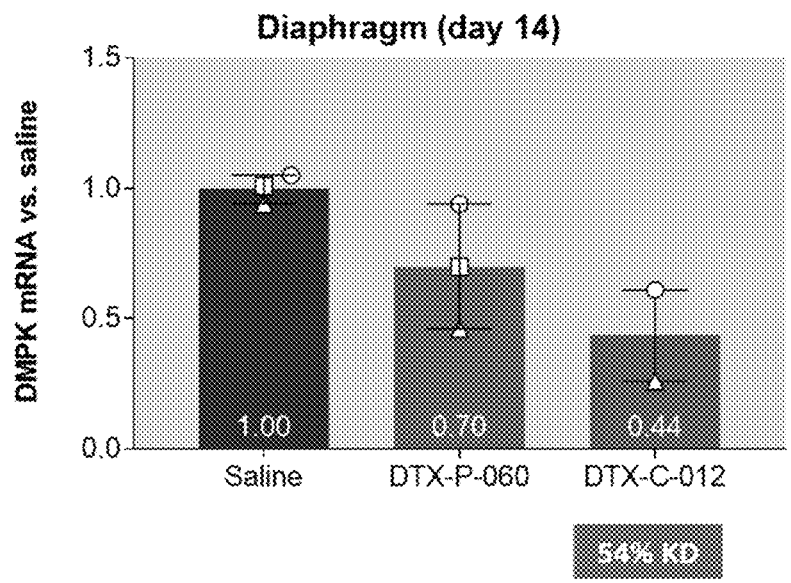
Figure 7H:
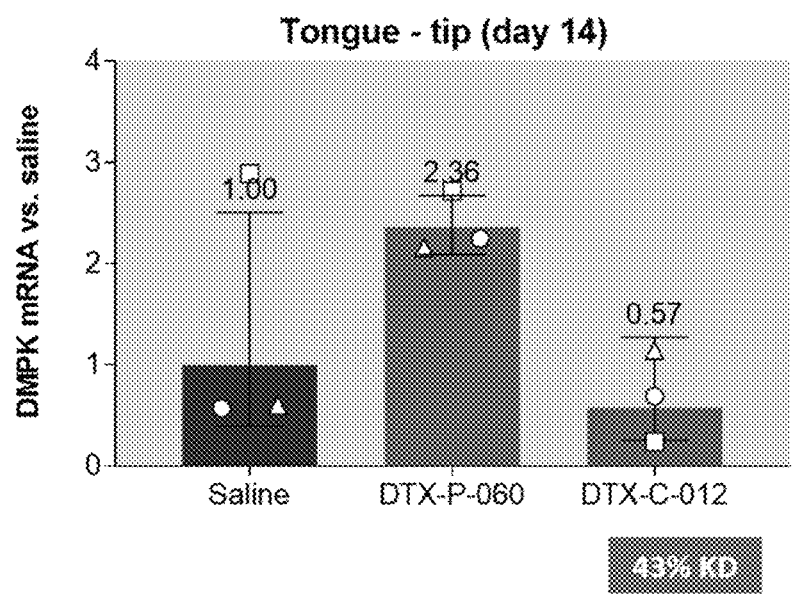
Figure 7I:
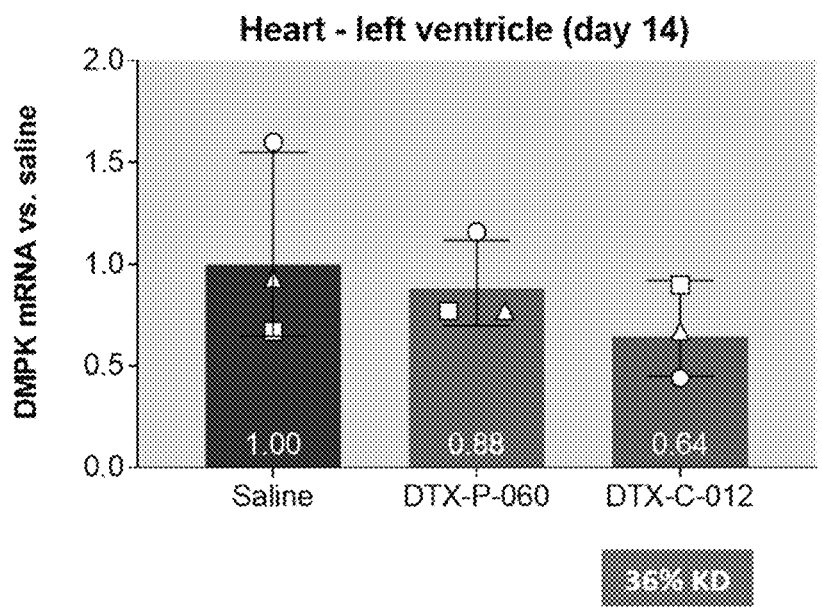
Figure 7J:
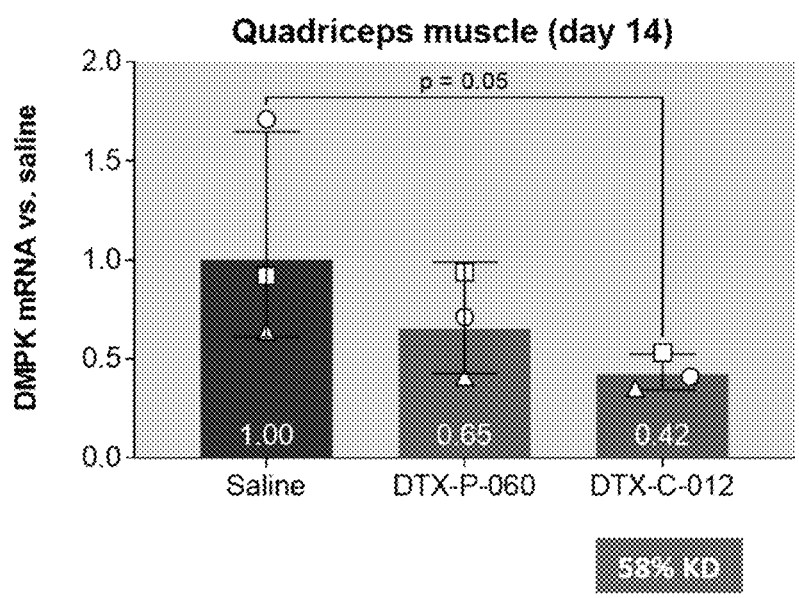
Figure 7K:
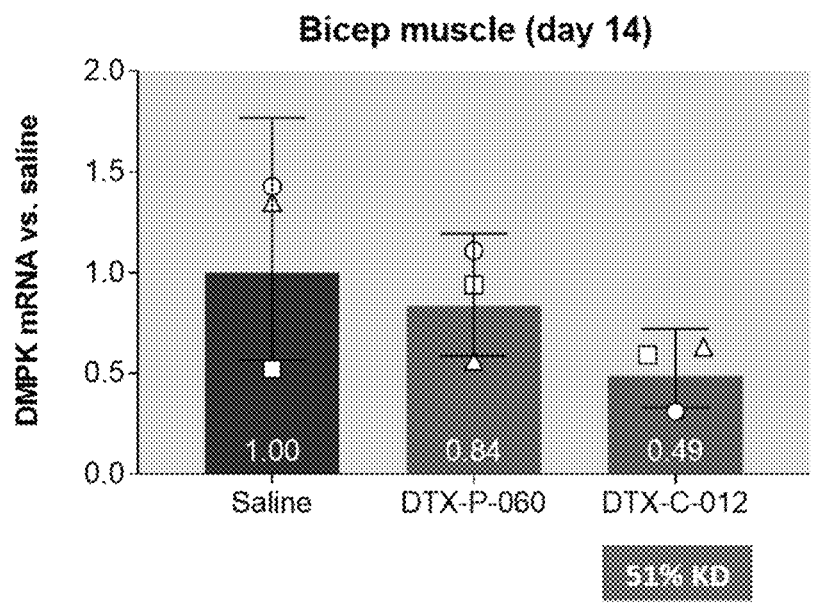
Figure 7L:
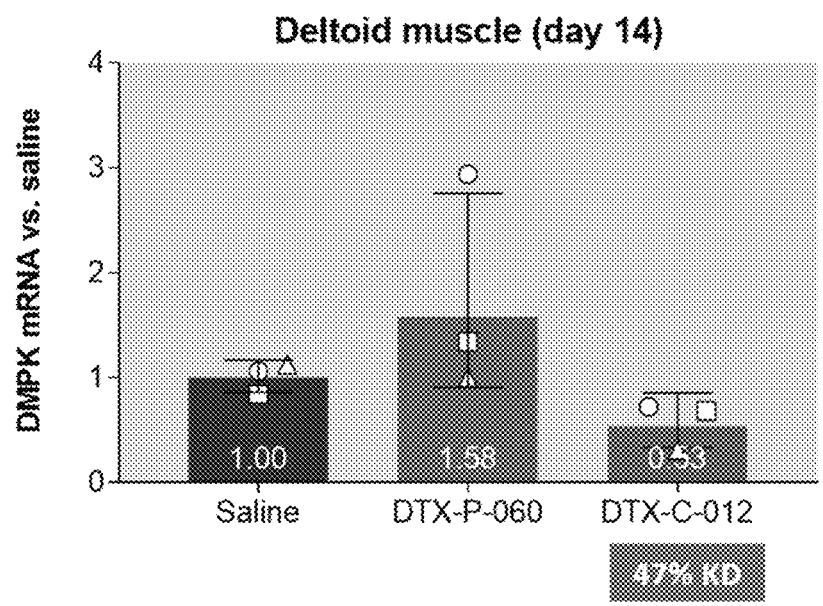
Figure 8A:
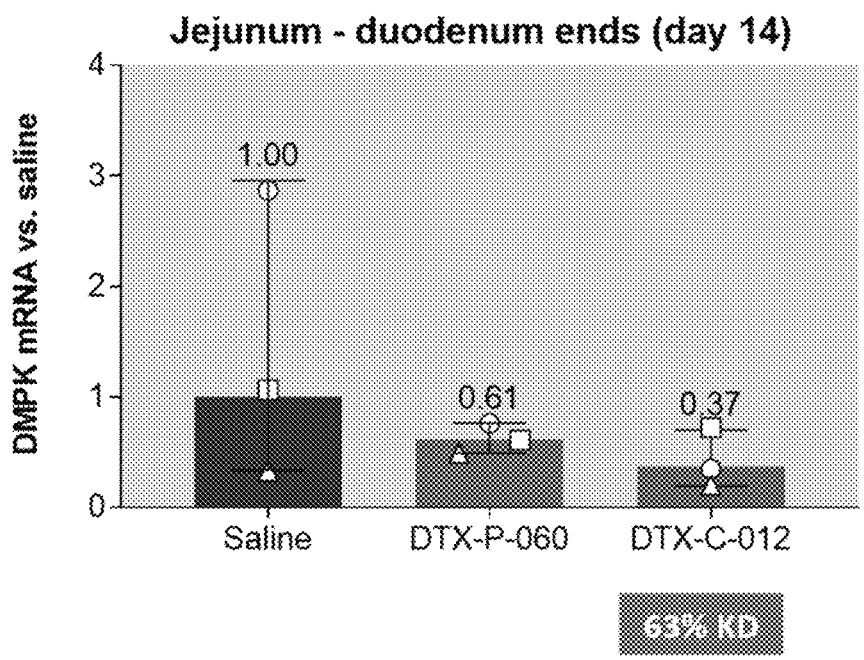
FIGS. 8A-8B depict non-limiting schematics showing the ability of a muscle targeting complex (DTX-C-012) comprising DTX-P-060 to reduce expression levels of DMPK in cynomolgus monkey smooth muscle tissues in vivo, relative to a vehicle experiment and compared to a naked DMPK ASO (DTX-P-060). (N=3 male cynomolgus monkeys)
Figure 8B:
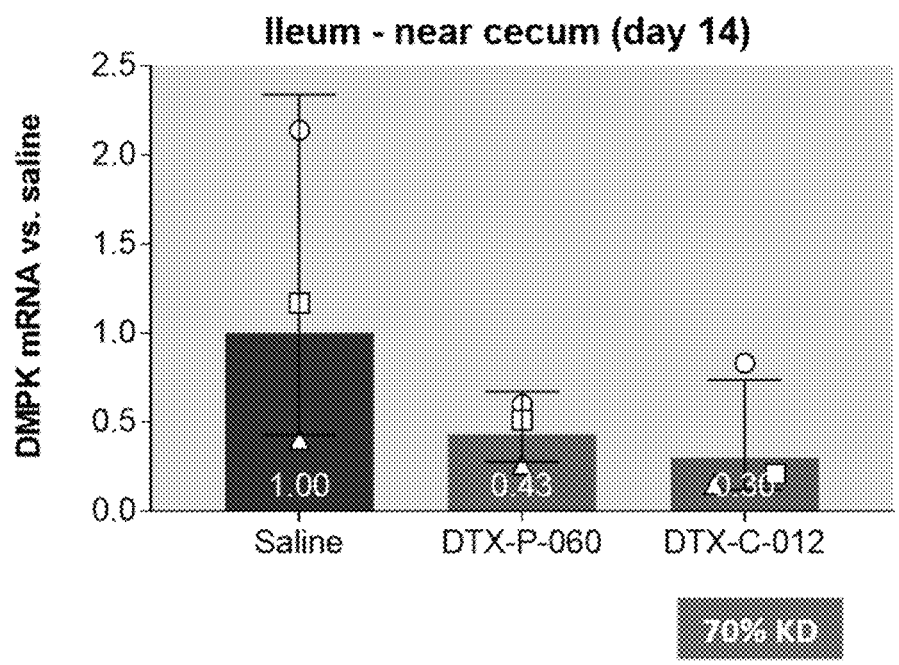
Figure 9A:
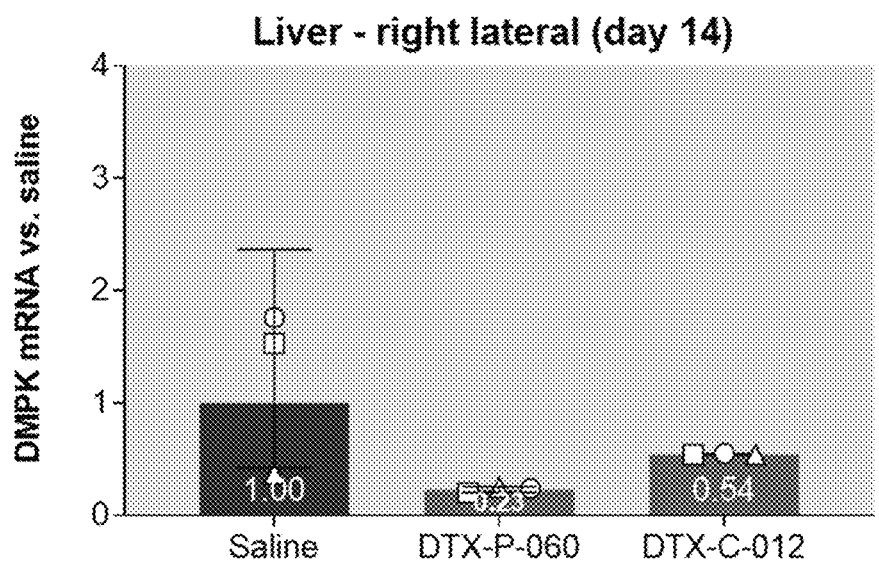
FIGS. 9A-9D depict non-limiting schematics showing the tissue selectivity of a muscle targeting complex (DTX-C-012) comprising DTX-P-060. The muscle targeting complex comprising DMPK-ASO does not reduce expression levels of DMPK in cynomolgus monkey liver, kidney, brain, or spleen tissues in vivo, relative to a vehicle experiment. (N=3 male cynomolgus monkeys)
Figure 9B:
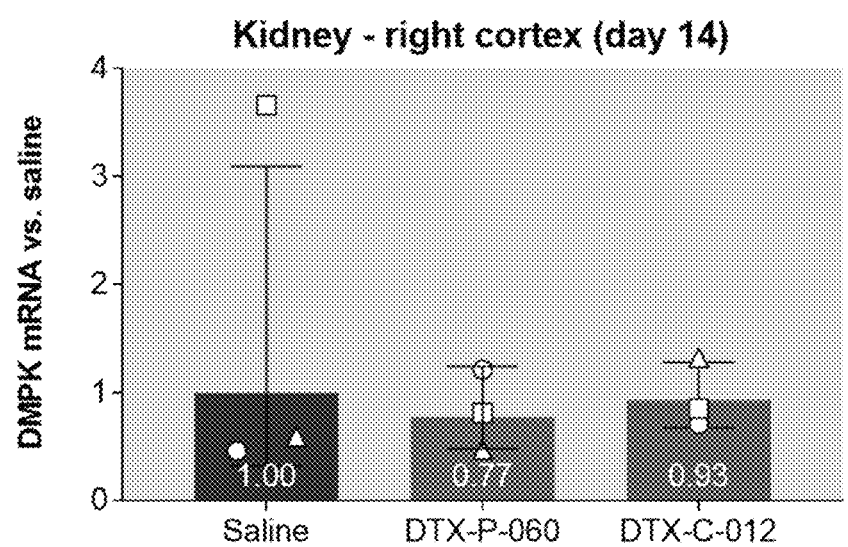
Figure 9C:
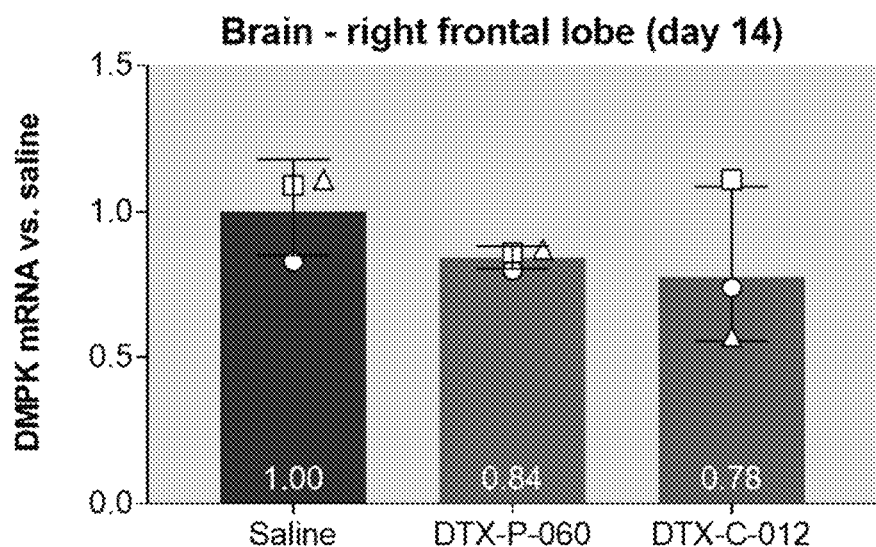
Figure 9D:
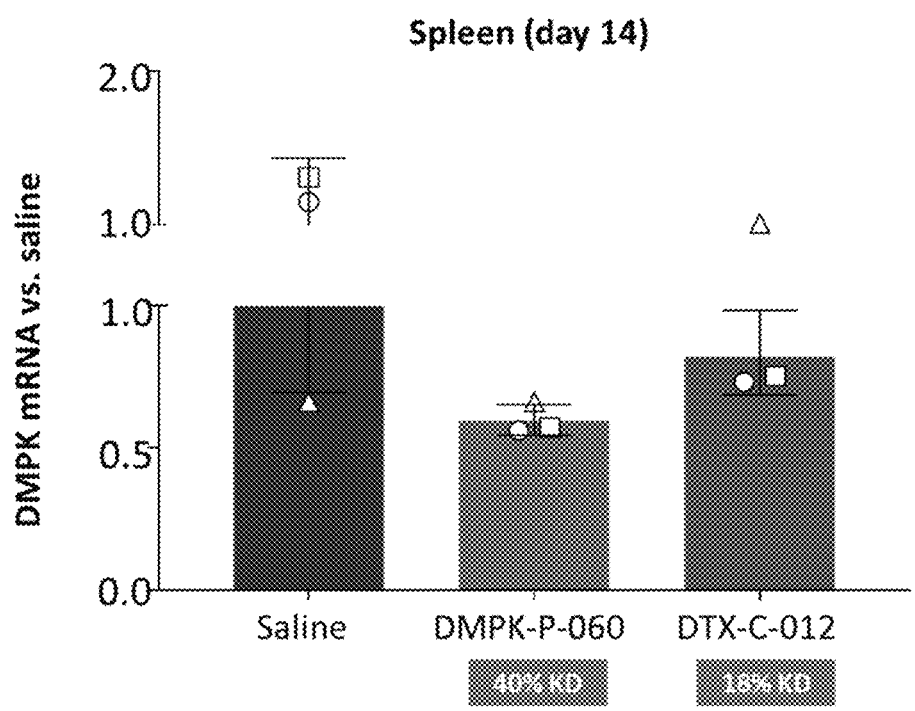
Figure 10:
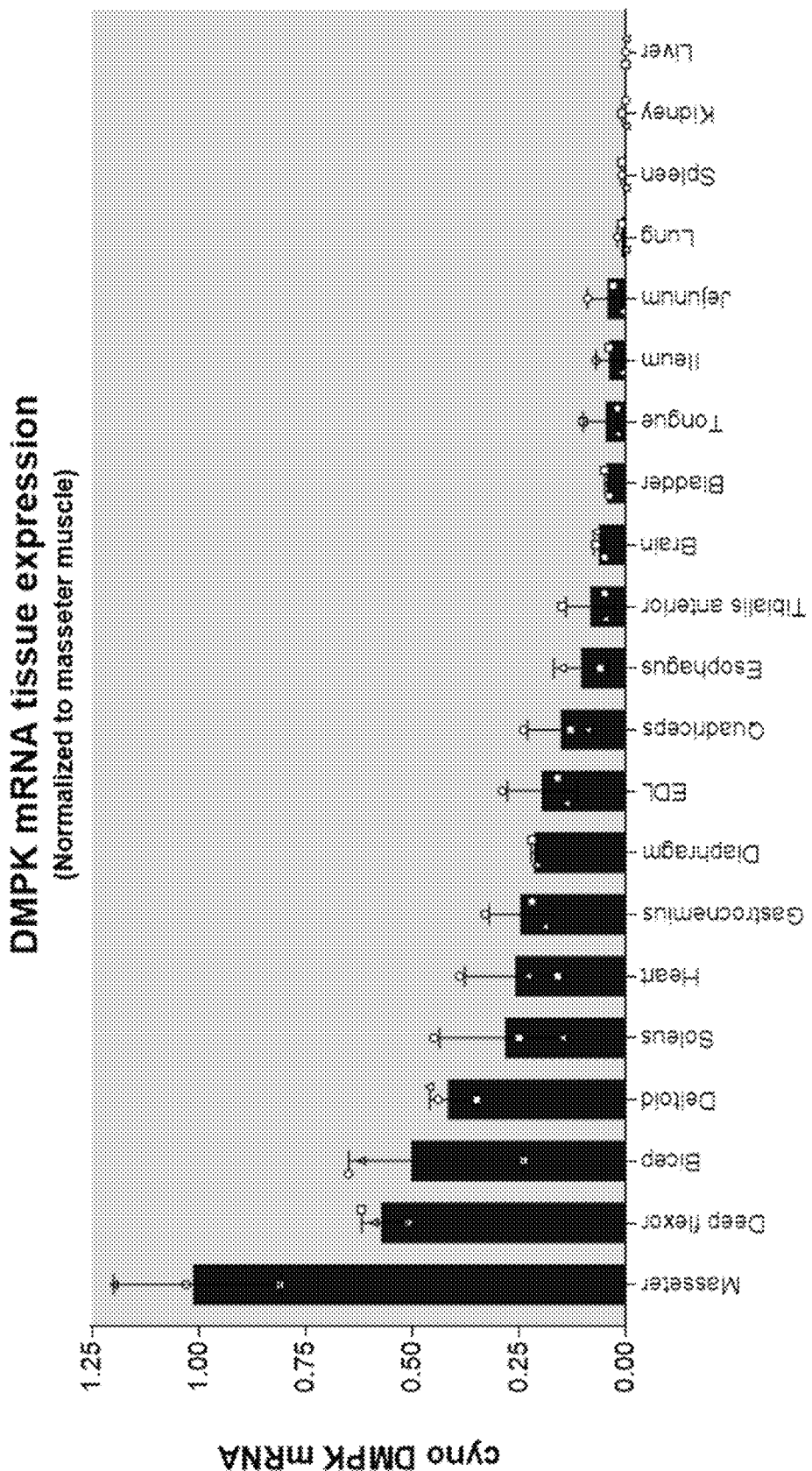
FIG. 10 shows normalized DMPK mRNA tissue expression levels across several tissue types in cynomolgus monkeys. (N=3 male cynomolgus monkeys)

Significant knockdown (KD) of DMPK mRNA expression using DTX-C-012 was observed in soleus, deep flexor, and masseter muscles relative to saline control, with 39% KD, 62% KD, and 41% KD, respectively (FIGS. 7A-7C). Robust knockdown of DMPK mRNA expression DTX-C-012 was further observed in gastrocnemius (62% KD; FIG. 7D), EDL (29% KD; FIG. 7E), tibialis anterior muscle (23% KD; FIG. 7F), diaphragm (54% KD; FIG. 7G), tongue (43% KD; FIG. 7H), heart muscle (36% KD; FIG. 7I), quadriceps (58% KD; FIG. 7J), bicep (51% KD; FIG. 7K), and deltoid muscles (47% KD; FIG. 7L). Knockdown of DMPK mRNA expression DTX-C-012 in smooth muscle was also observed in the intestine, with 63% KD at jejunum-duodenum ends (FIG. 8A) and 70% KD in ileum (FIG. 8B). Notably, naked DMPK ASO (i.e., not linked to a muscle-targeting agent), DTX-P-060, had minimal effects on DMPK expression levels relative to the vehicle control (i.e., little or no reduction in DMPK expression) for all assayed muscle tissue types. Monkeys treated with the DTX-C-012 complex demonstrated no change in DMPK expression in non-muscle tissues, such as liver, kidney, brain, and spleen tissues (FIGS. 9A-9D). Additional tissues were examined, as depicted in FIG. 10, which shows normalized DMPK mRNA tissue expression levels across several tissue types in cynomolgus monkeys. (N=3 male cynomolgus monkeys)

Figure 12:
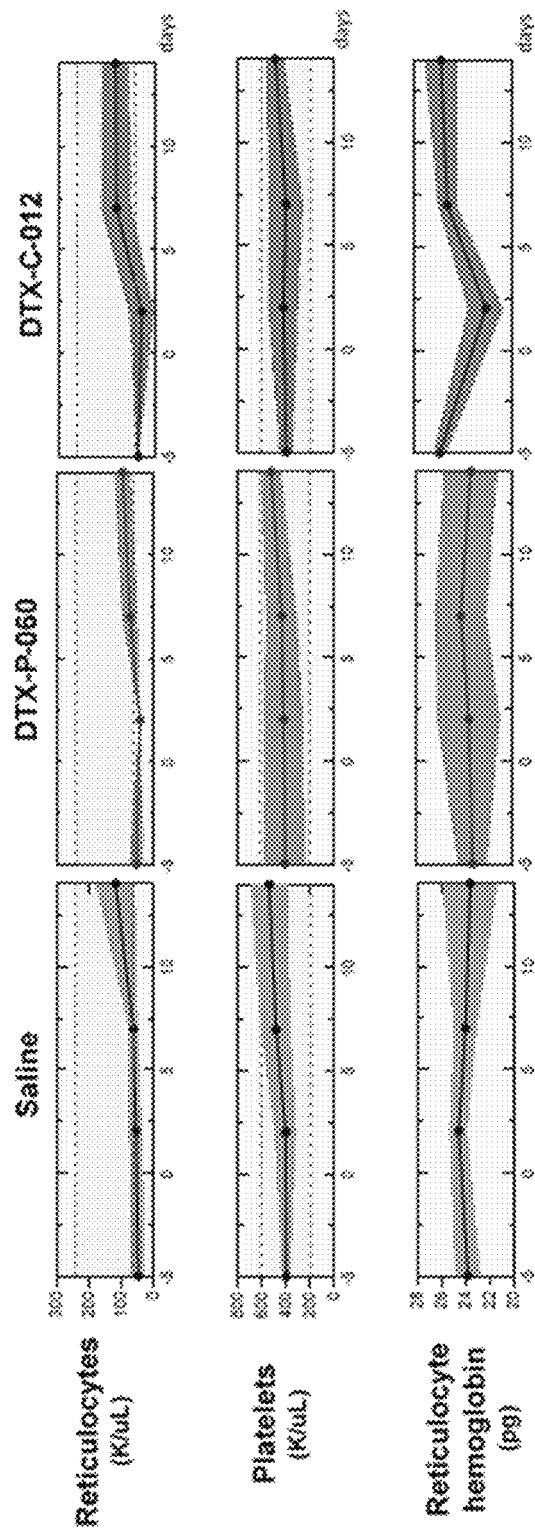
FIG. 12 shows that a single dose of a muscle targeting complex (DTX-C-012) comprising DTX-P-060 is safe and tolerated in cynomolgus monkeys. (N=3 male cynomolgus monkeys)

Prior to euthanization, all monkeys were tested for reticulocyte levels, platelet levels, hemoglobin expression, alanine aminotransferase (ALT) expression, aspartate aminotransferase (AST) expression, and blood urea nitrogen (BUN) levels on days 2, 7, and 14 after dosing. As shown in FIG. 12, monkeys dosed with antibody-oligonucleotide complex had normal reticulocyte levels, platelet levels, hemoglobin expression, alanine aminotransferase (ALT) expression, aspartate aminotransferase (AST) expression, and blood urea nitrogen (BUN) levels throughout the length of the experiment. These data show that a single dose of a complex comprising DTX-P-060 is safe and tolerated in cynomolgus monkeys.

These data demonstrate that the anti-transferrin receptor antibody of the DTX-C-012 complex enabled cellular internalization of the complex into muscle-specific tissues in an in vivo cynomolgus monkey model, thereby allowing the DMPK ASO (DTX-P-060) to inhibit expression of DMPK. These data further demonstrate that the DTX-C-012 complex is capable of specifically targeting muscle tissues for dose-dependent inhibition of DMPK without substantially impacting non-muscle tissues. This is direct contrast with the limited ability of DTX-P-060, a naked DMPK ASO (i.e., not linked to a muscle-targeting agent), to inhibit expression of DMPK in muscle tissues of an in vivo cynomolgus monkey model.

Figure 11A:
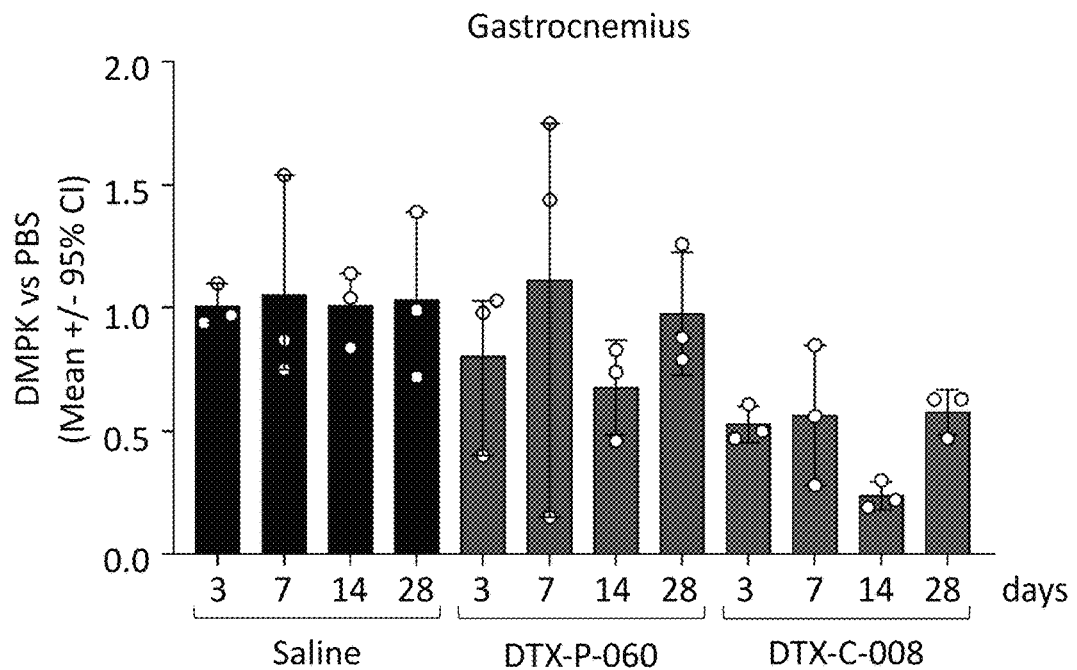
FIGS. 11A-11B depict non-limiting schematics showing the ability of a muscle targeting complex (DTX-C-008) comprising DTX-P-060 to reduce expression levels of DMPK in mouse muscle tissues in vivo for up to 28 days after dosing with DTX-C-008, relative to a vehicle experiment and compared to a naked DMPK ASO (DTX-P-060).
Figure 11B:
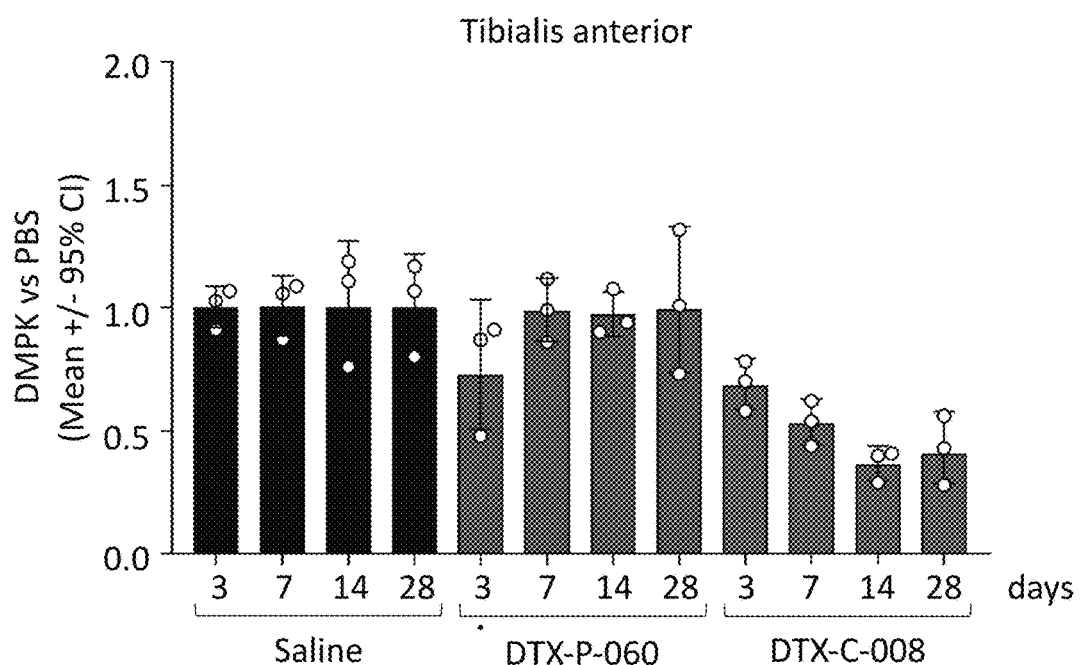

Example 6: Targeting DMPK in Mouse Muscle Tissues with a Muscle-Targeting Complex The muscle-targeting complex described in Example 2, DTX-C-008, was tested for time-dependent inhibition of DMPK in mouse tissues. C57BL/6 wild-type mice were intravenously injected with a single dose of a vehicle control (saline), DTX-P-060 (10 mg/kg of RNA), or DTX-C-008 (10 mg/kg of RNA) and euthanized after a prescribed period of time, as described in Table 2. Following euthanization, the mice were segmented into isolated tissue types and tissue samples were subsequently assayed for expression levels of DMPK (FIGS. 11A-11B).

TABLE 2

| | Experimental conditions | | |
|---|---|---|---|
| Group | Dosage | Days after injection before euthanization | Number of mice |
| 1 | Vehicle (saline) | 3 days | 3 |
| 2 | Vehicle (saline) | 7 days | 3 |
| 3 | Vehicle (saline) | 14 days | 3 |
| 4 | Vehicle (saline) | 28 days | 3 |
| 5 | DTX-P-060 | 3 days | 3 |
| 6 | DTX-P-060 | 7 days | 3 |
| 7 | DTX-P-060 | 14 days | 3 |
| 8 | DTX-P-060 | 28 days | 3 |
| 9 | DTX-C-008 | 3 days | 3 |
| 10 | DTX-C-008 | 7 days | 3 |
| 11 | DTX-C-008 | 14 days | 3 |
| 12 | DTX-C-008 | 28 days | 3 |

Mice treated with the DTX-C-008 complex demonstrated approximately 50% reduction in DMPK expression in gastrocnemius (FIG. 11A) and tibialis anterior (FIG. 11B) muscles for all of Groups 9-12 (β-28 days between injection and euthanization), relative to vehicle. Mice treated with the DTX-P-060 naked oligonucleotide did not demonstrate significant reduction in DMPK expression.

Equivalents and Terminology

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, optional features, modification and variation of the concepts herein disclosed may be resorted to by those skilled in the art, and that such modifications and variations are considered to be within the scope of this disclosure.

In addition, where features or aspects of the disclosure are described in terms of Markush groups or other grouping of alternatives, those skilled in the art will recognize that the disclosure is also thereby described in terms of any individual member or subgroup of members of the Markush group or other group.

It should be appreciated that, in some embodiments, sequences presented in the sequence listing may be referred to in describing the structure of an oligonucleotide or other nucleic acid. In such embodiments, the actual oligonucleotide or other nucleic acid may have one or more alternative nucleotides (e.g., an RNA counterpart of a DNA nucleotide or a DNA counterpart of an RNA nucleotide) and/or one or more modified nucleotides and/or one or more modified internucleotide linkages and/or one or more other modification compared with the specified sequence while retaining essentially same or similar complementary properties as the specified sequence.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:

1. A complex comprising an anti-transferrin receptor antibody covalently linked to a 5' end or a 3' end of an oligonucleotide,
wherein the anti-transferrin receptor antibody comprises a heavy chain variable region (VH) and a light chain variable region (VL), wherein:
the VH comprises a heavy chain complementarity determining region 1 (CDR-H1), a heavy chain complementarity determining region 2 (CDR-H2), and a heavy chain complementarity determining region 3 (CDR-H3) of a heavy chain variable region comprising the amino acid sequence of SEQ ID NO: 641, and comprises humanized framework regions,
the VL comprises a light chain complementarity determining region 1 (CDR-L1), a light chain complementarity determining region 2 (CDR-L2), and a light chain complementarity determining region 3 (CDR-L3) of a light chain variable region comprising the amino acid sequence of SEQ ID NO: 642, and comprises humanized framework regions,
wherein the oligonucleotide comprises one or more modifications and comprises an antisense strand comprising a region of complementarity of at least 15 nucleotides in length to an RNA encoded by a gene associated with a muscle disease, wherein the oligonucleotide is in the range of 15-30 nucleotides in length;
wherein the one or more modifications comprise a 2'-modified nucleoside selected from the group consisting of: a 2'-O-methyl nucleoside, a 2'-fluoro nucleoside, and combinations thereof, and/or comprise a modified backbone selected from a backbone comprising one or more phosphorothioate linkages and a phosphorodiamidate morpholino backbone.

2. The complex of claim 1, wherein the antisense strand is 20-27 nucleotides in length.

3. The complex of claim 2, wherein the region of complementarity is at least 18 nucleotides in length.

4. The complex of claim 2, wherein the region of complementarity is at least 19 nucleotides in length.

5. The complex of claim 4, wherein the oligonucleotide is double-stranded molecule and comprises the antisense strand hybridized to a sense strand.

6. The complex of claim 4, wherein the oligonucleotide is a single stranded antisense oligonucleotide.

7. The complex of claim 5, wherein each nucleoside of the oligonucleotide is selected from a 2'-O-methyl nucleoside and a 2'-fluoro nucleoside.

8. The complex of claim 7, wherein the oligonucleotide comprises a modified backbone comprising one or more phosphorothioate linkages.

9. The complex of claim 6, wherein the oligonucleotide is a phosphorodiamidate morpholino oligomer (PMO).

10. The complex of claim 1, wherein the CDR-H1, CDR-H2, CDR-H3, CDR-L1, CDR-L2, and CDR-L3 are according to the Chothia numbering system.

11. The complex of claim 10, wherein the anti-transferrin receptor antibody is in the form of a full-length IgG comprising a human IgG1 heavy chain constant region, or a functional variant thereof, and a human kappa light chain constant region.

12. The complex of claim 10, wherein the anti-transferrin receptor antibody comprises a human kappa light chain constant region and a human IgG1 heavy chain constant region comprising at least one amino acid substitution relative to a wild-type human IgG1 heavy chain constant region.

13. The complex of claim 11, wherein the full-length IgG comprises a heavy chain constant region comprising at least one amino acid substitution that reduces Fc receptor binding of the anti-transferrin receptor antibody.

14. The complex of claim 11, wherein the full-length IgG comprises two or more amino acid substitutions in a CH2 domain and two or more amino acid substitutions in a CH3 domain, relative to a full-length IgG comprising an IgG1 constant region having an amino acid sequence of SEQ ID NO: 37.

15. The complex of claim 12, wherein the anti-transferrin receptor antibody further comprises one or more sugar or carbohydrate molecules.

16. The complex of claim 15, wherein the one or more sugar or carbohydrate molecules comprise a fucose unit.

17. The complex of claim 12, wherein the complex is formable by a process comprising reacting a first electrophile of a linker precursor compound and a nucleophile of the anti-transferrin receptor antibody.

18. The complex of claim 17, wherein the nucleophile of the anti-transferrin receptor antibody is a thiol group of a cysteine residue of the anti-transferrin receptor antibody.

19. The complex of claim 17, wherein the first electrophile of the linker precursor compound is a maleimide moiety, and wherein the nucleophile of the anti-transferrin receptor antibody is a thiol-group of a cysteine residue of the anti-transferrin receptor antibody.

20. The complex of claim 19, wherein the maleimide moiety is present in a (maleimidomethyl)cyclohexane-1-carboxylate group of the linker precursor compound.

21. The complex of claim 19, wherein the complex is formable by a process comprising reacting a second electrophile of the linker precursor compound and a nucleophile covalently attached to the oligonucleotide.

22. The complex of claim 21, wherein the nucleophile covalently attached to the oligonucleotide comprises an aminoalkyl group.

23. The complex of claim 22, wherein the aminoalkyl group is a NH2-C6 group.

24. The complex of claim 21, wherein the nucleophile covalently attached to the oligonucleotide is covalently attached to a terminal phosphate group of the oligonucleotide.

25. The complex of claim 1, wherein the gene associated with a muscle disease is DUX4.

26. A method of delivering an oligonucleotide to a subject, the method comprising intravenously administering to the subject the complex of claim 1.

27. The method of claim 26, wherein the oligonucleotide is delivered to a skeletal muscle cell, a cardiac muscle cell, or a smooth muscle cell of the subject.

28. The method of claim 26, wherein the subject is human.

29. The method of claim 28, wherein the gene associated with a muscle disease is DUX4.

30. The method of claim 29, wherein the subject has Facioscapulohumeral Muscular Dystrophy (FSHD).

\* \* \* \* \*

SEQUENCE LISTING

```
Sequence total quantity: 997
SEQ ID NO: 1            moltype = AA  length = 760
FEATURE                 Location/Qualifiers
source                  1..760
                        mol_type = protein
                        organism = Homo sapiens
SEQUENCE: 1
MMDQARSAFS NLFGGEPLSY TRFSLARQVD GDNSHVEMKL AVDEEENADN NTKANVTKPK  60
RCSGSICYGT IAVIVFFLIG FMIGYLGYCK GVEPKTECER LAGTESPVRE EPGEDFPAAR  120
RLYWDDLKRK LSEKLDSTDF TGTIKLLNEN SYVPREAGSQ KDENLALYVE NQFREFKLSK  180
VWRDQHFVKI QVKDSAQNSV IIVDKNGRLV YLVENPGGYV AYSKAATVTG KLVHANFGTK  240
KDFEDLYTPV NGSIVIVRAG KITFAEKVAN AESLNAIGVL IYMDQTKFPI VNAELSFFGH  300
AHLGTGDPYT PGFPSFNHTQ FPPSRSSGLP NIPVQTISRA AAEKLFGNME GDCPSDWKTD  360
STCRMVTSES KNVKLTVSNV LKEIKILNIF GVIKGFVEPD AWGPGAAKSG  420
VGTALLLKLA QMFSDMVLKD GFQPSRSIIF ASWSAGDFGS VGATEWLEGY LSSLHLKAFT  480
YINLDKAVLG TSNFKVSASP LLYTLIEKTM QNVKHPVTGQ FLYQDSNWAS KVEKLTLDNA  540
AFPFLAYSGI PAVSFCFCED TDYPYLGTTM DTYKELIERI PELNKVARAA AEVAGQFVIK  600
LTHDVELNLD YERYNSQLLS FVRDLNQYRA DIKEMGLSVG WLYSARGDFF RATSRLTTDF  660
GNAEKTDRFV MKKLNDRVMR VEYHFLSPYV SPKESPFRHV FWGSGSHTLP ALLENLKLRK  720
QNNGAFNETL FRNQLALATW TIQGAANALS GDVWDIDNEF                       760

SEQ ID NO: 2            moltype = AA  length = 760
FEATURE                 Location/Qualifiers
source                  1..760
                        mol_type = protein
                        organism = Macaca mulatta
SEQUENCE: 2
MMDQARSAFS NLFGGEPLSY TRFSLARQVD GDNSHVEMKL GVDEEENTDN NTKPNGTKPK  60
RCGGNICYGT IAVIIFFLIG FMIGYLGYCK GVEPKTECER LAGTESPARE EPEEDFPAAP  120
RLYWDDLKRK LSEKLDTTDF TSTIKLLNEN LYVPREAGSQ KDENLALYIE NQFREFKLSK  180
VWRDQHFVKI QVKDSAQNSV IIVDKNGGLV YLVENPGGYV AYSKAATVTG KLVHANFGTK  240
KDFEDLDSPV NGSIVIVRAG KITFAEKVAN AESLNAIGVL IYMDQTKFPI VKADLSFFGH  300
AHLGTGDPYT PGFPSFNHTQ FPPSQSSGLP NIPVQTISRA AAEKLFGNME GDCPSDWKTD  360
STCKMVTSEN KSVKLTVSNV LKETKILNIF GVIKGFVEPD HYVVVGAQRD AWGPGAAKSS  420
VGTALLLKLA QMFSDMVLKD GFQPSRSIIF ASWSAGDFGS VGATEWLEGY LSSLHLKAFT  480
```

```
YINLDKAVLG TSNFKVSASP LLYTLIEKTM QDVKHPVTGR SLYQDSNWAS KVEKLTLDNA    540
APPFLAYSGI PAVSFCFCED TDYPYLGTTM DTYKELVERI PELNKVARAA AEVAGQFVIK    600
LTHDTELNLD YERYNSQLLL FLRDLNQYRA DVKEMGLSLQ WLYSARGDFF RATSRLTTDF    660
RNAEKRDKFV MKKLNDRVMR VEYYFLSPYV SPKESPFRHV FWGSGSHTLS ALLESLKLRR    720
QNNSAFNETL FRNQLALATW TIQGAANALS GDVWDIDNEF                         760

SEQ ID NO: 3             moltype = AA   length = 760
FEATURE                  Location/Qualifiers
source                   1..760
                         mol_type = protein
                         organism = Macaca fascicularis
SEQUENCE: 3
MMDQARSAFS NLFGGEPLSY TRFSLARQVD GDNSHVEMKL GVDEEENTDN NTKANGTKPK     60
RCGGNICYGT IAVIIFFLIG FMIGYLGYCK GVEPKTECER LAGTESPARE EPEEDFPAAP    120
RLYWDDLKRK LSEKLDTTDF TSTIKLLNEN LYVPREAGSQ KDENLALYIE NQFREFKLSK    180
VWRDQHFVKI QVKDSAQNSV IIVDKNGGLV YLVENPGGYV AYSKAATVTG KLVHANFGTK    240
KDFEDLDSPV NGSIVIVRAG KITFAEKVAN AESLNAIGVL IYMDQTKFPI VKADLSFFGH    300
AHLGTGDPYT PGFPSFNHTQ FPPSQSSGLP NIPVQTISRA AAEKLFGNME GDCPSDWKTD    360
STCKMVTSEN KSVKLTVSNV LKETKILNIF GVIKGFVEPD HYVVVGAQRD AWGPGAAKSS    420
VGTALLLKLA QMFSDMVLKD GFQPSRSIIF ASWSAGDFGS VGATEWLEGY LSSLHLKAFT    480
YINLDKAVLG TSNFKVSASP LLYTLIEKTM QDVKHPVTGR SLYQDSNWAS KVEKLTLDNA    540
APPFLAYSGI PAVSFCFCED TDYPYLGTTM DTYKELVERI PELNKVARAA AEVAGQFVIK    600
LTHDTELNLD YERYNSQLLL FLRDLNQYRA DVKEMGLSLQ WLYSARGDFF RATSRLTTDF    660
RNAEKRDKFV MKKLNDRVMR VEYYFLSPYV SPKESPFRHV FWGSGSHTLS ALLESLKLRR    720
QNNSAFNETL FRNQLALATW TIQGAANALS GDVWDIDNEF                         760

SEQ ID NO: 4             moltype = AA   length = 763
FEATURE                  Location/Qualifiers
source                   1..763
                         mol_type = protein
                         organism = Mus musculus
SEQUENCE: 4
MMDQARSAFS NLFGGEPLSY TRFSLARQVD GDNSHVEMKL AADEEENADN NMKASVRKPK     60
RFNGRLCFAA IALVIFFLIG FMSGYLGYCK RVEQKEECVK LAETEETDKS ETMETEDVPT    120
SSRLYWADLK TLLLSEKLNSI EFADTIKQLS QNTYTPREAG SQKDESLAYY IENQFHEFKF    180
SKVWRDEHYV KIQVKSSIGQ NMVTIVQSNG NLDPVESPEG YVAFSKPTEV SGKLVHANFG    240
TKKDFEELSY SVNGSLVIVR AGEITFAEKV ANAQSFNAIG VLIYMDKNKF PVVEADLALF    300
GHAHLGTGDP YTPGFPSFNH TQFPPSQSSG LPNIPVQTIS RAAAEKLFGK MEGSCPARWN    360
IDSSCKLELS QNQNVKLIVK NVLKERRILN IFGVIKGYEE PDRYVVVGAQ RDALGAGVAA    420
KSSVGTGLLL KLAQVFSDMI SKDGFRPSRS IIFASWTAGD FGAVGATEWL EGYLSSLHLK    480
AFTYINLDKV VLGTSNFKVS ASPLLYTLMG KIMQDVKHPV DGKSLYRDSN WISKVEKLSF    540
DNAAYPPLAY SGIPAVSFCF CEDADYPYLG TRLDTYEALT QKVPQLNQMV RTAAEVAGQL    600
IIKLTHDVEL NLDYEMYNSK LLSFMKDLNQ FKTDIRDMGL SLQWLYSARG DYFRATSRLT    660
TDFHNAEKTN RFVMREINDR IMKVEYHFLS PYVSPRESPF RHIFWGSGSH TLSALVENLK    720
LRQKNITAFN ETLFRNQLAL ATWTIQGVAN ALSGDIWNID NEF                     763

SEQ ID NO: 5             moltype = AA   length = 197
FEATURE                  Location/Qualifiers
REGION                   1..197
                         note = Synthetic polypeptide
source                   1..197
                         mol_type = protein
                         organism = synthetic construct
SEQUENCE: 5
FVKIQVKDSA QNSVIIVDKN GRLVYLVENP GGYVAYSKAA TVTGKLVHAN FGTKKDFEDL     60
YTPVNGSIVI VRAGKITFAE KVANAESLNA IGVLIYMDQT KFPIVNAELS FFGHAHLGTG    120
DPYTPGFPSF NHTQFPPSRS SGLPNIPVQT ISRAAAEKLF GNMEGDCPSD WKTDSTCRMV    180
TSESKNVKLT VSNVLKE                                                  197

SEQ ID NO: 6             moltype = AA   length = 7
FEATURE                  Location/Qualifiers
REGION                   1..7
                         note = Synthetic polypeptide
source                   1..7
                         mol_type = protein
                         organism = synthetic construct
SEQUENCE: 6
ASSLNIA                                                               7

SEQ ID NO: 7             moltype = AA   length = 12
FEATURE                  Location/Qualifiers
REGION                   1..12
                         note = Synthetic polypeptide
source                   1..12
                         mol_type = protein
                         organism = synthetic construct
SEQUENCE: 7
SKTFNTHPQS TP                                                        12
```

```
SEQ ID NO: 8            moltype = AA  length = 12
FEATURE                 Location/Qualifiers
REGION                  1..12
                        note = Synthetic polypeptide
source                  1..12
                        mol_type = protein
                        organism = synthetic construct
SEQUENCE: 8
TARGEHKEEE LI                                                                      12

SEQ ID NO: 9            moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 9
CQAQGQLVC                                                                           9

SEQ ID NO: 10           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 10
CSERSMNFC                                                                           9

SEQ ID NO: 11           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 11
CPKTRRVPC                                                                           9

SEQ ID NO: 12           moltype = AA  length = 20
FEATURE                 Location/Qualifiers
REGION                  1..20
                        note = Synthetic polypeptide
source                  1..20
                        mol_type = protein
                        organism = synthetic construct
SEQUENCE: 12
WLSEAGPVVT VRALRGTGSW                                                              20

SEQ ID NO: 13           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 13
CMQHSMRVC                                                                           9

SEQ ID NO: 14           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 14
DDTRHWG                                                                             7

SEQ ID NO: 15           moltype =     length =
SEQUENCE: 15
000

SEQ ID NO: 16           moltype = AA  length = 5
FEATURE                 Location/Qualifiers
source                  1..5
                        mol_type = protein
                        organism = synthetic construct
```

```
VARIANT              3
                     note = X can be any naturally occurring amino acid
SEQUENCE: 16
LPXTG                                                                    5

SEQ ID NO: 17        moltype = AA   length = 5
FEATURE              Location/Qualifiers
REGION               1..5
                     note = Synthetic polypeptide
source               1..5
                     mol_type = protein
                     organism = synthetic construct
SEQUENCE: 17
SYWMH                                                                    5

SEQ ID NO: 18        moltype = AA   length = 17
FEATURE              Location/Qualifiers
REGION               1..17
                     note = Synthetic polypeptide
source               1..17
                     mol_type = protein
                     organism = synthetic construct
SEQUENCE: 18
EINPTNGRTN YIEKFKS                                                       17

SEQ ID NO: 19        moltype = AA   length = 7
FEATURE              Location/Qualifiers
REGION               1..7
                     note = Synthetic polypeptide
source               1..7
                     mol_type = protein
                     organism = synthetic construct
SEQUENCE: 19
GTRAYHY                                                                  7

SEQ ID NO: 20        moltype = AA   length = 11
FEATURE              Location/Qualifiers
REGION               1..11
                     note = Synthetic polypeptide
source               1..11
                     mol_type = protein
                     organism = synthetic construct
SEQUENCE: 20
RASDNLYSNL A                                                             11

SEQ ID NO: 21        moltype = AA   length = 7
FEATURE              Location/Qualifiers
REGION               1..7
                     note = Synthetic polypeptide
source               1..7
                     mol_type = protein
                     organism = synthetic construct
SEQUENCE: 21
DATNLAD                                                                  7

SEQ ID NO: 22        moltype = AA   length = 9
FEATURE              Location/Qualifiers
REGION               1..9
                     note = Synthetic polypeptide
source               1..9
                     mol_type = protein
                     organism = synthetic construct
SEQUENCE: 22
QHFWGTPLT                                                                9

SEQ ID NO: 23        moltype = AA   length = 7
FEATURE              Location/Qualifiers
REGION               1..7
                     note = Synthetic polypeptide
source               1..7
                     mol_type = protein
                     organism = synthetic construct
SEQUENCE: 23
GYTFTSY                                                                  7

SEQ ID NO: 24        moltype = AA   length = 6
FEATURE              Location/Qualifiers
REGION               1..6
                     note = Synthetic polypeptide
```

```
source                  1..6
                        mol_type = protein
                        organism = synthetic construct
SEQUENCE: 24
NPTNGR                                                                          6

SEQ ID NO: 25           moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 25
TSYWMH                                                                          6

SEQ ID NO: 26           moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 26
WIGEINPTNG RTN                                                                 13

SEQ ID NO: 27           moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 27
ARGTRA                                                                          6

SEQ ID NO: 28           moltype = AA   length = 7
FEATURE                 Location/Qualifiers
REGION                  1..7
                        note = Synthetic polypeptide
source                  1..7
                        mol_type = protein
                        organism = synthetic construct
SEQUENCE: 28
YSNLAWY                                                                         7

SEQ ID NO: 29           moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 29
LLVYDATNLA                                                                     10

SEQ ID NO: 30           moltype = AA   length = 8
FEATURE                 Location/Qualifiers
REGION                  1..8
                        note = Synthetic polypeptide
source                  1..8
                        mol_type = protein
                        organism = synthetic construct
SEQUENCE: 30
QHFWGTPL                                                                        8

SEQ ID NO: 31           moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 31
QHFAGTPLT                                                                       9

SEQ ID NO: 32           moltype = AA   length = 8
FEATURE                 Location/Qualifiers
REGION                  1..8
```

```
                        note = Synthetic polypeptide
source                  1..8
                        mol_type = protein
                        organism = synthetic construct
SEQUENCE: 32
QHFAGTPL                                                                8

SEQ ID NO: 33           moltype = AA   length = 116
FEATURE                 Location/Qualifiers
REGION                  1..116
                        note = Synthetic polypeptide
source                  1..116
                        mol_type = protein
                        organism = synthetic construct
SEQUENCE: 33
QVQLQQPGAE LVKPGASVKL SCKASGYTFT SYWMHWVKQR PGQGLEWIGE INPTNGRTNY        60
IEKFKSKATL TVDKSSSTAY MQLSSLTSED SAVYYCARGT RAYHYWGQGT SVTVSS           116

SEQ ID NO: 34           moltype = AA   length = 107
FEATURE                 Location/Qualifiers
REGION                  1..107
                        note = Synthetic polypeptide
source                  1..107
                        mol_type = protein
                        organism = synthetic construct
SEQUENCE: 34
DIQMTQSPAS LSVSVGETVT ITCRASDNLY SNLAWYQQKQ GKSPQLLVYD ATNLADGVPS        60
RFSGSGSGTQ YSLKINSLQS EDFGTYYCQH FWGTPLTFGA GTKLELK                    107

SEQ ID NO: 35           moltype = AA   length = 116
FEATURE                 Location/Qualifiers
REGION                  1..116
                        note = Synthetic polypeptide
source                  1..116
                        mol_type = protein
                        organism = synthetic construct
SEQUENCE: 35
EVQLVQSGAE VKKPGASVKV SCKASGYTFT SYWMHWVRQA PGQRLEWIGE INPTNGRTNY        60
IEKFKSRATL TVDKSASTAY MELSSLRSED TAVYYCARGT RAYHYWGQGT MVTVSS           116

SEQ ID NO: 36           moltype = AA   length = 107
FEATURE                 Location/Qualifiers
REGION                  1..107
                        note = Synthetic polypeptide
source                  1..107
                        mol_type = protein
                        organism = synthetic construct
SEQUENCE: 36
DIQMTQSPSS LSASVGDRVT ITCRASDNLY SNLAWYQQKP GKSPKLLVYD ATNLADGVPS        60
RFSGSGSGTD YSLKINSLQS EDFGTYYCQH FWGTPLTFGA GTKLELK                    107

SEQ ID NO: 37           moltype = AA   length = 330
FEATURE                 Location/Qualifiers
REGION                  1..330
                        note = Synthetic polypeptide
source                  1..330
                        mol_type = protein
                        organism = synthetic construct
SEQUENCE: 37
ASTKGPSVFP LAPSSKSTSG GTAALGCLVK DYFPEPVTVS WNSGALTSGV HTFPAVLQSS        60
GLYSLSSVVT VPSSSLGTQT YICNVNHKPS NTKVDKKVEP KSCDKTHTCP PCPAPELLGG       120
PSVFLFPPKP KDTLMISRTP EVTCVVVDVS HEDPEVKFNW YVDGVEVHNA KTKPREEQYN       180
STYRVVSVLT VLHQDWLNGK EYKCKVSNKA LPAPIEKTIS KAKGQPREPQ VYTLPPSRDE       240
LTKNQVSLTC LVKGFYPSDI AVEWESNGQP ENNYKTTPPV LDSDGSFFLY SKLTVDKSRW       300
QQGNVFSCSV MHEALHNHYT QKSLSLSPGK                                       330

SEQ ID NO: 38           moltype = AA   length = 110
FEATURE                 Location/Qualifiers
REGION                  1..110
                        note = Synthetic polypeptide
source                  1..110
                        mol_type = protein
                        organism = synthetic construct
SEQUENCE: 38
ASTKGPSVFP LAPSSKSTSG GTAALGCLVK DYFPEPVTVS WNSGALTSGV HTFPAVLQSS        60
GLYSLSSVVT VPSSSLGTQT YICNVNHKPS NTKVDKKVEP KSCDKTHTCP                 110

SEQ ID NO: 39           moltype = AA   length = 446
FEATURE                 Location/Qualifiers
```

```
REGION                       1..446
                             note = Synthetic polypeptide
source                       1..446
                             mol_type = protein
                             organism = synthetic construct
SEQUENCE: 39
QVQLQQPGAE LVKPGASVKL SCKASGYTFT SYWMHWVKQR PGQGLEWIGE INPTNGRTNY    60
IEKFKSKATL TVDKSSSTAY MQLSSLTSED SAVYYCARGT RAYHYWGQGT SVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 40               moltype = AA  length = 226
FEATURE                     Location/Qualifiers
REGION                       1..226
                             note = Synthetic polypeptide
source                       1..226
                             mol_type = protein
                             organism = synthetic construct
SEQUENCE: 40
QVQLQQPGAE LVKPGASVKL SCKASGYTFT SYWMHWVKQR PGQGLEWIGE INPTNGRTNY    60
IEKFKSKATL TVDKSSSTAY MQLSSLTSED SAVYYCARGT RAYHYWGQGT SVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCP                 226

SEQ ID NO: 41               moltype = AA  length = 446
FEATURE                     Location/Qualifiers
REGION                       1..446
                             note = Synthetic polypeptide
source                       1..446
                             mol_type = protein
                             organism = synthetic construct
SEQUENCE: 41
EVQLVQSGAE VKKPGASVKV SCKASGYTFT SYWMHWVRQA PGQRLEWIGE INPTNGRTNY    60
IEKFKSRATL TVDKSASTAY MELSSLRSED TAVYYCARGT RAYHYWGQGT MVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 42               moltype = AA  length = 217
FEATURE                     Location/Qualifiers
REGION                       1..217
                             note = Synthetic polypeptide
source                       1..217
                             mol_type = protein
                             organism = synthetic construct
SEQUENCE: 42
DIQMTQSPSS LSASVGDRVT ITCRASDNLY SNLAWYQQKP GKSPKLLVYD ATNLADGVPS    60
RFSGSGSGTD YSLKINSLQS EDFGTYYCQH FWGTPLTFGA GTKLELKAST KGPSVFPLAP   120
SSKSTSGGTA ALGCLVKDYF PEPVTVSWNS GALTSGVHTF PAVLQSSGLY SLSSVVTVPS   180
SSLGTQTYIC NVNHKPSNTK VDKKVEPKSC DKTHTCP                           217

SEQ ID NO: 43               moltype = AA  length = 226
FEATURE                     Location/Qualifiers
REGION                       1..226
                             note = Synthetic polypeptide
source                       1..226
                             mol_type = protein
                             organism = synthetic construct
SEQUENCE: 43
QVQLQQPGAE LVKPGASVKL SCKASGYTFT SYWMHWVKQR PGQGLEWIGE INPTNGRTNY    60
IEKFKSKATL TVDKSSSTAY MQLSSLTSED SAVYYCARGT RAYHYWGQGT SVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCP                 226

SEQ ID NO: 44               moltype = AA  length = 226
FEATURE                     Location/Qualifiers
REGION                       1..226
                             note = Synthetic polypeptide
source                       1..226
                             mol_type = protein
                             organism = synthetic construct
SEQUENCE: 44
```

```
EVQLVQSGAE VKKPGASVKV SCKASGYTFT SYWMHWVRQA PGQRLEWIGE INPTNGRTNY   60
IEKFKSRATL TVDKSASTAY MELSSLRSED TAVYYCARGT RAYHYWGQGT MVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCP                 226

SEQ ID NO: 45           moltype = DNA   length = 2859
FEATURE                 Location/Qualifiers
source                  1..2859
                        mol_type = genomic DNA
                        organism = Homo sapiens
SEQUENCE: 45
agggggctg gaccaagggg tggggagaag gggaggaggc ctcggccggc cgcagagaga    60
agtggccaga gaggcccagg ggacagccag ggacaggcag acatgcagcc agggctccag  120
ggcctggaca ggggctgcca ggcctgtga caggaggacc cgcccggga                180
ggggccatgg tgctgcctgt ccaacatgtc agccgaggtg cggctgaggc ggctccagca  240
gctggtgttg gacccgggct tcctggggct ggagcccctg ctcgaccttc tcctgggcgt  300
ccaccaggag ctgggcgcct ccgaactggc ccaggacaag tacgtggccg acttcttgca  360
gtgggcggag cccatcgtgg tgaggcttaa ggaggtccga ctgcagaggg acgacttcga  420
gattctgaag gtgatcggac gcggggcgtt cagcgaggta gcggtagtga agatgaagca  480
gacgggccag gtgtatgcca tgaagatcat gaacaagtgg gacatgctga gaggggcga   540
ggtgtcgtgc ttccgtgagg agaggacgt gttggtgaat ggggaccggc ggtggatcac    600
gcagctgcac ttcgccttcc aggatgaaga ctacctgtac ctggtcatgg agtattacgt  660
gggcggggac ctgctgacac tgctgagcaa gtttggggga cggattccgg ccgagatggc  720
gcgcttctac ctggcggaga ttgtcatggc catagactcg gtgaccggc ttggctacgt    780
gcacagggac atcaaaccg caacatcct gctggaccgc tgtggccaca tccgcctggc    840
cgacttcggc tcttgcctca agctgcgggc agatgaacg cgcggtcgc tggtggctgt    900
gggcacccca gactacctgt cccccgagat cctgcaggct gtgggcggtg ggctgggac    960
aggcagctac gggcccgagt gtgactggtg ggcgctgggt gtattcgcct atgaaatgtt  1020
ctatgggcag acgcccttct acgcggattc cacggcggag acctatgca agatcgtcca  1080
ctacaaggag cacctctctc tgccgctggt ggacaaggg gtccctgagg aggctcgaga  1140
cttcattcag cggttgctgt gtccccgga gacacgcctg ggccggggtg gagcaggcga  1200
cttccggaca catcccttct tctttggcct cgactgggat ggtctccggg acagcgtgcc  1260
ccccttaca ccggatttcg aaggtgccac cgacacatgc aacttcgact tggtggagga   1320
cgggctcact gccatggaga cactgtcgga cattcggaa ggtgcgccgc tagggtcca    1380
cctgccttt gtgggctact cctactcctg catggccctc agggacagtg aggtcccagg  1440
ccccacaccc atggaactgg aggccgagca gctgcttgag ccacacgtgc aagcgcccag  1500
cctggagccc tcggtgtccc cacaggatga aacagctgaa gtggcagttc cagcggctgt  1560
ccctgcggca gaggctgagg ccgaggtgac gctgcggag ctccaggaag ccctggagga   1620
ggaggtgctc acccggacaga gcctgagccg ggagatggaa gccatccgca cggacaacca  1680
gaacttcgcc agtcaactac gcaggcagaa ggctcggaac cgggacctag aggcacacgt  1740
ccggcagttg caggagcgga tggagttgct gcaggcagag ggagcacag ctgtcacggg   1800
ggtccccagt ccccggggcca cggatccacc ttcccatcta gatggccccc cggccgtggc  1860
tgtggggcag tgccgcgctg tggggccagg cccccatgcac cgccactcg gctgctcccc   1920
tgccagggtc cctaggcctg gcctatcgga ggcgcttcc ctgctcctgt cgccgttgt    1980
tctgtctcgt gccgccgccc tgggctcat tgggttggtg gccccacgccg ggcaactcac   2040
cgcagtctgc cgccgcccag gagccgcccg cgctccctga accctagaac tgtcttcgac  2100
tccggggccc cgttggaaga ctgagtgccc ggggcacggc acagaagccg cgccaccgc    2160
ctgccagttc acaaccgctc cgagcgtggg tctccgccca gctccagtcc tgtgatccgg  2220
gcccgccccc tagcggccgg ggagggaggg gccgggtccg cggccggcga acggggctcg  2280
aagggtcctt gtaccggga atgctgctgc tgctgctgct gctgctgctg ctgctgctgc   2340
tgctgctgct gctgctgctg ctgggggat cacagaccat ttctttcttt cggccaggct   2400
gaggccctga cgtggatggg caaactgcag gcctgggaag gcagcaagcc gggccgtccg  2460
tgttccatcc tccacgcacc cccacctatc gttggttcgc aaagtgcaaa gctttcttgt  2520
gcatgacgcc ctgctctggg gagcgtctgg cgcgatctct gcctgcttac tcgggaaatt  2580
tgcttttgcc aaaccccgctt tttcggggat cccgcgcccc cctcctcact tgcgctgctc  2640
tcggagcccc agccggctcc gcccgcttcg gcggtttgga tatttattga cctcgtcctc  2700
cgactgctg acaggctaca ggaccccaa caacccaat ccacgttttg gatgcactga    2760
gaccccgaca ttcctcggta tttattgtct gtccccacct aggaccccca ccccgaccc   2820
tcgcgaataa aaggccctcc atctgcccaa agctctgga                         2859

SEQ ID NO: 46           moltype = DNA   length = 2683
FEATURE                 Location/Qualifiers
source                  1..2683
                        mol_type = genomic DNA
                        organism = Mus musculus
SEQUENCE: 46
gaactggcca gagagaccca agggatagtc agggacgggc agacatgcag ctagggttct    60
ggggcctgga caggggcagc caggccctgt gacgggaaga cccgcgagct ccggccgggg   120
aggggccatg gtgttgcctg cccaacatgt cagccgaagt gcggctgaag cagctccaga  180
agctggtgct ggaccaggc ttcctggga ctggagcccct gctcgacctt ctcctgggca    240
tccaccagga gctgggtgcc tctcacctag cccaggacaa gtatgtggcc gacttcttgc  300
agtgggtgga gcccattgca gcaaggctta aggaggtccg actgcagagg gatgattttg  360
agattttgaa ggtgatcggg cgtggggcgt tcagcgaggt agcggtggtg aagatgaaac  420
agacgggcca agtgtatgcc atgaaagatta tgaataagtg aagagaggcg              480
aggtgtcgtg cttccgggaa gaaagggatg tattagtgaa aggggaccgg cgctgggatca  540
cacagctgca ctttgccttc aggatgaga actacctgta cctggtcatg gaatactacg   600
tgggcgggga cctgctaacg ctgctgagca gtttggggga gcggatcccc gccgagatgg   660
ctcgcttcta cctggccgag attgtcatgg ccatagactc gtgcaccgg ctgggctacg    720
tgcacaggga catcaaacca gataacattc tgctggaccg atgtgggcac attcgcctgg   780
```

-continued

```
cagacttcgg ctcctgcctc aaactgcagc ctgatggaat ggtgaggtcg ctggtggctg   840
tgggcacccc ggactacctg tctcctgaga ttctgcaggc cgttggtgga gggcctgggg   900
caggcagcta cgggccagag tgtgactggt gggcactggg cgtgttcgcc tatgagatgt   960
tctatgggca gacccccttc tacgcggact ccacagccga gacatatgcc aagattgtgc  1020
actacaggga acacttgtcg ctgccgctgg cagacacagt tgtccccgag gaagctcagg  1080
acctcattcg tgggctgctg tgtcctgctg agataaggct aggtcgaggt ggggcagact  1140
tcgagggtgc cacggacaca tgcaatttcg atgtggtgga ggaccggctc actgccatgg  1200
tgagcggggg cggggagacg ctgtcagaca tgcaggaaga catgccccctt ggggtgcgcc  1260
tgcccttcgt gggctactcc tactgctgca tggccttcag agacaatcag gtcccggacc  1320
ccaccccttat ggaactagag gccctgcagt tgcctgtgtc agacttgcaa gggcttgact  1380
tgcagccccc agtgtcccca ccggatcaag tggctgaaga ggctgaccta gtggctgtcc  1440
ctgcccctgt ggctgaggca gagaccacgg taacgctgca gcagctccag gaagccctgg  1500
aagaagaggt tctcacccgg cagagcctga gccgcgagct ggaggccatc cggaccgcca  1560
accagaactt ctccagccaa ctacagggag ccgaggtccg aaaccgagac ctggaggcgc  1620
atgttcggca gctacaggaa cggatggaga tgctgcaggc cccaggagcc gcagccatca  1680
cgggggtccc cagtccccgg gccacggatc caccttccca tctagatggc ccccccggcc  1740
tggctgtggg ccagtgcccg ctggtggggc caggcccat gcaccgccgt cacctgctgc  1800
tccctgccag gatccctagg cctgcctat ccgaggcgcg ttgcctgctc ctgttccgg  1860
ctgctctggc tgctgccgcc acactgggct gcactgggtt ggtggcctat accggcggtc  1920
tcacccagt ctggtgtttc ccgggagcca ccttcgcccc ctgaaccctta agactccaag  1980
ccatctttca tttaggcctc ctaggaaggt cgagcgacca gggagcgacc caaagcgtct  2040
ctgtgcccat cgcgccccccc cccccccccc accgctccgc tccacacttc tgtgagcctg  2100
ggtccccacc cagctccgct cctgtgatcc aggcctgcca cctggcggcc ggggagggag  2160
gaacagggct cgtgcccagc acccctggtt cctgcagagc tggtagccac cgctgctgca  2220
gcagctgggg attcgccgac cttgctttac tcagccccga cgtggatggg caaactgctc  2280
agctcatccg atttcacttt ttcactctcc cagccatgca ttacaagcca taagcatgag  2340
cccctatttt ccaggacat cccattccca tagtgatgaa tcagcaagac ctctgccagc  2400
acacacggag tctttggctt cggacagcct cactcctggg ggttgctgca actccttccc  2460
cgtgtacacg tctgcactct aacaacggag ccacagctgc actccccct cccccaaagc  2520
agtgtgggta tttattgatc ttgttatctg actcactgac agactccggg acccacgttt  2580
tagatgcatt gagactcgac attcctcggt atttattgtc tgtccccacc tacgacctcc  2640
actcccgacc cttgcgaata aaatacttct ggtctgccct aaa                   2683

SEQ ID NO: 47          moltype = RNA   length = 20
FEATURE                Location/Qualifiers
misc_feature           1..20
                       note = Synthetic Polynucleotide
source                 1..20
                       mol_type = other RNA
                       organism = synthetic construct
SEQUENCE: 47
ggacggcccg gcttgctgcc                                                20

SEQ ID NO: 48          moltype = RNA   length = 20
FEATURE                Location/Qualifiers
misc_feature           1..20
                       note = Synthetic Polynucleotide
source                 1..20
                       mol_type = other RNA
                       organism = synthetic construct
SEQUENCE: 48
gggcccggat cacaggactg                                                20

SEQ ID NO: 49          moltype = RNA   length = 20
FEATURE                Location/Qualifiers
misc_feature           1..20
                       note = Synthetic Polynucleotide
source                 1..20
                       mol_type = other RNA
                       organism = synthetic construct
SEQUENCE: 49
caaacttgct cagcagtgtc                                                20

SEQ ID NO: 50          moltype = RNA   length = 20
FEATURE                Location/Qualifiers
misc_feature           1..20
                       note = Synthetic Polynucleotide
source                 1..20
                       mol_type = other RNA
                       organism = synthetic construct
SEQUENCE: 50
aaacttgctc agcagtgtca                                                20

SEQ ID NO: 51          moltype = RNA   length = 20
FEATURE                Location/Qualifiers
misc_feature           1..20
                       note = Synthetic Polynucleotide
source                 1..20
                       mol_type = other RNA
```

```
                            organism = synthetic construct
SEQUENCE: 51
cggatggcct ccatctcccg                                                    20

SEQ ID NO: 52               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 52
ctcggccgga atccgctccc                                                    20

SEQ ID NO: 53               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 53
tctcggccgg aatccgctcc                                                    20

SEQ ID NO: 54               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 54
tgctcagcag tgtcagcagg                                                    20

SEQ ID NO: 55               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 55
ttgtcgggtt tgatgtccct                                                    20

SEQ ID NO: 56               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 56
gttgtcgggt ttgatgtccc                                                    20

SEQ ID NO: 57               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 57
tccgccaggt agaagcgcgc                                                    20

SEQ ID NO: 58               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 58
catggcatac acctggcccg                                                    20

SEQ ID NO: 59               moltype = RNA   length = 20
FEATURE                     Location/Qualifiers
misc_feature                1..20
                            note = Synthetic Polynucleotide
source                      1..20
```

```
                            mol_type = other RNA
                            organism = synthetic construct
SEQUENCE: 59
aacttgctca gcagtgtcag                                                    20

SEQ ID NO: 60               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 60
cagctgcgtg atccaccgcc                                                    20

SEQ ID NO: 61               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 61
cgaatgtccg acagtgtctc                                                    20

SEQ ID NO: 62               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 62
gaagtcggcc aggcggatgt                                                    20

SEQ ID NO: 63               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 63
tgtcgggttt gatgtccctg                                                    20

SEQ ID NO: 64               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 64
ggatggcctc catctcccgg                                                    20

SEQ ID NO: 65               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 65
aggatgttgt cgggtttgat                                                    20

SEQ ID NO: 66               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 66
gtcgggtttg atgtccctgt                                                    20

SEQ ID NO: 67               moltype = RNA   length = 20
FEATURE                     Location/Qualifiers
misc_feature                1..20
                            note = Synthetic Polynucleotide
```

```
source                      1..20
                            mol_type = other RNA
                            organism = synthetic construct
SEQUENCE: 67
aatactccat gaccaggtac                                                        20

SEQ ID NO: 68               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 68
cttgttcatg atcttcatgg                                                        20

SEQ ID NO: 69               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 69
tcagtgcatc caaaacgtgg                                                        20

SEQ ID NO: 70               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 70
ctgtcccgga gaccatccca                                                        20

SEQ ID NO: 71               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 71
gggcctggga cctcactgtc                                                        20

SEQ ID NO: 72               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 72
cccacgtaat actccatgac                                                        20

SEQ ID NO: 73               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 73
ctctgccgca gggacagccg                                                        20

SEQ ID NO: 74               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 74
ctgtgcacgt agccaagccg                                                        20

SEQ ID NO: 75               moltype = RNA   length = 20
FEATURE                     Location/Qualifiers
misc_feature                1..20
```

```
                    note = Synthetic Polynucleotide
source              1..20
                    mol_type = other RNA
                    organism = synthetic construct
SEQUENCE: 75
tgcccatcca cgtcagggcc                                                    20

SEQ ID NO: 76       moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 76
agcgcctccg ataggccagg                                                    20

SEQ ID NO: 77       moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 77
tgtgcacgta gccaagccgg                                                    20

SEQ ID NO: 78       moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 78
gaccaggtac aggtagttct                                                    20

SEQ ID NO: 79       moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 79
ccatctcggc cggaatccgc                                                    20

SEQ ID NO: 80       moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 80
catctcggcc ggaatccgct                                                    20

SEQ ID NO: 81       moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 81
ttgccatagg tctccgccgt                                                    20

SEQ ID NO: 82       moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 82
acagcggtcc agcaggatgt                                                    20

SEQ ID NO: 83       moltype = RNA   length = 20
FEATURE             Location/Qualifiers
```

```
misc_feature              1..20
                          note = Synthetic Polynucleotide
source                    1..20
                          mol_type = other RNA
                          organism = synthetic construct
SEQUENCE: 83
aaagcgcctc cgataggcca                                                    20

SEQ ID NO: 84             moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 84
gccaaagaag aagggatgtg                                                    20

SEQ ID NO: 85             moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 85
cacgtaatac tccatgacca                                                    20

SEQ ID NO: 86             moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 86
atctcggccg gaatccgctc                                                    20

SEQ ID NO: 87             moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 87
gcttcatctt cactaccgct                                                    20

SEQ ID NO: 88             moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 88
gccatctcgg ccggaatccg                                                    20

SEQ ID NO: 89             moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 89
cagggacagc cgctggaact                                                    20

SEQ ID NO: 90             moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 90
atgacaatct ccgccaggta                                                    20

SEQ ID NO: 91             moltype = RNA   length = 20
```

```
FEATURE               Location/Qualifiers
misc_feature          1..20
                      note = Synthetic Polynucleotide
source                1..20
                      mol_type = other RNA
                      organism = synthetic construct
SEQUENCE: 91
ggccatgaca atctccgcca                                                    20

SEQ ID NO: 92         moltype = RNA  length = 20
FEATURE               Location/Qualifiers
misc_feature          1..20
                      note = Synthetic Polynucleotide
source                1..20
                      mol_type = other RNA
                      organism = synthetic construct
SEQUENCE: 92
atactccatg accaggtaca                                                    20

SEQ ID NO: 93         moltype = RNA  length = 20
FEATURE               Location/Qualifiers
misc_feature          1..20
                      note = Synthetic Polynucleotide
source                1..20
                      mol_type = other RNA
                      organism = synthetic construct
SEQUENCE: 93
gcctctgcct cgcgtagttg                                                    20

SEQ ID NO: 94         moltype = RNA  length = 20
FEATURE               Location/Qualifiers
misc_feature          1..20
                      note = Synthetic Polynucleotide
source                1..20
                      mol_type = other RNA
                      organism = synthetic construct
SEQUENCE: 94
gaatgtccga cagtgtctcc                                                    20

SEQ ID NO: 95         moltype = RNA  length = 20
FEATURE               Location/Qualifiers
misc_feature          1..20
                      note = Synthetic Polynucleotide
source                1..20
                      mol_type = other RNA
                      organism = synthetic construct
SEQUENCE: 95
cgttccatct gcccgcagct                                                    20

SEQ ID NO: 96         moltype = RNA  length = 20
FEATURE               Location/Qualifiers
misc_feature          1..20
                      note = Synthetic Polynucleotide
source                1..20
                      mol_type = other RNA
                      organism = synthetic construct
SEQUENCE: 96
ccttgtagtg gacgatcttg                                                    20

SEQ ID NO: 97         moltype = RNA  length = 20
FEATURE               Location/Qualifiers
misc_feature          1..20
                      note = Synthetic Polynucleotide
source                1..20
                      mol_type = other RNA
                      organism = synthetic construct
SEQUENCE: 97
atctccgcca ggtagaagcg                                                    20

SEQ ID NO: 98         moltype = RNA  length = 20
FEATURE               Location/Qualifiers
misc_feature          1..20
                      note = Synthetic Polynucleotide
source                1..20
                      mol_type = other RNA
                      organism = synthetic construct
SEQUENCE: 98
ctcaggctct gccgggtgag                                                    20
```

-continued

```
SEQ ID NO: 99              moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 99
tgcttcatct tcactaccgc                                                    20

SEQ ID NO: 100             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 100
gcaggatgtt gtcgggtttg                                                    20

SEQ ID NO: 101             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 101
ggcctcagcc tctgccgcag                                                    20

SEQ ID NO: 102             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 102
tgttgtcggg tttgatgtcc                                                    20

SEQ ID NO: 103             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 103
ccacgtaata ctccatgacc                                                    20

SEQ ID NO: 104             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 104
ccgttccatc tgcccgcagc                                                    20

SEQ ID NO: 105             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 105
ttcccgagta agcaggcaga                                                    20

SEQ ID NO: 106             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 106
tgatcttcat ggcatacacc                                                    20
```

```
SEQ ID NO: 107              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 107
agggacagcc gctggaactg                                                    20

SEQ ID NO: 108              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 108
gggtttgatg tccctgtgca                                                    20

SEQ ID NO: 109              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 109
tgacaatctc cgccaggtag                                                    20

SEQ ID NO: 110              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 110
cacagcggtc cagcaggatg                                                    20

SEQ ID NO: 111              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 111
gcgtagaagg gcgtctgccc                                                    20

SEQ ID NO: 112              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 112
ctcagcctct gccgcaggga                                                    20

SEQ ID NO: 113              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 113
gtctcagtgc atccaaaacg                                                    20

SEQ ID NO: 114              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 114
```

```
ggacgatctt gccataggtc                                                    20

SEQ ID NO: 115              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 115
tcagcagtgt cagcaggtcc                                                    20

SEQ ID NO: 116              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 116
gctcctgggc ggcgccagac                                                    20

SEQ ID NO: 117              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 117
agcaggatgt tgtcgggttt                                                    20

SEQ ID NO: 118              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 118
atccgctcct gcaactgccg                                                    20

SEQ ID NO: 119              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 119
aggagcaggg aaagcgcctc                                                    20

SEQ ID NO: 120              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 120
acacctggcc cgtctgcttc                                                    20

SEQ ID NO: 121              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 121
cccagcgccc accagtcaca                                                    20

SEQ ID NO: 122              moltype = RNA   length = 20
FEATURE                     Location/Qualifiers
misc_feature                1..20
                            note = Synthetic Polynucleotide
source                      1..20
                            mol_type = other RNA
                            organism = synthetic construct
```

```
SEQUENCE: 122
gctccctctg cctgcagcaa                                               20

SEQ ID NO: 123           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 123
gctcaggctc tgccgggtga                                               20

SEQ ID NO: 124           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 124
ttgatgtccc tgtgcacgta                                               20

SEQ ID NO: 125           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 125
gcctcagcct ctgccgcagg                                               20

SEQ ID NO: 126           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 126
ggtagttctc atcctggaag                                               20

SEQ ID NO: 127           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 127
cagcgcccac cagtcacact                                               20

SEQ ID NO: 128           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 128
cccaaacttg ctcagcagtg                                               20

SEQ ID NO: 129           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 129
cttgccatag gtctccgccg                                               20

SEQ ID NO: 130           moltype = RNA  length = 20
FEATURE                  Location/Qualifiers
misc_feature             1..20
                         note = Synthetic Polynucleotide
source                   1..20
                         mol_type = other RNA
```

```
                                organism = synthetic construct
SEQUENCE: 130
tacacctggc ccgtctgctt                                                  20

SEQ ID NO: 131          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 131
ccagcgccca ccagtcacac                                                  20

SEQ ID NO: 132          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 132
ggcctcagcc tggccgaaag                                                  20

SEQ ID NO: 133          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 133
aatctccgcc aggtagaagc                                                  20

SEQ ID NO: 134          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 134
atggcataca cctggcccgt                                                  20

SEQ ID NO: 135          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 135
ccatgacaat ctccgccagg                                                  20

SEQ ID NO: 136          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 136
tccccaaact tgctcagcag                                                  20

SEQ ID NO: 137          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 137
gatgttgtcg ggtttgatgt                                                  20

SEQ ID NO: 138          moltype = RNA   length = 20
FEATURE                 Location/Qualifiers
misc_feature            1..20
                        note = Synthetic Polynucleotide
source                  1..20
```

```
                        mol_type = other RNA
                        organism = synthetic construct
SEQUENCE: 138
gtttgcccat ccacgtcagg                                              20

SEQ ID NO: 139          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 139
cggacggccc ggcttgctgc                                              20

SEQ ID NO: 140          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 140
ctccgccagg tagaagcgcg                                              20

SEQ ID NO: 141          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 141
gtacaggtag ttctcatcct                                              20

SEQ ID NO: 142          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 142
agggcgtctg cccatagaac                                              20

SEQ ID NO: 143          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 143
tggccacagc ggtccagcag                                              20

SEQ ID NO: 144          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 144
cgtagttgac tggcgaagtt                                              20

SEQ ID NO: 145          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 145
tctgccgcag ggacagccgc                                              20

SEQ ID NO: 146          moltype = RNA   length = 20
FEATURE                 Location/Qualifiers
misc_feature            1..20
                        note = Synthetic Polynucleotide
```

```
source                      1..20
                            mol_type = other RNA
                            organism = synthetic construct
SEQUENCE: 146
aagcgcctcc gataggccag                                                    20

SEQ ID NO: 147              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 147
gacagaacaa cggcgaacag                                                    20

SEQ ID NO: 148              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 148
gctcagcagt gtcagcaggt                                                    20

SEQ ID NO: 149              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 149
atgatcttca tggcatacac                                                    20

SEQ ID NO: 150              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 150
tttgcccatc cacgtcaggg                                                    20

SEQ ID NO: 151              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 151
acttgctcag cagtgtcagc                                                    20

SEQ ID NO: 152              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 152
tgatgtccct gtgcacgtag                                                    20

SEQ ID NO: 153              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 153
aaataccgag gaatgtcggg                                                    20

SEQ ID NO: 154              moltype = RNA   length = 20
FEATURE                     Location/Qualifiers
misc_feature                1..20
```

```
                        note = Synthetic Polynucleotide
source                  1..20
                        mol_type = other RNA
                        organism = synthetic construct
SEQUENCE: 154
ggcgaataca cccagcgccc                                                    20

SEQ ID NO: 155          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 155
agacaataaa taccgaggaa                                                    20

SEQ ID NO: 156          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 156
cccgtctgct tcatcttcac                                                    20

SEQ ID NO: 157          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 157
ctgcctgcag caactccatc                                                    20

SEQ ID NO: 158          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 158
cctcagcctc tgccgcaggg                                                    20

SEQ ID NO: 159          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 159
gtgtccggaa gtcgcctgct                                                    20

SEQ ID NO: 160          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 160
tgcacgtgtg gctcaagcag                                                    20

SEQ ID NO: 161          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 161
gacaataaat accgaggaat                                                    20

SEQ ID NO: 162          moltype = RNA   length = 20
FEATURE                 Location/Qualifiers
```

```
misc_feature              1..20
                          note = Synthetic Polynucleotide
source                    1..20
                          mol_type = other RNA
                          organism = synthetic construct
SEQUENCE: 162
gccatgacaa tctccgccag                                                    20

SEQ ID NO: 163            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 163
gctgtcccgg agaccatccc                                                    20

SEQ ID NO: 164            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 164
catgaccagg tacaggtagt                                                    20

SEQ ID NO: 165            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 165
agcgcccacc agtcacactc                                                    20

SEQ ID NO: 166            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 166
tctcagtgca tccaaaacgt                                                    20

SEQ ID NO: 167            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 167
tttgggcaga tggagggcct                                                    20

SEQ ID NO: 168            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 168
gatgtccctg tgcacgtagc                                                    20

SEQ ID NO: 169            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 169
cagcagtgtc agcaggtccc                                                    20

SEQ ID NO: 170            moltype = RNA   length = 20
```

```
FEATURE                 Location/Qualifiers
misc_feature            1..20
                        note = Synthetic Polynucleotide
source                  1..20
                        mol_type = other RNA
                        organism = synthetic construct
SEQUENCE: 170
catgacaatc tccgccaggt                                                    20

SEQ ID NO: 171          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 171
acttgttcat gatcttcatg                                                    20

SEQ ID NO: 172          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 172
gtggaatccg cgtagaaggg                                                    20

SEQ ID NO: 173          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 173
tggccatgac aatctccgcc                                                    20

SEQ ID NO: 174          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 174
gggacagaca ataaataccg                                                    20

SEQ ID NO: 175          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 175
ccgctcccca aacttgctca                                                    20

SEQ ID NO: 176          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 176
cggctcaggc tctgccgggt                                                    20

SEQ ID NO: 177          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 177
ggctcctggg cggcgccaga                                                    20
```

```
SEQ ID NO: 178            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 178
tttcccgagt aagcaggcag                                                    20

SEQ ID NO: 179            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 179
ggatgttgtc gggtttgatg                                                    20

SEQ ID NO: 180            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 180
caggtagttc tcatcctgga                                                    20

SEQ ID NO: 181            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 181
tgcccataga acatttcata                                                    20

SEQ ID NO: 182            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 182
tagttctcat cctggaaggc                                                    20

SEQ ID NO: 183            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 183
atgtccctgt gcacgtagcc                                                    20

SEQ ID NO: 184            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 184
cgggcccgga tcacaggact                                                    20

SEQ ID NO: 185            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 185
tggacgatct tgccataggt                                                    20
```

```
SEQ ID NO: 186          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 186
gttggccggc gtgggccacc                                                      20

SEQ ID NO: 187          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 187
ctcagtgcat ccaaaacgtg                                                      20

SEQ ID NO: 188          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 188
tcgaagttgc atgtgtcggt                                                      20

SEQ ID NO: 189          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 189
tggaacacgg acggcccggc                                                      20

SEQ ID NO: 190          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 190
ccgagagcag cgcaagtgag                                                      20

SEQ ID NO: 191          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 191
tcctgcaact gccggacgtg                                                      20

SEQ ID NO: 192          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 192
tcaccaacac gtccctctcc                                                      20

SEQ ID NO: 193          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 193
```

```
tgcctgcagc aactccatcc                                               20

SEQ ID NO: 194          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 194
ttggccggcg tgggccacca                                               20

SEQ ID NO: 195          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 195
gagcctctgc ctcgcgtagt                                               20

SEQ ID NO: 196          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 196
aagggcgtct gcccatagaa                                               20

SEQ ID NO: 197          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 197
acagacaata aataccgagg                                               20

SEQ ID NO: 198          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 198
ggacagacaa taaataccga                                               20

SEQ ID NO: 199          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 199
acgtgtgcct ctaggtcccg                                               20

SEQ ID NO: 200          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 200
ggcacgagac agaacaacgg                                               20

SEQ ID NO: 201          moltype = RNA   length = 20
FEATURE                 Location/Qualifiers
misc_feature            1..20
                        note = Synthetic Polynucleotide
source                  1..20
                        mol_type = other RNA
                        organism = synthetic construct
```

```
SEQUENCE: 201
tgaccaggta caggtagttc                                                    20

SEQ ID NO: 202          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 202
ctctgccggg tgagcacctc                                                    20

SEQ ID NO: 203          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 203
gacaatctcc gccaggtaga                                                    20

SEQ ID NO: 204          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 204
tctccgccag gtagaagcgc                                                    20

SEQ ID NO: 205          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 205
ctctgcctcg cgtagttgac                                                    20

SEQ ID NO: 206          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 206
ctttgggcag atggagggcc                                                    20

SEQ ID NO: 207          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 207
acaggtagtt ctcatcctgg                                                    20

SEQ ID NO: 208          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 208
ccaaacttgc tcagcagtgt                                                    20

SEQ ID NO: 209          moltype = RNA  length = 20
FEATURE                 Location/Qualifiers
misc_feature            1..20
                        note = Synthetic Polynucleotide
source                  1..20
                        mol_type = other RNA
```

```
                        organism = synthetic construct
SEQUENCE: 209
tcgggtttga tgtccctgtg                                                    20

SEQ ID NO: 210          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 210
ggcttgctgc cttcccaggc                                                    20

SEQ ID NO: 211          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 211
tacaggtagt tctcatcctg                                                    20

SEQ ID NO: 212          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 212
ttgcccatcc acgtcagggc                                                    20

SEQ ID NO: 213          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 213
aggtacaggt agttctcatc                                                    20

SEQ ID NO: 214          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 214
gacagacaat aaataccgag                                                    20

SEQ ID NO: 215          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 215
tagaacattt cataggcgaa                                                    20

SEQ ID NO: 216          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 216
agggcctttt attcgcgagg                                                    20

SEQ ID NO: 217          moltype = RNA  length = 20
FEATURE                 Location/Qualifiers
misc_feature            1..20
                        note = Synthetic Polynucleotide
source                  1..20
```

```
                        mol_type = other RNA
                        organism = synthetic construct
SEQUENCE: 217
gcctcgcgta gttgactggc                                               20

SEQ ID NO: 218          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 218
ccagcaggat gttgtcgggt                                               20

SEQ ID NO: 219          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 219
gtagttgact ggcgaagttc                                               20

SEQ ID NO: 220          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 220
tgcggatggc ctccatctcc                                               20

SEQ ID NO: 221          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 221
acaatctccg ccaggtagaa                                               20

SEQ ID NO: 222          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 222
gcgaatacac ccagcgccca                                               20

SEQ ID NO: 223          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 223
gtagttctca tcctggaagg                                               20

SEQ ID NO: 224          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 224
ggctcaggct ctgccgggtg                                               20

SEQ ID NO: 225          moltype = RNA   length = 20
FEATURE                 Location/Qualifiers
misc_feature            1..20
                        note = Synthetic Polynucleotide
```

```
source                  1..20
                        mol_type = other RNA
                        organism = synthetic construct
SEQUENCE: 225
ccattcacca acacgtccct                                                    20

SEQ ID NO: 226          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 226
accaggtaca ggtagttctc                                                    20

SEQ ID NO: 227          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 227
ctgcagtttg cccatccacg                                                    20

SEQ ID NO: 228          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 228
ttgttcatga tcttcatggc                                                    20

SEQ ID NO: 229          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 229
tttgatgtcc ctgtgcacgt                                                    20

SEQ ID NO: 230          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 230
gcggtccagc aggatgttgt                                                    20

SEQ ID NO: 231          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 231
gtctatggcc atgacaatct                                                    20

SEQ ID NO: 232          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 232
ggagcaggga aagcgcctcc                                                    20

SEQ ID NO: 233          moltype = RNA   length = 20
FEATURE                 Location/Qualifiers
misc_feature            1..20
```

```
                    note = Synthetic Polynucleotide
source              1..20
                    mol_type = other RNA
                    organism = synthetic construct
SEQUENCE: 233
tgcctcgcgt agttgactgg                                                    20

SEQ ID NO: 234      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 234
gcggatggcc tccatctccc                                                    20

SEQ ID NO: 235      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 235
tttcataggc gaatacaccc                                                    20

SEQ ID NO: 236      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 236
gcctgtcagc gagtcggagg                                                    20

SEQ ID NO: 237      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 237
ccacttcagc tgtttcatcc                                                    20

SEQ ID NO: 238      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 238
catccgctcc tgcaactgcc                                                    20

SEQ ID NO: 239      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 239
tctagggttc agggagcgcg                                                    20

SEQ ID NO: 240      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 240
caccaacacg tccctctcct                                                    20

SEQ ID NO: 241      moltype = RNA   length = 20
FEATURE             Location/Qualifiers
```

```
                        misc_feature          1..20
                                              note = Synthetic Polynucleotide
                        source                1..20
                                              mol_type = other RNA
                                              organism = synthetic construct
                        SEQUENCE: 241
                        caggagcagg gaaagcgcct                                                20

SEQ ID NO: 242        moltype = RNA   length = 20
                        FEATURE               Location/Qualifiers
                        misc_feature          1..20
                                              note = Synthetic Polynucleotide
                        source                1..20
                                              mol_type = other RNA
                                              organism = synthetic construct
                        SEQUENCE: 242
                        caatctccgc caggtagaag                                                20

SEQ ID NO: 243        moltype = RNA   length = 20
                        FEATURE               Location/Qualifiers
                        misc_feature          1..20
                                              note = Synthetic Polynucleotide
                        source                1..20
                                              mol_type = other RNA
                                              organism = synthetic construct
                        SEQUENCE: 243
                        atgttgtcgg gtttgatgtc                                                20

SEQ ID NO: 244        moltype = RNA   length = 20
                        FEATURE               Location/Qualifiers
                        misc_feature          1..20
                                              note = Synthetic Polynucleotide
                        source                1..20
                                              mol_type = other RNA
                                              organism = synthetic construct
                        SEQUENCE: 244
                        ccatccgctc ctgcaactgc                                                20

SEQ ID NO: 245        moltype = RNA   length = 20
                        FEATURE               Location/Qualifiers
                        misc_feature          1..20
                                              note = Synthetic Polynucleotide
                        source                1..20
                                              mol_type = other RNA
                                              organism = synthetic construct
                        SEQUENCE: 245
                        gcgtcacctc ggcctcagcc                                                20

SEQ ID NO: 246        moltype = RNA   length = 20
                        FEATURE               Location/Qualifiers
                        misc_feature          1..20
                                              note = Synthetic Polynucleotide
                        source                1..20
                                              mol_type = other RNA
                                              organism = synthetic construct
                        SEQUENCE: 246
                        gagggccttt tattcgcgag                                                20

SEQ ID NO: 247        moltype = RNA   length = 20
                        FEATURE               Location/Qualifiers
                        misc_feature          1..20
                                              note = Synthetic Polynucleotide
                        source                1..20
                                              mol_type = other RNA
                                              organism = synthetic construct
                        SEQUENCE: 247
                        agcggcagag agaggtgctc                                                20

SEQ ID NO: 248        moltype = RNA   length = 20
                        FEATURE               Location/Qualifiers
                        misc_feature          1..20
                                              note = Synthetic Polynucleotide
                        source                1..20
                                              mol_type = other RNA
                                              organism = synthetic construct
                        SEQUENCE: 248
                        catccaaaac gtggattggg                                                20

SEQ ID NO: 249        moltype = RNA   length = 20
```

```
FEATURE                 Location/Qualifiers
misc_feature            1..20
                        note = Synthetic Polynucleotide
source                  1..20
                        mol_type = other RNA
                        organism = synthetic construct
SEQUENCE: 249
ttgggcagat ggagggcctt                                           20

SEQ ID NO: 250          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 250
cctctgcctc gcgtagttga                                           20

SEQ ID NO: 251          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 251
acagaacaac ggcgaacagg                                           20

SEQ ID NO: 252          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 252
caggatgttg tcgggtttga                                           20

SEQ ID NO: 253          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 253
cggcctcagc ctctgccgca                                           20

SEQ ID NO: 254          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 254
cagcaggatg ttgtcgggtt                                           20

SEQ ID NO: 255          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 255
gcagagagag gtgctccttg                                           20

SEQ ID NO: 256          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 256
tccagttcca tgggtgtggg                                           20
```

```
SEQ ID NO: 257          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 257
cctcagcctg gccgaaagaa                                                     20

SEQ ID NO: 258          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 258
gggccttta ttcgcgaggg                                                      20

SEQ ID NO: 259          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 259
gtcggccagg cggatgtggc                                                     20

SEQ ID NO: 260          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 260
gcttgctgcc ttcccaggcc                                                     20

SEQ ID NO: 261          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 261
ggtccagcag gatgttgtcg                                                     20

SEQ ID NO: 262          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 262
cggagaccat cccagtcgag                                                     20

SEQ ID NO: 263          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 263
tctgcctcgc gtagttgact                                                     20

SEQ ID NO: 264          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 264
aggtagttct catcctggaa                                                     20
```

```
SEQ ID NO: 265           moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 265
tccttgtagt ggacgatctt                                                    20

SEQ ID NO: 266           moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 266
gcatccaaaa cgtggattgg                                                    20

SEQ ID NO: 267           moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 267
gtccagcagg atgttgtcgg                                                    20

SEQ ID NO: 268           moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 268
agctcccgca gcgtcacctc                                                    20

SEQ ID NO: 269           moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 269
cgagagcagc gcaagtgagg                                                    20

SEQ ID NO: 270           moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 270
cagggaaagc gcctccgata                                                    20

SEQ ID NO: 271           moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 271
atttcatagg cgaatacacc                                                    20

SEQ ID NO: 272           moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 272
```

-continued

```
tcggccaggc ggatgtggcc                                              20

SEQ ID NO: 273        moltype = RNA   length = 20
FEATURE               Location/Qualifiers
misc_feature          1..20
                      note = Synthetic Polynucleotide
source                1..20
                      mol_type = other RNA
                      organism = synthetic construct
SEQUENCE: 273
aagggatgtg tccggaagtc                                              20

SEQ ID NO: 274        moltype = RNA   length = 20
FEATURE               Location/Qualifiers
misc_feature          1..20
                      note = Synthetic Polynucleotide
source                1..20
                      mol_type = other RNA
                      organism = synthetic construct
SEQUENCE: 274
cttgtagtgg acgatcttgc                                              20

SEQ ID NO: 275        moltype = RNA   length = 20
FEATURE               Location/Qualifiers
misc_feature          1..20
                      note = Synthetic Polynucleotide
source                1..20
                      mol_type = other RNA
                      organism = synthetic construct
SEQUENCE: 275
agtcggccag gcggatgtgg                                              20

SEQ ID NO: 276        moltype = RNA   length = 20
FEATURE               Location/Qualifiers
misc_feature          1..20
                      note = Synthetic Polynucleotide
source                1..20
                      mol_type = other RNA
                      organism = synthetic construct
SEQUENCE: 276
gcctcagcct ggccgaaaga                                              20

SEQ ID NO: 277        moltype = RNA   length = 20
FEATURE               Location/Qualifiers
misc_feature          1..20
                      note = Synthetic Polynucleotide
source                1..20
                      mol_type = other RNA
                      organism = synthetic construct
SEQUENCE: 277
agcgtcacct cggcctcagc                                              20

SEQ ID NO: 278        moltype = RNA   length = 20
FEATURE               Location/Qualifiers
misc_feature          1..20
                      note = Synthetic Polynucleotide
source                1..20
                      mol_type = other RNA
                      organism = synthetic construct
SEQUENCE: 278
cagcggcaga gagaggtgct                                              20

SEQ ID NO: 279        moltype = RNA   length = 20
FEATURE               Location/Qualifiers
misc_feature          1..20
                      note = Synthetic Polynucleotide
source                1..20
                      mol_type = other RNA
                      organism = synthetic construct
SEQUENCE: 279
ccagcggcag agagaggtgc                                              20

SEQ ID NO: 280        moltype = RNA   length = 20
FEATURE               Location/Qualifiers
misc_feature          1..20
                      note = Synthetic Polynucleotide
source                1..20
                      mol_type = other RNA
                      organism = synthetic construct
```

```
SEQUENCE: 280
ttgtagtgga cgatcttgcc                                                    20

SEQ ID NO: 281          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 281
agggaaagcg cctccgatag                                                    20

SEQ ID NO: 282          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 282
gggaaagcgc ctccgatagg                                                    20

SEQ ID NO: 283          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 283
ggcagcaagc cgggccgtcc                                                    20

SEQ ID NO: 284          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 284
cagtcctgtg atccgggccc                                                    20

SEQ ID NO: 285          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 285
gacactgctg agcaagtttg                                                    20

SEQ ID NO: 286          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 286
tgacactgct gagcaagttt                                                    20

SEQ ID NO: 287          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 287
cgggagatgg aggccatccg                                                    20

SEQ ID NO: 288          moltype = DNA   length = 20
FEATURE                 Location/Qualifiers
misc_feature            1..20
                        note = Synthetic Polynucleotide
source                  1..20
                        mol_type = other DNA
```

```
                              organism = synthetic construct
SEQUENCE: 288
gggagcggat tccggccgag                                              20

SEQ ID NO: 289         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 289
ggagcggatt ccggccgaga                                              20

SEQ ID NO: 290         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 290
cctgctgaca ctgctgagca                                              20

SEQ ID NO: 291         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 291
agggacatca aacccgacaa                                              20

SEQ ID NO: 292         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 292
gggacatcaa acccgacaac                                              20

SEQ ID NO: 293         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 293
gcgcgcttct acctggcgga                                              20

SEQ ID NO: 294         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 294
cgggccaggt gtatgccatg                                              20

SEQ ID NO: 295         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 295
ctgacactgc tgagcaagtt                                              20

SEQ ID NO: 296         moltype = DNA   length = 20
FEATURE                Location/Qualifiers
misc_feature           1..20
                       note = Synthetic Polynucleotide
source                 1..20
```

```
                        mol_type = other DNA
                        organism = synthetic construct
SEQUENCE: 296
ggcggtggat cacgcagctg                                               20

SEQ ID NO: 297          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 297
gagacactgt cggacattcg                                               20

SEQ ID NO: 298          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 298
acatccgcct ggccgacttc                                               20

SEQ ID NO: 299          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 299
cagggacatc aaacccgaca                                               20

SEQ ID NO: 300          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 300
ccgggagatg gaggccatcc                                               20

SEQ ID NO: 301          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 301
atcaaacccg acaacatcct                                               20

SEQ ID NO: 302          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 302
acagggacat caaacccgac                                               20

SEQ ID NO: 303          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 303
gtacctggtc atggagtatt                                               20

SEQ ID NO: 304          moltype = DNA   length = 20
FEATURE                 Location/Qualifiers
misc_feature            1..20
                        note = Synthetic Polynucleotide
```

```
source                  1..20
                        mol_type = other DNA
                        organism = synthetic construct
SEQUENCE: 304
ccatgaagat catgaacaag                                                   20

SEQ ID NO: 305          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 305
ccacgttttg gatgcactga                                                   20

SEQ ID NO: 306          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 306
tgggatggtc tccgggacag                                                   20

SEQ ID NO: 307          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 307
gacagtgagg tcccaggccc                                                   20

SEQ ID NO: 308          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 308
gtcatggagt attacgtggg                                                   20

SEQ ID NO: 309          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 309
cggctgtccc tgcggcagag                                                   20

SEQ ID NO: 310          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 310
cggcttggct acgtgcacag                                                   20

SEQ ID NO: 311          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 311
ggccctgacg tggatgggca                                                   20

SEQ ID NO: 312          moltype = DNA   length = 20
FEATURE                 Location/Qualifiers
misc_feature            1..20
```

```
                    note = Synthetic Polynucleotide
source              1..20
                    mol_type = other DNA
                    organism = synthetic construct
SEQUENCE: 312
cctggcctat cggaggcgct                                                     20

SEQ ID NO: 313      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 313
ccggcttggc tacgtgcaca                                                     20

SEQ ID NO: 314      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 314
agaactacct gtacctggtc                                                     20

SEQ ID NO: 315      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 315
gcggattccg gccgagatgg                                                     20

SEQ ID NO: 316      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 316
agcggattcc ggccgagatg                                                     20

SEQ ID NO: 317      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 317
acggcggaga cctatggcaa                                                     20

SEQ ID NO: 318      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 318
acatcctgct ggaccgctgt                                                     20

SEQ ID NO: 319      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 319
tggcctatcg gaggcgcttt                                                     20

SEQ ID NO: 320      moltype = DNA  length = 20
FEATURE             Location/Qualifiers
```

```
                         -continued misc_feature             1..20
                         note = Synthetic Polynucleotide
source                   1..20
                         mol_type = other DNA
                         organism = synthetic construct
SEQUENCE: 320
cacatccctt cttctttggc                                                   20

SEQ ID NO: 321           moltype = DNA  length = 20
FEATURE                  Location/Qualifiers
misc_feature             1..20
                         note = Synthetic Polynucleotide
source                   1..20
                         mol_type = other DNA
                         organism = synthetic construct
SEQUENCE: 321
tggtcatgga gtattacgtg                                                   20

SEQ ID NO: 322           moltype = DNA  length = 20
FEATURE                  Location/Qualifiers
misc_feature             1..20
                         note = Synthetic Polynucleotide
source                   1..20
                         mol_type = other DNA
                         organism = synthetic construct
SEQUENCE: 322
gagcggattc cggccgagat                                                   20

SEQ ID NO: 323           moltype = DNA  length = 20
FEATURE                  Location/Qualifiers
misc_feature             1..20
                         note = Synthetic Polynucleotide
source                   1..20
                         mol_type = other DNA
                         organism = synthetic construct
SEQUENCE: 323
agcggtagtg aagatgaagc                                                   20

SEQ ID NO: 324           moltype = DNA  length = 20
FEATURE                  Location/Qualifiers
misc_feature             1..20
                         note = Synthetic Polynucleotide
source                   1..20
                         mol_type = other DNA
                         organism = synthetic construct
SEQUENCE: 324
cggattccgg ccgagatggc                                                   20

SEQ ID NO: 325           moltype = DNA  length = 20
FEATURE                  Location/Qualifiers
misc_feature             1..20
                         note = Synthetic Polynucleotide
source                   1..20
                         mol_type = other DNA
                         organism = synthetic construct
SEQUENCE: 325
agttccagcg gctgtccctg                                                   20

SEQ ID NO: 326           moltype = DNA  length = 20
FEATURE                  Location/Qualifiers
misc_feature             1..20
                         note = Synthetic Polynucleotide
source                   1..20
                         mol_type = other DNA
                         organism = synthetic construct
SEQUENCE: 326
tacctggcgg agattgtcat                                                   20

SEQ ID NO: 327           moltype = DNA  length = 20
FEATURE                  Location/Qualifiers
misc_feature             1..20
                         note = Synthetic Polynucleotide
source                   1..20
                         mol_type = other DNA
                         organism = synthetic construct
SEQUENCE: 327
tggcggagat tgtcatggcc                                                   20

SEQ ID NO: 328           moltype = DNA  length = 20
```

```
FEATURE                 Location/Qualifiers
misc_feature            1..20
                        note = Synthetic Polynucleotide
source                  1..20
                        mol_type = other DNA
                        organism = synthetic construct
SEQUENCE: 328
tgtacctggt catggagtat                                               20

SEQ ID NO: 329          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 329
caactacgcg aggcagaggc                                               20

SEQ ID NO: 330          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 330
ggagacactg tcggacattc                                               20

SEQ ID NO: 331          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 331
agctgcgggc agatggaacg                                               20

SEQ ID NO: 332          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 332
caagatcgtc cactacaagg                                               20

SEQ ID NO: 333          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 333
cgcttctacc tggcggagat                                               20

SEQ ID NO: 334          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 334
ctcacccggc agagcctgag                                               20

SEQ ID NO: 335          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 335
gcggtagtga agatgaagca                                               20
```

```
SEQ ID NO: 336           moltype = DNA    length = 20
FEATURE                  Location/Qualifiers
misc_feature             1..20
                         note = Synthetic Polynucleotide
source                   1..20
                         mol_type = other DNA
                         organism = synthetic construct
SEQUENCE: 336
caaacccgac aacatcctgc                                                20

SEQ ID NO: 337           moltype = DNA    length = 20
FEATURE                  Location/Qualifiers
misc_feature             1..20
                         note = Synthetic Polynucleotide
source                   1..20
                         mol_type = other DNA
                         organism = synthetic construct
SEQUENCE: 337
ctgcggcaga ggctgaggcc                                                20

SEQ ID NO: 338           moltype = DNA    length = 20
FEATURE                  Location/Qualifiers
misc_feature             1..20
                         note = Synthetic Polynucleotide
source                   1..20
                         mol_type = other DNA
                         organism = synthetic construct
SEQUENCE: 338
ggacatcaaa cccgacaaca                                                20

SEQ ID NO: 339           moltype = DNA    length = 20
FEATURE                  Location/Qualifiers
misc_feature             1..20
                         note = Synthetic Polynucleotide
source                   1..20
                         mol_type = other DNA
                         organism = synthetic construct
SEQUENCE: 339
ggtcatggag tattacgtgg                                                20

SEQ ID NO: 340           moltype = DNA    length = 20
FEATURE                  Location/Qualifiers
misc_feature             1..20
                         note = Synthetic Polynucleotide
source                   1..20
                         mol_type = other DNA
                         organism = synthetic construct
SEQUENCE: 340
gctgcgggca gatggaacgg                                                20

SEQ ID NO: 341           moltype = DNA    length = 20
FEATURE                  Location/Qualifiers
misc_feature             1..20
                         note = Synthetic Polynucleotide
source                   1..20
                         mol_type = other DNA
                         organism = synthetic construct
SEQUENCE: 341
tctgcctgct tactcgggaa                                                20

SEQ ID NO: 342           moltype = DNA    length = 20
FEATURE                  Location/Qualifiers
misc_feature             1..20
                         note = Synthetic Polynucleotide
source                   1..20
                         mol_type = other DNA
                         organism = synthetic construct
SEQUENCE: 342
ggtgtatgcc atgaagatca                                                20

SEQ ID NO: 343           moltype = DNA    length = 20
FEATURE                  Location/Qualifiers
misc_feature             1..20
                         note = Synthetic Polynucleotide
source                   1..20
                         mol_type = other DNA
                         organism = synthetic construct
SEQUENCE: 343
cagttccagc ggctgtccct                                                20
```

```
SEQ ID NO: 344          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 344
tgcacaggga catcaaaccc                                                    20

SEQ ID NO: 345          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 345
ctacctggcg gagattgtca                                                    20

SEQ ID NO: 346          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 346
catcctgctg gaccgctgtg                                                    20

SEQ ID NO: 347          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 347
gggcagacgc ccttctacgc                                                    20

SEQ ID NO: 348          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 348
tccctgcggc agaggctgag                                                    20

SEQ ID NO: 349          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 349
cgttttggat gcactgagac                                                    20

SEQ ID NO: 350          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 350
gacctatggc aagatcgtcc                                                    20

SEQ ID NO: 351          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 351
```

```
ggacctgctg acactgctga                                                   20

SEQ ID NO: 352         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 352
gtctggcgcc gcccaggagc                                                   20

SEQ ID NO: 353         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 353
aaacccgaca acatcctgct                                                   20

SEQ ID NO: 354         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 354
cggcagttgc aggagcggat                                                   20

SEQ ID NO: 355         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 355
gaggcgcttt ccctgctcct                                                   20

SEQ ID NO: 356         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 356
gaagcagacg ggccaggtgt                                                   20

SEQ ID NO: 357         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 357
tgtgactggt gggcgctggg                                                   20

SEQ ID NO: 358         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 358
ttgctgcagg cagagggagc                                                   20

SEQ ID NO: 359         moltype = DNA  length = 20
FEATURE                Location/Qualifiers
misc_feature           1..20
                       note = Synthetic Polynucleotide
source                 1..20
                       mol_type = other DNA
                       organism = synthetic construct
```

SEQUENCE: 359
tcacccggca gagcctgagc                                                    20

SEQ ID NO: 360          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 360
tacgtgcaca gggacatcaa                                                    20

SEQ ID NO: 361          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 361
cctgcggcag aggctgaggc                                                    20

SEQ ID NO: 362          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 362
cttccaggat gagaactacc                                                    20

SEQ ID NO: 363          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 363
agtgtgactg gtgggcgctg                                                    20

SEQ ID NO: 364          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 364
cactgctgag caagtttggg                                                    20

SEQ ID NO: 365          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 365
cggcggagac ctatggcaag                                                    20

SEQ ID NO: 366          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 366
aagcagacgg gccaggtgta                                                    20

SEQ ID NO: 367          moltype = DNA  length = 20
FEATURE                 Location/Qualifiers
misc_feature            1..20
                        note = Synthetic Polynucleotide
source                  1..20
                        mol_type = other DNA

```
                        organism = synthetic construct
SEQUENCE: 367
gtgtgactgg tgggcgctgg                                                   20

SEQ ID NO: 368          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 368
ctttcggcca ggctgaggcc                                                   20

SEQ ID NO: 369          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 369
gcttctacct ggcggagatt                                                   20

SEQ ID NO: 370          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 370
acgggccagg tgtatgccat                                                   20

SEQ ID NO: 371          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 371
cctggcggag attgtcatgg                                                   20

SEQ ID NO: 372          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 372
ctgctgagca agtttgggga                                                   20

SEQ ID NO: 373          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 373
acatcaaacc cgacaacatc                                                   20

SEQ ID NO: 374          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 374
cctgacgtgg atgggcaaac                                                   20

SEQ ID NO: 375          moltype = DNA   length = 20
FEATURE                 Location/Qualifiers
misc_feature            1..20
                        note = Synthetic Polynucleotide
source                  1..20
```

```
                            mol_type = other DNA
                            organism = synthetic construct
SEQUENCE: 375
gcagcaagcc gggccgtccg                                                    20

SEQ ID NO: 376              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 376
cgcgcttcta cctggcggag                                                    20

SEQ ID NO: 377              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 377
aggatgagaa ctacctgtac                                                    20

SEQ ID NO: 378              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 378
gttctatggg cagacgccct                                                    20

SEQ ID NO: 379              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 379
ctgctggacc gctgtggcca                                                    20

SEQ ID NO: 380              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 380
aacttcgcca gtcaactacg                                                    20

SEQ ID NO: 381              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 381
gcggctgtcc ctgcggcaga                                                    20

SEQ ID NO: 382              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 382
ctggcctatc ggaggcgctt                                                    20

SEQ ID NO: 383              moltype = DNA   length = 20
FEATURE                     Location/Qualifiers
misc_feature                1..20
                            note = Synthetic Polynucleotide
```

```
source                  1..20
                        mol_type = other DNA
                        organism = synthetic construct
SEQUENCE: 383
ctgttcgccg ttgttctgtc                                               20

SEQ ID NO: 384          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 384
acctgctgac actgctgagc                                               20

SEQ ID NO: 385          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 385
gtgtatgcca tgaagatcat                                               20

SEQ ID NO: 386          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 386
ccctgacgtg gatgggcaaa                                               20

SEQ ID NO: 387          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 387
gctgacactg ctgagcaagt                                               20

SEQ ID NO: 388          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 388
ctacgtgcac agggacatca                                               20

SEQ ID NO: 389          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 389
cccgacattc ctcggtattt                                               20

SEQ ID NO: 390          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 390
gggcgctggg tgtattcgcc                                               20

SEQ ID NO: 391          moltype = DNA   length = 20
FEATURE                 Location/Qualifiers
misc_feature            1..20
```

```
                    note = Synthetic Polynucleotide
source              1..20
                    mol_type = other DNA
                    organism = synthetic construct
SEQUENCE: 391
ttcctcggta tttattgtct                                                     20

SEQ ID NO: 392      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 392
gtgaagatga agcagacggg                                                     20

SEQ ID NO: 393      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 393
gatggagttg ctgcaggcag                                                     20

SEQ ID NO: 394      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 394
ccctgcggca gaggctgagg                                                     20

SEQ ID NO: 395      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 395
agcaggcgac ttccggacac                                                     20

SEQ ID NO: 396      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 396
ctgcttgagc cacacgtgca                                                     20

SEQ ID NO: 397      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 397
attcctcggt atttattgtc                                                     20

SEQ ID NO: 398      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 398
ctggcggaga ttgtcatggc                                                     20

SEQ ID NO: 399      moltype = DNA  length = 20
FEATURE             Location/Qualifiers
```

```
misc_feature          1..20
                      note = Synthetic Polynucleotide
source                1..20
                      mol_type = other DNA
                      organism = synthetic construct
SEQUENCE: 399
gggatggtct ccgggacagc                                              20

SEQ ID NO: 400        moltype = DNA   length = 20
FEATURE               Location/Qualifiers
misc_feature          1..20
                      note = Synthetic Polynucleotide
source                1..20
                      mol_type = other DNA
                      organism = synthetic construct
SEQUENCE: 400
actacctgta cctggtcatg                                              20

SEQ ID NO: 401        moltype = DNA   length = 20
FEATURE               Location/Qualifiers
misc_feature          1..20
                      note = Synthetic Polynucleotide
source                1..20
                      mol_type = other DNA
                      organism = synthetic construct
SEQUENCE: 401
gagtgtgact ggtgggcgct                                              20

SEQ ID NO: 402        moltype = DNA   length = 20
FEATURE               Location/Qualifiers
misc_feature          1..20
                      note = Synthetic Polynucleotide
source                1..20
                      mol_type = other DNA
                      organism = synthetic construct
SEQUENCE: 402
acgttttgga tgcactgaga                                              20

SEQ ID NO: 403        moltype = DNA   length = 20
FEATURE               Location/Qualifiers
misc_feature          1..20
                      note = Synthetic Polynucleotide
source                1..20
                      mol_type = other DNA
                      organism = synthetic construct
SEQUENCE: 403
aggccctcca tctgcccaaa                                              20

SEQ ID NO: 404        moltype = DNA   length = 20
FEATURE               Location/Qualifiers
misc_feature          1..20
                      note = Synthetic Polynucleotide
source                1..20
                      mol_type = other DNA
                      organism = synthetic construct
SEQUENCE: 404
gctacgtgca cagggacatc                                              20

SEQ ID NO: 405        moltype = DNA   length = 20
FEATURE               Location/Qualifiers
misc_feature          1..20
                      note = Synthetic Polynucleotide
source                1..20
                      mol_type = other DNA
                      organism = synthetic construct
SEQUENCE: 405
gggacctgct gacactgctg                                              20

SEQ ID NO: 406        moltype = DNA   length = 20
FEATURE               Location/Qualifiers
misc_feature          1..20
                      note = Synthetic Polynucleotide
source                1..20
                      mol_type = other DNA
                      organism = synthetic construct
SEQUENCE: 406
acctggcgga gattgtcatg                                              20

SEQ ID NO: 407        moltype = DNA   length = 20
```

```
FEATURE                 Location/Qualifiers
misc_feature            1..20
                        note = Synthetic Polynucleotide
source                  1..20
                        mol_type = other DNA
                        organism = synthetic construct
SEQUENCE: 407
catgaagatc atgaacaagt                                                   20

SEQ ID NO: 408          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 408
cccttctacg cggattccac                                                   20

SEQ ID NO: 409          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 409
ggcggagatt gtcatggcca                                                   20

SEQ ID NO: 410          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 410
cggtatttat tgtctgtccc                                                   20

SEQ ID NO: 411          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 411
tgagcaagtt tggggagcgg                                                   20

SEQ ID NO: 412          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 412
acccggcaga gcctgagccg                                                   20

SEQ ID NO: 413          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 413
tctggcgccg cccaggagcc                                                   20

SEQ ID NO: 414          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 414
ctgcctgctt actcgggaaa                                                   20
```

```
SEQ ID NO: 415            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 415
catcaaaccc gacaacatcc                                                  20

SEQ ID NO: 416            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 416
tccaggatga gaactacctg                                                  20

SEQ ID NO: 417            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 417
tatgaaatgt tctatgggca                                                  20

SEQ ID NO: 418            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 418
gccttccagg atgagaacta                                                  20

SEQ ID NO: 419            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 419
ggctacgtgc acagggacat                                                  20

SEQ ID NO: 420            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 420
agtcctgtga tccgggcccg                                                  20

SEQ ID NO: 421            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 421
acctatggca agatcgtcca                                                  20

SEQ ID NO: 422            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 422
ggtggcccac gccggccaac                                                  20
```

-continued

```
SEQ ID NO: 423          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 423
cacgttttgg atgcactgag                                                    20

SEQ ID NO: 424          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 424
accgacacat gcaacttcga                                                    20

SEQ ID NO: 425          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 425
gccgggccgt ccgtgttcca                                                    20

SEQ ID NO: 426          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 426
ctcacttgcg ctgctctcgg                                                    20

SEQ ID NO: 427          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 427
cacgtccggc agttgcagga                                                    20

SEQ ID NO: 428          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 428
ggagagggac gtgttggtga                                                    20

SEQ ID NO: 429          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 429
ggatggagtt gctgcaggca                                                    20

SEQ ID NO: 430          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 430
```

```
tggtggccca cgccggccaa                                                  20

SEQ ID NO: 431          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 431
actacgcgag gcagaggctc                                                  20

SEQ ID NO: 432          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 432
ttctatgggc agacgccctt                                                  20

SEQ ID NO: 433          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 433
cctcggtatt tattgtctgt                                                  20

SEQ ID NO: 434          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 434
tcggtattta ttgtctgtcc                                                  20

SEQ ID NO: 435          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 435
cgggacctag aggcacacgt                                                  20

SEQ ID NO: 436          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 436
ccgttgttct gtctcgtgcc                                                  20

SEQ ID NO: 437          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 437
gaactacctg tacctggtca                                                  20

SEQ ID NO: 438          moltype = DNA   length = 20
FEATURE                 Location/Qualifiers
misc_feature            1..20
                        note = Synthetic Polynucleotide
source                  1..20
                        mol_type = other DNA
                        organism = synthetic construct
```

```
SEQUENCE: 438
gaggtgctca cccggcagag                                               20

SEQ ID NO: 439          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 439
tctacctggc ggagattgtc                                               20

SEQ ID NO: 440          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 440
gcgcttctac ctggcggaga                                               20

SEQ ID NO: 441          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 441
gtcaactacg cgaggcagag                                               20

SEQ ID NO: 442          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 442
ggccctccat ctgcccaaag                                               20

SEQ ID NO: 443          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 443
ccaggatgag aactacctgt                                               20

SEQ ID NO: 444          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 444
acactgctga gcaagtttgg                                               20

SEQ ID NO: 445          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 445
cacagggaca tcaaacccga                                               20

SEQ ID NO: 446          moltype = DNA  length = 20
FEATURE                 Location/Qualifiers
misc_feature            1..20
                        note = Synthetic Polynucleotide
source                  1..20
                        mol_type = other DNA
```

```
                            organism = synthetic construct
SEQUENCE: 446
gcctgggaag gcagcaagcc                                                   20

SEQ ID NO: 447              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 447
caggatgaga actacctgta                                                   20

SEQ ID NO: 448              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 448
gccctgacgt ggatgggcaa                                                   20

SEQ ID NO: 449              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 449
gatgagaact acctgtacct                                                   20

SEQ ID NO: 450              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 450
ctcggtattt attgtctgtc                                                   20

SEQ ID NO: 451              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 451
ttcgcctatg aaatgttcta                                                   20

SEQ ID NO: 452              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 452
cctcgcgaat aaaaggccct                                                   20

SEQ ID NO: 453              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 453
gccagtcaac tacgcgaggc                                                   20

SEQ ID NO: 454              moltype = DNA   length = 20
FEATURE                     Location/Qualifiers
misc_feature                1..20
                            note = Synthetic Polynucleotide
source                      1..20
```

-continued

```
                        mol_type = other DNA
                        organism = synthetic construct
SEQUENCE: 454
acccgacaac atcctgctgg                                                    20

SEQ ID NO: 455          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 455
gaacttcgcc agtcaactac                                                    20

SEQ ID NO: 456          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 456
ggagatggag gccatccgca                                                    20

SEQ ID NO: 457          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 457
ttctacctgg cggagattgt                                                    20

SEQ ID NO: 458          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 458
tgggcgctgg gtgtattcgc                                                    20

SEQ ID NO: 459          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 459
ccttccagga tgagaactac                                                    20

SEQ ID NO: 460          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 460
cacccggcag agcctgagcc                                                    20

SEQ ID NO: 461          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 461
agggacgtgt tggtgaatgg                                                    20

SEQ ID NO: 462          moltype = DNA   length = 20
FEATURE                 Location/Qualifiers
misc_feature            1..20
                        note = Synthetic Polynucleotide
```

```
source                  1..20
                        mol_type = other DNA
                        organism = synthetic construct
SEQUENCE: 462
gagaactacc tgtacctggt                                                     20

SEQ ID NO: 463          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 463
cgtggatggg caaactgcag                                                     20

SEQ ID NO: 464          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 464
gccatgaaga tcatgaacaa                                                     20

SEQ ID NO: 465          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 465
acgtgcacag ggacatcaaa                                                     20

SEQ ID NO: 466          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 466
acaacatcct gctggaccgc                                                     20

SEQ ID NO: 467          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 467
agattgtcat ggccatagac                                                     20

SEQ ID NO: 468          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 468
ggaggcgctt tccctgctcc                                                     20

SEQ ID NO: 469          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 469
ccagtcaact acgcgaggca                                                     20

SEQ ID NO: 470          moltype = DNA  length = 20
FEATURE                 Location/Qualifiers
misc_feature            1..20
```

```
                    note = Synthetic Polynucleotide
source              1..20
                    mol_type = other DNA
                    organism = synthetic construct
SEQUENCE: 470
gggagatgga ggccatccgc                                                          20

SEQ ID NO: 471      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 471
gggtgtattc gcctatgaaa                                                          20

SEQ ID NO: 472      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 472
cctccgactc gctgacaggc                                                          20

SEQ ID NO: 473      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 473
ggatgaaaca gctgaagtgg                                                          20

SEQ ID NO: 474      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 474
ggcagttgca ggagcggatg                                                          20

SEQ ID NO: 475      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 475
cgcgctccct gaaccctaga                                                          20

SEQ ID NO: 476      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 476
aggagaggga cgtgttggtg                                                          20

SEQ ID NO: 477      moltype = DNA  length = 20
FEATURE             Location/Qualifiers
misc_feature        1..20
                    note = Synthetic Polynucleotide
source              1..20
                    mol_type = other DNA
                    organism = synthetic construct
SEQUENCE: 477
aggcgctttc cctgctcctg                                                          20

SEQ ID NO: 478      moltype = DNA  length = 20
FEATURE             Location/Qualifiers
```

```
misc_feature              1..20
                          note = Synthetic Polynucleotide
source                    1..20
                          mol_type = other DNA
                          organism = synthetic construct
SEQUENCE: 478
cttctacctg gcggagattg                                                20

SEQ ID NO: 479            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 479
gacatcaaac ccgacaacat                                                20

SEQ ID NO: 480            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 480
gcagttgcag gagcggatgg                                                20

SEQ ID NO: 481            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 481
ggctgaggcc gaggtgacgc                                                20

SEQ ID NO: 482            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 482
ctcgcgaata aaaggccctc                                                20

SEQ ID NO: 483            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 483
gagcacctct ctctgccgct                                                20

SEQ ID NO: 484            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 484
cccaatccac gttttggatg                                                20

SEQ ID NO: 485            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 485
aaggccctcc atctgcccaa                                                20

SEQ ID NO: 486            moltype = DNA  length = 20
```

```
FEATURE                 Location/Qualifiers
misc_feature            1..20
                        note = Synthetic Polynucleotide
source                  1..20
                        mol_type = other DNA
                        organism = synthetic construct
SEQUENCE: 486
tcaactacgc gaggcagagg                                              20

SEQ ID NO: 487          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 487
cctgttcgcc gttgttctgt                                              20

SEQ ID NO: 488          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 488
tcaaacccga caacatcctg                                              20

SEQ ID NO: 489          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 489
tgcggcagag gctgaggccg                                              20

SEQ ID NO: 490          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 490
aacccgacaa catcctgctg                                              20

SEQ ID NO: 491          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 491
caaggagcac ctctctctgc                                              20

SEQ ID NO: 492          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 492
cccacaccca tggaactgga                                              20

SEQ ID NO: 493          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 493
ttctttcggc caggctgagg                                              20
```

| | | |
|---|---|---|
| SEQ ID NO: 494<br>FEATURE<br>misc_feature<br>source | moltype = DNA   length = 20<br>Location/Qualifiers<br>1..20<br>note = Synthetic Polynucleotide<br>1..20<br>mol_type = other DNA<br>organism = synthetic construct | |
| SEQUENCE: 494<br>ccctcgcgaa taaaaggccc | | 20 |
| SEQ ID NO: 495<br>FEATURE<br>misc_feature<br>source | moltype = DNA   length = 20<br>Location/Qualifiers<br>1..20<br>note = Synthetic Polynucleotide<br>1..20<br>mol_type = other DNA<br>organism = synthetic construct | |
| SEQUENCE: 495<br>gccacatccg cctggccgac | | 20 |
| SEQ ID NO: 496<br>FEATURE<br>misc_feature<br>source | moltype = DNA   length = 20<br>Location/Qualifiers<br>1..20<br>note = Synthetic Polynucleotide<br>1..20<br>mol_type = other DNA<br>organism = synthetic construct | |
| SEQUENCE: 496<br>ggcctgggaa ggcagcaagc | | 20 |
| SEQ ID NO: 497<br>FEATURE<br>misc_feature<br>source | moltype = DNA   length = 20<br>Location/Qualifiers<br>1..20<br>note = Synthetic Polynucleotide<br>1..20<br>mol_type = other DNA<br>organism = synthetic construct | |
| SEQUENCE: 497<br>cgacaacatc ctgctggacc | | 20 |
| SEQ ID NO: 498<br>FEATURE<br>misc_feature<br>source | moltype = DNA   length = 20<br>Location/Qualifiers<br>1..20<br>note = Synthetic Polynucleotide<br>1..20<br>mol_type = other DNA<br>organism = synthetic construct | |
| SEQUENCE: 498<br>ctcgactggg atggtctccg | | 20 |
| SEQ ID NO: 499<br>FEATURE<br>misc_feature<br>source | moltype = DNA   length = 20<br>Location/Qualifiers<br>1..20<br>note = Synthetic Polynucleotide<br>1..20<br>mol_type = other DNA<br>organism = synthetic construct | |
| SEQUENCE: 499<br>agtcaactac gcgaggcaga | | 20 |
| SEQ ID NO: 500<br>FEATURE<br>misc_feature<br>source | moltype = DNA   length = 20<br>Location/Qualifiers<br>1..20<br>note = Synthetic Polynucleotide<br>1..20<br>mol_type = other DNA<br>organism = synthetic construct | |
| SEQUENCE: 500<br>ttccaggatg agaactacct | | 20 |
| SEQ ID NO: 501<br>FEATURE<br>misc_feature<br>source | moltype = DNA   length = 20<br>Location/Qualifiers<br>1..20<br>note = Synthetic Polynucleotide<br>1..20<br>mol_type = other DNA<br>organism = synthetic construct | |
| SEQUENCE: 501<br>aagatcgtcc actacaagga | | 20 |

```
SEQ ID NO: 502            moltype = DNA   length = 20
FEATURE                   Location/Qualifiers
misc_feature              1..20
                          note = Synthetic Polynucleotide
source                    1..20
                          mol_type = other DNA
                          organism = synthetic construct
SEQUENCE: 502
ccaatccacg ttttggatgc                                                    20

SEQ ID NO: 503            moltype = DNA   length = 20
FEATURE                   Location/Qualifiers
misc_feature              1..20
                          note = Synthetic Polynucleotide
source                    1..20
                          mol_type = other DNA
                          organism = synthetic construct
SEQUENCE: 503
ccgacaacat cctgctggac                                                    20

SEQ ID NO: 504            moltype = DNA   length = 20
FEATURE                   Location/Qualifiers
misc_feature              1..20
                          note = Synthetic Polynucleotide
source                    1..20
                          mol_type = other DNA
                          organism = synthetic construct
SEQUENCE: 504
gaggtgacgc tgcgggagct                                                    20

SEQ ID NO: 505            moltype = DNA   length = 20
FEATURE                   Location/Qualifiers
misc_feature              1..20
                          note = Synthetic Polynucleotide
source                    1..20
                          mol_type = other DNA
                          organism = synthetic construct
SEQUENCE: 505
cctcacttgc gctgctctcg                                                    20

SEQ ID NO: 506            moltype = DNA   length = 20
FEATURE                   Location/Qualifiers
misc_feature              1..20
                          note = Synthetic Polynucleotide
source                    1..20
                          mol_type = other DNA
                          organism = synthetic construct
SEQUENCE: 506
tatcggaggc gctttccctg                                                    20

SEQ ID NO: 507            moltype = DNA   length = 20
FEATURE                   Location/Qualifiers
misc_feature              1..20
                          note = Synthetic Polynucleotide
source                    1..20
                          mol_type = other DNA
                          organism = synthetic construct
SEQUENCE: 507
ggtgtattcg cctatgaaat                                                    20

SEQ ID NO: 508            moltype = DNA   length = 20
FEATURE                   Location/Qualifiers
misc_feature              1..20
                          note = Synthetic Polynucleotide
source                    1..20
                          mol_type = other DNA
                          organism = synthetic construct
SEQUENCE: 508
ggccacatcc gcctggccga                                                    20

SEQ ID NO: 509            moltype = DNA   length = 20
FEATURE                   Location/Qualifiers
misc_feature              1..20
                          note = Synthetic Polynucleotide
source                    1..20
                          mol_type = other DNA
                          organism = synthetic construct
SEQUENCE: 509
```

```
gacttccgga cacatccctt                                              20

SEQ ID NO: 510         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 510
gcaagatcgt ccactacaag                                              20

SEQ ID NO: 511         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 511
ccacatccgc ctggccgact                                              20

SEQ ID NO: 512         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 512
tctttcggcc aggctgaggc                                              20

SEQ ID NO: 513         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 513
gctgaggccg aggtgacgct                                              20

SEQ ID NO: 514         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 514
agcacctctc tctgccgctg                                              20

SEQ ID NO: 515         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 515
gcacctctct ctgccgctgg                                              20

SEQ ID NO: 516         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 516
ggcaagatcg tccactacaa                                              20

SEQ ID NO: 517         moltype = DNA  length = 20
FEATURE                Location/Qualifiers
misc_feature           1..20
                       note = Synthetic Polynucleotide
source                 1..20
                       mol_type = other DNA
                       organism = synthetic construct
```

```
SEQUENCE: 517
ctatcggagg cgctttccct                                             20

SEQ ID NO: 518           moltype = DNA  length = 20
FEATURE                  Location/Qualifiers
misc_feature             1..20
                         note = Synthetic Polynucleotide
source                   1..20
                         mol_type = other DNA
                         organism = synthetic construct
SEQUENCE: 518
cctatcggag gcgctttccc                                             20

SEQ ID NO: 519           moltype = DNA  length = 1275
FEATURE                  Location/Qualifiers
source                   1..1275
                         mol_type = genomic DNA
                         organism = Homo sapiens
SEQUENCE: 519
atggccctcc cgacaccctc ggacagcacc ctccccgcgg aagcccgggg acgaggacgg   60
cgacggagac tcgtttggac cccgagccaa agcgaggccc tgcgagcctg ctttgagcgg  120
aacccgtacc cgggcatcgc caccagagaa cggctggccc aggccatcgg cattccggag  180
cccagggtcc agatttggtt tcagaatgag aggtcacgcc agctgaggca gcaccggcgg  240
gaatctcggc cctggcccgg gagacgcggc ccgccagaag gccggcgaaa gcggaccgcc  300
gtcaccggat cccagaccgc cctgctcctc cgagcctttg agaaggatcg cttcccaggc  360
atcgccgccc gggaggagct ggccagagag acgggccggc cggagtccag gattcagatc  420
tggtttcaga atcgaagggc caggcacccg ggacagggtg gcagggcgcc cgcgcaggca  480
ggcggcctgt gcagcgcggc ccccggcggg ggtcaccctg ctccctcgtg ggtcgccttc  540
gcccacaccg gcgcgtgggg aacgggcgtt cccgcacccc acgtgccctg cgcgcctggg  600
gctctcccac aggggcttt cgtgagccag gcagcgaggg cgccccccgc gctgcagccc  660
agccaggccg cgccggcaga ggggatctcc caacctgccc cggcgcgcgg ggatttcgcg  720
tacgccgccc cggctcctcc ggacggggcg ctctcccacc ctcaggctcc tcggtggcct  780
ccgcacccgg gcaaaagccg ggaggaccgg gacccgcagc gcgacggcct gccgggcccc  840
tgcgcggtgg cacagcctgg gccgctcaa gcggggccgc agggccaagg ggtgcttgcg  900
ccacccacgt cccaggggag tccgtggtgg ggctggggca ggtcgccggg  960
gcggcgtggg aaccccaagc cggggcagct ccacctcccc agcccgcgcc ccggacgcc  1020
tccgcctccg cgcggcaggg gcagatgcaa ggcatcccgg cgcctcccca ggcgctccag  1080
gagccggcgc cctggtctgc actcccctgc ggcctgctgc tggatgagct cctggcgagc  1140
ccggagtttc tgcagcaggc gcaacctctc ctagaaacgg aggcccgggg ggagctggag  1200
gcctcggaag aggccgcctc gctggaagca cccctcagcg aggaagaata ccgggctctg  1260
ctggaggagc tttag                                                  1275

SEQ ID NO: 520           moltype = DNA  length = 2024
FEATURE                  Location/Qualifiers
source                   1..2024
                         mol_type = genomic DNA
                         organism = Mus musculus
SEQUENCE: 520
atggcagaag ctggcagccc tgttggtggc agtggtgtgg cacgggaatc ccggcggcgc   60
aggaagacgg tttggcaggc ctggcaagag caggccctgc tatcaacttt caagaagaag  120
agatacctga gcttcaagga gaggaaggag ctggccaaga gaatggggt ctcagattgc  180
cgcatccgcg tgtggtttca gaaccgcagg aatcgcagtg gagaggaggg gcatgcctca  240
aagaggtcca tcagaggctc caggcggcta gcctcgccac agctccagga gagcttgga  300
tccaggccac agggtagagg catgcgctca tctggcagaa ggcctcgcac tcgactcacc  360
tcgctacagc tcaggatcct agggcaagcc tttgagagga acccacgacc aggcttttgt  420
accagggagg agctggcgcg tgacacaggg ttgcccgagg acacgatcca catatgtttt  480
caaaaccgaa gagctcggcg gcgccacagg aggggcaggc ccacagctca agatcaagac  540
ttgctggcgt cacaagggtc ggatgggcc cctgcaggtc cggaaggcag agagcgtgaa  600
ggtgccagg agaacttgtt gccacaggaa gaagcaggaa gatcgggcat ggatacctcg  660
agccctagcg acttgccctc ctttctgcgga gagtccagc cttccaagt ggcacagccc  720
cgtggagcag gccaacaaga gccccccact cgagcaggca acgcaggctc tctgaaccc  780
ctccttgatc agctgctgga tgaagtccaa gtagaagagc ctgctccagc ccctctgaat  840
ttggatggag accctggtgg cagggtgcat gaaggttccc aggagagctt ttggccacag  900
gaagaagcag gaagtacagg catgatact tctagccaca gcgactcaaa ctccttctgc  960
agagagtccc agccttccca gtgggacag cctgtggag cgggccaaga agatgcccgc 1020
actcaagcag acagcacagg ccctctgaa ctccctcctcc ttgatcaact gctgacgaa  1080
gtccaaagg aagagcatgt gccagtccca ctggattggg gtagaaatcc tggcagcagg  1140
gagcatgaag gttcccagga cagcttactg ccctcgagg aagcagtaaa ttcgggcatg  1200
gatacctcga tcccctagcat ctggccaacc ttctgcagag aatccagcc tccccaagtg  1260
gcacagccct ctggaccagg ccaagcacag gccccactc aaggtggggaa cacgaccccc  1320
ctggagctct cctctatca actgttgat gaagtccaag tagaagagca tgctccagcc  1380
cctctgaatt gggatgtaga tcctggtggc agggtgcatg aaggttcgtg ggagagcttt  1440
tggcacagg aagaagcagg aagtacaggc tggatactt caagcccag cgactcaaac  1500
tccttcttca gagagtccaa gccttcccca gtggcacagc gcgtgcaagaa cccgccagaa  1560
gatgcccgca ctcaagcaga cagcacaggc cctctggaac tcctcctctt tgatcaactg  1620
ctggacgaag tccaaaagga agagcatgtg ccagccccac tggattggg tagaaatcct  1680
ggcagcatga gcatgaagg ttcccaggac agcttactgc cctgagga agcagcaaat  1740
tcggcaggg atacctcgat ccctagcatc tggcagcct tctgcagaaa tcccagcct  1800
ccccaagtgg cacagccctc tggaccaggc caagcacagg cccccattca aggtggggaac  1860
```

```
acggaccccc tggagctctt ccttgatcaa ctgctgaccg aagtccaact tgaggagcag   1920
gggcctgccc ctgtgaatgt ggaggaaaca tgggagcaaa tggacacaac acctatctgc   1980
ctctcacttc agaagaatat cagactcttc tagatatgct ctga                    2024
```

| | | |
|---|---|---|
| SEQ ID NO: 521 | moltype = DNA  length = 25 | |
| FEATURE | Location/Qualifiers | |
| misc_feature | 1..25 | |
| | note = Synthetic Polynucleotide | |
| source | 1..25 | |
| | mol_type = other DNA | |
| | organism = synthetic construct | |

```
SEQUENCE: 521
gggcatttta atatatctct gaact                                           25
```

| | | |
|---|---|---|
| SEQ ID NO: 522 | moltype = DNA  length = 25 | |
| FEATURE | Location/Qualifiers | |
| misc_feature | 1..25 | |
| | note = Synthetic Polynucleotide | |
| source | 1..25 | |
| | mol_type = other DNA | |
| | organism = synthetic construct | |

```
SEQUENCE: 522
agttcagaga tatattaaaa tgccc                                           25
```

| | | |
|---|---|---|
| SEQ ID NO: 523 | moltype = DNA  length = 25 | |
| FEATURE | Location/Qualifiers | |
| misc_feature | 1..25 | |
| | note = Synthetic | |
| source | 1..25 | |
| | mol_type = other DNA | |
| | organism = synthetic construct | |

```
SEQUENCE: 523
cctcttacct cagttacaat ttata                                           25
```

| | | |
|---|---|---|
| SEQ ID NO: 524 | moltype = RNA  length = 21 | |
| FEATURE | Location/Qualifiers | |
| misc_feature | 1..21 | |
| | note = Synthetic | |
| source | 1..21 | |
| | mol_type = other RNA | |
| | organism = synthetic construct | |
| modified_base | 1 | |
| | mod_base = OTHER | |
| | note = modified by 2prime Fluoro | |
| modified_base | 2 | |
| | mod_base = cm | |
| modified_base | 3 | |
| | mod_base = OTHER | |
| | note = modified by 2prime Fluoro | |
| modified_base | 4 | |
| | mod_base = um | |
| modified_base | 5 | |
| | mod_base = OTHER | |
| | note = modified by 2prime Fluoro | |
| modified_base | 6 | |
| | mod_base = um | |
| modified_base | 7 | |
| | mod_base = OTHER | |
| | note = modified by 2prime Fluoro | |
| modified_base | 8 | |
| | mod_base = OTHER | |
| | note = modified by 2prime OMe | |
| modified_base | 9 | |
| | mod_base = OTHER | |
| | note = modified by 2prime Fluoro | |
| modified_base | 10 | |
| | mod_base = um | |
| modified_base | 11 | |
| | mod_base = OTHER | |
| | note = modified by 2prime Fluoro | |
| modified_base | 12 | |
| | mod_base = um | |
| modified_base | 13 | |
| | mod_base = OTHER | |
| | note = modified by 2prime Fluoro | |
| modified_base | 14 | |
| | mod_base = gm | |
| modified_base | 15 | |
| | mod_base = OTHER | |

```
                              note = modified by 2prime Fluoro
modified_base                 16
                              mod_base = um
modified_base                 17
                              mod_base = OTHER
                              note = modified by 2prime Fluoro
modified_base                 18
                              mod_base = um
modified_base                 19
                              mod_base = OTHER
                              note = modified by 2prime Fluoro
modified_base                 20
                              mod_base = OTHER
                              note = modified by 2prime OMe
modified_base                 21
                              mod_base = OTHER
                              note = modified by 2prime Fluoro
SEQUENCE: 524
tcctatgact gtagatttta t                                           21

SEQ ID NO: 525                moltype = RNA  length = 23
FEATURE                       Location/Qualifiers
misc_feature                  1..23
                              note = Synthetic
source                        1..23
                              mol_type = other RNA
                              organism = synthetic construct
modified_base                 1
                              mod_base = OTHER
                              note = modified by 2prime OMe
modified_base                 2
                              mod_base = OTHER
                              note = modified by 2prime Fluoro
modified_base                 3
                              mod_base = OTHER
                              note = modified by 2prime OMe
modified_base                 4
                              mod_base = OTHER
                              note = modified by 2prime Fluoro
modified_base                 5
                              mod_base = OTHER
                              note = modified by 2prime OMe
modified_base                 6
                              mod_base = OTHER
                              note = modified by 2prime Fluoro
modified_base                 7
                              mod_base = um
modified_base                 8
                              mod_base = OTHER
                              note = modified by 2prime Fluoro
modified_base                 9
                              mod_base = um
modified_base                 10
                              mod_base = OTHER
                              note = modified by 2prime Fluoro
modified_base                 11
                              mod_base = cm
modified_base                 12
                              mod_base = OTHER
                              note = modified by 2prime Fluoro
modified_base                 13
                              mod_base = gm
modified_base                 14
                              mod_base = OTHER
                              note = modified by 2prime Fluoro
modified_base                 15
                              mod_base = cm
modified_base                 16
                              mod_base = OTHER
                              note = modified by 2prime Fluoro
modified_base                 17
                              mod_base = um
modified_base                 18
                              mod_base = OTHER
                              note = modified by 2prime Fluoro
modified_base                 19
                              mod_base = gm
modified_base                 20
                              mod_base = OTHER
```

```
                    note = modified by 2prime Fluoro
modified_base       21
                    mod_base = OTHER
                    note = modified by 2prime OMe
modified_base       21..23
                    mod_base = OTHER
                    note = phosphorothioate linkage
modified_base       22
                    mod_base = OTHER
                    note = modified by 2prime Fluoro
modified_base       23
                    mod_base = um
SEQUENCE: 525
ataaaatcta cagtcatagg aat                                               23

SEQ ID NO: 526      moltype = RNA   length = 21
FEATURE             Location/Qualifiers
misc_feature        1..21
                    note = Synthetic
source              1..21
                    mol_type = other RNA
                    organism = synthetic construct
modified_base       1
                    mod_base = OTHER
                    note = modified by 2prime Fluoro
modified_base       2
                    mod_base = gm
modified_base       3
                    mod_base = OTHER
                    note = modified by 2prime Fluoro
modified_base       4
                    mod_base = OTHER
                    note = modified by 2prime OMe
modified_base       5
                    mod_base = OTHER
                    note = modified by 2prime Fluoro
modified_base       6
                    mod_base = um
modified_base       7
                    mod_base = OTHER
                    note = modified by 2prime Fluoro
modified_base       8
                    mod_base = OTHER
                    note = modified by 2prime OMe
modified_base       9
                    mod_base = OTHER
                    note = modified by 2prime Fluoro
modified_base       10
                    mod_base = cm
modified_base       11
                    mod_base = OTHER
                    note = modified by 2prime Fluoro
modified_base       12
                    mod_base = um
modified_base       13
                    mod_base = OTHER
                    note = modified by 2prime Fluoro
modified_base       14
                    mod_base = um
modified_base       15
                    mod_base = OTHER
                    note = modified by 2prime Fluoro
modified_base       16
                    mod_base = um
modified_base       17
                    mod_base = OTHER
                    note = modified by 2prime Fluoro
modified_base       18
                    mod_base = cm
modified_base       19
                    mod_base = OTHER
                    note = modified by 2prime Fluoro
modified_base       20
                    mod_base = um
modified_base       21
                    mod_base = OTHER
                    note = modified by 2prime Fluoro
SEQUENCE: 526
tgtaataacc atatctacct t                                                 21
```

```
SEQ ID NO: 527         moltype = RNA   length = 23
FEATURE                Location/Qualifiers
misc_feature           1..23
                       note = Synthetic
source                 1..23
                       mol_type = other RNA
                       organism = synthetic construct
modified_base          1
                       mod_base = OTHER
                       note = modified by 2prime OMe
modified_base          2
                       mod_base = OTHER
                       note = modified by 2prime Fluoro
modified_base          3
                       mod_base = gm
modified_base          4
                       mod_base = OTHER
                       note = modified by 2prime Fluoro
modified_base          5
                       mod_base = um
modified_base          6
                       mod_base = OTHER
                       note = modified by 2prime Fluoro
modified_base          7
                       mod_base = gm
modified_base          8
                       mod_base = OTHER
                       note = modified by 2prime Fluoro
modified_base          9
                       mod_base = um
modified_base          10
                       mod_base = OTHER
                       note = modified by 2prime Fluoro
modified_base          11
                       mod_base = um
modified_base          12
                       mod_base = OTHER
                       note = modified by 2prime Fluoro
modified_base          13
                       mod_base = gm
modified_base          14
                       mod_base = OTHER
                       note = modified by 2prime Fluoro
modified_base          15
                       mod_base = um
modified_base          16
                       mod_base = OTHER
                       note = modified by 2prime Fluoro
modified_base          17
                       mod_base = um
modified_base          18
                       mod_base = OTHER
                       note = modified by 2prime Fluoro
modified_base          19
                       mod_base = OTHER
                       note = modified by 2prime OMe
modified_base          20
                       mod_base = OTHER
                       note = modified by 2prime Fluoro
modified_base          21
                       mod_base = OTHER
                       note = modified by 2prime OMe
modified_base          21..23
                       mod_base = OTHER
                       note = phosphorothioate linkage
modified_base          22
                       mod_base = OTHER
                       note = modified by 2prime Fluoro
modified_base          23
                       mod_base = OTHER
                       note = modified by 2prime OMe
SEQUENCE: 527
aaggtagata tggttattac aaa                                              23

SEQ ID NO: 528         moltype = DNA   length = 1710
FEATURE                Location/Qualifiers
source                 1..1710
                       mol_type = genomic DNA
```

```
                           organism = Homo sapiens
SEQUENCE: 528
atggccctcc cgacaccctc ggacagcacc ctccccgcgg aagcccgggg acgaggacgg      60
cgacggagac tcgtttggac cccgagccaa agcgaggccc tgcgagcctg ctttgagcgg     120
aacccgtacc cgggcatcgc caccagagaa cggctgaagg aggccatcgg cattccggag     180
cccagggtcc agatttggtt tcagaatgag aggtcacgcc agctgaggca gcaccgcgg     240
gaatctcggc cctggcccgg gagacgcggc ccgccagaag gccggcgaaa gcggaccgcc     300
gtcaccggat cccagaccgc cctgctcctc cgagcctttg agaaggatcg ctttccaggc     360
atcgccgccc gggaggagct ggccagagag acgggctcc cggagtccag gattcagatc      420
tggtttcaga atcgaagggc caggcacccg ggacagggtg gcagggcgcc cgcgcaggca     480
ggcggcctgt gcagcgcggc ccccggcggg ggtcacctg ctccctcgtg ggtcgccttc      540
gcccacaccg gcgcgtgggg aacggggctt cccgcacccc acgtgccctg cgcgcctggg     600
gctctcccac aggggctttt cgtgagccag gcagcgaggg ccgcccccgc gctgcagccc     660
agccaggccg cgccggcaga ggggatctcc caacctgccc cggcgcgggg ggatttcgcc     720
tacgccgccc cggctcctcc ggacggggcg ctctcccacc ctcaggctcc tcgctggcct     780
ccgcacccgg gcaaaagccg ggaggaccgg gaccccagc gcgacggcct gccgggcccc      840
tgcgcggtgg cacagcctgg gcccgctcaa gcggggcgc agggcaagg ggtgcttgcg       900
ccacccacgt cccaggggag tccgtggtgg ggctggggcc gggtccccca ggtcgccggg     960
gcggcgtggg aaccccaagc cggggcagct ccacctcccc agcccgcgcc ccggacgcc     1020
tccgcctccg cgcggcaggg gcagatgcaa ggcatcccgg cgccctccca ggcgctccag    1080
gagccggcgc cctggtctgc actccctgc ggcctgctgc tggatgagct cctggcgagc     1140
ccggagtttc tgcagcaggc gcaacctctc ctagaaacgg aggcccgggg ggagctggag    1200
gcctcggaag aggccgcctc gctggaagca cccctcagcg aggaagaata ccgggctctg    1260
ctggaggagc tttaggacgc ggggttggga cggggtcggg tggttcgggg cagggcggtg    1320
gcctctcttt cgcggggaac acctggctgg ctacggaggg gcgtgtctcc gccccgcccc    1380
ctccaccggg ctgaccggcc tgggattcct gccttctagg tctaggcccg gtgagagact    1440
ccacaccgcg gagaactgcc attctttcct gggcatcccg gggatcccag agccggccca    1500
ggtaccagca gacctgcgcg cagtgcgcac cccggctgac gtgcaaggga gctcgctggc    1560
ctctctgtgc ccttgttctt ccgtgaaatt ctggctgaat gtctcccccc accttccgac    1620
gctgtctagg caaacctgga ttagagttac atctcctgga tgattagttc agatatatat    1680
taaaatgccc cctccctgtg gatcctatag                                     1710

SEQ ID NO: 529         moltype = AA  length = 248
FEATURE                Location/Qualifiers
source                 1..248
                       mol_type = protein
                       organism = synthetic construct
SEQUENCE: 529
DYKDIVMTQS HKFMSTSVGD RVSITCKASQ DVGTAVAWYQ QKPGQSPKLL IYWASTRHTG      60
VPDRFTGSGS GTDFTLTISN VQSEDLADYF CQQYSSYLTF GAGTKLELKR GGGGSGGGGS     120
GGGGSGGGGS EVMLVESGGD LVKPGGSLKL SCAASGFTFS SYGMSWVRQT PDKRLEWVAT     180
ISSGGSYTYY PDSVKGRFTI SRDNAKNTLY LQMSSLKSED TAMYYCALLR SDWYFDVWGA     240
GTTVTVSS                                                              248

SEQ ID NO: 530         moltype = AA  length = 245
FEATURE                Location/Qualifiers
source                 1..245
                       mol_type = protein
                       organism = synthetic construct
SEQUENCE: 530
DYKDIVITQS HKFMSTSVGD RVSITCKASQ DVSTAVAWYQ QKPGQSPKLL IYSASYRYTG      60
VPDRFTGSGS GTDFTFTISS VQAEDLAVYY CQQHYSTPYT FGGGTKLEIK RGGGGSGGGG     120
SGGGGSGGGG SQVQLQQSGA ELVRPGASVT LSCKASGYTF TDYEMHWVKQ TPVHGLEWIG     180
AIDPETGGTA YNQKFKGKAT LTADKSSSTA YMELRSLTSE DSAVYYCTGW GFDYWGQGTT     240
LTVSS                                                                 245

SEQ ID NO: 531         moltype = AA  length = 247
FEATURE                Location/Qualifiers
source                 1..247
                       mol_type = protein
                       organism = synthetic construct
SEQUENCE: 531
DYKDIVMTQS HKFMSTSVGD RVSITCKASQ DVGTAVAWYQ QKPGQSPKLL IYWASTRHTG      60
VPDRFTGSGS GTDFTLTISN VQSEDLADYF CQQYSSYPYT FGGGTKLEIK RGGGGSGGGG     120
SGGGGSGGGG SQVQLQQPGS ELVRPGASVK LSCKASGYTF TSYWMHWVKQ RPGQGLEWIG     180
NIYPGSGSTN YDEKFKSKAT LTVDTSSSTA YMQLSSLTSE DSAVYYCTRG ATALDYWGQG     240
TTLTVSS                                                               247

SEQ ID NO: 532         moltype = AA  length = 131
FEATURE                Location/Qualifiers
source                 1..131
                       mol_type = protein
                       organism = synthetic construct
SEQUENCE: 532
QVQLQESGPG LVKPSETLSL TCTVSAGSIS STSTSYYWGW IRQSPGKGLE WIGSIYYSGR      60
TYYNPSLKSR VTISVDRPNN QFSLKVSSVT AADSAVYYCA RHRRVLLWIG ELLDDYDRDV     120
WGQGTMVTVS S                                                          131

SEQ ID NO: 533         moltype = AA  length = 5
```

```
FEATURE              Location/Qualifiers
source               1..5
                     mol_type = protein
                     organism = synthetic construct
SEQUENCE: 533
DYAMH                                                                       5

SEQ ID NO: 534       moltype = AA  length = 17
FEATURE              Location/Qualifiers
source               1..17
                     mol_type = protein
                     organism = synthetic construct
SEQUENCE: 534
GISTYFGRTN YNQKFKG                                                         17

SEQ ID NO: 535       moltype = AA  length = 10
FEATURE              Location/Qualifiers
source               1..10
                     mol_type = protein
                     organism = synthetic construct
SEQUENCE: 535
GLSGNYVMDY                                                                 10

SEQ ID NO: 536       moltype = AA  length = 15
FEATURE              Location/Qualifiers
source               1..15
                     mol_type = protein
                     organism = synthetic construct
SEQUENCE: 536
RASESWDSYG NSFMH                                                           15

SEQ ID NO: 537       moltype = AA  length = 7
FEATURE              Location/Qualifiers
source               1..7
                     mol_type = protein
                     organism = synthetic construct
SEQUENCE: 537
RASNLES                                                                     7

SEQ ID NO: 538       moltype = AA  length = 9
FEATURE              Location/Qualifiers
source               1..9
                     mol_type = protein
                     organism = synthetic construct
SEQUENCE: 538
QQSNEAPPT                                                                   9

SEQ ID NO: 539       moltype = AA  length = 60
FEATURE              Location/Qualifiers
source               1..60
                     mol_type = protein
                     organism = synthetic construct
SEQUENCE: 539
QVQLQQSGPE LVRPGVSVKI SCKGSGYTFT DYAMHWVKQS HAKSLEWIGG ISTYFGRTNY          60

SEQ ID NO: 540       moltype = AA  length = 111
FEATURE              Location/Qualifiers
source               1..111
                     mol_type = protein
                     organism = synthetic construct
SEQUENCE: 540
DIVLTQSPAS LAVSLGQRAT ISCRASESVD DYGNSFMHWY QQKPGQPPKL LIYRASNLES          60
GIPARFSGSG SRTDFTLTIN PVEADDVATY YCQQSNEAPP TFGGGTKLEI R                  111

SEQ ID NO: 541       moltype = AA  length = 5
FEATURE              Location/Qualifiers
source               1..5
                     mol_type = protein
                     organism = synthetic construct
SEQUENCE: 541
DYGMH                                                                       5

SEQ ID NO: 542       moltype = AA  length = 17
FEATURE              Location/Qualifiers
source               1..17
                     mol_type = protein
                     organism = synthetic construct
SEQUENCE: 542
VISPYSGRTN YNQNFKG                                                         17
```

```
SEQ ID NO: 543         moltype = AA  length = 10
FEATURE                Location/Qualifiers
source                 1..10
                       mol_type = protein
                       organism = synthetic construct
SEQUENCE: 543
GLSGNYVVDY                                                              10

SEQ ID NO: 544         moltype = AA  length = 15
FEATURE                Location/Qualifiers
source                 1..15
                       mol_type = protein
                       organism = synthetic construct
SEQUENCE: 544
RASESWDSYG NSFMH                                                        15

SEQ ID NO: 545         moltype = AA  length = 7
FEATURE                Location/Qualifiers
source                 1..7
                       mol_type = protein
                       organism = synthetic construct
SEQUENCE: 545
RASNLES                                                                 7

SEQ ID NO: 546         moltype = AA  length = 9
FEATURE                Location/Qualifiers
source                 1..9
                       mol_type = protein
                       organism = synthetic construct
SEQUENCE: 546
QQSNEGPPT                                                               9

SEQ ID NO: 547         moltype = AA  length = 119
FEATURE                Location/Qualifiers
source                 1..119
                       mol_type = protein
                       organism = synthetic construct
SEQUENCE: 547
QVQLQQSGPE LVRPGVSVKI SCKGSGYTFT DYGMHWVKQS HAKSLEWIGV ISPYSGRTNY       60
NQNFKGKATM TVDKSSSTAY LELARLTSED SAIYYCARGL SGNYVVDYWG QGTSVTVSS       119

SEQ ID NO: 548         moltype = AA  length = 111
FEATURE                Location/Qualifiers
source                 1..111
                       mol_type = protein
                       organism = synthetic construct
SEQUENCE: 548
DIVLTQSPAS LAVSLGQRAT ISCRASESVD SYGNSFMHWY QQKPGQPPKL LIYRASNLES       60
GIPARFSGSG SRTDFTLTIN PVEADDVATY YCQQSNEGPP TFGGGTKLEI K               111

SEQ ID NO: 549         moltype = AA  length = 5
FEATURE                Location/Qualifiers
source                 1..5
                       mol_type = protein
                       organism = synthetic construct
SEQUENCE: 549
DYAMH                                                                   5

SEQ ID NO: 550         moltype = AA  length = 17
FEATURE                Location/Qualifiers
source                 1..17
                       mol_type = protein
                       organism = synthetic construct
SEQUENCE: 550
VISFYSGKTN YNQKFMG                                                      17

SEQ ID NO: 551         moltype = AA  length = 10
FEATURE                Location/Qualifiers
source                 1..10
                       mol_type = protein
                       organism = synthetic construct
SEQUENCE: 551
GLSGNYVMDY                                                              10

SEQ ID NO: 552         moltype = AA  length = 15
FEATURE                Location/Qualifiers
source                 1..15
                       mol_type = protein
```

```
                                organism = synthetic construct
SEQUENCE: 552
RASESWDSYG NSFMH                                                           15

SEQ ID NO: 553          moltype = AA   length = 7
FEATURE                 Location/Qualifiers
source                  1..7
                        mol_type = protein
                        organism = synthetic construct
SEQUENCE: 553
RASNLES                                                                     7

SEQ ID NO: 554          moltype = AA   length = 9
FEATURE                 Location/Qualifiers
source                  1..9
                        mol_type = protein
                        organism = synthetic construct
SEQUENCE: 554
QQSNEGPPT                                                                   9

SEQ ID NO: 555          moltype = AA   length = 119
FEATURE                 Location/Qualifiers
source                  1..119
                        mol_type = protein
                        organism = synthetic construct
SEQUENCE: 555
QVQLQQSGPE LVRPGVSVKI SCKGSGYTVT DYAMHWVKQS HAKSLEWIGV ISFYSGKTNY           60
NQKFMGKATM TVDKSSSTAY MELARLTSED SAIYYCARGL SGNYVMDYWG QGTSVTVSS           119

SEQ ID NO: 556          moltype = AA   length = 111
FEATURE                 Location/Qualifiers
source                  1..111
                        mol_type = protein
                        organism = synthetic construct
SEQUENCE: 556
DIVLTQSPAS LAVSLGQRAT ISCRASESVD SYGNSFMHWY QQKPGQPPKL LIYRASNLES           60
GIPARFSGSG SRTDFTLTIN PVEADDVATY YCQQSNEGPP TFGGGTKLEI K                   111

SEQ ID NO: 557          moltype = AA   length = 5
FEATURE                 Location/Qualifiers
source                  1..5
                        mol_type = protein
                        organism = synthetic construct
SEQUENCE: 557
DYGMH                                                                       5

SEQ ID NO: 558          moltype = AA   length = 17
FEATURE                 Location/Qualifiers
source                  1..17
                        mol_type = protein
                        organism = synthetic construct
SEQUENCE: 558
VISPYSGKTN YSQKFKG                                                         17

SEQ ID NO: 559          moltype = AA   length = 10
FEATURE                 Location/Qualifiers
source                  1..10
                        mol_type = protein
                        organism = synthetic construct
SEQUENCE: 559
GLSGNFVMDF                                                                 10

SEQ ID NO: 560          moltype = AA   length = 15
FEATURE                 Location/Qualifiers
source                  1..15
                        mol_type = protein
                        organism = synthetic construct
SEQUENCE: 560
RASESWDSYG NSFMH                                                           15

SEQ ID NO: 561          moltype = AA   length = 7
FEATURE                 Location/Qualifiers
source                  1..7
                        mol_type = protein
                        organism = synthetic construct
SEQUENCE: 561
RASNLES                                                                     7

SEQ ID NO: 562          moltype = AA   length = 9
```

```
FEATURE                 Location/Qualifiers
source                  1..9
                        mol_type = protein
                        organism = synthetic construct
SEQUENCE: 562
QHSNEDPPT                                                                      9

SEQ ID NO: 563          moltype = AA   length = 119
FEATURE                 Location/Qualifiers
source                  1..119
                        mol_type = protein
                        organism = synthetic construct
SEQUENCE: 563
QVQLQQSGPE LVRPGVAVKI SCKGSGYKFI DYGMHWVKQS HTKSLQWIGV ISPYSGKTNY              60
SQKFKGKATM TVDKSSSTAY MELARLTSED SAIYYCARGL SGNFVMDFWG QGTSVTVSS              119

SEQ ID NO: 564          moltype = AA   length = 111
FEATURE                 Location/Qualifiers
source                  1..111
                        mol_type = protein
                        organism = synthetic construct
SEQUENCE: 564
DIVLTQSPAS LAVSLGQRAT ISCRASESVD SYGPSFMHWY QQKPGQPPKL LIYRASNLES              60
GIPARFSGSG SRTDFTLTIN PVEADDVATY YCQHSNEDPP TFGGGTRLEI K                      111

SEQ ID NO: 565          moltype = AA   length = 5
FEATURE                 Location/Qualifiers
source                  1..5
                        mol_type = protein
                        organism = synthetic construct
SEQUENCE: 565
DYAMH                                                                          5

SEQ ID NO: 566          moltype = AA   length = 17
FEATURE                 Location/Qualifiers
source                  1..17
                        mol_type = protein
                        organism = synthetic construct
SEQUENCE: 566
GISTYFGRTN YNQKFKG                                                            17

SEQ ID NO: 567          moltype = AA   length = 10
FEATURE                 Location/Qualifiers
source                  1..10
                        mol_type = protein
                        organism = synthetic construct
SEQUENCE: 567
GLSGNYVMDY                                                                    10

SEQ ID NO: 568          moltype = AA   length = 15
FEATURE                 Location/Qualifiers
source                  1..15
                        mol_type = protein
                        organism = synthetic construct
SEQUENCE: 568
RASESWDSYG NSFMH                                                              15

SEQ ID NO: 569          moltype = AA   length = 7
FEATURE                 Location/Qualifiers
source                  1..7
                        mol_type = protein
                        organism = synthetic construct
SEQUENCE: 569
RASNLES                                                                        7

SEQ ID NO: 570          moltype = AA   length = 9
FEATURE                 Location/Qualifiers
source                  1..9
                        mol_type = protein
                        organism = synthetic construct
SEQUENCE: 570
QQSNEAPPT                                                                      9

SEQ ID NO: 571          moltype = AA   length = 119
FEATURE                 Location/Qualifiers
source                  1..119
                        mol_type = protein
                        organism = synthetic construct
SEQUENCE: 571
```

```
QVQLQQSGPE LVRPGVSVKI SCKGSGYTFT DYAMHWVKQS HAKSLEWIGG ISTYFGRTNY    60
NQKFKGRATM TVDKSSSTAY MELARLTSED SALYYCARGL SGNYVMDYWG QGTSVTVSS    119

SEQ ID NO: 572          moltype = AA   length = 111
FEATURE                 Location/Qualifiers
source                  1..111
                        mol_type = protein
                        organism = synthetic construct
SEQUENCE: 572
DIVLTQSPAS LAVSLGQRAT ISCRASESVD DYGNSFMHWY QQKPGQPPKL LIYRASNLES    60
GIPARFSGSG SRTDFTLTIN PVEADDVATY YCQQSNEAPP TFGGGTKLEI R             111

SEQ ID NO: 573          moltype = AA   length = 17
FEATURE                 Location/Qualifiers
source                  1..17
                        mol_type = protein
                        organism = synthetic construct
SEQUENCE: 573
EINPTNGRTN YNENFKS                                                    17

SEQ ID NO: 574          moltype = AA   length = 7
FEATURE                 Location/Qualifiers
source                  1..7
                        mol_type = protein
                        organism = synthetic construct
SEQUENCE: 574
GTRAYHF                                                               7

SEQ ID NO: 575          moltype = AA   length = 11
FEATURE                 Location/Qualifiers
source                  1..11
                        mol_type = protein
                        organism = synthetic construct
SEQUENCE: 575
RASENIYSNL A                                                          11

SEQ ID NO: 576          moltype = AA   length = 7
FEATURE                 Location/Qualifiers
source                  1..7
                        mol_type = protein
                        organism = synthetic construct
SEQUENCE: 576
AATDLAD                                                               7

SEQ ID NO: 577          moltype = AA   length = 116
FEATURE                 Location/Qualifiers
source                  1..116
                        mol_type = protein
                        organism = synthetic construct
SEQUENCE: 577
QVQLQQPGAE LVRPGAAVKL SCKASGYTFT SYWMHWVKQR PGQGLEWIGE INPTNGRTNY    60
NENFKSKATL TVDKSSSTAY MQLSSLTSED SAVYYCARGT RAYHFWGQGT SVTVSS        116

SEQ ID NO: 578          moltype = AA   length = 107
FEATURE                 Location/Qualifiers
source                  1..107
                        mol_type = protein
                        organism = synthetic construct
SEQUENCE: 578
DIQLTQTPAS LSVSVGETVT ITCRASENIY SNLAWYQQKQ GKSPQLLVYA ATDLADGVPS    60
RFRGSGSGTQ YSLKINSLQS EDFGSYYCQH FWGTPLTFGA GTKLELI                  107

SEQ ID NO: 579          moltype = AA   length = 17
FEATURE                 Location/Qualifiers
source                  1..17
                        mol_type = protein
                        organism = synthetic construct
SEQUENCE: 579
EINPINGRTN YSEKFKK                                                    17

SEQ ID NO: 580          moltype = AA   length = 11
FEATURE                 Location/Qualifiers
source                  1..11
                        mol_type = protein
                        organism = synthetic construct
SEQUENCE: 580
RASDNIYSNL A                                                          11

SEQ ID NO: 581          moltype = AA   length = 7
```

```
FEATURE                 Location/Qualifiers
source                  1..7
                        mol_type = protein
                        organism = synthetic construct
SEQUENCE: 581
AATNLAD                                                                         7

SEQ ID NO: 582          moltype = AA   length = 9
FEATURE                 Location/Qualifiers
source                  1..9
                        mol_type = protein
                        organism = synthetic construct
SEQUENCE: 582
QHFWGTPLM                                                                       9

SEQ ID NO: 583          moltype = AA   length = 116
FEATURE                 Location/Qualifiers
source                  1..116
                        mol_type = protein
                        organism = synthetic construct
SEQUENCE: 583
QVQLQQPGAE LVKPGASVKL SCKASGYTFA SYWMHWVKQR PGQGLEWIGE INPINGRTNY              60
SEKFKKKATL TVDKSSSTAY MQLSSLTSED SAVYYCARGT RAYHYWGQGT SVTVSS                  116

SEQ ID NO: 584          moltype = AA   length = 107
FEATURE                 Location/Qualifiers
source                  1..107
                        mol_type = protein
                        organism = synthetic construct
SEQUENCE: 584
DIQMTQSPAS LSVSVGETVT ITCRASDNIY SNLAWYQQKQ GKSPQLLVYA ATNLADGVPS              60
RFSGSGSGTQ YSLKINSLQS EDFGSYYCQH FWGTPLMFGS GTKLELK                            107

SEQ ID NO: 585          moltype = AA   length = 17
FEATURE                 Location/Qualifiers
source                  1..17
                        mol_type = protein
                        organism = synthetic construct
SEQUENCE: 585
EINPSNGRTN YNETFKS                                                              17

SEQ ID NO: 586          moltype = AA   length = 11
FEATURE                 Location/Qualifiers
source                  1..11
                        mol_type = protein
                        organism = synthetic construct
SEQUENCE: 586
RASDNIYSNL A                                                                    11

SEQ ID NO: 587          moltype = AA   length = 7
FEATURE                 Location/Qualifiers
source                  1..7
                        mol_type = protein
                        organism = synthetic construct
SEQUENCE: 587
AVTNLAD                                                                         7

SEQ ID NO: 588          moltype = AA   length = 116
FEATURE                 Location/Qualifiers
source                  1..116
                        mol_type = protein
                        organism = synthetic construct
SEQUENCE: 588
QVQLQQPGAE LVKPGASVKL SCKASGYTFT SYWMHWVKQR PGQGLEWIGE INPSNGRTNY              60
NETFKSKATL TVDKSSSTAY MQLSSLTSED SAVYYCARGT RAYHYWGQGT SVTVSS                  116

SEQ ID NO: 589          moltype = AA   length = 107
FEATURE                 Location/Qualifiers
source                  1..107
                        mol_type = protein
                        organism = synthetic construct
SEQUENCE: 589
DIQMTQSPAS LSVSVGETVT ITCRASDNIY SNLAWYQQKQ GKSPQLLVYA VTNLADGVPS              60
RFSGSGSGTQ YSLKINSLQS EDFGSYYCQH FWGTPLTFGA GTKLELK                            107

SEQ ID NO: 590          moltype = AA   length = 6
FEATURE                 Location/Qualifiers
source                  1..6
                        mol_type = protein
```

```
                                -continued organism = synthetic construct
SEQUENCE: 590
SEYAWN                                                                  6

SEQ ID NO: 591          moltype = AA   length = 16
FEATURE                 Location/Qualifiers
source                  1..16
                        mol_type = protein
                        organism = synthetic construct
SEQUENCE: 591
YISYSGTTSY NPSLKS                                                      16

SEQ ID NO: 592          moltype = AA   length = 13
FEATURE                 Location/Qualifiers
source                  1..13
                        mol_type = protein
                        organism = synthetic construct
SEQUENCE: 592
YGYGNPATRY FDV                                                         13

SEQ ID NO: 593          moltype = AA   length = 11
FEATURE                 Location/Qualifiers
source                  1..11
                        mol_type = protein
                        organism = synthetic construct
SEQUENCE: 593
RASKSISKYL A                                                           11

SEQ ID NO: 594          moltype = AA   length = 7
FEATURE                 Location/Qualifiers
source                  1..7
                        mol_type = protein
                        organism = synthetic construct
SEQUENCE: 594
SGSTLQS                                                                 7

SEQ ID NO: 595          moltype = AA   length = 9
FEATURE                 Location/Qualifiers
source                  1..9
                        mol_type = protein
                        organism = synthetic construct
SEQUENCE: 595
QQHNEYPWT                                                               9

SEQ ID NO: 596          moltype = AA   length = 124
FEATURE                 Location/Qualifiers
source                  1..124
                        mol_type = protein
                        organism = synthetic construct
SEQUENCE: 596
VHDVQLQESG PGLVKPSQSL SLTCTVTGNS ITSEYAWNWI RQFPGNKLEW MGYISYSGTT       60
SYNPSLKSRI SITRDTSKNQ LFLQLNSVTT EDTATYFCAR YGYGNPATRY FDVWGAGTTV      120
TVSS                                                                  124

SEQ ID NO: 597          moltype = AA   length = 107
FEATURE                 Location/Qualifiers
source                  1..107
                        mol_type = protein
                        organism = synthetic construct
SEQUENCE: 597
DVQITQSPSY LTASPGETIT INCRASKSIS KYLAWYQEKP GKTNKLLIYS GSTLQSGIPS       60
RFSGSGSGTD FTLTISNLEP EDFAMYYCQQ HNEYPWTFGG GTKLEIK                   107

SEQ ID NO: 598          moltype = AA   length = 17
FEATURE                 Location/Qualifiers
source                  1..17
                        mol_type = protein
                        organism = synthetic construct
SEQUENCE: 598
NIYPGSGSTK YDERFKS                                                     17

SEQ ID NO: 599          moltype = AA   length = 11
FEATURE                 Location/Qualifiers
source                  1..11
                        mol_type = protein
                        organism = synthetic construct
SEQUENCE: 599
GGYDSRAWFA Y                                                           11
```

```
SEQ ID NO: 600          moltype = AA   length = 15
FEATURE                 Location/Qualifiers
source                  1..15
                        mol_type = protein
                        organism = synthetic construct
SEQUENCE: 600
RARQSVSTSS YSFMH                                                          15

SEQ ID NO: 601          moltype = AA   length = 7
FEATURE                 Location/Qualifiers
source                  1..7
                        mol_type = protein
                        organism = synthetic construct
SEQUENCE: 601
YASIQES                                                                   7

SEQ ID NO: 602          moltype = AA   length = 9
FEATURE                 Location/Qualifiers
source                  1..9
                        mol_type = protein
                        organism = synthetic construct
SEQUENCE: 602
QHTWEIPFT                                                                 9

SEQ ID NO: 603          moltype = AA   length = 120
FEATURE                 Location/Qualifiers
source                  1..120
                        mol_type = protein
                        organism = synthetic construct
SEQUENCE: 603
QVQLQQPGSE LVRPGASVKL SCKASGYTFT SYWMHWVKQR HGQGLEWIGN IYPGSGSTKY          60
DERFKSKGTL TVDTSSSTAY MHLSSLTSED SAVYYCTRGG YDSRAWFAYW GQGTLVTVSA         120

SEQ ID NO: 604          moltype = AA   length = 111
FEATURE                 Location/Qualifiers
source                  1..111
                        mol_type = protein
                        organism = synthetic construct
SEQUENCE: 604
DIVLTQSPAS LAVSLGQRAT ISCRARQSVS TSSYSFMHWY RQKAGQPPKL LIKYASIQES          60
GVPARFSGSG SGTDFTLNIL PVEEEDTATY YCQHTWEIPF TFGSGTKLEI K                  111

SEQ ID NO: 605          moltype = AA   length = 17
FEATURE                 Location/Qualifiers
source                  1..17
                        mol_type = protein
                        organism = synthetic construct
SEQUENCE: 605
NIYPGSGSTK YDEKRKS                                                        17

SEQ ID NO: 606          moltype = AA   length = 11
FEATURE                 Location/Qualifiers
source                  1..11
                        mol_type = protein
                        organism = synthetic construct
SEQUENCE: 606
GGYDSRAWFA H                                                              11

SEQ ID NO: 607          moltype = AA   length = 15
FEATURE                 Location/Qualifiers
source                  1..15
                        mol_type = protein
                        organism = synthetic construct
SEQUENCE: 607
RAROSVSTSS YSFMH                                                          15

SEQ ID NO: 608          moltype = AA   length = 7
FEATURE                 Location/Qualifiers
source                  1..7
                        mol_type = protein
                        organism = synthetic construct
SEQUENCE: 608
YASIQES                                                                   7

SEQ ID NO: 609          moltype = AA   length = 9
FEATURE                 Location/Qualifiers
source                  1..9
                        mol_type = protein
                        organism = synthetic construct
```

```
SEQUENCE: 609
QHTWEIPFT                                                                       9

SEQ ID NO: 610         moltype = AA  length = 120
FEATURE                Location/Qualifiers
source                 1..120
                       mol_type = protein
                       organism = synthetic construct
SEQUENCE: 610
QVQLQQPGSE LVRPGASVKL SCKASGYTFT SYWMHWVKQR HGQGLEWIGN IYPGSGSTKY   60
DEKFKSKGTL TVDTSSSTAY MHLSSLTSED SAVYYCTRGG YDSRAWFAHW GQGTLVTVSA  120

SEQ ID NO: 611         moltype = AA  length = 111
FEATURE                Location/Qualifiers
source                 1..111
                       mol_type = protein
                       organism = synthetic construct
SEQUENCE: 611
DIVLTQSPAS LAVSLGQRAT ISCRARQSVS TSSYSFMHWY QQKPGQPPKL LIKYASIQES   60
GVPARFSGSG SGTDFTLNIL PVEEEDTATY YCQHTWEIPF TFGSGTNLEI K          111

SEQ ID NO: 612         moltype = AA  length = 5
FEATURE                Location/Qualifiers
source                 1..5
                       mol_type = protein
                       organism = synthetic construct
SEQUENCE: 612
DYYMY                                                                           5

SEQ ID NO: 613         moltype = AA  length = 17
FEATURE                Location/Qualifiers
source                 1..17
                       mol_type = protein
                       organism = synthetic construct
SEQUENCE: 613
SISNGGDNTY YPDTVKG                                                             17

SEQ ID NO: 614         moltype = AA  length = 15
FEATURE                Location/Qualifiers
source                 1..15
                       mol_type = protein
                       organism = synthetic construct
SEQUENCE: 614
QGALYDGYYR GAMDY                                                               15

SEQ ID NO: 615         moltype = AA  length = 12
FEATURE                Location/Qualifiers
source                 1..12
                       mol_type = protein
                       organism = synthetic construct
SEQUENCE: 615
TTSSSWPSSY FH                                                                  12

SEQ ID NO: 616         moltype = AA  length = 7
FEATURE                Location/Qualifiers
source                 1..7
                       mol_type = protein
                       organism = synthetic construct
SEQUENCE: 616
STSNLAS                                                                         7

SEQ ID NO: 617         moltype = AA  length = 9
FEATURE                Location/Qualifiers
source                 1..9
                       mol_type = protein
                       organism = synthetic construct
SEQUENCE: 617
HQYHRSPFT                                                                       9

SEQ ID NO: 618         moltype = AA  length = 124
FEATURE                Location/Qualifiers
source                 1..124
                       mol_type = protein
                       organism = synthetic construct
SEQUENCE: 618
EVKLVESGGG LVQPGGFLKL SCATSGFTFS DYYMYWVRQT PEKRLEWVAS ISNGGDNTYY   60
PDTVKGRFTI SRDNAKNTLY LQMSRLKSED TAMYYCARQG ALYDGYYRGA MDYWGQGTSV  120
TVSS                                                              124
```

```
SEQ ID NO: 619          moltype = AA   length = 108
FEATURE                 Location/Qualifiers
source                  1..108
                        mol_type = protein
                        organism = synthetic construct
SEQUENCE: 619
QIVLTQSPAI MSASLGGRVT MTCTTSSSVP SSYFHWYQQK PGSSPKLWIY STSNLASGVP      60
ARFSGSGSGT SYSLTISSME AEDAATYYCH QYHRSPFTFG SGTKLEIK                  108

SEQ ID NO: 620          moltype = AA   length = 5
FEATURE                 Location/Qualifiers
source                  1..5
                        mol_type = protein
                        organism = synthetic construct
SEQUENCE: 620
NYWIE                                                                   5

SEQ ID NO: 621          moltype = AA   length = 17
FEATURE                 Location/Qualifiers
source                  1..17
                        mol_type = protein
                        organism = synthetic construct
SEQUENCE: 621
EILPGSGSTK YNEKFKG                                                     17

SEQ ID NO: 622          moltype = AA   length = 12
FEATURE                 Location/Qualifiers
source                  1..12
                        mol_type = protein
                        organism = synthetic construct
SEQUENCE: 622
RGGYGYDGEF AY                                                          12

SEQ ID NO: 623          moltype = AA   length = 11
FEATURE                 Location/Qualifiers
source                  1..11
                        mol_type = protein
                        organism = synthetic construct
SEQUENCE: 623
RAGQDITNYL N                                                           11

SEQ ID NO: 624          moltype = AA   length = 7
FEATURE                 Location/Qualifiers
source                  1..7
                        mol_type = protein
                        organism = synthetic construct
SEQUENCE: 624
YTSRLHS                                                                 7

SEQ ID NO: 625          moltype = AA   length = 9
FEATURE                 Location/Qualifiers
source                  1..9
                        mol_type = protein
                        organism = synthetic construct
SEQUENCE: 625
QQANTLPYT                                                               9

SEQ ID NO: 626          moltype = AA   length = 121
FEATURE                 Location/Qualifiers
source                  1..121
                        mol_type = protein
                        organism = synthetic construct
SEQUENCE: 626
QVQLQQSGAE LMKPGASVKI SCKAAGYTFS NYWIEWVKQR PGHGLEWIGE ILPGSGSTKY      60
NEKFKGKATF TADTSSNTAY MQLSSLTSED SAVYYCARRG GYGYDGEFAY WGQGTLVTVS     120
A                                                                     121

SEQ ID NO: 627          moltype = AA   length = 107
FEATURE                 Location/Qualifiers
source                  1..107
                        mol_type = protein
                        organism = synthetic construct
SEQUENCE: 627
DIQMTQTTSS LSASLGDRVT INCRAGQDIT NYLNWFQQKP DGTVKLLIYY TSRLHSGVPS      60
RFSGSGSGTD YSLTITNLEQ EDIATYFCQQ ANTLPYTFGG GTKLEIK                   107

SEQ ID NO: 628          moltype = AA   length = 8
FEATURE                 Location/Qualifiers
source                  1..8
```

```
                            mol_type = protein
                            organism = synthetic construct
SEQUENCE: 628
GYTFTNYW                                                                   8

SEQ ID NO: 629              moltype = AA   length = 8
FEATURE                     Location/Qualifiers
source                      1..8
                            mol_type = protein
                            organism = synthetic construct
SEQUENCE: 629
INPINGRS                                                                   8

SEQ ID NO: 630              moltype = AA   length = 9
FEATURE                     Location/Qualifiers
source                      1..9
                            mol_type = protein
                            organism = synthetic construct
SEQUENCE: 630
ARGTRAMHY                                                                  9

SEQ ID NO: 631              moltype = AA   length = 6
FEATURE                     Location/Qualifiers
source                      1..6
                            mol_type = protein
                            organism = synthetic construct
SEQUENCE: 631
ENIYNN                                                                     6

SEQ ID NO: 632              moltype = AA   length = 5
FEATURE                     Location/Qualifiers
source                      1..5
                            mol_type = protein
                            organism = synthetic construct
SEQUENCE: 632
NYWMH                                                                      5

SEQ ID NO: 633              moltype = AA   length = 17
FEATURE                     Location/Qualifiers
source                      1..17
                            mol_type = protein
                            organism = synthetic construct
SEQUENCE: 633
EINPINGRSN YGERFKT                                                        17

SEQ ID NO: 634              moltype = AA   length = 7
FEATURE                     Location/Qualifiers
source                      1..7
                            mol_type = protein
                            organism = synthetic construct
SEQUENCE: 634
GTRAMHY                                                                    7

SEQ ID NO: 635              moltype = AA   length = 11
FEATURE                     Location/Qualifiers
source                      1..11
                            mol_type = protein
                            organism = synthetic construct
SEQUENCE: 635
RTSENIYNNL A                                                              11

SEQ ID NO: 636              moltype = AA   length = 7
FEATURE                     Location/Qualifiers
source                      1..7
                            mol_type = protein
                            organism = synthetic construct
SEQUENCE: 636
AATNLAD                                                                    7

SEQ ID NO: 637              moltype = AA   length = 7
FEATURE                     Location/Qualifiers
source                      1..7
                            mol_type = protein
                            organism = synthetic construct
SEQUENCE: 637
GYTFTNY                                                                    7

SEQ ID NO: 638              moltype = AA   length = 5
FEATURE                     Location/Qualifiers
```

```
source                  1..5
                        mol_type = protein
                        organism = synthetic construct
SEQUENCE: 638
TRAMH                                                                       5

SEQ ID NO: 639          moltype = AA   length = 7
FEATURE                 Location/Qualifiers
source                  1..7
                        mol_type = protein
                        organism = synthetic construct
SEQUENCE: 639
SENIYNN                                                                     7

SEQ ID NO: 640          moltype = AA   length = 6
FEATURE                 Location/Qualifiers
source                  1..6
                        mol_type = protein
                        organism = synthetic construct
SEQUENCE: 640
FWGTPL                                                                      6

SEQ ID NO: 641          moltype = AA   length = 116
FEATURE                 Location/Qualifiers
source                  1..116
                        mol_type = protein
                        organism = synthetic construct
SEQUENCE: 641
QVQLQQPGAE LVKPGASVKL SCKASGYTFT NYWMHWVKQR PGQGLEWIGE INPINGRSNY           60
GERFKTKATL TVDKSSSTAY MQLSSLTSED SAVYYCARGT RAMHYWGQGT SVTVSS              116

SEQ ID NO: 642          moltype = AA   length = 107
FEATURE                 Location/Qualifiers
source                  1..107
                        mol_type = protein
                        organism = synthetic construct
SEQUENCE: 642
DIQMTQSPAS LSVSVGETVT ITCRTSENIY NNLAWYQQKQ GKSPQLLVYA ATNLADGVPS           60
RFSGSGSGTQ YSLKINSLQS EDFGNYYCQH FWGTPLTFGA GTKLELK                       107

SEQ ID NO: 643          moltype = AA   length = 10
FEATURE                 Location/Qualifiers
source                  1..10
                        mol_type = protein
                        organism = synthetic construct
SEQUENCE: 643
GFTFSNYGMH                                                                 10

SEQ ID NO: 644          moltype = AA   length = 17
FEATURE                 Location/Qualifiers
source                  1..17
                        mol_type = protein
                        organism = synthetic construct
SEQUENCE: 644
MIYYDSSKMN YADTVKG                                                         17

SEQ ID NO: 645          moltype = AA   length = 9
FEATURE                 Location/Qualifiers
source                  1..9
                        mol_type = protein
                        organism = synthetic construct
SEQUENCE: 645
PTSHYVVDV                                                                   9

SEQ ID NO: 646          moltype = AA   length = 11
FEATURE                 Location/Qualifiers
source                  1..11
                        mol_type = protein
                        organism = synthetic construct
SEQUENCE: 646
QASQDIGNWL A                                                               11

SEQ ID NO: 647          moltype = AA   length = 7
FEATURE                 Location/Qualifiers
source                  1..7
                        mol_type = protein
                        organism = synthetic construct
SEQUENCE: 647
GATSLAD                                                                     7
```

```
SEQ ID NO: 648            moltype = AA   length = 9
FEATURE                   Location/Qualifiers
source                    1..9
                          mol_type = protein
                          organism = synthetic construct
SEQUENCE: 648
LQAYNTPWT                                                              9

SEQ ID NO: 649            moltype = AA   length = 117
FEATURE                   Location/Qualifiers
source                    1..117
                          mol_type = protein
                          organism = synthetic construct
SEQUENCE: 649
EVQLVWSGGG LVQPQNSLTL SCVASGFTFS NYGMHWRQAP KKGLEWIAMI YYDSSKMNYA      60
DTVKGRFTIS RDNSKNTLYL EMNSLRSEDT AMYYCAVPTS HYVVDVWGQG VSVTVSS        117

SEQ ID NO: 650            moltype = AA   length = 108
FEATURE                   Location/Qualifiers
source                    1..108
                          mol_type = protein
                          organism = synthetic construct
SEQUENCE: 650
DIQMTQSPAS LSASLEEIVT ITCQASQDIG NWLAWYQQKP GKSPQLLIYG ATSLADGVPS      60
RFSGSRSGTQ FSLKISRVQV EDIGIYYCLQ AYNTPWTFGG GTKLELKR                  108

SEQ ID NO: 651            moltype = AA   length = 60
FEATURE                   Location/Qualifiers
source                    1..60
                          mol_type = protein
                          organism = Mus musculus
SEQUENCE: 651
MEFGLSWLFL VAILKGVQCE VQLQQSGTVL ARPGASVKMS CKASGYSFTI YWIHWVKQRP      60

SEQ ID NO: 652            moltype = AA   length = 130
FEATURE                   Location/Qualifiers
source                    1..130
                          mol_type = protein
                          organism = Mus musculus
SEQUENCE: 652
MDMRVPAQLL GLLLLWLPGA RCDVQITQSP SYLAASPGET IIINCRASKS ISKYLAWYQE      60
KPGKTNKLLI YSGSTLQSGI PSRFSGSGSG TDFTLTISSL EPQDFAMYYC QQHNEYPWTF     120
GGGTKLEIKR                                                            130

SEQ ID NO: 653            moltype = RNA   length = 19
FEATURE                   Location/Qualifiers
source                    1..19
                          mol_type = other RNA
                          organism = synthetic construct
modified_base             3
                          mod_base = OTHER
                          note = may be thymine
modified_base             5
                          mod_base = OTHER
                          note = may be thymine
modified_base             14
                          mod_base = OTHER
                          note = may be thymine
SEQUENCE: 653
ggtctaggcc cggtgagag                                                   19

SEQ ID NO: 654            moltype = RNA   length = 19
FEATURE                   Location/Qualifiers
source                    1..19
                          mol_type = other RNA
                          organism = synthetic construct
modified_base             3
                          mod_base = OTHER
                          note = may be thymine
modified_base             7..8
                          mod_base = OTHER
                          note = may be thymine
modified_base             13..14
                          mod_base = OTHER
                          note = may be thymine
modified_base             18
                          mod_base = OTHER
                          note = may be thymine
```

```
                                      -continued
SEQUENCE: 654
cctggattag agttacatc                                               19

SEQ ID NO: 655        moltype = DNA  length = 25
FEATURE               Location/Qualifiers
source                1..25
                      mol_type = other DNA
                      organism = synthetic construct
SEQUENCE: 655
cttctaggtc taggcccggt gagag                                        25

SEQ ID NO: 656        moltype = RNA  length = 25
FEATURE               Location/Qualifiers
source                1..25
                      mol_type = other RNA
                      organism = synthetic construct
modified_base         2
                      mod_base = OTHER
                      note = may be thymine
modified_base         4
                      mod_base = OTHER
                      note = may be thymine
modified_base         14
                      mod_base = OTHER
                      note = may be thymine
modified_base         20
                      mod_base = OTHER
                      note = may be thymine
SEQUENCE: 656
ctctcaccgg gcctagacct agaag                                        25

SEQ ID NO: 657        moltype = RNA  length = 35
FEATURE               Location/Qualifiers
source                1..35
                      mol_type = other RNA
                      organism = synthetic construct
modified_base         14
                      mod_base = OTHER
                      note = may be thymine
modified_base         18
                      mod_base = OTHER
                      note = may be thymine
modified_base         22
                      mod_base = OTHER
                      note = may be thymine
modified_base         34
                      mod_base = OTHER
                      note = may be thymine
SEQUENCE: 657
cgcggggaac acctggctgg ctacggaggg gcgtg                             35

SEQ ID NO: 658        moltype = RNA  length = 35
FEATURE               Location/Qualifiers
source                1..35
                      mol_type = other RNA
                      organism = synthetic construct
modified_base         4..5
                      mod_base = OTHER
                      note = may be thymine
modified_base         7
                      mod_base = OTHER
                      note = may be thymine
modified_base         11
                      mod_base = OTHER
                      note = may be thymine
modified_base         13
                      mod_base = OTHER
                      note = may be thymine
modified_base         22
                      mod_base = OTHER
                      note = may be thymine
modified_base         30
                      mod_base = OTHER
                      note = may be thymine
SEQUENCE: 658
gccttctagg tctaggcccg gtgagagact ccaca                             35

SEQ ID NO: 659        moltype = DNA  length = 38
FEATURE               Location/Qualifiers
```

```
source                  1..38
                        mol_type = other DNA
                        organism = synthetic construct
SEQUENCE: 659
gctccacgcc ctctgcaagg gacctgttgc tcgcgtgt                                38

SEQ ID NO: 660          moltype = DNA  length = 40
FEATURE                 Location/Qualifiers
source                  1..40
                        mol_type = other DNA
                        organism = synthetic construct
SEQUENCE: 660
ctgggattcc tgccttctag gtctaggccc ggtgagagac                              40

SEQ ID NO: 661          moltype = DNA  length = 60
FEATURE                 Location/Qualifiers
source                  1..60
                        mol_type = other DNA
                        organism = synthetic construct
SEQUENCE: 661
cgggttccac gctccttcgc cctctgcaag gggacctgtt gctcgcgtgt ctcccgcccc        60

SEQ ID NO: 662          moltype = DNA  length = 60
FEATURE                 Location/Qualifiers
source                  1..60
                        mol_type = other DNA
                        organism = synthetic construct
SEQUENCE: 662
agtcaagaca gcggcttcca gtttccatag aattactgga gaacctcaga gagccagccc       60

SEQ ID NO: 663          moltype = DNA  length = 59
FEATURE                 Location/Qualifiers
source                  1..59
                        mol_type = other DNA
                        organism = synthetic construct
SEQUENCE: 663
gctgaccggc ctgggattcc tgccactagg tctaggcccg gtgagagact ccacaccgc        59

SEQ ID NO: 664          moltype = DNA  length = 3635
FEATURE                 Location/Qualifiers
source                  1..3635
                        mol_type = genomic DNA
                        organism = Homo sapiens
SEQUENCE: 664
tcctggcggc tgcgaggttt cactgcaggg gcgccagtgg gctcagtgac gctgcggcct       60
ccttctgcct aggtcccaac gcttcggggc agggtgcgg tcttgcaata ggaagccgag       120
cgtcttgcaa gcttcccgtc gggcaccagc tactcggccc cgcaccctac ctggtgcatt      180
ccctagacac ctccggggtc cctacctgga gatccccgga gccccccttc ctgcgccagc      240
catgccttta aaccgcactt tgtccatgtc ctcactgcca ggactggagg actgggagga      300
tgaattcgac ctggagaacg cagtgctctt cgaagtggcc tgggaggtgg ctaacaaggt      360
gggtggcatc tacacggttgc tgcagacgaa ggcgaaggtg acaggggacg aatggggcga     420
caactacttc ctggtggggc cgtacacgga gcagggcgtg aggacccagg tggaactgct      480
ggaggccccc acccccggccc tgaagaggac actggattcc atgaacagca agggctgcaa     540
ggtgtatttc gggcgctggc tgatcgaggg aggccctctg tggtgctcc tggacgtggg       600
tgcctcagct tgggccctgg agcgctggaa gggagagctt tgggatacct gcaacatcgg      660
agtgccgtgg tacgaccgcg aggccaacga cgctgtcctc tttggctttc tgaccacctg      720
gttcctgggt gagttcctgg cacagagtga ggagaagcca catgtggttg ctcacttcca      780
tgagtggttg gcaggcgttg gactctgcct gtgtcgtgcc cggcgactgc ctgtagcaac      840
catcttcacc acccatgcca cgctgctggg gcgctacctg tgtgccggtg ccgtggactt      900
ctacaacaac ctggagaact tcaacgtgga caaggaagca ggggagaggc agatactacca     960
ccgatactgc atgaaagggg cggcagccca ctgcgctcac gtcttcacta ctgtgtccca    1020
gatcaccgcc atcgaggcac agcacttgct caagaggaaa ccagatattg tgaccccaa     1080
tgggctgaat gtgaagaagt tttctgccat gcatgagttc cagaacctcc atgctcagag    1140
caaggctcga atccaggagt ttgtgcgggg ccattttat gggcatctgg acttcaactt     1200
ggacaagacc ttatacttct ttatcgccgg ccgctatgag ttctccaaca agggtgctga    1260
cgtcttcctg gaggcattgg ctcggctcaa ctatctgctc agagtgaacg gcagcgagca    1320
gacagtggtt gccttcttca tcatgccagc gcggaccaac aatttcaacg tggaaaccct    1380
caaaggccaa gctgtgcgca aacagctttg ggacacggcc aacacggtga aggaaaagtt    1440
cgggaggaag ctttatgaat ccttactggt tgggagcctt cccgacatga acaagatgct    1500
ggataaggaa gacttcacta tgatgaagag agccatcttt gcaacgcagc ggcagtcttt    1560
cccccctgtg tgcacccaca atatgctgga tgactcctca gacccatcc tgaccatcat     1620
ccgccgaatc ggcctcttca atagcagtgc cgacaggggt aaggtgattt ccacccggga   1680
gttcctctcc tccacaagcc cctgctccc tgtggactat gaggagttgg tccgtggctg    1740
tcaccttgga tcttccccct cctactatga gccttgggc tacacaccgg tcagtgcac     1800
ggttatggga atccccagta tctccaccaa tctctccggc ttcggctgct catggaggga    1860
acacatcgca gaccctcag cttacggtat tacattctt gaccggcggt tccgcagcct     1920
ggatgattcc tgctcgcagc tcacctcctt cctctacagt ttctgtcagc agagccggcg    1980
gcagcgtatc atccagcgga accgcacgga gcgcctctcc gaccttctgg actggaaata   2040
cctaggccgg tactatatgt ctgcgcgcca catggcgctg tccaaggcct ttccagagca    2100
```

-continued

```
cttcacctac gagcccaacg aggcggatgc ggcccagggg taccgctacc cacggccagc   2160
ctcggtgcca ccgtcgccct cgctgtcacg acactccagc ccgcaccaga gtgaggacga   2220
ggaggatccc cggaacgggc cgctggagga agacggcgag cgctacgatg aggacgagga   2280
ggccgccaag gaccggcgca acatccgtgc accagagtgg ccgcgccgag cgtcctgcac   2340
ctcctccacc agccggcagca agcgcaactc tgttggacacg gccacctcca gctcactcag   2400
caccccgagc gagcccctca gcccaccag ctccctgggc gaggagcgta actaagtccg   2460
ccccaccaca ctccccgcct gtcctgcctc tctgctccag agagaggatg cagagggtg   2520
ctgctcctaa accccgctc cagatctgca ctgggtgtgg ccccgcagtg cccccaccca   2580
gtccgccaaa cactccaccc cctccagctc cagtttccaa gttcctgcac tccagaatcc   2640
acaaagccgt gcctttctct ggctccagaa tatgcataat cagcgccctg gagtcccctg   2700
ggcctggacc gcttcccaga ggccaggaat ctgccattac tctgcggtgg tgccagaggt   2760
tttaggaaac ctggcatggt gctttcaggt ctggggcttt tagagccccc cgtgtggctt   2820
acaaattcta cagcatacag agcaggccac gctcaggccc ggcatgcggg ccaccaagtt   2880
ctggaaacca cgtggtgtcc ctgcgaatgg ggcgatcaag tccagagccg gggcacttc   2940
agagtttgaa ggtaactgag agcagatggt cctccatttc aactccagaa gtggggctct   3000
gggagggatg ttctagccct ccctggcatg tcagagccag gctctgcctg gaggatccct   3060
ccatccggct cctgtcatcc cctacacttt ggccaagcaa gaggtggtag aaccacttgg   3120
ctgctcattc cttctggagg acacacagtc tcagtccaga tgccttcctg tcttctggc   3180
cctttctgga ccagatccta ctcttccttt ctaaatctga gatctccctc cagggaatcc   3240
gcctgcagag gacagagctg gctgtcttcc cccacccta acctggctta ttcccaactg   3300
ctctgcccac tgtgaaacca ctaggttcta ggtcctggct tctagatctg gaaccttacc   3360
acgttactgc atactgatcc cttttcccatg atccagaact gaggtcactg ggttctagaa   3420
cccccacatt tacctcgagg ctcttccatc cccaaactgt gccctgcctt cagctttggt   3480
gaaagggagg gccctcatg tgtgctgtgc tgtgtctgca ccgcttggtt tgcagttgag   3540
aggggagggc aggaggggtg tgattggagt gtgtccggag atgagatgaa aaaaatacat   3600
ctatatttaa gaatcccaaa aaaaaaaaaa aaaaa                              3635
```

SEQ ID NO: 665          moltype = DNA   length = 3681
FEATURE                 Location/Qualifiers
source                  1..3681
                        mol_type = genomic DNA
                        organism = Mus musculus

SEQUENCE: 665

```
actgcagctg cccgcccgat tcagtgtctc agctcaccct acctgagtcg gagcgctctg   60
gggcggggt gcggtcgtgc aataggaagc ggagcgcctt gcaagcttcc cctgggacac   120
ccgctaactc taccggtcac caagtctgct gcgttcccag ccgatctctc tggttttcag   180
ttttggtgct cgaagtcccc tgcccgcagt agccatgcct ctcagccgca gtctctctgt   240
gtcctcgctt ccaggattgg aagactggga ggatgaattc gaccccgaga acgcagtgct   300
tttcggggtg gcctgggagg tggccaacaa ggtgggtggc atctacactg tgctgcagaa   360
gaaggcgaag gtgacagggg atgaatgggg tgacaactac tatctggtgg gaccatacac   420
ggagcagggt gtgaggacgc aggtagagct cctggagccc ccaactccgg aactgaagag   480
gactttggat tccatgaaca gcaagggttg taaggtgtat tttgggcgtt ggctgatcga   540
ggggggaccc ctagtggtgc tcctggatgt aggagcctca gcttgggccc tggagcgctg   600
gaagggtgag cttgggacca cctgcaacat cggggtaccc tggtacgacc gcgaggccaa   660
tgacgctgtc ctgttcggct tcctcaccac ctggttcctg ggtgagttcc tggcccagaa   720
cgaagagaag ccgtatgtgg ttgcccactt ccacgaatgg ttggctggcg ttggtctgtg   780
tctgtgccgt gcccggcgct tgccggtggc aaccatcttc accactcatg ccacgtctgc   840
ggggcgctac ctgtgtgctg cgcgtgtgga cttctacaac aacctggaga atttcaatgt   900
agacaaggaa gcaggagaga ggcagatcta tcaccggtac tgcatggagc gtgcagcagc   960
tcactgtgcc catgtcttca ctaccgtatc ccagatcacc gcaatcgagg ctcaacacct   1020
ccttaagaga aaaccagata ttgtgacccc caacgtgctg aatgtgaaga agtctctgc   1080
tatgcacgaa ttccagaacc ttcatgctca gagcaaagca cgaatccagg aatttgtgcc   1140
tggccatttt tatgggcacc tggacttcaa cctagacaag actttgtatt tctttatcgc   1200
tggccgctat gagttttcca acaagggagc tgatgtgttc ctggaggcat ggcccggct   1260
caactatctg ctcagagtga atggcagtga gcaaaagctt gtcgcattct tcatcatgcc   1320
ggcccggacc aataatttca acgtggaaac cctgaagggc caagccgtgc gcaaacaact   1380
atgggacaca gccaatacag tcaaggagaa atttgggagg aagctctacg aatccctttt   1440
agtggggagc ctcccggaca tgaacaagat gctggacaag gaggacttca ctatgatgaa   1500
gagagccatc tttgccactc agcggcagtc ttttcccacca gtgtgcaccc acaacatgct   1560
ggacgactcc tcagacccca tcttgaccac catccgccga attggcctt tcaacagcag   1620
tgccgaccgt gtgaaggtga ttttttcaccc agaattcctt tcttcacaa gccctctcct   1680
ccccgtggat tatgaggaat ttgttccgcg ctgtcacctt ggggtcttcc cctcctacta   1740
tgagccctgg ggctacacac cagcggagtg cactgtcatg gcatcccca gcatctccac   1800
caacctctcc ggcctttggct gctttatgga ggaacacatc gcagatccct cagcttacgg   1860
catttacatt ctggatcgga ggttccgcag cctggatgat tcatgctcac agctcacctc   1920
cttcctgtac agcttctgcc agcagagccg gcgacagcgc atcatccagc ggaaccgcac   1980
agaacggttc tcgacttgc tagattgaa gtacctgggc cggtactaca tgtctgcgcg   2040
ccacatggct ctggccaagg cctttccaga ccacttcacc tatgaacccc atgaggtaga   2100
tgcgacccag gggtaccgt acccacgacc agcctccgtc ccgccgtcgc cctcactgtc   2160
tcgacactcc agcccacacc agagtgagga tgaggaagag ccacgggatg gacccctggg   2220
ggaagacagt gagcgttatg atgaggaaga ggaggctgcc aaggaccgcc gcaacatccg   2280
ggcacctgag tggccacgca gggctcctg ttcctcctcc acaggtggca gcaagagaag   2340
caactcggtg gacactgggc cctccagctc actcagcaca cccactgagc ccctgagtcc   2400
taccagttcc ctgggtgagg agcgcaacta agctcccacc tcagatcccat tccctgcctg   2460
tccagtgctc ctctcgcaga gggcctatgc agatgggagg gtgcctgaac ccactccag   2520
actcttgagt gggaccccta cccagtgtgg tccatagcct aacctctgtt tcagacactc   2580
cagcccttga gctccaatct tggagttccc gcactcacg ccgccgtgcc tttcttggat   2640
tgcaggatgc attctttgtg cactgatctg gagtctccag gcttagactg ggtcccgag   2700
gccaggcatc tgccattgtt tttcaatgcc agaggtttta ggacactgg tttattggct   2760
```

-continued

```
tccaggctgt ggcttcttcg tttgatccta taatcataca gagtatgctt tgctcaggcc  2820
tgcctctggg accacctcat gttgattct gtgtggcttc ccgaatcagc caagttcaga   2880
gttaggacat ttcagggatt aacataattg aaaatcagcc tgcaaggtag ctcagtagct  2940
ctgtcgacag attgcttgtc tagcatgccc gaagccctgg gatctaactc tagaacctca  3000
taaacctggt gcggtgatac acatctgtaa tcccagcact cggtaggtag aggtagacgg  3060
atcaagagtt aaaggccatc atcctctgct acatagggag ttcaaggcca aactgggcaa  3120
catgagacac tgtctcaaaa gcaaagtaaa ggtggtggaa tgctcacggt cctccatttc  3180
aacccacgac tgcgatgctg ggacatgctg caaggttggc ctccctgggt gtgttcttca  3240
aaggagcatg cggagttgga ccagacacct ttctgccttt tttctggacc agacccttctt 3300
ttccttggtc cagtgtcccc tctagggaat gcctccattg agggcagaat gtctgtcaac  3360
cccacaagtg ctcagcccac tgtgaaacca ctgggttctg ggtcccagtg gctgaatcag  3420
gagtcttttg tcactgtgct gcaccccggt cccctttcct gatacaaaac cgagcccacc  3480
ggcttcttga agccccacat gtacctgag gcctttctgc ctgcaagctt cagtgaatgg   3540
gcgggcccct cctcacgtgt gctgtgtctg gcccagtgcc tttggtttgc atttgggagg  3600
gggagggcag aaggtgtgtg attggagtgt gtctagagat gaaaaaaaaa aaagaaaat   3660
acacctgtat ttaagaatgc c                                            3681

SEQ ID NO: 666        moltype = RNA   length = 19
FEATURE               Location/Qualifiers
source                1..19
                      mol_type = other RNA
                      organism = synthetic construct
SEQUENCE: 666
cttcctggat ggcttcaat                                                19

SEQ ID NO: 667        moltype = RNA   length = 19
FEATURE               Location/Qualifiers
source                1..19
                      mol_type = other RNA
                      organism = synthetic construct
SEQUENCE: 667
gtacattaag atggacttc                                                19

SEQ ID NO: 668        moltype = RNA   length = 30
FEATURE               Location/Qualifiers
source                1..30
                      mol_type = other RNA
                      organism = synthetic construct
SEQUENCE: 668
tatctggata ggtggtatca agatctgtaa                                    30

SEQ ID NO: 669        moltype = RNA   length = 25
FEATURE               Location/Qualifiers
source                1..25
                      mol_type = other RNA
                      organism = synthetic construct
SEQUENCE: 669
atgtaactga aaatgttctt cttta                                         25

SEQ ID NO: 670        moltype = RNA   length = 30
FEATURE               Location/Qualifiers
source                1..30
                      mol_type = other RNA
                      organism = synthetic construct
SEQUENCE: 670
tggataggtg gtatcaacat ctgtaagcac                                    30

SEQ ID NO: 671        moltype = RNA   length = 22
FEATURE               Location/Qualifiers
source                1..22
                      mol_type = other RNA
                      organism = synthetic construct
SEQUENCE: 671
gataggtggt atcaacatct gt                                            22

SEQ ID NO: 672        moltype = RNA   length = 30
FEATURE               Location/Qualifiers
source                1..30
                      mol_type = other RNA
                      organism = synthetic construct
SEQUENCE: 672
tatctggata ggtggtatca acatctgtaa                                    30

SEQ ID NO: 673        moltype = RNA   length = 25
FEATURE               Location/Qualifiers
source                1..25
                      mol_type = other RNA
                      organism = synthetic construct
SEQUENCE: 673
```
aaacttggaa gagtgatgtg atgta                                              25

SEQ ID NO: 674         moltype = RNA   length = 27
FEATURE                Location/Qualifiers
source                 1..27
                       mol_type = other RNA
                       organism = synthetic construct
SEQUENCE: 674
gctcacttgt tgaggcaaaa cttggaa                                            27

SEQ ID NO: 675         moltype = RNA   length = 25
FEATURE                Location/Qualifiers
source                 1..25
                       mol_type = other RNA
                       organism = synthetic construct
SEQUENCE: 675
gccttggcaa catttccact tcctg                                              25

SEQ ID NO: 676         moltype = RNA   length = 25
FEATURE                Location/Qualifiers
source                 1..25
                       mol_type = other RNA
                       organism = synthetic construct
SEQUENCE: 676
tacacacttt acctgttgag aatag                                              25

SEQ ID NO: 677         moltype = RNA   length = 24
FEATURE                Location/Qualifiers
source                 1..24
                       mol_type = other RNA
                       organism = synthetic construct
SEQUENCE: 677
gataggtggt atcaacatct gtaa                                               24

SEQ ID NO: 678         moltype = RNA   length = 21
FEATURE                Location/Qualifiers
source                 1..21
                       mol_type = other RNA
                       organism = synthetic construct
SEQUENCE: 678
gataggtggt atcaacatct g                                                  21

SEQ ID NO: 679         moltype = RNA   length = 25
FEATURE                Location/Qualifiers
source                 1..25
                       mol_type = other RNA
                       organism = synthetic construct
SEQUENCE: 679
gataggtggt atcaacatct gtaag                                              25

SEQ ID NO: 680         moltype = RNA   length = 20
FEATURE                Location/Qualifiers
source                 1..20
                       mol_type = other RNA
                       organism = synthetic construct
SEQUENCE: 680
ggtggtatca acatctgtaa                                                    20

SEQ ID NO: 681         moltype = RNA   length = 20
FEATURE                Location/Qualifiers
source                 1..20
                       mol_type = other RNA
                       organism = synthetic construct
SEQUENCE: 681
gtatcaacat ctgtaagcac                                                    20

SEQ ID NO: 682         moltype = RNA   length = 30
FEATURE                Location/Qualifiers
source                 1..30
                       mol_type = other RNA
                       organism = synthetic construct
misc_difference        27
                       note = n can be any nucleotide
SEQUENCE: 682
cggctaattt cagagggcgc tttcttngac                                         30

SEQ ID NO: 683         moltype = RNA   length = 26
FEATURE                Location/Qualifiers
source                 1..26

```
SEQUENCE: 683
acagtggtgc tgagatagta taggcc                                        26

SEQ ID NO: 684         moltype = RNA   length = 22
FEATURE                Location/Qualifiers
source                 1..22
                       mol_type = other RNA
                       organism = synthetic construct
SEQUENCE: 684
taggccactt tgttgctctt gc                                            22

SEQ ID NO: 685         moltype = RNA   length = 19
FEATURE                Location/Qualifiers
source                 1..19
                       mol_type = other RNA
                       organism = synthetic construct
SEQUENCE: 685
ttcagagggc gctttcttc                                                19

SEQ ID NO: 686         moltype = RNA   length = 30
FEATURE                Location/Qualifiers
source                 1..30
                       mol_type = other RNA
                       organism = synthetic construct
SEQUENCE: 686
tcttcaggtg caccttctgt ttctcaatct                                    30

SEQ ID NO: 687         moltype = RNA   length = 30
FEATURE                Location/Qualifiers
source                 1..30
                       mol_type = other RNA
                       organism = synthetic construct
SEQUENCE: 687
tctgtgatac tcttcaggtg caccttctgt                                    30

SEQ ID NO: 688         moltype = RNA   length = 21
FEATURE                Location/Qualifiers
source                 1..21
                       mol_type = other RNA
                       organism = synthetic construct
SEQUENCE: 688
tcttctgctc gggaggtgac a                                             21

SEQ ID NO: 689         moltype = RNA   length = 20
FEATURE                Location/Qualifiers
source                 1..20
                       mol_type = other RNA
                       organism = synthetic construct
SEQUENCE: 689
ccagttacta ttcagaagac                                               20

SEQ ID NO: 690         moltype = RNA   length = 20
FEATURE                Location/Qualifiers
source                 1..20
                       mol_type = other RNA
                       organism = synthetic construct
SEQUENCE: 690
tcttcaggtg caccttctgt                                               20

SEQ ID NO: 691         moltype = RNA   length = 18
FEATURE                Location/Qualifiers
source                 1..18
                       mol_type = other RNA
                       organism = synthetic construct
SEQUENCE: 691
tgctgctgtc ttcttgct                                                 18

SEQ ID NO: 692         moltype = RNA   length = 19
FEATURE                Location/Qualifiers
source                 1..19
                       mol_type = other RNA
                       organism = synthetic construct
SEQUENCE: 692
ttgttaactt tttcccatt                                                19

SEQ ID NO: 693         moltype = RNA   length = 20
FEATURE                Location/Qualifiers
```

```
source                  1..20
                        mol_type = other RNA
                        organism = synthetic construct
SEQUENCE: 693
tgttaacttt ttcccattgg                                                     20

SEQ ID NO: 694          moltype = RNA   length = 20
FEATURE                 Location/Qualifiers
source                  1..20
                        mol_type = other RNA
                        organism = synthetic construct
SEQUENCE: 694
cattttgtta actttttccc                                                     20

SEQ ID NO: 695          moltype = RNA   length = 19
FEATURE                 Location/Qualifiers
source                  1..19
                        mol_type = other RNA
                        organism = synthetic construct
SEQUENCE: 695
ctgtagcttc acccttttcc                                                     19

SEQ ID NO: 696          moltype = RNA   length = 26
FEATURE                 Location/Qualifiers
source                  1..26
                        mol_type = other RNA
                        organism = synthetic construct
SEQUENCE: 696
gagagcttcc tgtagcttca cccttt                                              26

SEQ ID NO: 697          moltype = RNA   length = 28
FEATURE                 Location/Qualifiers
source                  1..28
                        mol_type = other RNA
                        organism = synthetic construct
SEQUENCE: 697
tcctgtagct tcacccttcc cacaggcg                                            28

SEQ ID NO: 698          moltype = RNA   length = 20
FEATURE                 Location/Qualifiers
source                  1..20
                        mol_type = other RNA
                        organism = synthetic construct
SEQUENCE: 698
tgtgttacct acccttgtcg                                                     20

SEQ ID NO: 699          moltype = RNA   length = 27
FEATURE                 Location/Qualifiers
source                  1..27
                        mol_type = other RNA
                        organism = synthetic construct
SEQUENCE: 699
tagactatct tttatattct gtaatat                                             27

SEQ ID NO: 700          moltype = RNA   length = 29
FEATURE                 Location/Qualifiers
source                  1..29
                        mol_type = other RNA
                        organism = synthetic construct
SEQUENCE: 700
gagagcttcc tgtagcttca cccttttcca                                          29

SEQ ID NO: 701          moltype = RNA   length = 31
FEATURE                 Location/Qualifiers
source                  1..31
                        mol_type = other RNA
                        organism = synthetic construct
SEQUENCE: 701
ttcctgtagc ttcacccttt ccacaggcgt t                                        31

SEQ ID NO: 702          moltype = RNA   length = 23
FEATURE                 Location/Qualifiers
source                  1..23
                        mol_type = other RNA
                        organism = synthetic construct
SEQUENCE: 702
agcttcctgt agcttcaccc ttt                                                 23

SEQ ID NO: 703          moltype = RNA   length = 29
```

```
FEATURE                 Location/Qualifiers
source                  1..29
                        mol_type = other RNA
                        organism = synthetic construct
SEQUENCE: 703
ggagagagct tcctgtagct tcacccttt                                        29

SEQ ID NO: 704          moltype = RNA   length = 23
FEATURE                 Location/Qualifiers
source                  1..23
                        mol_type = other RNA
                        organism = synthetic construct
SEQUENCE: 704
gagagcttcc tgtagcttca ccc                                              23

SEQ ID NO: 705          moltype = RNA   length = 25
FEATURE                 Location/Qualifiers
source                  1..25
                        mol_type = other RNA
                        organism = synthetic construct
SEQUENCE: 705
tatgtgttac ctaccttgt cggtc                                             25

SEQ ID NO: 706          moltype = RNA   length = 20
FEATURE                 Location/Qualifiers
source                  1..20
                        mol_type = other RNA
                        organism = synthetic construct
SEQUENCE: 706
ggagagagct tcctgtagct                                                  20

SEQ ID NO: 707          moltype = RNA   length = 23
FEATURE                 Location/Qualifiers
source                  1..23
                        mol_type = other RNA
                        organism = synthetic construct
SEQUENCE: 707
tcacccttc cacaggcgtt gca                                               23

SEQ ID NO: 708          moltype = RNA   length = 28
FEATURE                 Location/Qualifiers
source                  1..28
                        mol_type = other RNA
                        organism = synthetic construct
SEQUENCE: 708
gctgggagag agcttcctgt agcttcac                                         28

SEQ ID NO: 709          moltype = RNA   length = 28
FEATURE                 Location/Qualifiers
source                  1..28
                        mol_type = other RNA
                        organism = synthetic construct
SEQUENCE: 709
tgttacctac ccttgtcggt ccttgtac                                         28

SEQ ID NO: 710          moltype = RNA   length = 28
FEATURE                 Location/Qualifiers
source                  1..28
                        mol_type = other RNA
                        organism = synthetic construct
SEQUENCE: 710
ctgctgtctt cttgctatga ataatgtc                                         28

SEQ ID NO: 711          moltype = RNA   length = 28
FEATURE                 Location/Qualifiers
source                  1..28
                        mol_type = other RNA
                        organism = synthetic construct
SEQUENCE: 711
ggcgttgcac tttgcaatgc tgctgtct                                         28

SEQ ID NO: 712          moltype = RNA   length = 28
FEATURE                 Location/Qualifiers
source                  1..28
                        mol_type = other RNA
                        organism = synthetic construct
SEQUENCE: 712
ttggaaatca agctgggaga gagcttcc                                         28
```

```
SEQ ID NO: 713          moltype = RNA   length = 28
FEATURE                 Location/Qualifiers
source                  1..28
                        mol_type = other RNA
                        organism = synthetic construct
SEQUENCE: 713
ctaccettgt cggtccttgt acattttg                                              28

SEQ ID NO: 714          moltype = RNA   length = 28
FEATURE                 Location/Qualifiers
source                  1..28
                        mol_type = other RNA
                        organism = synthetic construct
SEQUENCE: 714
gtcaatccga cctgagcttt gttgtaga                                              28

SEQ ID NO: 715          moltype = RNA   length = 27
FEATURE                 Location/Qualifiers
source                  1..27
                        mol_type = other RNA
                        organism = synthetic construct
SEQUENCE: 715
cttgctatga ataatgtcaa tccgacc                                               27

SEQ ID NO: 716          moltype = RNA   length = 28
FEATURE                 Location/Qualifiers
source                  1..28
                        mol_type = other RNA
                        organism = synthetic construct
SEQUENCE: 716
tatatgtgtt acctaccctt gtcggtcc                                              28

SEQ ID NO: 717          moltype = RNA   length = 20
FEATURE                 Location/Qualifiers
source                  1..20
                        mol_type = other RNA
                        organism = synthetic construct
SEQUENCE: 717
tttgtgtctt tctgagaaac                                                       20

SEQ ID NO: 718          moltype = RNA   length = 20
FEATURE                 Location/Qualifiers
source                  1..20
                        mol_type = other RNA
                        organism = synthetic construct
SEQUENCE: 718
aaagacttac cttaagatac                                                       20

SEQ ID NO: 719          moltype = RNA   length = 20
FEATURE                 Location/Qualifiers
source                  1..20
                        mol_type = other RNA
                        organism = synthetic construct
SEQUENCE: 719
atctgtcaaa tcgcctgcag                                                       20

SEQ ID NO: 720          moltype = RNA   length = 19
FEATURE                 Location/Qualifiers
source                  1..19
                        mol_type = other RNA
                        organism = synthetic construct
SEQUENCE: 720
cgccgccatt tctcaacag                                                        19

SEQ ID NO: 721          moltype = RNA   length = 20
FEATURE                 Location/Qualifiers
source                  1..20
                        mol_type = other RNA
                        organism = synthetic construct
SEQUENCE: 721
tttgtattta gcatgttccc                                                       20

SEQ ID NO: 722          moltype = RNA   length = 17
FEATURE                 Location/Qualifiers
source                  1..17
                        mol_type = other RNA
                        organism = synthetic construct
SEQUENCE: 722
ccgccatttc tcaacag                                                          17
```

```
SEQ ID NO: 723          moltype = RNA   length = 21
FEATURE                 Location/Qualifiers
source                  1..21
                        mol_type = other RNA
                        organism = synthetic construct
SEQUENCE: 723
ttctcaggaa tttgtgtctt t                                                   21

SEQ ID NO: 724          moltype = RNA   length = 11
FEATURE                 Location/Qualifiers
source                  1..11
                        mol_type = other RNA
                        organism = synthetic construct
SEQUENCE: 724
gacaactctt t                                                              11

SEQ ID NO: 725          moltype = RNA   length = 20
FEATURE                 Location/Qualifiers
source                  1..20
                        mol_type = other RNA
                        organism = synthetic construct
SEQUENCE: 725
tcagcttctg ttagccactg                                                     20

SEQ ID NO: 726          moltype = RNA   length = 24
FEATURE                 Location/Qualifiers
source                  1..24
                        mol_type = other RNA
                        organism = synthetic construct
SEQUENCE: 726
tgttcagctt ctgttagcca ctga                                                24

SEQ ID NO: 727          moltype = RNA   length = 27
FEATURE                 Location/Qualifiers
source                  1..27
                        mol_type = other RNA
                        organism = synthetic construct
SEQUENCE: 727
ctgttcagct tctgttagcc actgatt                                             27

SEQ ID NO: 728          moltype = RNA   length = 30
FEATURE                 Location/Qualifiers
source                  1..30
                        mol_type = other RNA
                        organism = synthetic construct
SEQUENCE: 728
ttctcaacag atctgtcaaa tcgcctgcag                                          30

SEQ ID NO: 729          moltype = RNA   length = 25
FEATURE                 Location/Qualifiers
source                  1..25
                        mol_type = other RNA
                        organism = synthetic construct
SEQUENCE: 729
gccactgatt aaatatcttt atatc                                               25

SEQ ID NO: 730          moltype = RNA   length = 30
FEATURE                 Location/Qualifiers
source                  1..30
                        mol_type = other RNA
                        organism = synthetic construct
SEQUENCE: 730
tctgttagcc actgattaaa tatctttata                                          30

SEQ ID NO: 731          moltype = RNA   length = 31
FEATURE                 Location/Qualifiers
source                  1..31
                        mol_type = other RNA
                        organism = synthetic construct
SEQUENCE: 731
gagaaactgt tcagcttctg ttagccactg a                                        31

SEQ ID NO: 732          moltype = RNA   length = 31
FEATURE                 Location/Qualifiers
source                  1..31
                        mol_type = other RNA
                        organism = synthetic construct
SEQUENCE: 732
```

```
tctttctgag aaactgttca gcttctgtta g                              31

SEQ ID NO: 733         moltype = RNA   length = 26
FEATURE                Location/Qualifiers
source                 1..26
                       mol_type = other RNA
                       organism = synthetic construct
SEQUENCE: 733
cagatctgtc aaatcgcctg caggta                                    26

SEQ ID NO: 734         moltype = RNA   length = 26
FEATURE                Location/Qualifiers
source                 1..26
                       mol_type = other RNA
                       organism = synthetic construct
SEQUENCE: 734
caacagatct gtcaaatcgc ctgcag                                    26

SEQ ID NO: 735         moltype = RNA   length = 33
FEATURE                Location/Qualifiers
source                 1..33
                       mol_type = other RNA
                       organism = synthetic construct
SEQUENCE: 735
aaactgttca gcttctgtta gccactgatt aaa                            33

SEQ ID NO: 736         moltype = RNA   length = 31
FEATURE                Location/Qualifiers
source                 1..31
                       mol_type = other RNA
                       organism = synthetic construct
SEQUENCE: 736
gaaactgttc agcttctgtt agccactgat t                              31

SEQ ID NO: 737         moltype = RNA   length = 28
FEATURE                Location/Qualifiers
source                 1..28
                       mol_type = other RNA
                       organism = synthetic construct
SEQUENCE: 737
aaactgttca gcttctgtta gccactga                                  28

SEQ ID NO: 738         moltype = RNA   length = 28
FEATURE                Location/Qualifiers
source                 1..28
                       mol_type = other RNA
                       organism = synthetic construct
SEQUENCE: 738
tgagaaactg ttcagcttct gttagcca                                  28

SEQ ID NO: 739         moltype = RNA   length = 32
FEATURE                Location/Qualifiers
source                 1..32
                       mol_type = other RNA
                       organism = synthetic construct
SEQUENCE: 739
ttctgagaaa ctgttcagct tctgttagcc ac                             32

SEQ ID NO: 740         moltype = RNA   length = 26
FEATURE                Location/Qualifiers
source                 1..26
                       mol_type = other RNA
                       organism = synthetic construct
SEQUENCE: 740
ttctgagaaa ctgttcagct tctgtt                                    26

SEQ ID NO: 741         moltype = RNA   length = 25
FEATURE                Location/Qualifiers
source                 1..25
                       mol_type = other RNA
                       organism = synthetic construct
SEQUENCE: 741
gatctgtcaa atcgcctgca ggtaa                                     25

SEQ ID NO: 742         moltype = RNA   length = 25
FEATURE                Location/Qualifiers
source                 1..25
                       mol_type = other RNA
                       organism = synthetic construct
```

-continued

```
SEQUENCE: 742
ataatgaaaa cgccgccatt tctca                                              25

SEQ ID NO: 743          moltype = RNA  length = 25
FEATURE                 Location/Qualifiers
source                  1..25
                        mol_type = other RNA
                        organism = synthetic construct
SEQUENCE: 743
aaactgttca gcttctgtta gccac                                              25

SEQ ID NO: 744          moltype = RNA  length = 25
FEATURE                 Location/Qualifiers
source                  1..25
                        mol_type = other RNA
                        organism = synthetic construct
SEQUENCE: 744
ttgtgtcttt ctgagaaact gttca                                              25

SEQ ID NO: 745          moltype = RNA  length = 25
FEATURE                 Location/Qualifiers
source                  1..25
                        mol_type = other RNA
                        organism = synthetic construct
SEQUENCE: 745
ccaattctca ggaatttgtg tcttt                                              25

SEQ ID NO: 746          moltype = RNA  length = 25
FEATURE                 Location/Qualifiers
source                  1..25
                        mol_type = other RNA
                        organism = synthetic construct
SEQUENCE: 746
atcgcctgca ggtaaaagca tatgg                                              25

SEQ ID NO: 747          moltype = RNA  length = 30
FEATURE                 Location/Qualifiers
source                  1..30
                        mol_type = other RNA
                        organism = synthetic construct
SEQUENCE: 747
tgaaaacgcc gccatttctc aacagatctg                                         30

SEQ ID NO: 748          moltype = RNA  length = 30
FEATURE                 Location/Qualifiers
source                  1..30
                        mol_type = other RNA
                        organism = synthetic construct
SEQUENCE: 748
cataatgaaa acgccgccat ttctcaacag                                         30

SEQ ID NO: 749          moltype = RNA  length = 30
FEATURE                 Location/Qualifiers
source                  1..30
                        mol_type = other RNA
                        organism = synthetic construct
SEQUENCE: 749
tgttcagctt ctgttagcca ctgattaaat                                         30

SEQ ID NO: 750          moltype = RNA  length = 24
FEATURE                 Location/Qualifiers
source                  1..24
                        mol_type = other RNA
                        organism = synthetic construct
SEQUENCE: 750
cagatctgtc aaatcgcctg cagg                                               24

SEQ ID NO: 751          moltype = RNA  length = 27
FEATURE                 Location/Qualifiers
source                  1..27
                        mol_type = other RNA
                        organism = synthetic construct
SEQUENCE: 751
caacagatct gtcaaatcgc ctgcagg                                            27

SEQ ID NO: 752          moltype = RNA  length = 29
FEATURE                 Location/Qualifiers
source                  1..29
                        mol_type = other RNA
```

-continued

```
                        organism = synthetic construct
SEQUENCE: 752
ctcaacagat ctgtcaaatc gcctgcagg                                              29

SEQ ID NO: 753          moltype = RNA   length = 23
FEATURE                 Location/Qualifiers
source                  1..23
                        mol_type = other RNA
                        organism = synthetic construct
SEQUENCE: 753
gatctgtcaa atcgcctgca ggt                                                    23

SEQ ID NO: 754          moltype = RNA   length = 22
FEATURE                 Location/Qualifiers
source                  1..22
                        mol_type = other RNA
                        organism = synthetic construct
SEQUENCE: 754
gatctgtcaa atcgcctgca gg                                                     22

SEQ ID NO: 755          moltype = RNA   length = 21
FEATURE                 Location/Qualifiers
source                  1..21
                        mol_type = other RNA
                        organism = synthetic construct
SEQUENCE: 755
gatctgtcaa atcgcctgca g                                                      21

SEQ ID NO: 756          moltype = RNA   length = 25
FEATURE                 Location/Qualifiers
source                  1..25
                        mol_type = other RNA
                        organism = synthetic construct
SEQUENCE: 756
cagatctgtc aaatcgcctg caggt                                                  25

SEQ ID NO: 757          moltype = RNA   length = 23
FEATURE                 Location/Qualifiers
source                  1..23
                        mol_type = other RNA
                        organism = synthetic construct
SEQUENCE: 757
cagatctgtc aaatcgcctg cag                                                    23

SEQ ID NO: 758          moltype = RNA   length = 25
FEATURE                 Location/Qualifiers
source                  1..25
                        mol_type = other RNA
                        organism = synthetic construct
SEQUENCE: 758
gtgtctttct gagaaactgt tcagc                                                  25

SEQ ID NO: 759          moltype = RNA   length = 28
FEATURE                 Location/Qualifiers
source                  1..28
                        mol_type = other RNA
                        organism = synthetic construct
SEQUENCE: 759
gagaaactgt tcagcttctg ttagccac                                               28

SEQ ID NO: 760          moltype = RNA   length = 28
FEATURE                 Location/Qualifiers
source                  1..28
                        mol_type = other RNA
                        organism = synthetic construct
SEQUENCE: 760
gaaactgttc agcttctgtt agccactg                                               28

SEQ ID NO: 761          moltype = RNA   length = 24
FEATURE                 Location/Qualifiers
source                  1..24
                        mol_type = other RNA
                        organism = synthetic construct
SEQUENCE: 761
ctgttcagct tctgttagcc actg                                                   24

SEQ ID NO: 762          moltype = RNA   length = 27
FEATURE                 Location/Qualifiers
source                  1..27
```

```
                            mol_type = other RNA
                            organism = synthetic construct
SEQUENCE: 762
atctgtcaaa tcgcctgcag gtaaaag                                        27

SEQ ID NO: 763              moltype = RNA   length = 29
FEATURE                     Location/Qualifiers
source                      1..29
                            mol_type = other RNA
                            organism = synthetic construct
SEQUENCE: 763
gatctgtcaa atcgcctgca ggtaaaagc                                      29

SEQ ID NO: 764              moltype = RNA   length = 19
FEATURE                     Location/Qualifiers
source                      1..19
                            mol_type = other RNA
                            organism = synthetic construct
SEQUENCE: 764
gctgaattat ttcttcccc                                                 19

SEQ ID NO: 765              moltype = RNA   length = 19
FEATURE                     Location/Qualifiers
source                      1..19
                            mol_type = other RNA
                            organism = synthetic construct
SEQUENCE: 765
tttttctgtc tgacagctg                                                 19

SEQ ID NO: 766              moltype = RNA   length = 18
FEATURE                     Location/Qualifiers
source                      1..18
                            mol_type = other RNA
                            organism = synthetic construct
SEQUENCE: 766
tctgttttg aggattgc                                                   18

SEQ ID NO: 767              moltype = RNA   length = 17
FEATURE                     Location/Qualifiers
source                      1..17
                            mol_type = other RNA
                            organism = synthetic construct
SEQUENCE: 767
ccaccgcaga ttcaggc                                                   17

SEQ ID NO: 768              moltype = RNA   length = 17
FEATURE                     Location/Qualifiers
source                      1..17
                            mol_type = other RNA
                            organism = synthetic construct
SEQUENCE: 768
gcccaatgcc atcctgg                                                   17

SEQ ID NO: 769              moltype = RNA   length = 17
FEATURE                     Location/Qualifiers
source                      1..17
                            mol_type = other RNA
                            organism = synthetic construct
SEQUENCE: 769
tttgcagacc tcctgcc                                                   17

SEQ ID NO: 770              moltype = RNA   length = 17
FEATURE                     Location/Qualifiers
source                      1..17
                            mol_type = other RNA
                            organism = synthetic construct
SEQUENCE: 770
cagtttgccg ctgccca                                                   17

SEQ ID NO: 771              moltype = RNA   length = 20
FEATURE                     Location/Qualifiers
source                      1..20
                            mol_type = other RNA
                            organism = synthetic construct
SEQUENCE: 771
gttgcattca atgttctgac                                                20

SEQ ID NO: 772              moltype = RNA   length = 21
FEATURE                     Location/Qualifiers
```

```
source                  1..21
                        mol_type = other RNA
                        organism = synthetic construct
SEQUENCE: 772
attttttcctg tagaatactg g                                              21

SEQ ID NO: 773          moltype = RNA   length = 34
FEATURE                 Location/Qualifiers
source                  1..34
                        mol_type = other RNA
                        organism = synthetic construct
SEQUENCE: 773
gctgcccaat gcgatcctgg agttcctgta agat                                 34

SEQ ID NO: 774          moltype = RNA   length = 28
FEATURE                 Location/Qualifiers
source                  1..28
                        mol_type = other RNA
                        organism = synthetic construct
SEQUENCE: 774
gctgcccaat gccatcctgg agttcctg                                        28

SEQ ID NO: 775          moltype = RNA   length = 31
FEATURE                 Location/Qualifiers
source                  1..31
                        mol_type = other RNA
                        organism = synthetic construct
SEQUENCE: 775
gctgcccaat gccatcctgg agttcctgta a                                    31

SEQ ID NO: 776          moltype = RNA   length = 31
FEATURE                 Location/Qualifiers
source                  1..31
                        mol_type = other RNA
                        organism = synthetic construct
SEQUENCE: 776
caatgccatc ctggagttcc tgtaagatac c                                    31

SEQ ID NO: 777          moltype = RNA   length = 32
FEATURE                 Location/Qualifiers
source                  1..32
                        mol_type = other RNA
                        organism = synthetic construct
SEQUENCE: 777
gctgcccaat gccatcctgg agttcctgta ag                                   32

SEQ ID NO: 778          moltype = RNA   length = 30
FEATURE                 Location/Qualifiers
source                  1..30
                        mol_type = other RNA
                        organism = synthetic construct
SEQUENCE: 778
ccaatgccat cctggagttc ctgtaagata                                      30

SEQ ID NO: 779          moltype = RNA   length = 39
FEATURE                 Location/Qualifiers
source                  1..39
                        mol_type = other RNA
                        organism = synthetic construct
SEQUENCE: 779
ttgccgctgc ccaatgccat cctggagttc ctgtaagat                            39

SEQ ID NO: 780          moltype = RNA   length = 34
FEATURE                 Location/Qualifiers
source                  1..34
                        mol_type = other RNA
                        organism = synthetic construct
SEQUENCE: 780
gctgcccaat gccatcctgg agttcctgta agat                                 34

SEQ ID NO: 781          moltype = RNA   length = 27
FEATURE                 Location/Qualifiers
source                  1..27
                        mol_type = other RNA
                        organism = synthetic construct
SEQUENCE: 781
caatgccatc ctggagttcc tgtaaga                                         27

SEQ ID NO: 782          moltype = RNA   length = 26
```

```
FEATURE             Location/Qualifiers
source              1..26
                    mol_type = other RNA
                    organism = synthetic construct
SEQUENCE: 782
cagtttgccg ctgcccaatg ccatcc                                        26

SEQ ID NO: 783      moltype = RNA   length = 24
FEATURE             Location/Qualifiers
source              1..24
                    mol_type = other RNA
                    organism = synthetic construct
SEQUENCE: 783
cttccccagt tgcattcaat gttc                                          24

SEQ ID NO: 784      moltype = RNA   length = 23
FEATURE             Location/Qualifiers
source              1..23
                    mol_type = other RNA
                    organism = synthetic construct
SEQUENCE: 784
ctggcatctg tttttgagga ttg                                           23

SEQ ID NO: 785      moltype = RNA   length = 20
FEATURE             Location/Qualifiers
source              1..20
                    mol_type = other RNA
                    organism = synthetic construct
SEQUENCE: 785
ttagatctgt cgccctacct                                               20

SEQ ID NO: 786      moltype = RNA   length = 39
FEATURE             Location/Qualifiers
source              1..39
                    mol_type = other RNA
                    organism = synthetic construct
SEQUENCE: 786
gctgcccaat gccatcctgg agttcctgta agataccaa                          39

SEQ ID NO: 787      moltype = RNA   length = 34
FEATURE             Location/Qualifiers
source              1..34
                    mol_type = other RNA
                    organism = synthetic construct
SEQUENCE: 787
gcccaatgcc atcctggagt tcctgtaaga tacc                               34

SEQ ID NO: 788      moltype = RNA   length = 25
FEATURE             Location/Qualifiers
source              1..25
                    mol_type = other RNA
                    organism = synthetic construct
SEQUENCE: 788
catcctggag ttcctgtaag atacc                                         25

SEQ ID NO: 789      moltype = RNA   length = 28
FEATURE             Location/Qualifiers
source              1..28
                    mol_type = other RNA
                    organism = synthetic construct
SEQUENCE: 789
tgccatcctg gagttcctgt aagatacc                                      28

SEQ ID NO: 790      moltype = RNA   length = 25
FEATURE             Location/Qualifiers
source              1..25
                    mol_type = other RNA
                    organism = synthetic construct
SEQUENCE: 790
tgccatcctg gagttcctgt aagat                                         25

SEQ ID NO: 791      moltype = RNA   length = 28
FEATURE             Location/Qualifiers
source              1..28
                    mol_type = other RNA
                    organism = synthetic construct
SEQUENCE: 791
caatgccatc ctggagttcc tgtaagat                                      28
```

```
SEQ ID NO: 792          moltype = RNA   length = 31
FEATURE                 Location/Qualifiers
source                  1..31
                        mol_type = other RNA
                        organism = synthetic construct
SEQUENCE: 792
gcccaatgcc atcctggagt tcctgtaaga t                                      31

SEQ ID NO: 793          moltype = RNA   length = 28
FEATURE                 Location/Qualifiers
source                  1..28
                        mol_type = other RNA
                        organism = synthetic construct
SEQUENCE: 793
gcccaatgcc atcctggagt tcctgtaa                                          28

SEQ ID NO: 794          moltype = RNA   length = 34
FEATURE                 Location/Qualifiers
source                  1..34
                        mol_type = other RNA
                        organism = synthetic construct
SEQUENCE: 794
gccgctgccc aatgacatcc tggagttcct gtaa                                   34

SEQ ID NO: 795          moltype = RNA   length = 25
FEATURE                 Location/Qualifiers
source                  1..25
                        mol_type = other RNA
                        organism = synthetic construct
SEQUENCE: 795
gccatcctgg agttcctgta agata                                             25

SEQ ID NO: 796          moltype = RNA   length = 25
FEATURE                 Location/Qualifiers
source                  1..25
                        mol_type = other RNA
                        organism = synthetic construct
SEQUENCE: 796
ccaatgccat cctggagttc ctgta                                             25

SEQ ID NO: 797          moltype = RNA   length = 25
FEATURE                 Location/Qualifiers
source                  1..25
                        mol_type = other RNA
                        organism = synthetic construct
SEQUENCE: 797
ctgacaacag tttgccgctg cccaa                                             25

SEQ ID NO: 798          moltype = RNA   length = 25
FEATURE                 Location/Qualifiers
source                  1..25
                        mol_type = other RNA
                        organism = synthetic construct
SEQUENCE: 798
tttgaggatt gctgaattat ttctt                                             25

SEQ ID NO: 799          moltype = RNA   length = 30
FEATURE                 Location/Qualifiers
source                  1..30
                        mol_type = other RNA
                        organism = synthetic construct
SEQUENCE: 799
cagtttgccg ctgcccaatg ccatcctgga                                        30

SEQ ID NO: 800          moltype = RNA   length = 30
FEATURE                 Location/Qualifiers
source                  1..30
                        mol_type = other RNA
                        organism = synthetic construct
SEQUENCE: 800
ttgccgctgc ccaatgccat cctggagttc                                        30

SEQ ID NO: 801          moltype = RNA   length = 25
FEATURE                 Location/Qualifiers
source                  1..25
                        mol_type = other RNA
                        organism = synthetic construct
SEQUENCE: 801
tttgccgctg cccaatgcca tcctg                                             25
```

```
SEQ ID NO: 802          moltype = RNA   length = 22
FEATURE                 Location/Qualifiers
source                  1..22
                        mol_type = other RNA
                        organism = synthetic construct
SEQUENCE: 802
ccaatgccat cctggagttc ct                                                22

SEQ ID NO: 803          moltype = RNA   length = 29
FEATURE                 Location/Qualifiers
source                  1..29
                        mol_type = other RNA
                        organism = synthetic construct
SEQUENCE: 803
cccaatgcca tcctggagtt cctgtaaga                                         29

SEQ ID NO: 804          moltype = RNA   length = 28
FEATURE                 Location/Qualifiers
source                  1..28
                        mol_type = other RNA
                        organism = synthetic construct
SEQUENCE: 804
ccgctgccca atgccatcct ggagttcc                                          28

SEQ ID NO: 805          moltype = RNA   length = 30
FEATURE                 Location/Qualifiers
source                  1..30
                        mol_type = other RNA
                        organism = synthetic construct
SEQUENCE: 805
cccaatgcca tcctggagtt cctgtaagat                                        30

SEQ ID NO: 806          moltype = RNA   length = 30
FEATURE                 Location/Qualifiers
source                  1..30
                        mol_type = other RNA
                        organism = synthetic construct
SEQUENCE: 806
ccgctgccca atgccatcct ggagttcctg                                        30

SEQ ID NO: 807          moltype = RNA   length = 30
FEATURE                 Location/Qualifiers
source                  1..30
                        mol_type = other RNA
                        organism = synthetic construct
SEQUENCE: 807
tgcccaatgc catcctggag ttcctgtaag                                        30

SEQ ID NO: 808          moltype = RNA   length = 28
FEATURE                 Location/Qualifiers
source                  1..28
                        mol_type = other RNA
                        organism = synthetic construct
SEQUENCE: 808
cccaatgcca tcctggagtt cctgtaag                                          28

SEQ ID NO: 809          moltype = RNA   length = 28
FEATURE                 Location/Qualifiers
source                  1..28
                        mol_type = other RNA
                        organism = synthetic construct
SEQUENCE: 809
tgcccaatgc catcctggag ttcctgta                                          28

SEQ ID NO: 810          moltype = RNA   length = 22
FEATURE                 Location/Qualifiers
source                  1..22
                        mol_type = other RNA
                        organism = synthetic construct
SEQUENCE: 810
caatgccatc ctggagttcc tg                                                22

SEQ ID NO: 811          moltype = RNA   length = 29
FEATURE                 Location/Qualifiers
source                  1..29
                        mol_type = other RNA
                        organism = synthetic construct
SEQUENCE: 811
```

```
agcctctcgc tcactcaccc tgcaaagga                                              29

SEQ ID NO: 812           moltype = RNA   length = 29
FEATURE                  Location/Qualifiers
source                   1..29
                         mol_type = other RNA
                         organism = synthetic construct
SEQUENCE: 812
ccactcagag ctcagatctt ctaacttcc                                              29

SEQ ID NO: 813           moltype = RNA   length = 27
FEATURE                  Location/Qualifiers
source                   1..27
                         mol_type = other RNA
                         organism = synthetic construct
SEQUENCE: 813
cttccactca gagctcagat cttctaa                                                27

SEQ ID NO: 814           moltype = RNA   length = 25
FEATURE                  Location/Qualifiers
source                   1..25
                         mol_type = other RNA
                         organism = synthetic construct
SEQUENCE: 814
gggatccagt atacttacag gctcc                                                  25

SEQ ID NO: 815           moltype = RNA   length = 17
FEATURE                  Location/Qualifiers
source                   1..17
                         mol_type = other RNA
                         organism = synthetic construct
SEQUENCE: 815
ctcagagctc agatctt                                                           17

SEQ ID NO: 816           moltype = RNA   length = 15
FEATURE                  Location/Qualifiers
source                   1..15
                         mol_type = other RNA
                         organism = synthetic construct
SEQUENCE: 816
ggctgctttg ccctc                                                             15

SEQ ID NO: 817           moltype = RNA   length = 27
FEATURE                  Location/Qualifiers
source                   1..27
                         mol_type = other RNA
                         organism = synthetic construct
SEQUENCE: 817
ctcagatctt ctaacttcct ctttaac                                                27

SEQ ID NO: 818           moltype = RNA   length = 29
FEATURE                  Location/Qualifiers
source                   1..29
                         mol_type = other RNA
                         organism = synthetic construct
SEQUENCE: 818
ctcagagctc agatcttcta acttcctct                                              29

SEQ ID NO: 819           moltype = RNA   length = 27
FEATURE                  Location/Qualifiers
source                   1..27
                         mol_type = other RNA
                         organism = synthetic construct
SEQUENCE: 819
cgccttccac tcagagctca gatcttc                                                27

SEQ ID NO: 820           moltype = RNA   length = 27
FEATURE                  Location/Qualifiers
source                   1..27
                         mol_type = other RNA
                         organism = synthetic construct
SEQUENCE: 820
tcagctcttg aagtaaacgg tttaccg                                                27

SEQ ID NO: 821           moltype = RNA   length = 27
FEATURE                  Location/Qualifiers
source                   1..27
                         mol_type = other RNA
                         organism = synthetic construct
```

```
SEQUENCE: 821
tttgccctca gctcttgaag taaacgg                                               27

SEQ ID NO: 822          moltype = RNA   length = 27
FEATURE                 Location/Qualifiers
source                  1..27
                        mol_type = other RNA
                        organism = synthetic construct
SEQUENCE: 822
ggctgctttg ccctcagctc ttgaagt                                               27

SEQ ID NO: 823          moltype = RNA   length = 26
FEATURE                 Location/Qualifiers
source                  1..26
                        mol_type = other RNA
                        organism = synthetic construct
SEQUENCE: 823
caggagctag gtcaggctgc tttgcc                                                26

SEQ ID NO: 824          moltype = RNA   length = 25
FEATURE                 Location/Qualifiers
source                  1..25
                        mol_type = other RNA
                        organism = synthetic construct
SEQUENCE: 824
tccaatagtg gtcagtccag gagct                                                 25

SEQ ID NO: 825          moltype = RNA   length = 27
FEATURE                 Location/Qualifiers
source                  1..27
                        mol_type = other RNA
                        organism = synthetic construct
SEQUENCE: 825
aaagagaatg ggatccagta tacttac                                               27

SEQ ID NO: 826          moltype = RNA   length = 27
FEATURE                 Location/Qualifiers
source                  1..27
                        mol_type = other RNA
                        organism = synthetic construct
SEQUENCE: 826
aaatagctag agccaaagag aatggga                                               27

SEQ ID NO: 827          moltype = RNA   length = 33
FEATURE                 Location/Qualifiers
source                  1..33
                        mol_type = other RNA
                        organism = synthetic construct
SEQUENCE: 827
ggctgctttg ccctcagctc ttgaagtaaa cgg                                        33

SEQ ID NO: 828          moltype = RNA   length = 30
FEATURE                 Location/Qualifiers
source                  1..30
                        mol_type = other RNA
                        organism = synthetic construct
SEQUENCE: 828
aggctgcttt gccctcagct cttgaagtaa                                            30

SEQ ID NO: 829          moltype = RNA   length = 30
FEATURE                 Location/Qualifiers
source                  1..30
                        mol_type = other RNA
                        organism = synthetic construct
SEQUENCE: 829
gtcaggctgc tttgccctca gctcttgaag                                            30

SEQ ID NO: 830          moltype = RNA   length = 30
FEATURE                 Location/Qualifiers
source                  1..30
                        mol_type = other RNA
                        organism = synthetic construct
SEQUENCE: 830
aggtcaggct gctttgccct cagctcttga                                            30

SEQ ID NO: 831          moltype = RNA   length = 25
FEATURE                 Location/Qualifiers
source                  1..25
                        mol_type = other RNA
```

```
                              organism = synthetic construct
SEQUENCE: 831
cagagctcag atcttctaac ttcct                                            25

SEQ ID NO: 832         moltype = RNA  length = 25
FEATURE                Location/Qualifiers
source                 1..25
                       mol_type = other RNA
                       organism = synthetic construct
SEQUENCE: 832
cttacaggct ccaatagtgg tcagt                                            25

SEQ ID NO: 833         moltype = RNA  length = 25
FEATURE                Location/Qualifiers
source                 1..25
                       mol_type = other RNA
                       organism = synthetic construct
SEQUENCE: 833
atgggatcca gtatacttac aggct                                            25

SEQ ID NO: 834         moltype = RNA  length = 25
FEATURE                Location/Qualifiers
source                 1..25
                       mol_type = other RNA
                       organism = synthetic construct
SEQUENCE: 834
agagaatggg atccagtata cttac                                            25

SEQ ID NO: 835         moltype = RNA  length = 27
FEATURE                Location/Qualifiers
source                 1..27
                       mol_type = other RNA
                       organism = synthetic construct
SEQUENCE: 835
aacttcctct ttaacagaaa agcatac                                          27

SEQ ID NO: 836         moltype = RNA  length = 23
FEATURE                Location/Qualifiers
source                 1..23
                       mol_type = other RNA
                       organism = synthetic construct
SEQUENCE: 836
ctcatacctt ctgcttgatg atc                                              23

SEQ ID NO: 837         moltype = RNA  length = 20
FEATURE                Location/Qualifiers
source                 1..20
                       mol_type = other RNA
                       organism = synthetic construct
SEQUENCE: 837
tcaaggaaga tggcatttct                                                  20

SEQ ID NO: 838         moltype = RNA  length = 20
FEATURE                Location/Qualifiers
source                 1..20
                       mol_type = other RNA
                       organism = synthetic construct
SEQUENCE: 838
gaaagccagt cggtaagttc                                                  20

SEQ ID NO: 839         moltype = RNA  length = 15
FEATURE                Location/Qualifiers
source                 1..15
                       mol_type = other RNA
                       organism = synthetic construct
SEQUENCE: 839
cacccaccat caccc                                                       15

SEQ ID NO: 840         moltype = RNA  length = 23
FEATURE                Location/Qualifiers
source                 1..23
                       mol_type = other RNA
                       organism = synthetic construct
SEQUENCE: 840
cctctgtgat tttataactt gat                                              23

SEQ ID NO: 841         moltype = RNA  length = 20
FEATURE                Location/Qualifiers
source                 1..20
```

```
                              mol_type = other RNA
                              organism = synthetic construct
SEQUENCE: 841
tgatatcctc aaggtcaccc                                                 20

SEQ ID NO: 842            moltype = RNA  length = 30
FEATURE                   Location/Qualifiers
source                    1..30
                          mol_type = other RNA
                          organism = synthetic construct
SEQUENCE: 842
ggtacctcca acatcaagga agatggcatt                                      30

SEQ ID NO: 843            moltype = RNA  length = 26
FEATURE                   Location/Qualifiers
source                    1..26
                          mol_type = other RNA
                          organism = synthetic construct
SEQUENCE: 843
atttctagtt tggagatggc agtttc                                          26

SEQ ID NO: 844            moltype = RNA  length = 26
FEATURE                   Location/Qualifiers
source                    1..26
                          mol_type = other RNA
                          organism = synthetic construct
SEQUENCE: 844
catcaaggaa gatggcattt ctagtt                                          26

SEQ ID NO: 845            moltype = RNA  length = 26
FEATURE                   Location/Qualifiers
source                    1..26
                          mol_type = other RNA
                          organism = synthetic construct
SEQUENCE: 845
gagcaggtac ctccaacatc aaggaa                                          26

SEQ ID NO: 846            moltype = RNA  length = 30
FEATURE                   Location/Qualifiers
source                    1..30
                          mol_type = other RNA
                          organism = synthetic construct
SEQUENCE: 846
ctccaacatc aaggaagatg gcatttctag                                      30

SEQ ID NO: 847            moltype = RNA  length = 25
FEATURE                   Location/Qualifiers
source                    1..25
                          mol_type = other RNA
                          organism = synthetic construct
SEQUENCE: 847
accagagtaa cagtctgagt aggag                                           25

SEQ ID NO: 848            moltype = RNA  length = 25
FEATURE                   Location/Qualifiers
source                    1..25
                          mol_type = other RNA
                          organism = synthetic construct
SEQUENCE: 848
caccagagta acagtctgag tagga                                           25

SEQ ID NO: 849            moltype = RNA  length = 25
FEATURE                   Location/Qualifiers
source                    1..25
                          mol_type = other RNA
                          organism = synthetic construct
SEQUENCE: 849
tcaccagagt aacagtctga gtagg                                           25

SEQ ID NO: 850            moltype = RNA  length = 25
FEATURE                   Location/Qualifiers
source                    1..25
                          mol_type = other RNA
                          organism = synthetic construct
SEQUENCE: 850
gtcaccagag taacagtctg agtag                                           25

SEQ ID NO: 851            moltype = RNA  length = 26
FEATURE                   Location/Qualifiers
```

```
source                  1..26
                        mol_type = other RNA
                        organism = synthetic construct
SEQUENCE: 851
accagagtaa cagtctgagt aggagc                                              26

SEQ ID NO: 852          moltype = RNA   length = 24
FEATURE                 Location/Qualifiers
source                  1..24
                        mol_type = other RNA
                        organism = synthetic construct
SEQUENCE: 852
ttctgtccaa gcccggttga aatc                                                24

SEQ ID NO: 853          moltype = RNA   length = 30
FEATURE                 Location/Qualifiers
source                  1..30
                        mol_type = other RNA
                        organism = synthetic construct
SEQUENCE: 853
acatcaagga agatggcatt tctagtttgg                                          30

SEQ ID NO: 854          moltype = RNA   length = 25
FEATURE                 Location/Qualifiers
source                  1..25
                        mol_type = other RNA
                        organism = synthetic construct
SEQUENCE: 854
acatcaagga agatggcatt tctag                                               25

SEQ ID NO: 855          moltype = RNA   length = 25
FEATURE                 Location/Qualifiers
source                  1..25
                        mol_type = other RNA
                        organism = synthetic construct
SEQUENCE: 855
atcatttttt ctcatacctt ctgct                                               25

SEQ ID NO: 856          moltype = RNA   length = 21
FEATURE                 Location/Qualifiers
source                  1..21
                        mol_type = other RNA
                        organism = synthetic construct
SEQUENCE: 856
cacccaccat caccctctgt g                                                   21

SEQ ID NO: 857          moltype = RNA   length = 22
FEATURE                 Location/Qualifiers
source                  1..22
                        mol_type = other RNA
                        organism = synthetic construct
SEQUENCE: 857
atcatctcgt tgatatcctc aa                                                  22

SEQ ID NO: 858          moltype = RNA   length = 28
FEATURE                 Location/Qualifiers
source                  1..28
                        mol_type = other RNA
                        organism = synthetic construct
SEQUENCE: 858
ctccaacatc aaggaagatg gcatttct                                            28

SEQ ID NO: 859          moltype = RNA   length = 25
FEATURE                 Location/Qualifiers
source                  1..25
                        mol_type = other RNA
                        organism = synthetic construct
SEQUENCE: 859
catcaaggaa gatggcattt ctagt                                               25

SEQ ID NO: 860          moltype = RNA   length = 18
FEATURE                 Location/Qualifiers
source                  1..18
                        mol_type = other RNA
                        organism = synthetic construct
SEQUENCE: 860
ttgctggtct tgttttttc                                                      18

SEQ ID NO: 861          moltype = RNA   length = 16
```

```
FEATURE                Location/Qualifiers
source                 1..16
                       mol_type = other RNA
                       organism = synthetic construct
SEQUENCE: 861
ccgtaatgat tgttct                                                         16

SEQ ID NO: 862         moltype = RNA   length = 18
FEATURE                Location/Qualifiers
source                 1..18
                       mol_type = other RNA
                       organism = synthetic construct
SEQUENCE: 862
gctggtcttg tttttcaa                                                       18

SEQ ID NO: 863         moltype = RNA   length = 20
FEATURE                Location/Qualifiers
source                 1..20
                       mol_type = other RNA
                       organism = synthetic construct
SEQUENCE: 863
tggtcttgtt tttcaaattt                                                     20

SEQ ID NO: 864         moltype = RNA   length = 20
FEATURE                Location/Qualifiers
source                 1..20
                       mol_type = other RNA
                       organism = synthetic construct
SEQUENCE: 864
gtcttgtttt tcaaattttg                                                     20

SEQ ID NO: 865         moltype = RNA   length = 20
FEATURE                Location/Qualifiers
source                 1..20
                       mol_type = other RNA
                       organism = synthetic construct
SEQUENCE: 865
cttgtttttc aaattttggg                                                     20

SEQ ID NO: 866         moltype = RNA   length = 19
FEATURE                Location/Qualifiers
source                 1..19
                       mol_type = other RNA
                       organism = synthetic construct
SEQUENCE: 866
tgtttttcaa attttgggc                                                      19

SEQ ID NO: 867         moltype = RNA   length = 33
FEATURE                Location/Qualifiers
source                 1..33
                       mol_type = other RNA
                       organism = synthetic construct
SEQUENCE: 867
tccaactggg gacgcctctg ttccaaatcc tgc                                      33

SEQ ID NO: 868         moltype = RNA   length = 21
FEATURE                Location/Qualifiers
source                 1..21
                       mol_type = other RNA
                       organism = synthetic construct
SEQUENCE: 868
tcctgcattg ttgcctgtaa g                                                   21

SEQ ID NO: 869         moltype = RNA   length = 30
FEATURE                Location/Qualifiers
source                 1..30
                       mol_type = other RNA
                       organism = synthetic construct
SEQUENCE: 869
tccaactggg gacgcctctg ttccaaatcc                                          30

SEQ ID NO: 870         moltype = RNA   length = 21
FEATURE                Location/Qualifiers
source                 1..21
                       mol_type = other RNA
                       organism = synthetic construct
SEQUENCE: 870
actggggacg cctctgttcc a                                                   21
```

```
SEQ ID NO: 871            moltype = RNA   length = 20
FEATURE                   Location/Qualifiers
source                    1..20
                          mol_type = other RNA
                          organism = synthetic construct
SEQUENCE: 871
ccgtaatgat tgttctagcc                                                       20

SEQ ID NO: 872            moltype = RNA   length = 20
FEATURE                   Location/Qualifiers
source                    1..20
                          mol_type = other RNA
                          organism = synthetic construct
SEQUENCE: 872
tgttaaaaaa cttacttcga                                                       20

SEQ ID NO: 873            moltype = RNA   length = 18
FEATURE                   Location/Qualifiers
source                    1..18
                          mol_type = other RNA
                          organism = synthetic construct
SEQUENCE: 873
ctgttgcctc cggttctg                                                         18

SEQ ID NO: 874            moltype = RNA   length = 18
FEATURE                   Location/Qualifiers
source                    1..18
                          mol_type = other RNA
                          organism = synthetic construct
SEQUENCE: 874
ttggctctgg cctgtcct                                                         18

SEQ ID NO: 875            moltype = RNA   length = 33
FEATURE                   Location/Qualifiers
source                    1..33
                          mol_type = other RNA
                          organism = synthetic construct
SEQUENCE: 875
ttcaactgtt gcctccggtt ctgaaggtgt tct                                        33

SEQ ID NO: 876            moltype = RNA   length = 25
FEATURE                   Location/Qualifiers
source                    1..25
                          mol_type = other RNA
                          organism = synthetic construct
SEQUENCE: 876
tacttcatcc cactgattct gaatt                                                 25

SEQ ID NO: 877            moltype = RNA   length = 25
FEATURE                   Location/Qualifiers
source                    1..25
                          mol_type = other RNA
                          organism = synthetic construct
SEQUENCE: 877
ctgaaggtgt tcttgtactt catcc                                                 25

SEQ ID NO: 878            moltype = RNA   length = 25
FEATURE                   Location/Qualifiers
source                    1..25
                          mol_type = other RNA
                          organism = synthetic construct
SEQUENCE: 878
ctgttgcctc cggttctgaa ggtgt                                                 25

SEQ ID NO: 879            moltype = RNA   length = 30
FEATURE                   Location/Qualifiers
source                    1..30
                          mol_type = other RNA
                          organism = synthetic construct
SEQUENCE: 879
ctgttgcctc cggttctgaa ggtgttcttg                                            30

SEQ ID NO: 880            moltype = RNA   length = 30
FEATURE                   Location/Qualifiers
source                    1..30
                          mol_type = other RNA
                          organism = synthetic construct
SEQUENCE: 880
caactgttgc ctccggttct gaaggtgttc                                            30
```

```
SEQ ID NO: 881          moltype = RNA   length = 30
FEATURE                 Location/Qualifiers
source                  1..30
                        mol_type = other RNA
                        organism = synthetic construct
SEQUENCE: 881
ttgcctccgg ttctgaaggt gttcttgtac                                        30

SEQ ID NO: 882          moltype = RNA   length = 25
FEATURE                 Location/Qualifiers
source                  1..25
                        mol_type = other RNA
                        organism = synthetic construct
SEQUENCE: 882
gttgcctccg ttctgaagg tgttc                                              25

SEQ ID NO: 883          moltype = RNA   length = 23
FEATURE                 Location/Qualifiers
source                  1..23
                        mol_type = other RNA
                        organism = synthetic construct
SEQUENCE: 883
ctccggttct gaaggtgttc ttg                                               23

SEQ ID NO: 884          moltype = RNA   length = 22
FEATURE                 Location/Qualifiers
source                  1..22
                        mol_type = other RNA
                        organism = synthetic construct
SEQUENCE: 884
ctccggttct gaaggtgttc tt                                                22

SEQ ID NO: 885          moltype = RNA   length = 21
FEATURE                 Location/Qualifiers
source                  1..21
                        mol_type = other RNA
                        organism = synthetic construct
SEQUENCE: 885
ctccggttct gaaggtgttc t                                                 21

SEQ ID NO: 886          moltype = RNA   length = 20
FEATURE                 Location/Qualifiers
source                  1..20
                        mol_type = other RNA
                        organism = synthetic construct
SEQUENCE: 886
ctccggttct gaaggtgttc                                                   20

SEQ ID NO: 887          moltype = RNA   length = 19
FEATURE                 Location/Qualifiers
source                  1..19
                        mol_type = other RNA
                        organism = synthetic construct
SEQUENCE: 887
ctccggttct gaaggtgtt                                                    19

SEQ ID NO: 888          moltype = RNA   length = 25
FEATURE                 Location/Qualifiers
source                  1..25
                        mol_type = other RNA
                        organism = synthetic construct
SEQUENCE: 888
cattcaactg ttgcctccgg ttctg                                             25

SEQ ID NO: 889          moltype = RNA   length = 24
FEATURE                 Location/Qualifiers
source                  1..24
                        mol_type = other RNA
                        organism = synthetic construct
SEQUENCE: 889
ctgttgcctc cggttctgaa ggtg                                              24

SEQ ID NO: 890          moltype = RNA   length = 31
FEATURE                 Location/Qualifiers
source                  1..31
                        mol_type = other RNA
                        organism = synthetic construct
SEQUENCE: 890
```

```
cattcaactg ttgcctccgg ttctgaaggt g                                  31

SEQ ID NO: 891         moltype = RNA   length = 21
FEATURE                Location/Qualifiers
source                 1..21
                       mol_type = other RNA
                       organism = synthetic construct
SEQUENCE: 891
tactaacctt ggtttctgtg a                                             21

SEQ ID NO: 892         moltype = RNA   length = 27
FEATURE                Location/Qualifiers
source                 1..27
                       mol_type = other RNA
                       organism = synthetic construct
SEQUENCE: 892
tgtataggga ccctccttcc atgactc                                       27

SEQ ID NO: 893         moltype = RNA   length = 25
FEATURE                Location/Qualifiers
source                 1..25
                       mol_type = other RNA
                       organism = synthetic construct
SEQUENCE: 893
ctaaccttgg tttctgtgat tttct                                         25

SEQ ID NO: 894         moltype = RNA   length = 27
FEATURE                Location/Qualifiers
source                 1..27
                       mol_type = other RNA
                       organism = synthetic construct
SEQUENCE: 894
ggtatctttg atactaacct tggtttc                                       27

SEQ ID NO: 895         moltype = RNA   length = 22
FEATURE                Location/Qualifiers
source                 1..22
                       mol_type = other RNA
                       organism = synthetic construct
SEQUENCE: 895
attctttcaa ctagaataaa ag                                            22

SEQ ID NO: 896         moltype = RNA   length = 25
FEATURE                Location/Qualifiers
source                 1..25
                       mol_type = other RNA
                       organism = synthetic construct
SEQUENCE: 896
gattctgaat tctttcaact agaat                                         25

SEQ ID NO: 897         moltype = RNA   length = 20
FEATURE                Location/Qualifiers
source                 1..20
                       mol_type = other RNA
                       organism = synthetic construct
SEQUENCE: 897
atcccactga ttctgaattc                                               20

SEQ ID NO: 898         moltype = RNA   length = 22
FEATURE                Location/Qualifiers
source                 1..22
                       mol_type = other RNA
                       organism = synthetic construct
SEQUENCE: 898
aaccgagacc ggacaggatt ct                                            22

SEQ ID NO: 899         moltype = RNA   length = 20
FEATURE                Location/Qualifiers
source                 1..20
                       mol_type = other RNA
                       organism = synthetic construct
SEQUENCE: 899
ctgttgcagt aatctatgag                                               20

SEQ ID NO: 900         moltype = RNA   length = 23
FEATURE                Location/Qualifiers
source                 1..23
                       mol_type = other RNA
                       organism = synthetic construct
```

```
SEQUENCE: 900
tgccattgtt tcatcagctc ttt                                              23

SEQ ID NO: 901          moltype = RNA   length = 20
FEATURE                 Location/Qualifiers
source                  1..20
                        mol_type = other RNA
                        organism = synthetic construct
SEQUENCE: 901
tgcagtaatc tatgagtttc                                                  20

SEQ ID NO: 902          moltype = RNA   length = 20
FEATURE                 Location/Qualifiers
source                  1..20
                        mol_type = other RNA
                        organism = synthetic construct
SEQUENCE: 902
tcctgtagga cattggcagt                                                  20

SEQ ID NO: 903          moltype = RNA   length = 18
FEATURE                 Location/Qualifiers
source                  1..18
                        mol_type = other RNA
                        organism = synthetic construct
SEQUENCE: 903
gagtcttcta ggagcctt                                                    18

SEQ ID NO: 904          moltype = RNA   length = 25
FEATURE                 Location/Qualifiers
source                  1..25
                        mol_type = other RNA
                        organism = synthetic construct
SEQUENCE: 904
ggccaaacct cggcttacct gaaat                                            25

SEQ ID NO: 905          moltype = RNA   length = 20
FEATURE                 Location/Qualifiers
source                  1..20
                        mol_type = other RNA
                        organism = synthetic construct
SEQUENCE: 905
ggccaaacct cggcttacct                                                  20

SEQ ID NO: 906          moltype = RNA   length = 29
FEATURE                 Location/Qualifiers
source                  1..29
                        mol_type = other RNA
                        organism = synthetic construct
SEQUENCE: 906
aatcagctgg gagagagctt cctgtagct                                        29

SEQ ID NO: 907          moltype = RNA   length = 26
FEATURE                 Location/Qualifiers
source                  1..26
                        mol_type = other RNA
                        organism = synthetic construct
SEQUENCE: 907
tcgttcttct gtcgtcgtaa cgtttc                                           26

SEQ ID NO: 908          moltype = RNA   length = 16
FEATURE                 Location/Qualifiers
source                  1..16
                        mol_type = other RNA
                        organism = synthetic construct
SEQUENCE: 908
caccgattgt cttcga                                                      16

SEQ ID NO: 909          moltype = RNA   length = 17
FEATURE                 Location/Qualifiers
source                  1..17
                        mol_type = other RNA
                        organism = synthetic construct
SEQUENCE: 909
cccttgtacg atttatg                                                     17

SEQ ID NO: 910          moltype = RNA   length = 18
FEATURE                 Location/Qualifiers
source                  1..18
                        mol_type = other RNA
```

| | |
|---|---|
| | organism = synthetic construct |
| SEQUENCE: 910 | |
| tctgtgttta aggactct | 18 |
| | |
| SEQ ID NO: 911 | moltype = RNA length = 31 |
| FEATURE | Location/Qualifiers |
| source | 1..31 |
| | mol_type = other RNA |
| | organism = synthetic construct |
| SEQUENCE: 911 | |
| gccgctgccc aatgccatcc tggagttcct g | 31 |
| | |
| SEQ ID NO: 912 | moltype = RNA length = 29 |
| FEATURE | Location/Qualifiers |
| source | 1..29 |
| | mol_type = other RNA |
| | organism = synthetic construct |
| SEQUENCE: 912 | |
| attagatctg tcgccctacc tcttttttc | 29 |
| | |
| SEQ ID NO: 913 | moltype = RNA length = 27 |
| FEATURE | Location/Qualifiers |
| source | 1..27 |
| | mol_type = other RNA |
| | organism = synthetic construct |
| SEQUENCE: 913 | |
| tgtcgcccta cctctttttt ctgtctg | 27 |
| | |
| SEQ ID NO: 914 | moltype = RNA length = 25 |
| FEATURE | Location/Qualifiers |
| source | 1..25 |
| | mol_type = other RNA |
| | organism = synthetic construct |
| SEQUENCE: 914 | |
| gcccaatgcc atcctggagt tcctg | 25 |
| | |
| SEQ ID NO: 915 | moltype = RNA length = 30 |
| FEATURE | Location/Qualifiers |
| source | 1..30 |
| | mol_type = other RNA |
| | organism = synthetic construct |
| SEQUENCE: 915 | |
| gagcctctcg ctcactcacc ctgcaaagga | 30 |
| | |
| SEQ ID NO: 916 | moltype = RNA length = 36 |
| FEATURE | Location/Qualifiers |
| source | 1..36 |
| | mol_type = other RNA |
| | organism = synthetic construct |
| SEQUENCE: 916 | |
| atcattttt ctcataccttt ctgctaggag ctaaaa | 36 |
| | |
| SEQ ID NO: 917 | moltype = RNA length = 26 |
| FEATURE | Location/Qualifiers |
| source | 1..26 |
| | mol_type = other RNA |
| | organism = synthetic construct |
| SEQUENCE: 917 | |
| ggaagctaag gaagaagctg agcagg | 26 |
| | |
| SEQ ID NO: 918 | moltype = DNA length = 6054 |
| FEATURE | Location/Qualifiers |
| source | 1..6054 |
| | mol_type = genomic DNA |
| | organism = Homo sapiens |
| SEQUENCE: 918 | |
| cagcccctga gaccaggtct ggctccacag ctctgtcctg ctctgtgtct ttccctgctg | 60 |
| ctctcaggtc ccctgcaggc cttggcccct ttcctcatct gtagacacac ttgagtagcc | 120 |
| caggcacagc catgggagat tcggagatgg cagtcttttgg ggctgccgcc ccctacctgc | 180 |
| gcaagtcaga gaaggagcgg ctagaagcgc agaccaggcc ttttgacctc aagaaggatg | 240 |
| tcttcgtgcc tgatgacaaa caggagtttg tcaaggccaa gatcgtgtct cgagagggtg | 300 |
| gcaaagtcac tgccgagacc gagtatggca agacagtgac cgtgaaggag gaccaggtga | 360 |
| tgcagcagaa cccacccaag ttcgacaaaa tcgaggacat ggccatgctg accttcctgc | 420 |
| atgagccgc ggtgctctac aacctcaagg atcgctacgg ctcctggatg atctacacct | 480 |
| actcgggcct cttctgtgtc accgtcaacc cttacaagtg gctgccggtg tacactcctg | 540 |
| aggtggtggc tgcctaccgg ggcaagaaga ggagcgaggc cccgccccac atcttctcca | 600 |
| tctccgacaa cgcctatcag tacatgctga cagacagaga aaaccagtcc atcctgatca | 660 |
| ccggagaatc cggagcaggg aagacagtca acaccaagag ggtcatccag tactttgctg | 720 |
| ttattgcagc cattggggac cgcagcaaga aggaccagag cccgggcaag ggcacccttgg | 780 |

```
aggaccagat catccaggcc aaccctgctc tggaggcctt tggcaatgcc aagaccgtcc  840
ggaacgacaa ctcctcccgc ttcgggaaat tcattcgaat tcattttggg gcaacaggaa  900
agttggcatc tgcagacata gagacctatc ttctggaaaa atccagagtt attttccagc  960
tgaaagcaga gagagattat cacatttttct accaaatcct gtctaacaaa aagcctgagc 1020
tgctggacat gctgctgatc accaacaacc cctacgatta tgcattcatc tcccaaggag 1080
agaccaccgt ggcctccatt gatgacgctg aggagctcat ggccactgat aacgcttttg 1140
atgtgctggg cttcacttca gaggagaaaa actccatgta taagctgaca ggcgccatca 1200
tgcactttgg aaacatgaag ttcaagctga agcagcggga ggagcaggcg gagccagacg 1260
gcactgaaga ggctgacaag tctgcctacc tcatgggggct gaactcagcc gacctgctca 1320
aggggctgtg ccaccctcgg gtgaaagtgg gcaatgagta cgtcaccaag gggcagaatg 1380
tccagcaggt gatatatgcc actggggcac tggccaaggc agtgtatgag aggatgttca 1440
actgatggt gacgcgcatc aatgccaccc tggagaccaa gcagccacgc cagtacttca 1500
taggagtcct ggacatcgct ggcttcgaga tcttcgattt caacagcttt gagcagctct 1560
gcatcaactt caccaacgag aagctgcagc agttcttcaa ccaccacatg tttgtgctgg 1620
agcaggagga gtacaagaag agggcatcg agtggacatt cattgacttt ggcatggacc 1680
tgcaggcctg cattgacctc atcgagaagc ccatgggcat catgtccatc ctggaagagg 1740
agtgcatgtt ccccaaggcc accgacatga ccttcaaggc caagctgttt gacaaccacc 1800
tgggcaaatc cgccaacttc cagaagccac gcaatatcaa ggggaagcct gaagcccact 1860
tctccctgat ccactatgcc ggcatcgtgg actacaacat cattggctgg ctgcagaaga 1920
acaaggatcc tctcaatgag actgtcgtgg gcttgtatca gaagtcttcc ctcaagctgc 1980
tcagcaccct gtttgccaac tatgctgggg ctgatgcgcc tattgagaag ggcaaaggca 2040
aggccaagaa aggctcgtcc tttcagactg tgtcagctct cacagaggaa aatctgaaca 2100
agctgatgac caacttgcgc tccacccatc cccactttgt acgttgtatc atccctaatg 2160
agacaaagtc tccaggggtg atggacaacc ccctggtcat gcaccagctg cgctgcaatg 2220
gtgtgctgga gggcatccgc atctgcagga aaggcttccc caaccgcatc ctctacgggg 2280
acttccggca gaggtatcgc atcctgaacc cagcgggccat ccctgagggga cagttcattg 2340
atagcaggaa gggggcagag aagctgctca gctcccctga cattgatcac aaccagtaca 2400
agtttggcca caccaaggtg ttcttcaagg ccgggctgct ggggctgctg gaggaaatga 2460
gggacgagag gctgagccgc atcatcacgc gtatccaggc ccagtcccga ggtgtgctcg 2520
ccagaatgga gtacaaaaag ctgctggaac gtagagactc cctgctggta atccagtgga 2580
acattcgggc cttcatgggg gtcaagaatt ggccctggat gaagctctac ttcaagatca 2640
agccgctgct gaagagtgca gaaagagaga aggagatggc ctccatgaag gaggagttca 2700
cacgcctcaa agaggcgcta gagaagtccg aggctcgccg caaggagctg aggagaaga 2760
tggtgtccct gctgcaggag aagaatgacc tgcagctcca agtgcaggcg gaacaagaca 2820
acctggcaga tgctgaggag cgctgtgatc agctgatcaa aaacaagatt cagctggagg 2880
ccaaggtgaa ggagatgaac gagaggctgg aggatgagga ggagatgaat gctgagctca 2940
ctgccaagaa gcgcaagctg gaagatgagt gctcagagct caaaagggac atcgatgatc 3000
tggagctgac actggccaaa gtggagaagg agaaacacgc aacagagaac aaggtgaaaa 3060
acctgacaga ggagatggct gggctggatg agatcattgc caagctgacc aaggagaaga 3120
aagctctgca gagggcccac caacaggctc tggatgacct tcaggccgag gaggacaagg 3180
tcaacaccct gactaaggcc aaagtcaagc tggagcagca agtggatgat ctggaaggat 3240
ccctggagca agagaagaag gtgcgcatgg acctggagca agcgaagcgg aagctggagg 3300
gcgacctgaa gctgacccag gagagcatca tggacctgga gaatgacaag cagcagctgg 3360
atgagcggct gaaaaaaaaa gactttgagc tgaatgctct caacgcaagg attgaggatg 3420
aacaggccct cggcagccag ctgcagaaga agctcaagga gcttcaggca cgcatcgagg 3480
agctggagga ggagctggag gccgagcgca ccgccagggc taaggtggag aagctgcgct 3540
cagacctgtc tcgggagctg gaagagatca gcgagcgact ggaagagcgc agcgggggca 3600
cgtccgtgca gatcgagatg aacaagaagc gcgaggccga gttccagaag atgcggcggg 3660
acctggagga ggccacgctg cagcacgagg ccactgccgc ggccctgcgc aagaagcacg 3720
ccgacagcgt ggccgagctg ggcgagcaga tcgacaacct gcagcgggtg aagcagaagc 3780
tggagaagga gaaagcgag ttcaagctgg agctggatga cgtcacctcc aacatggagg 3840
agatcatcaa ggccaaggct aacctggaga agatgtgccg gaccttggaa gaccagatga 3900
atgagcaccg gagcaaggcg gaggagaccc agcgttctgt caacgacctc accagccagc 3960
gggccaagtt gcaaaccgag aatggtgagc tgtcccggca gctggatgag aaggaggcac 4020
tgatctccca gctgacccga ggcaagctca cctacacccca gcgctggaag gacctcaaga 4080
ggcagctgga ggaggaggtt aaggcgaaga acgcccctggc ccacgcactg cagtcggccc 4140
ggcatgactg cgacctgctg cgggagcagt acgaggagga gacggaggcc aaggccgagc 4200
tgcagcgcgt ccttttccaag gccaactcgg aggtggccca gtggaggacc aagtatgaga 4260
cggacgccat tcagcggact gaggagctcg aggaggccaa gaagaagctg gcccagcggc 4320
tgcaggaagc tgaggaggcc gtgggagctg ttaatgccaa gtgctcctcg ctggagaaga 4380
ccaagcaccg gctacagaat gagatcgagg acttgatggt ggacgtagag cgctccaatg 4440
ctgctgctgc agccctggac aagaagcaga ggaacttcga caagatcctg gccgagtgga 4500
agcagaagta tgaggagtcg cagtcggagc tggagtcctc gcagaaggag gctcgctccc 4560
tcagcacaga gctcttcaaa ctcaagaacg cctatgagga gtccctggaa catctggaga 4620
ccttcaagcg ggagaacaaa aacctgcagg aggagatctc cgacttgact gagcagttgg 4680
gttccagcgg aaagactatc atgagctggg agaaggtccg aaagcagctg gaggccgaga 4740
agatggagct gcagtcagcc ctggaggagg ccgaggcctc cctggagcac gaggagggca 4800
agatcctccg ggcccagctg gagttcaacc agatcaaggc agatcgag cggaagctgg 4860
cagagaagga cgaggagatg gaacaggcca agcgcaacct gcgggtg gtggactcgg 4920
tgcagacctc cctggacgca gagacacgca gccgcaacga ggccctgagg gtgaagaaga 4980
agatggaagg agacctcaat gagatacgaga tccagctcag ccacgccaac cgcatggccg 5040
ccgaggccca gaagcaagtc aagagcctcc agagcttgtt gaaggacacc cagattcagc 5100
tggacgatgc agtccgtgcc aacgacgacc tgaaggagaa catcgccatc gtggagcggc 5160
gcaacaacct gctgcaggct gagctgggag agttgcgtgc ccagagcgga cagcagaaga 5220
ggtcccggaa gctggcggag caggagctga ttgagactag tgagcgggtg cagctgctgc 5280
attcccagaa caccagcctc atcaaccaga gaagaagat ggatgctgac ctgtcccagc 5340
tccagactga agtggaggag gcagtgcagg agtgcaggaa tgctgaggag aaggccaaga 5400
aggccatcac ggatgccgcc atgatggcag aggagctgaa aaggagcag gacaccgcg 5460
cccacctgga gcgcatgaag aagaacatgg aacagaccat taaggacctg cagcaccggc 5520
```

```
tggacgaagc cgagcagatc gccctcaagg gcggcaagaa gcagctgcag aagctggaag  5580
cgcgggtgcg ggagctggag aatgagctgg aggccgagca gaagcgcaac gcagagtcgg  5640
tgaagggcat gaggaagagc gagcggcgca tcaaggagct cacctaccag acggaggagg  5700
acaggaaaaa cctgctgcgg ctgcaggacc tggtagacaa gctgcagcta aaggtcaagg  5760
cctacaagcg ccaggccgag gaggcggagg agcaagccaa caccaacctg tccaagttcc  5820
gcaaggtgca gcacgagctg gatgaggcag aggagcgggc ggacatcgcc gagtcccagg  5880
tcaacaagct gcgggccaag agccgtgaca ttggcacgaa gggcttgaat gaggagtagc  5940
tttgccacat cttgatctgc tcagccctgg aggtgccagc aaagcccat gctggagcct   6000
gtgtaacagc tccttgggag gaagcagaat aaagcaattt tccttgaagc cgag         6054

SEQ ID NO: 919        moltype = DNA   length = 6313
FEATURE               Location/Qualifiers
source                1..6313
                      mol_type = genomic DNA
                      organism = Mus musculus
SEQUENCE: 919
gctagggact gggtgcaggt gggggatggg gcaccctgct gccccatata tacagcccct  60
gagaccaggt ctggctctga gcattctcct gctgtttcct tacttgctac cctcaggtag  120
gagtgggagc tggaggcttc cctctgggat aaggggctcc aggttcagga agtgattcct  180
ctagaacagc agcgggcttc tggcatgtag taccaggtta tcattgaaca ctcctgtgca  240
gatctaaata cgcatgcttg tgccgtagga atgtgggagc ccaagtgttc caaggtggct  300
ccgagaaagg aagcctcagc agaggagtac agctcttcta caggtcaggg cttacctctc  360
tatcactaga cacgtttgag aatccaaggc tcagccatgg cggatgcaga gatggctgca  420
tttggggctg cagccccctt cctgcggaag tctgagaagg agaggctgga ggcacagacc  480
aggccctttg acctcaagaa agatgttttt gtgcccgatg acaagaaga gtttgtcaag  540
gccaagatcg tgtcccgaga gggtgcaaa gtcactgctg agacggaaa tggcaagacg  600
gtgactgtga aggaggacca ggtgatgcag cagaacccac ccaagttcga caagatcgag  660
gacatggcca tgctgacctt cctgcatgag ccggctgtgc tgtacaacct caaggagcgc  720
tacgcttcct ggatgatcta tacctactcg ggcctcttct gcgtcaccgt caaccccta c  780
aagtgcctgc ctgtgtacaa tgcggaagtg gtggctgcca ccggggcaa gaagaggagc  840
gaggcccctc ctcacatctt ctccatctct gacaacgcct atcagtacat gctgacagat  900
cgggagaatc agtccatcct catcaccgga gaatccggag ctgggaagac tgtcaacact  960
aagagggtca tccaatattt tgctgttatt gccgccattg ggaccgcag caagaaggac  1020
cagaccccag gcaagggtac cctggaagat caaatcatcc aagcaaccc tgctctgaag  1080
gcctttggca atgccaagac agttcggaat gacaactcct ctcgatttgg gaaattcatc  1140
cgaatccatt ttgggcaac aggaaagttg gcatctgcag acatagagac ctaccttctg  1200
gaaaaatcca gggttatttt ccagctgaaa gcagaaagag attatcacat tttctaccaa  1260
atcctgtcta ataaaaagcc tgagcttcta gacatgctgc tgatcaccaa caccccctac  1320
gattatgcgt tcatctccca aggagagacg actgtggaca tccattgatga tctgaagag   1380
ctcatggcca cggatagcgc cttttgacgtg ctgggcttca ctccagaaga gaagaactcc  1440
atttacaagc tgacaggcgc catcatgcac ttttggaaaca tgaagttcaa gcagaagcag  1500
cgggaggagc aggcggaacc agacggcact gaagaggctg acaaatcagc ctacctcatg  1560
gggctgaact cagccgcatc gcttaagggg tcgtgccatc ctagagtcaa agtgggcaac  1620
gagtacgtca ccaaggggca gaatgtccag caggtgtcat acgccatcgg ggcactggcc  1680
aagtcagtgt acgagaagat gttcaactgg atggtgacac gcatcaatgc aaccctggag  1740
accaagcagc cgcgccagta cttcataggt gtcctggaca ttgccggctt tgagatcttc  1800
gatttcaaca gctttgagca gctgtgcatc aacttcacca atgagaagct gcagcagttc  1860
ttcaaccacc acatgttcgt gctggagcag gaggagtaca agaaggaggg cattgagtgg  1920
accttcatag acttcggcat ggactttgcag gcctgcattg acctcatcga gaagcccatg  1980
ggcatcatgt ccatccttga ggaggagtgc atgttcccca aggccacaga catgaccttc  2040
aaggccaagc tgtacgacaa ccacctgggc aagtccaaca cttccagaa gcctcgaaat  2100
gtcaaggggga agcaggaagc ccacttctct ttggtccact atgctggcac tgtggactac  2160
aatatcctgg gctggctaca aaagaacaag gacccactca atgagacggt ggtgggtttg  2220
taccagaagt cttccctcaa gctgctcagc aatctatttg ccaactatgc tggagctgat  2280
gccccggcgg acaaaggcaa aggcaaggca aagaaaggct catccttca gaccgtgtct  2340
gctctgcaca gagaaaatct gaacaaactt atgacaaact tgcgctccac gcaccctcac  2400
tttgtacgct gcatcatccc caatgagaca aagtctccag gggtgatgga caaccccctg  2460
gtcatgcacc agctgcgatg caatggcgtg ctggagggta tccgcatctg caggaagggc  2520
ttcccaacc gcattctcta tggggacttc gtgcagaggt atcgcatcct gaacccagca  2580
gccatccctg aggggcaatt cattgatagc aggaaagggg ctgagaaact gctgggctcc  2640
ctggacattg accacaacca atacaagttt ggtcacacca aggtgttctt caaggcgggc  2700
ctgctggggc tgctggagga gatgcgtgat gagaggctga gccgcatcat caccagaatc  2760
caggcccagt cccgaggtgt gctctccaga atggagttca gaagctgct ggagcgcaga   2820
gactccctgc tgattatcca gtggaacatt agggccttca tcgggtgtaa gaattggcca  2880
tggatgaagc tctacttcaa gatcaagccg ctgctgaaga gcgggagac ggagaaggag   2940
atggccacca tgaaggagga gtttgggcga tcaaagatg cactagaga gtctgaggct   3000
cgccgcaagg agctggagga gaagatggtg tccctgctgc aggagaagaa tgacctgcag  3060
ctccaagtgc aggcggagaca agacaacttg gcggatgcag aggagcgctg tgaccagctg  3120
atcaagaaca agatctgget ggaggccaag gtgaaggaga tgactgaggac gctggaggac  3180
gaggaggaga tgaatgccga gctcactgcc aagaagcgca agctggaaga tgagtgctca  3240
gagctcaagc gggatatcga tgacctggag ctgacgctgg ccaaggtgga aaggaaaag   3300
catgcaacag agaacaaggt gaaaaacctg acagaggaga tggctggtt ggatgagatc  3360
attgtcaagc tgacaaagga gaaaaagct ctgcaagagg cccaccagca ggctctggat  3420
gacctgcagg ctgaggaaga caaggtcaat actctgacca aggccaaggt caaggctgag  3480
cagcaggtgg atgatctgga gggatccctg gagcaggaa agaaggtgcg catggaccta  3540
gagcgagcca agcggaagct ggagggagac ctgaagctga cgcaggagag catcatggac  3600
ctggagaatg acaagcagca gttggatgag cgactcaaaa agaaggactt tgagttaaat  3660
gcactcaatg ccaggattga ggatgagcaa gccctgggca gtcagctgca agaagaagtc  3720
aaggagcttc aggcacgcat cgaggagctg gaggaggagc tggaggccga gcgcacagcc  3780
```

```
cgggccaagg tggagaagct gcgctctgac ctgtcccggg agctggagga gatcagtgaa   3840
aggctggagg aggcaggcgg ggccacatcc gtgcagatag agatgaacaa gaagcgcgag   3900
gccgagttcc agaagatgcg gcgggacctg gaggaggcca cgctgcagca cgaggccacg   3960
gcggcggccc tgcgcaagaa gcatgccgac agcgtggcgg agctgggcga gcagatcgac   4020
aacctccagc gggtgaaaca gaagctggag aaagagaaaa gcgagttcaa gctggagctg   4080
gatgacgtca cctccaacat ggagcagatc atcaaggcca aggctaacct ggagaagatg   4140
tgccggacct tggaagacca gatgaatgag caccggagca aggccgagga gacgcagcgt   4200
tctgtcaatg acctcaccag ccagcgggcc aagctgcaga cagagaatgg ggagctgtcc   4260
cggcagctgg aggaggaagga ggctctgatc tctcagctaa cccgaggcaa gctcacatat   4320
acacagcagc tggaggacct caagaggcaa ctggaggagg aggtcaaggc caagaacgca   4380
ctggcccacg cactgcagtc agcacggcat gattgtgacc tgctgaggga acagtatgag   4440
gaggagacag aggccaaggc tgagctacag cgagtcctgt ccaaggccaa ttcagaggtg   4500
gcccagtgga ggaccaagta tgagacggat gccatacaga ggacagagga gctggaggaa   4560
gccaagaaga agctggctca gaggctgcag gatgcagagg agcagtggga ggctgtcaat   4620
gccaagtgtt cctctctgga gaagaccaag cacaggctgc agaatgagat cgaggacctg   4680
atggtgacgg tggagcgctc caatgccgcc gccgcagccc tggacaagaa gcagaggaac   4740
tttgacaaga tcctggctga gtggaagcag aagtatgagg agtcgcagtc agagctggag   4800
tcttcccaga aggaggcgcg ctccctgagc acagagctct tcaagctcaa gaacgcctat   4860
gaggagtctc tggagcacct agagaccttc aagcggagaa acaagaacct ccaggaggag   4920
atctcagacc tgactgagca gctgggctcc acggggaaga gcatccatga gctgaagaag   4980
atccgaaagc aactggaggc cgagaagctg gagctgcagt cggccctgga ggaggctgag   5040
gcctccctgg agcacgagga gggcaagatc ctccgcgccc agctagagtt caaccagatc   5100
aaggcagaga ttgaaaggaa gctggcagag aaggatgagg agatggagaa ggccaagcgc   5160
aaccacctgc ggatggtgga ctccctgcag acctccctgg atgcggagac acgcagccgc   5220
aatgaggccc tgcgggtgaa gaagaagatg gagggcgacc tcaacgagat ggagatccaa   5280
ctcagccatg ccaaccgtat ggctgctgga gcccagaaaa agtgaagag cctccagagt   5340
ctgctgaagg acactcaaat ccagctggat gatgctgtcc gtgccaatga cgacctgaaa   5400
gagaacatcg ccatcgtgga acggcgcaac aacctgctgc aggcggagct ggaggagctt   5460
cgggctgtgt tggagcagac ggagcggtct cggaagctgg cagagcagga gctgattgag   5520
accagcgagc gggtgcagct gctgcactcg cagaaccaca gcctcatcaa ccagaagaag   5580
aagatggatg cagacctatc ccagctccaa acagaagtag aggaggcagt gcaggagtgt   5640
aggaacgcag aggagaaggc caagaaggct atcacagatg ccgccatgat ggctgaggag   5700
ctgaagaagg agcaggacac cagcgcccac ctggagcgca tgaagaagaa catggagcag   5760
accatcaagg acttgcagca ccgtctggac gaggcagagc agatcgccct caagggcggc   5820
aagaagcagc tgcagaagct ggaggcccgg gtccggggag ctggagaatga gctggaggct   5880
gagcaaaagc gcaatgcaga gtcagtgaag ggcatgagga gagtgagcg gcgcatcaag   5940
gagctcacct accagacaga ggaagacagg aagaacctac tgcggctgca ggacctggtg   6000
gacaagctgc agctgaaggt gaaggcctac aagcgccagg ctgaggaggc ggaggagcag   6060
gccaacacca acctgtccaa gttccgcaag gtgcagcacg actggatga ggcggaggag   6120
agggcggaca tcgccgagtc ccaggtcaac aagctgcggg ccaagagccg ggacattggt   6180
gccaagggcc tgaatgagga gtagctcttg tgctacccag ctccaagggt gcccgtgaag   6240
ccctcagacc tggagccttt gcaacagccc tttaggtgga agcagaataa agcaatttc   6300
cttaaagcca aaa                                                      6313

SEQ ID NO: 920         moltype = DNA   length = 16
FEATURE                Location/Qualifiers
source                 1..16
                       mol_type = other DNA
                       organism = synthetic construct
SEQUENCE: 920
tctcctcacg gaagca                                                   16

SEQ ID NO: 921         moltype = DNA   length = 16
FEATURE                Location/Qualifiers
source                 1..16
                       mol_type = other DNA
                       organism = synthetic construct
SEQUENCE: 921
ctctcctcac ggaagc                                                   16

SEQ ID NO: 922         moltype = DNA   length = 16
FEATURE                Location/Qualifiers
source                 1..16
                       mol_type = other DNA
                       organism = synthetic construct
SEQUENCE: 922
cctctcctca cggaag                                                   16

SEQ ID NO: 923         moltype = DNA   length = 16
FEATURE                Location/Qualifiers
source                 1..16
                       mol_type = other DNA
                       organism = synthetic construct
SEQUENCE: 923
aaacttgctc agcagt                                                   16

SEQ ID NO: 924         moltype = DNA   length = 16
FEATURE                Location/Qualifiers
source                 1..16
```

```
                         mol_type = other DNA
                         organism = synthetic construct
SEQUENCE: 924
caaacttgct cagcag                                                       16

SEQ ID NO: 925           moltype = DNA   length = 16
FEATURE                  Location/Qualifiers
source                   1..16
                         mol_type = other DNA
                         organism = synthetic construct
SEQUENCE: 925
ccaaacttgc tcagca                                                       16

SEQ ID NO: 926           moltype = DNA   length = 16
FEATURE                  Location/Qualifiers
source                   1..16
                         mol_type = other DNA
                         organism = synthetic construct
SEQUENCE: 926
cccaaacttg ctcagc                                                       16

SEQ ID NO: 927           moltype = DNA   length = 16
FEATURE                  Location/Qualifiers
source                   1..16
                         mol_type = other DNA
                         organism = synthetic construct
SEQUENCE: 927
ccccaaactt gctcag                                                       16

SEQ ID NO: 928           moltype = DNA   length = 16
FEATURE                  Location/Qualifiers
source                   1..16
                         mol_type = other DNA
                         organism = synthetic construct
SEQUENCE: 928
tccccaaact tgctca                                                       16

SEQ ID NO: 929           moltype = DNA   length = 16
FEATURE                  Location/Qualifiers
source                   1..16
                         mol_type = other DNA
                         organism = synthetic construct
SEQUENCE: 929
gtttgatgtc cctgtg                                                       16

SEQ ID NO: 930           moltype = DNA   length = 16
FEATURE                  Location/Qualifiers
source                   1..16
                         mol_type = other DNA
                         organism = synthetic construct
SEQUENCE: 930
ggtttgatgt ccctgt                                                       16

SEQ ID NO: 931           moltype = DNA   length = 16
FEATURE                  Location/Qualifiers
source                   1..16
                         mol_type = other DNA
                         organism = synthetic construct
SEQUENCE: 931
gggtttgatg tccctg                                                       16

SEQ ID NO: 932           moltype = DNA   length = 16
FEATURE                  Location/Qualifiers
source                   1..16
                         mol_type = other DNA
                         organism = synthetic construct
SEQUENCE: 932
acagcctgca ggatct                                                       16

SEQ ID NO: 933           moltype = DNA   length = 16
FEATURE                  Location/Qualifiers
source                   1..16
                         mol_type = other DNA
                         organism = synthetic construct
SEQUENCE: 933
cacagcctgc aggatc                                                       16

SEQ ID NO: 934           moltype = DNA   length = 16
FEATURE                  Location/Qualifiers
```

```
source                        1..16
                              mol_type = other DNA
                              organism = synthetic construct
SEQUENCE: 934
ccacagcctg caggat                                                              16

SEQ ID NO: 935                moltype = DNA   length = 16
FEATURE                       Location/Qualifiers
source                        1..16
                              mol_type = other DNA
                              organism = synthetic construct
SEQUENCE: 935
cccacagcct gcagga                                                              16

SEQ ID NO: 936                moltype = DNA   length = 16
FEATURE                       Location/Qualifiers
source                        1..16
                              mol_type = other DNA
                              organism = synthetic construct
SEQUENCE: 936
gcccacagcc tgcagg                                                              16

SEQ ID NO: 937                moltype = DNA   length = 16
FEATURE                       Location/Qualifiers
source                        1..16
                              mol_type = other DNA
                              organism = synthetic construct
SEQUENCE: 937
cgcccacagc ctgcag                                                              16

SEQ ID NO: 938                moltype = DNA   length = 16
FEATURE                       Location/Qualifiers
source                        1..16
                              mol_type = other DNA
                              organism = synthetic construct
SEQUENCE: 938
ccgcccacag cctgca                                                              16

SEQ ID NO: 939                moltype = DNA   length = 16
FEATURE                       Location/Qualifiers
source                        1..16
                              mol_type = other DNA
                              organism = synthetic construct
SEQUENCE: 939
accgcccaca gcctgc                                                              16

SEQ ID NO: 940                moltype = DNA   length = 16
FEATURE                       Location/Qualifiers
source                        1..16
                              mol_type = other DNA
                              organism = synthetic construct
SEQUENCE: 940
caccgcccac agcctg                                                              16

SEQ ID NO: 941                moltype = DNA   length = 16
FEATURE                       Location/Qualifiers
source                        1..16
                              mol_type = other DNA
                              organism = synthetic construct
SEQUENCE: 941
ccaccgccca cagcct                                                              16

SEQ ID NO: 942                moltype = DNA   length = 16
FEATURE                       Location/Qualifiers
source                        1..16
                              mol_type = other DNA
                              organism = synthetic construct
SEQUENCE: 942
cccaccgccc acagcc                                                              16

SEQ ID NO: 943                moltype = DNA   length = 16
FEATURE                       Location/Qualifiers
source                        1..16
                              mol_type = other DNA
                              organism = synthetic construct
SEQUENCE: 943
gcccaccgcc cacagc                                                              16

SEQ ID NO: 944                moltype = DNA   length = 16
```

```
                        -continued

FEATURE             Location/Qualifiers
source              1..16
                    mol_type = other DNA
                    organism = synthetic construct
SEQUENCE: 944
ccaggcccac cgccca                                                      16

SEQ ID NO: 945      moltype = DNA   length = 16
FEATURE             Location/Qualifiers
source              1..16
                    mol_type = other DNA
                    organism = synthetic construct
SEQUENCE: 945
cccaggccca ccgccc                                                      16

SEQ ID NO: 946      moltype = DNA   length = 16
FEATURE             Location/Qualifiers
source              1..16
                    mol_type = other DNA
                    organism = synthetic construct
SEQUENCE: 946
tcccaggccc accgcc                                                      16

SEQ ID NO: 947      moltype = DNA   length = 16
FEATURE             Location/Qualifiers
source              1..16
                    mol_type = other DNA
                    organism = synthetic construct
SEQUENCE: 947
tgcctgtccc aggccc                                                      16

SEQ ID NO: 948      moltype = DNA   length = 16
FEATURE             Location/Qualifiers
source              1..16
                    mol_type = other DNA
                    organism = synthetic construct
SEQUENCE: 948
ctgcctgtcc caggcc                                                      16

SEQ ID NO: 949      moltype = DNA   length = 16
FEATURE             Location/Qualifiers
source              1..16
                    mol_type = other DNA
                    organism = synthetic construct
SEQUENCE: 949
gctgcctgtc ccaggc                                                      16

SEQ ID NO: 950      moltype = DNA   length = 16
FEATURE             Location/Qualifiers
source              1..16
                    mol_type = other DNA
                    organism = synthetic construct
SEQUENCE: 950
ggtggcacct tcgaaa                                                      16

SEQ ID NO: 951      moltype = DNA   length = 16
FEATURE             Location/Qualifiers
source              1..16
                    mol_type = other DNA
                    organism = synthetic construct
SEQUENCE: 951
cggtggcacc ttcgaa                                                      16

SEQ ID NO: 952      moltype = DNA   length = 16
FEATURE             Location/Qualifiers
source              1..16
                    mol_type = other DNA
                    organism = synthetic construct
SEQUENCE: 952
tcggtggcac cttcga                                                      16

SEQ ID NO: 953      moltype = DNA   length = 16
FEATURE             Location/Qualifiers
source              1..16
                    mol_type = other DNA
                    organism = synthetic construct
SEQUENCE: 953
agtgagcccg tcctcc                                                      16
```

```
SEQ ID NO: 954           moltype = DNA   length = 16
FEATURE                  Location/Qualifiers
source                   1..16
                         mol_type = other DNA
                         organism = synthetic construct
SEQUENCE: 954
cagtgagccc gtcctc                                                         16

SEQ ID NO: 955           moltype = DNA   length = 16
FEATURE                  Location/Qualifiers
source                   1..16
                         mol_type = other DNA
                         organism = synthetic construct
SEQUENCE: 955
gcagtgagcc cgtcct                                                         16

SEQ ID NO: 956           moltype = DNA   length = 16
FEATURE                  Location/Qualifiers
source                   1..16
                         mol_type = other DNA
                         organism = synthetic construct
SEQUENCE: 956
tcccgaatgt ccgaca                                                         16

SEQ ID NO: 957           moltype = DNA   length = 16
FEATURE                  Location/Qualifiers
source                   1..16
                         mol_type = other DNA
                         organism = synthetic construct
SEQUENCE: 957
ttcccgaatg tccgac                                                         16

SEQ ID NO: 958           moltype = DNA   length = 16
FEATURE                  Location/Qualifiers
source                   1..16
                         mol_type = other DNA
                         organism = synthetic construct
SEQUENCE: 958
cttcccgaat gtccga                                                         16

SEQ ID NO: 959           moltype = DNA   length = 16
FEATURE                  Location/Qualifiers
source                   1..16
                         mol_type = other DNA
                         organism = synthetic construct
SEQUENCE: 959
ccttcccgaa tgtccg                                                         16

SEQ ID NO: 960           moltype = DNA   length = 16
FEATURE                  Location/Qualifiers
source                   1..16
                         mol_type = other DNA
                         organism = synthetic construct
SEQUENCE: 960
accttcccga atgtcc                                                         16

SEQ ID NO: 961           moltype = DNA   length = 16
FEATURE                  Location/Qualifiers
source                   1..16
                         mol_type = other DNA
                         organism = synthetic construct
SEQUENCE: 961
caccttcccg aatgtc                                                         16

SEQ ID NO: 962           moltype = DNA   length = 16
FEATURE                  Location/Qualifiers
source                   1..16
                         mol_type = other DNA
                         organism = synthetic construct
SEQUENCE: 962
gcaccttccc gaatgt                                                         16

SEQ ID NO: 963           moltype = DNA   length = 16
FEATURE                  Location/Qualifiers
source                   1..16
                         mol_type = other DNA
                         organism = synthetic construct
SEQUENCE: 963
cgcaccttcc cgaatg                                                         16
```

```
SEQ ID NO: 964           moltype = DNA  length = 16
FEATURE                  Location/Qualifiers
source                   1..16
                         mol_type = other DNA
                         organism = synthetic construct
SEQUENCE: 964
atccgctcct gcaact                                                          16

SEQ ID NO: 965           moltype = DNA  length = 16
FEATURE                  Location/Qualifiers
source                   1..16
                         mol_type = other DNA
                         organism = synthetic construct
SEQUENCE: 965
catccgctcc tgcaac                                                          16

SEQ ID NO: 966           moltype = DNA  length = 16
FEATURE                  Location/Qualifiers
source                   1..16
                         mol_type = other DNA
                         organism = synthetic construct
SEQUENCE: 966
ccatccgctc ctgcaa                                                          16

SEQ ID NO: 967           moltype = DNA  length = 16
FEATURE                  Location/Qualifiers
source                   1..16
                         mol_type = other DNA
                         organism = synthetic construct
SEQUENCE: 967
gctccctctg cctgca                                                          16

SEQ ID NO: 968           moltype = DNA  length = 16
FEATURE                  Location/Qualifiers
source                   1..16
                         mol_type = other DNA
                         organism = synthetic construct
SEQUENCE: 968
aggtggatcc gtggcc                                                          16

SEQ ID NO: 969           moltype = DNA  length = 16
FEATURE                  Location/Qualifiers
source                   1..16
                         mol_type = other DNA
                         organism = synthetic construct
SEQUENCE: 969
gggaaggtgg atccgt                                                          16

SEQ ID NO: 970           moltype = DNA  length = 16
FEATURE                  Location/Qualifiers
source                   1..16
                         mol_type = other DNA
                         organism = synthetic construct
SEQUENCE: 970
acaggagcag ggaaag                                                          16

SEQ ID NO: 971           moltype = DNA  length = 16
FEATURE                  Location/Qualifiers
source                   1..16
                         mol_type = other DNA
                         organism = synthetic construct
SEQUENCE: 971
cagactgcgg tgagtt                                                          16

SEQ ID NO: 972           moltype = DNA  length = 16
FEATURE                  Location/Qualifiers
source                   1..16
                         mol_type = other DNA
                         organism = synthetic construct
SEQUENCE: 972
ggctcctggg cggcgc                                                          16

SEQ ID NO: 973           moltype = DNA  length = 16
FEATURE                  Location/Qualifiers
source                   1..16
                         mol_type = other DNA
                         organism = synthetic construct
SEQUENCE: 973
```

```
ggcggctcct gggcgg                                                          16

SEQ ID NO: 974         moltype = DNA   length = 16
FEATURE                Location/Qualifiers
source                 1..16
                       mol_type = other DNA
                       organism = synthetic construct SEQUENCE: 974
cgcgggcggc tcctgg                                                          16

SEQ ID NO: 975         moltype = DNA   length = 16
FEATURE                Location/Qualifiers
source                 1..16
                       mol_type = other DNA
                       organism = synthetic construct SEQUENCE: 975
gagcgcgggc ggctcc                                                          16

SEQ ID NO: 976         moltype = DNA   length = 16
FEATURE                Location/Qualifiers
source                 1..16
                       mol_type = other DNA
                       organism = synthetic construct SEQUENCE: 976
ggttcaggga gcgcgg                                                          16

SEQ ID NO: 977         moltype = DNA   length = 16
FEATURE                Location/Qualifiers
source                 1..16
                       mol_type = other DNA
                       organism = synthetic construct SEQUENCE: 977
agttctaggg ttcagg                                                          16

SEQ ID NO: 978         moltype = DNA   length = 16
FEATURE                Location/Qualifiers
source                 1..16
                       mol_type = other DNA
                       organism = synthetic construct SEQUENCE: 978
cagttctagg gttcag                                                          16

SEQ ID NO: 979         moltype = DNA   length = 16
FEATURE                Location/Qualifiers
source                 1..16
                       mol_type = other DNA
                       organism = synthetic construct SEQUENCE: 979
acagttctag ggttca                                                          16

SEQ ID NO: 980         moltype = DNA   length = 16
FEATURE                Location/Qualifiers
source                 1..16
                       mol_type = other DNA
                       organism = synthetic construct SEQUENCE: 980
gacagttcta gggttc                                                          16

SEQ ID NO: 981         moltype = DNA   length = 16
FEATURE                Location/Qualifiers
source                 1..16
                       mol_type = other DNA
                       organism = synthetic construct SEQUENCE: 981
agacagttct agggtt                                                          16

SEQ ID NO: 982         moltype = DNA   length = 16
FEATURE                Location/Qualifiers
source                 1..16
                       mol_type = other DNA
                       organism = synthetic construct SEQUENCE: 982
aagacagttc tagggt                                                          16

SEQ ID NO: 983         moltype = DNA   length = 16
FEATURE                Location/Qualifiers
source                 1..16
                       mol_type = other DNA
                       organism = synthetic construct
```

```
SEQUENCE: 983
gaagacagtt ctaggg                                                          16

SEQ ID NO: 984         moltype = DNA   length = 16
FEATURE                Location/Qualifiers
source                 1..16
                       mol_type = other DNA
                       organism = synthetic construct
SEQUENCE: 984
cgaagacagt tctagg                                                          16

SEQ ID NO: 985         moltype = DNA   length = 16
FEATURE                Location/Qualifiers
source                 1..16
                       mol_type = other DNA
                       organism = synthetic construct
SEQUENCE: 985
tcgaagacag ttctag                                                          16

SEQ ID NO: 986         moltype = DNA   length = 16
FEATURE                Location/Qualifiers
source                 1..16
                       mol_type = other DNA
                       organism = synthetic construct
SEQUENCE: 986
gtcgaagaca gttcta                                                          16

SEQ ID NO: 987         moltype = DNA   length = 16
FEATURE                Location/Qualifiers
source                 1..16
                       mol_type = other DNA
                       organism = synthetic construct
SEQUENCE: 987
agtcgaagac agttct                                                          16

SEQ ID NO: 988         moltype = DNA   length = 16
FEATURE                Location/Qualifiers
source                 1..16
                       mol_type = other DNA
                       organism = synthetic construct
SEQUENCE: 988
gagtcgaaga cagttc                                                          16

SEQ ID NO: 989         moltype = DNA   length = 16
FEATURE                Location/Qualifiers
source                 1..16
                       mol_type = other DNA
                       organism = synthetic construct
SEQUENCE: 989
ggagtcgaag acagtt                                                          16

SEQ ID NO: 990         moltype = DNA   length = 16
FEATURE                Location/Qualifiers
source                 1..16
                       mol_type = other DNA
                       organism = synthetic construct
SEQUENCE: 990
cggagtcgaa gacagt                                                          16

SEQ ID NO: 991         moltype = DNA   length = 16
FEATURE                Location/Qualifiers
source                 1..16
                       mol_type = other DNA
                       organism = synthetic construct
SEQUENCE: 991
ccggagtcga agacag                                                          16

SEQ ID NO: 992         moltype = DNA   length = 16
FEATURE                Location/Qualifiers
source                 1..16
                       mol_type = other DNA
                       organism = synthetic construct
SEQUENCE: 992
cccggagtcg aagaca                                                          16

SEQ ID NO: 993         moltype = DNA   length = 16
FEATURE                Location/Qualifiers
source                 1..16
                       mol_type = other DNA
```

```
                        organism = synthetic construct
SEQUENCE: 993
ccccggagtc gaagac                                                           16

SEQ ID NO: 994          moltype = DNA  length = 16
FEATURE                 Location/Qualifiers
source                  1..16
                        mol_type = other DNA
                        organism = synthetic construct
SEQUENCE: 994
gccccggagt cgaaga                                                           16

SEQ ID NO: 995          moltype = DNA  length = 16
FEATURE                 Location/Qualifiers
source                  1..16
                        mol_type = other DNA
                        organism = synthetic construct
SEQUENCE: 995
ggccccggag tcgaag                                                           16

SEQ ID NO: 996          moltype = DNA  length = 16
FEATURE                 Location/Qualifiers
source                  1..16
                        mol_type = other DNA
                        organism = synthetic construct
SEQUENCE: 996
gggccccgga gtcgaa                                                           16

SEQ ID NO: 997          moltype = DNA  length = 16
FEATURE                 Location/Qualifiers
source                  1..16
                        mol_type = other DNA
                        organism = synthetic construct
SEQUENCE: 997
acaataaata ccgagg                                                           16
```